(12) United States Patent
Sugiura et al.

(10) Patent No.: US 9,828,406 B2
(45) Date of Patent: Nov. 28, 2017

(54) ANTITUMOR AGENT

(75) Inventors: Reiko Sugiura, Osaka (JP); Osamu Muraoka, Osaka (JP); Nozomi Tsutsui, Osaka (JP); Ayako Kita, Osaka (JP); Tatsuki Kunoh, Osaka (JP)

(73) Assignee: KINKI UNIVERSITY, Osaka (JP)

( * ) Notice: Subject to any disclaimer, the term of this patent is extended or adjusted under 35 U.S.C. 154(b) by 161 days.

(21) Appl. No.: 14/122,308

(22) PCT Filed: May 28, 2012

(86) PCT No.: PCT/JP2012/063686
§ 371 (c)(1),
(2), (4) Date: Dec. 23, 2013

(87) PCT Pub. No.: WO2012/165394
PCT Pub. Date: Dec. 6, 2012

(65) Prior Publication Data
US 2014/0121175 A1    May 1, 2014

(30) Foreign Application Priority Data

May 27, 2011 (JP) ................................ 2011-119797
Apr. 20, 2012 (JP) ................................ 2012-097198

(51) Int. Cl.
| | |
|---|---|
| *C07H 13/06* | (2006.01) |
| *A61K 31/7012* | (2006.01) |
| *A61K 31/7032* | (2006.01) |
| *A61K 45/06* | (2006.01) |

(52) U.S. Cl.
CPC ......... *C07H 13/06* (2013.01); *A61K 31/7012* (2013.01); *A61K 31/7032* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,849,716 A | 12/1998 | Akimoto et al. | |
| 6,153,736 A | 11/2000 | Bittman et al. | |
| 6,472,158 B1 | 10/2002 | Vertesy et al. | |
| 6,573,246 B1 | 6/2003 | Bittman et al. | |
| 2002/0022597 A1 | 2/2002 | Yamazaki et al. | |
| 2006/0165630 A1 | 7/2006 | Rubinstenn et al. | |

FOREIGN PATENT DOCUMENTS

| | | |
|---|---|---|
| DE | 19802450 A1 | 7/1999 |
| JP | 11-514992 | 12/1999 |
| JP | 2006-504752 | 2/2006 |
| JP | 2008-260715 | 10/2008 |
| JP | 2009-126820 | 6/2009 |
| WO | WO 1994/009020 | 4/1994 |
| WO | WO 2000/052020 | 9/2000 |
| WO | WO 2011/112889 | 9/2011 |

OTHER PUBLICATIONS

Crich, D. et al., Tetrahedron, "Synthesis of the mannosyl erythritol lipid MEL A; confirmation of the configuration of the meso-erythritol moiety", 2002, vol. 58, pp. 35-44.*
Faramarzi, M. A. et al., Steroids, "Microbial transformation of hydrocortisone by Acremonium strictum PTCC 5282", 2002, vol. 67, pp. 869-872.*
Tran, M. A. et al., Pigment Cell Melanoma Res., "Use of Liposomes as Drug Delivery Vehicles for Treatment of Melanoma", 2009, vol. 22, issue 4, pp. 388-399.*
Schell, W. A. et al., Journal of Clinical Microbiology, "Fatal, Disseminated Acremonium strictum Infection in a Neutropenic Host", 1996, pp. 1333-1336.*
Acumedia, "Sabouraud Dextrose Broth (7617)" product information, published Nov. 2010; also available at http://www.neogen.com/Acumedia/pdf/ProdInfo/7617_Pl.pdf.*
Extended European Search Report dated Feb. 16, 2015 issued in European Patent Application No. 12792042.9.
Konishi, M., et al. (2007), "A yeast glycolipid biosurfactant, mannosylerythritol lipid, shows high binding affinity towards lectins on a self-assembled monolayer system", *Biotechnol Lett*, 29:473-480.
Sugiura, R., et al. (2012), "Acremomannolipin A, the potential calcium signal modulator with a characteristic glycolipid structure from the filamentous fungus *Acremonium strictum* ", *Bioorganic & Medicinal Chemistry Letters*, 22: 6735-6739.
Tsutsui, N. et al. (2014), "Structure-activity relationship studies on acremomannolipin A, the potent calcium signal modulator with a novel glycolipid structure 2: Role of the alditol side chain stereochemistry", *Bioorganic & Medicinal Chemistry*, 22: 945-959.
Office Action dated Dec. 23, 2014 issued in Chinese Patent Application No. 201280025929.9—with English translation.
International Preliminary Report on Patentability dated Dec. 12, 2013 issued in PCT Application No. PCT/JP2012/063686.
Crich, D., et al. Enhanced Diastereoselectivity in β-Mannopyranosylation through the Use of Sterically Minimal Propargyl Ether Protecting Groups, *J. Org. Chem.*, vol. 71 (2006), pp. 3064-3070.
He, Y., et al. An iterative acetylene-epoxide coupling strategy for the total synthesis of longimicin C, *Tetrahedron Letters*, vol. 46 (2005), pp. 5393-5397.

(Continued)

*Primary Examiner* — Layla D Berry
*Assistant Examiner* — Bahar Craigo
(74) *Attorney, Agent, or Firm* — Harness, Dickey and Pierce, P.L.C.

(57) ABSTRACT

The invention is intended to provide an excellent antitumor agent. An antitumor agent contains a glycolipid glycoside compound represented by Formula (1) or a pharmacologically acceptable salt thereof as an active ingredient:

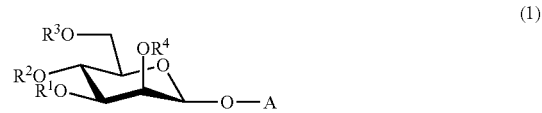

in the formula, $R^1$ to $R^4$ are the same as or different from each other and represent an alkanoyl group or a hydrogen atom, and A represents a sugar alcohol residue or a polyol residue.

2 Claims, 6 Drawing Sheets

(56) References Cited

OTHER PUBLICATIONS

Ishiwata, S. et al. Molecular Genetic Approach to Identify Inhibitors of Signal Transduction Pathways: Fission Yeast as a Model System for Drug Discovery, *Source Book of Models for Biomedical Research,* (2007) pp. 439-443.

Ma, Y., et al. Rho2 Is a Target of the Farnesyltransferase Cpp1 and Acts Upstream of Pmk1 Mitogen-activated Protein Kinase Signaling in Fission Yeast, *Molecular Biology of the Cell,* vol. 17 (2006), pp. 5028-5037.

Nishizono, N., et al. A novel method for the synthesis of 4'-thiopyrimidine nucleosides using hypervalent iodine compounds, *Org. Biomol. Chem.,* vol. 1 (2003), pp. 3692-3697.

Sugiura, R. et al. pmp1+, a suppressor of calcineurin deficiency, encodes a novel MAP kinase phosphatase in fission yeast, *The EMBO Journal,* vol. 17, No. 1 (1998), pp. 140-148.

Sugiura, R. et al. The MAPK kinase Pek1 acts as a phosphorylation-dependent molecular switch, *Nature,* vol. 399 (1999), pp. 479-483.

Sugiura, R. et al. Feedback regulation of MAPK signalling by an RNA-binding protein, *Nature,* vol. 424 (2003), pp. 961-965.

Yoshida, T., et al. A calcineurin-like gene ppb1+ in fission yeast: mutant defects in cytokinesis, cell polarity, mating and spindle pole body positioning, *Journal of Cell Science,* vol. 107 (1994), pp. 1725-1735.

Zhao, X., et al. Mannosyleiythritol Lipid Is a Potent Inducer of Apoptosis and Differentiation of Mouse Melanoma Cells in Culture, *Cancer Research,* vol. 59 (1999), pp. 482-486.

International Search Report (English Version) dated Jun. 19, 2012 issued in PCT Application No. PCT/JP2012/063686.

Office Action dated Mar. 29, 2016 issued in Japanese Patent Application No. 2012-121422 (with English concise explanation).

\* cited by examiner (g)

(h)

(i)

(j)

(k)

(l)

(s)

(t)

(u)

(v)

(w)

(x)

ANTITUMOR AGENT

PRIORITY STATEMENT

This application is a national stage application under 35 U.S.C. §371 of PCT International Application No. PCT/JP2012/063686 which has an International filing date of May 2012. PCT/JP2012/063868 claims priority under 35 U.S.C. §119 to Japanese Application No. 2011-119797 filed on 27 May 2011 and to Japanese Application No. 2012-097198 filed on 20 Apr. 2012. The contents of each application recited above are incorporated herein by reference in their entirety.

TECHNICAL FIELD

The present invention relates to an antitumor agent containing a novel glycolipid glycoside compound or a pharmacologically acceptable salt thereof as an active ingredient.

BACKGROUND ART

The invention relates to an antitumor agent containing a novel compound discovered by a new screening method that the inventors of the invention have developed, as an active ingredient. The compound, which has a pentitol and a hexitol chain as an aglycone, and in which all hydroxyl groups of a mannose ring which is a mother nucleus are esterified with medium chain fatty acids, is particularly an excellent novel glycolipid glycoside which inhibits a proliferation of tumor cells and are useful as an antitumor agent.

The glycolipid glycoside of the invention has been unknown to have an antitumor action.

As a sugar fatty acid ester compound is known a compound in which all hydroxyl groups of a mannose ring became a fatty acid ester is known (Patent Literature 1).

CITATION LIST

Patent Literature

Patent Literature 1: Japanese Unexamined Patent Publication JP-A 2006-504752

SUMMARY OF INVENTION

Technical Problem

A compound of Patent Literature 1, in terms of not having a glycoside bond, is clearly different from the glycolipid glycoside compound of the invention, is used for treatment of seborrheic dry skin and does not have an antitumor action.

The invention is intended to provide an excellent antitumor agent.

Solution to Problem

That is, the invention provides an antitumor agent containing a glycolipid glycoside compound represented by Formula (1) or a pharmacologically acceptable salt thereof as an active ingredient:

[Chem. 1]

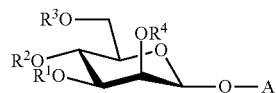

(1)

(in the formula, $R^1$ to $R^4$ are the same as or different from each other and represent an alkanoyl group or a hydrogen atom, and A represents a sugar alcohol residue or a polyol residue.)

Additionally, in the invention, in Formula (1), $R^1$ to $R^4$ are the same as or different from each other and are a lower to higher alkanoyl group or a hydrogen atom, and A is a sugar alcohol residue or a polyol residue.

Further, in the invention, in Formula (1), $R^1$ to $R^4$ are the same as or different from each other and are an alkanoyl group having 3 to 16 carbon atoms or a hydrogen atom, and A is a sugar alcohol residue having 4 to 7 carbon atoms or a polyol residue having 2 to 3 carbon atoms.

Additionally, in the invention, the antitumor agent further contains a glycolipid glycoside compound represented by Formula (1a) or a pharmacologically acceptable salt thereof as an active ingredient:

[Chem. 2]

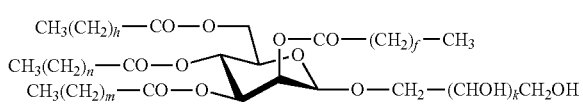

(1a)

(in the formula, f, h, m and n represent an integer of 0 to 14, and k represents an integer of 0 to 5, respectively.)

Additionally, in Formula (1a), f, h, m and n represent an integer of 2 to 8, and $-CH_2(CHOH)_kCH_2OH$ is a sugar alcohol residue having 4 to 7 carbon atoms or a glycerin residue.

Further, the invention provides an antitumor agent containing a glycolipid glycoside compound represented by Formula (1) or a pharmacologically acceptable salt thereof, and an antitumor agent as active ingredients:

[Chem. 3]

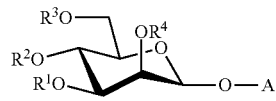

(1)

(in the formula, $R^1$ to $R^4$ are the same as or different from each other and represent an alkanoyl group or a hydrogen atom, and A represents a sugar alcohol residue or a polyol residue.)

Advantageous Effects of Invention

The glycolipid glycoside compound represented by Formula (1) or a pharmacologically acceptable salt thereof exhibits proliferation inhibitory effect on various tumor cells and is useful as an antitumor agent.

In addition, the antitumor agent containing a glycolipid glycoside compound represented by Formula (1) or a pharmacologically acceptable salt thereof and an antitumor agent as active ingredients synergistically exhibits proliferation inhibitory effect on a tumor cell compared to a case of singly using a glycoside compound (1) or an antitumor agent respectively, and is useful as an antitumor agent.

The objects, features and advantages of the invention become further apparent by the following detailed description and drawings.

BRIEF DESCRIPTION OF DRAWINGS

FIG. 2(a) is a chemical formula of a glycolipid glycoside compound obtained in Preparation Example 1, FIG. 2(b) is a chemical formula obtained in Preparation Example 2, FIG. 2(c) is a chemical formula obtained in Preparation Example 3, FIG. 2(d) is a chemical formula obtained in Preparation Example 4, FIG. 2(e) is a chemical formula obtained in Preparation Example 5, and FIG. 2(f) is a chemical formula obtained in Preparation Example 6;

FIG. 3(g) and FIG. 3(h) are chemical formulae of the glycolipid glycoside compounds obtained in Preparation Example 7, FIG. 3(i) is a chemical formula obtained in Preparation Example 8, FIG. 3(j) is a chemical formula obtained in Preparation Example 9, FIG. 3(k) is a chemical formula obtained in Preparation Example 10 and FIG. 3(l) is a chemical formula obtained in Preparation Example 11;

FIG. 4(m) is a chemical formula of a glycolipid glycoside compound obtained in Preparation Example 12, FIG. 4(n) is a chemical formula obtained in Preparation Example 13, FIG. 4(o) is a chemical formula obtained in Preparation Example 16, FIG. 4(p) is a chemical formula obtained in Preparation Example 17, FIG. 4(q) is a chemical formula obtained in Preparation Example 18, and FIG. 4(r) is a chemical formula obtained in Preparation Example 19;

FIG. 5(s) is a chemical formula of a glycolipid glycoside compound obtained in Preparation Example 20, FIG. 5(t) is a chemical formula obtained in Preparation Example 21, FIG. 5(u) is a chemical formula obtained in Preparation Example 22, FIG. 5(v) is a chemical formula obtained in Preparation Example 23, FIG. 5(w) is a chemical formula obtained in Preparation Example 24 and FIG. 5(x) is a chemical formula obtained in Preparation Example 25; FIG. 6(y) is a chemical formula of a glycolipid glycoside compound obtained in Preparation Example 28.

DESCRIPTION OF EMBODIMENTS

Figure 1:
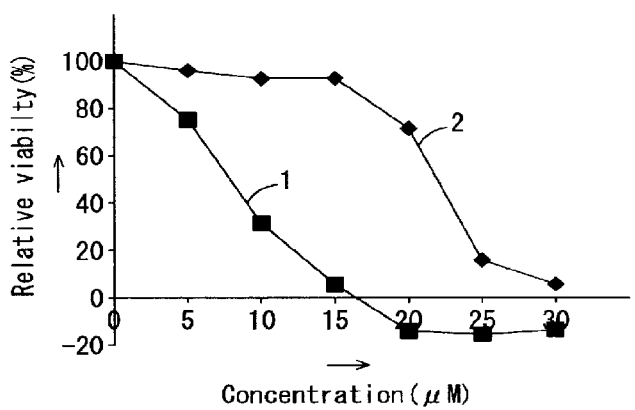
FIG. 1 is a graph comparing concentration and cell proliferation inhibition rate of a glycoside compound (1) (Preparation Example 24) with respect to normal embryonic kidney-derived cells (HEK293F) and human acute lymphoblastic leukemia T-cells (Molt-4), and in the figure, line 1 shows a proliferation curve of the human acute lymphoblastic leukemia T-cell (Molt-4) and line 2 shows a proliferation curve of the normal embryonic kidney-derived cell (HEK293F)
Figure 2:
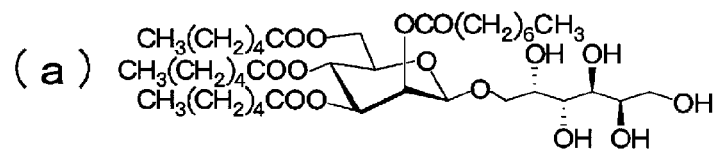
FIG. 2 are chemical formulae of glycolipid glycoside compounds obtained in Preparation Examples of the invention, and in the figure.
Figure 2:
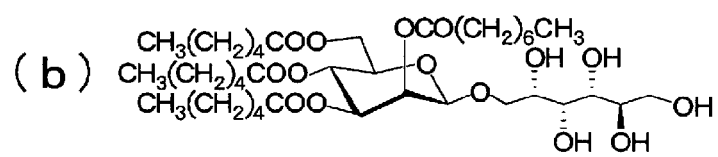
Figure 2:
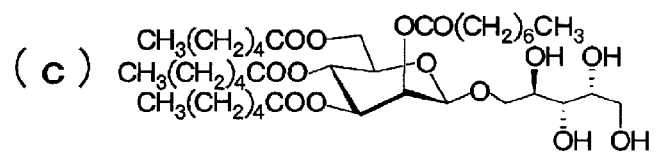
Figure 2:
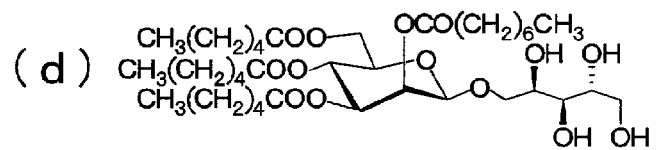
Figure 2:
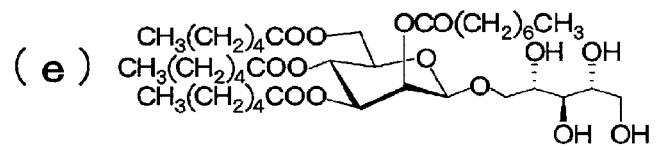
Figure 2:
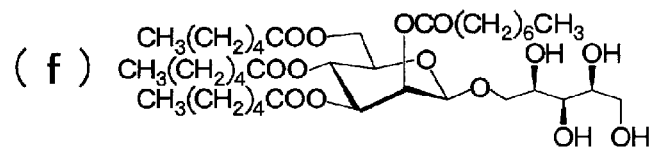
Figure 3:
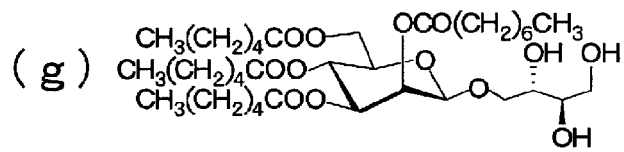
FIG. 3 are chemical formulae of glycolipid glycoside compounds obtained in Preparation Examples of the invention, and in the figure.
Figure 3:
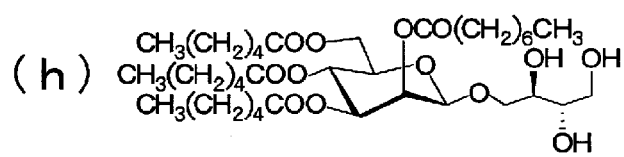
Figure 3:
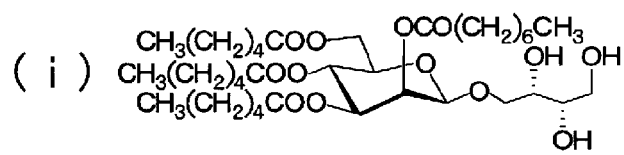
Figure 3:
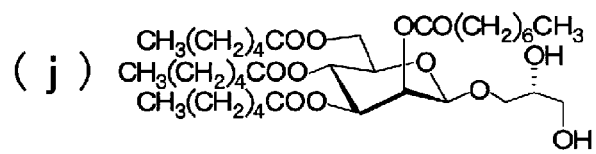
Figure 3:
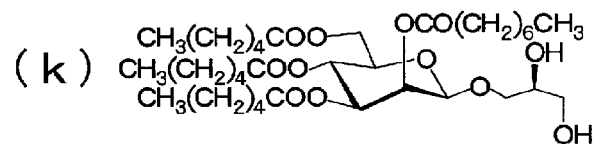
Figure 3:
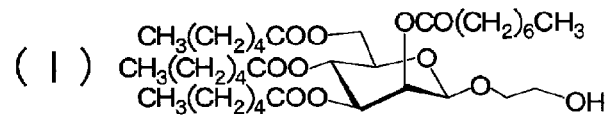
Figure 4:
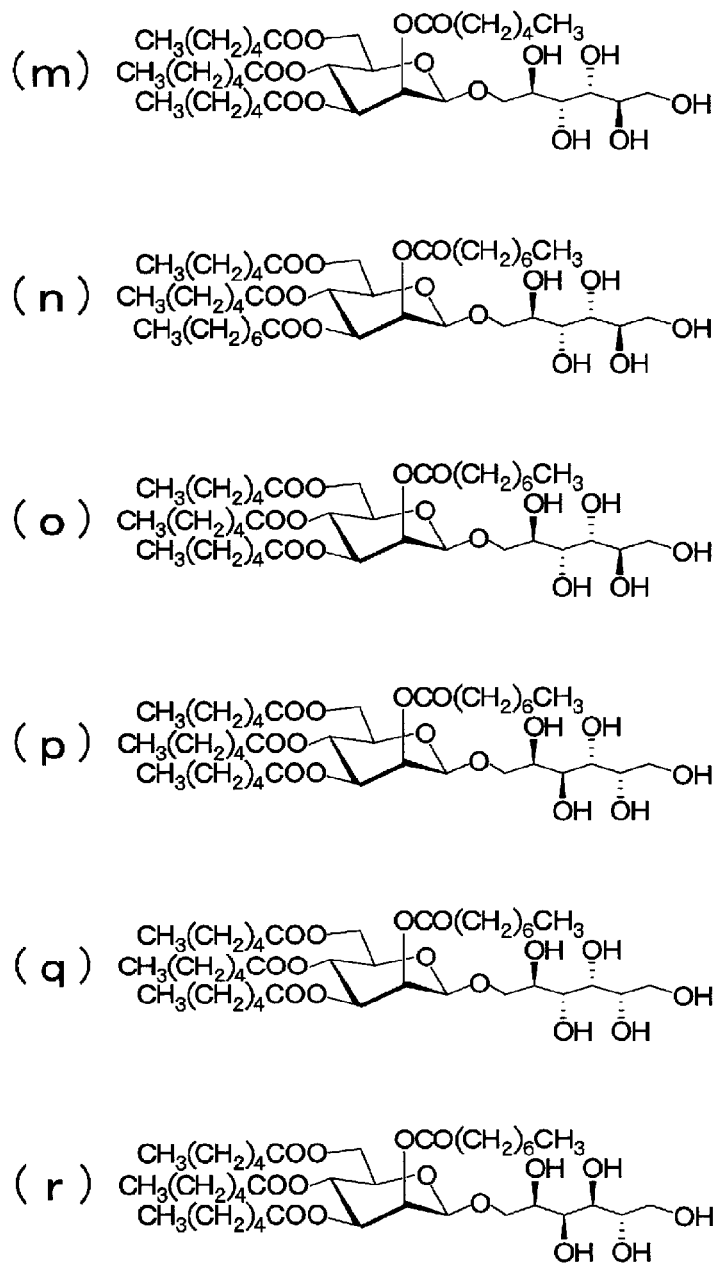
FIG. 4 are chemical formulae of glycolipid glycoside compounds obtained in Preparation Examples of the invention, and in the figure.
Figure 5:
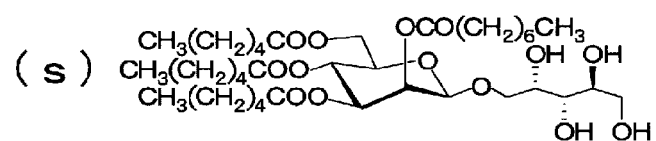
FIG. 5 are chemical formulae of glycolipid glycoside compounds obtained in Preparation Examples of the invention, and in the figure.
Figure 5:
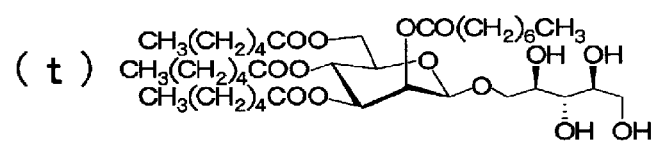
Figure 5:
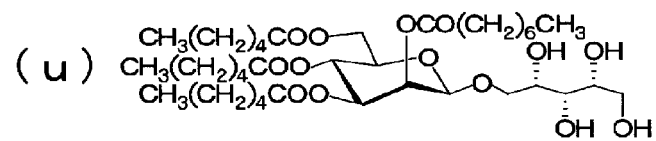
Figure 5:
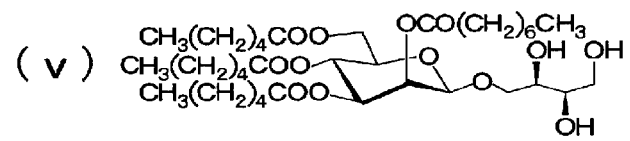
Figure 5:
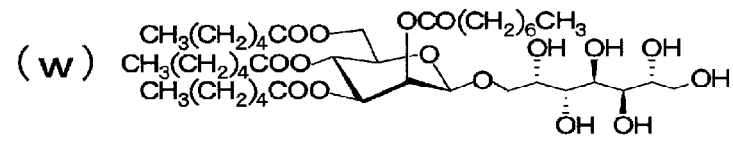
Figure 5:
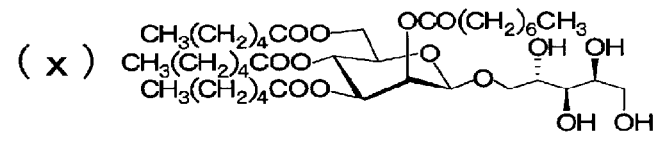
Figure 6:
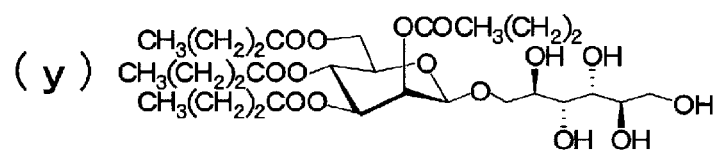
FIG. 6 is a chemical formula of a glycolipid glycoside compound obtained in Preparation Example of the invention, and in the figure.

Hereinafter, the preferred embodiments of the invention will be described in detail with reference to the drawings.

The invention is characterized in that the antitumor agent contains a glycolipid glycoside compound represented by Formula (1) or a pharmacologically acceptable salt thereof as an active ingredient:

[Chem. 4]

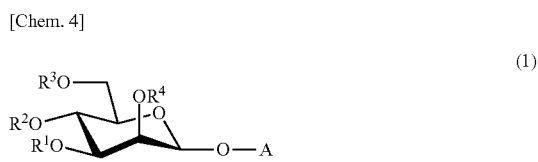

(in the formula, $R^1$ to $R^4$ are the same as or different from each other and represent an alkanoyl group or a hydrogen atom, and A represents a sugar alcohol residue or a polyol residue.)

In a glycolipid glycoside compound (hereinafter, referred to as a glycoside compound (1)) which is an active ingredient and represented by the above formula (1), $R^1$ to $R^4$, are the same or different, represent a higher or lower alkanoyl group or a hydrogen atom, and A is a sugar alcohol residue or a polyol residue.

In a glycoside compound (1), as an alkanoyl group represented by $R^1$ to $R^4$, an alkanoyl group having 20 or less carbon atoms is exemplified. For example, an alkanoyl group having 3 to 18 carbon atoms such as a formyl group, an acetyl group, a propionyl group, a butanoyl group, a pentanoyl group, a hexanoyl group, a heptanoyl group, an octanoyl group, a nonanoyl group, a decanoyl group, an undecanoyl group, a dodecanoyl group, a tridecanoyl group, a tetradecanoyl group, a pentadecanoyl group, a hexadecanoyl group, a heptadecanoyl group, an octadecanoyl group or the like is preferable, and a propionyl group, a butanoyl group, a pentanoyl group, a hexanoyl group, a heptanoyl group, an octanoyl group or a hexadecanoyl group are particularly preferable.

In a glycoside compound (1), a glycoside bond may be an α-glycoside bond or a β-glycoside bond, however, a β-glycoside bond is desirable in terms of the antitumor effect.

In a glycoside compound (1), a sugar alcohol residue or a polyol residue represented by A is a compound in which one hydroxyl group has been eliminated from a sugar alcohol or a polyol.

As the sugar alcohols, sugar alcohols having 4 to 7 carbon atoms are exemplified. Specifically, for example, sugar alcohols having 4 carbon atoms such as erythritol, threitol and the like, sugar alcohols having 5 carbon atoms such as ribitol, arabinitol, xylitol and the like, sugar alcohols having 6 carbon atoms such as sorbitol, mannitol, galactitol and the like, and sugar alcohols having 7 carbon atoms such as perseitol, volemitol, D-glycero-D-glucoheptitol and the like are exemplified.

These sugar or sugar alcohols have various optical isomers or stereoisomers, however, any one may be used in the invention. However, in terms of the antitumor effect, for example, compounds having stereochemistry such as D-glucose as hexitol and L-arabinose as pentitol are preferable.

Furthermore, as the polyol, divalent or trivalent alcohols having 2 to 3 carbon atoms such as ethylene glycol and glycerine are exemplified.

Among them, the sugar alcohol residues such as erythritol, threitol, ribitol, arabinitol, xylitol, sorbitol, mannitol, and galactitol, and the polyol residues such as ethylene glycol and glycerine are preferable, and erythritol, threitol, xylitol, sorbitol, and galactitol residues are particularly preferable.

As a glycoside compound (1), a preferable compound is a glycolipid glycoside compound in which $R^1$ to $R^4$ are the same as or different from each other and are an alkanoyl group having 1 to 18 carbon atoms such as a formyl group, an acetyl group, a propionyl group, a butanoyl group, a pentanoyl group, a hexanoyl group, a heptanoyl group, an octanoyl group, a nonanoyl group, a decanoyl group, an undecanoyl group, a dodecanoyl group, a tridecanoyl group, a tetradecanoyl group, a pentadecanoyl group, a hexadecanoyl group, a heptadecanoyl group, an octadecanoyl group or the like, and sugar alcohols are sugar alcohol residues having 4 to 7 carbon atoms such as sugar alcohols having 4 carbon atoms such as erythritol and threitol, sugar alcohols having 5 carbon atoms such as ribitol, arabinitol, and xylitol, sugar alcohols having 6 carbon atoms such as sorbitol, mannitol, and galactitol, sugar alcohols having 7 carbon atoms such as perseitol, volemitol, and D-glycero-D-glucoheptitol, or divalent or trivalent alcohol residues having 2 to 3 carbon atoms such as ethylene glycol and glycerine, and the glycoside bond is a β-glycoside bond.

Moreover, as more preferable glycoside compound, compounds represented by the above formula (1a) are exemplified. For example, glycolipid glycoside compounds in which, in Formula (1), the alkanoyl group represented by $R^1$ to $R^4$ is a propionyl group, a butanoyl group, a pentanoyl group, a hexanoyl group, a heptanoyl group, an octanoyl group or hexadecanoyl group, and A is a sugar alcohol residue having 4 to 7 carbon atoms such as a sugar alcohol having 4 carbon atoms such as erythritol, or threitol, a sugar alcohol having 5 carbon atoms such as ribitol, arabinitol, or xylitol, a sugar alcohol having 6 carbon atoms such as sorbitol, mannitol, or galactitol, or a sugar alcohol having 7 carbon atoms such as perseitol, volemitol, or D-glycero-D-glucoheptitol, or a glycerine residue are exemplified.

In particular, the alkanoyl group represented by $R^1$ to $R^4$ may be an alkanoyl group having 4 to 10 carbon atoms.

Examples of compounds of the invention include, for example:

D-galactitolyl 3,4,6-tri-O-hexanoyl-2-O-octanoyl-β-D-mannopyranoside (D-galactitol-1-yl 3,4,6-tri-O-hexanoyl-2-O-octanoyl-β-D-mannopyranoside), D-glucitol-1-yl 3,4,6-tri-O-hexanoyl-2-O-octanoyl-β-D-mannopyranoside, D-lixitolyl 3,4,6-tri-O-hexanoyl-2-O-octanoyl-β-D-mannopyranoside (D-arabinitol-5-yl 3,4,6-tri-O-hexanoyl-2-O-octanoyl-β-D-mannopyranoside), D-arabitolyl 3,4,6-tri-O-hexanoyl-2-O-octanoyl-β-D-mannopyranoside (D-arabinitol-1-yl 3,4,6-tri-O-hexanoyl-2-O-octanoyl-β-D-mannopyranoside), D-ribitolyl 3,4,6-tri-O-hexanoyl-2-O-octanoyl-β-D-mannopyranoside (D-ribitol-1-yl 3,4,6-tri-O-hexanoyl-2-O-octanoyl-β-D-mannopyranoside), L-xylitolyl 3,4,6-tri-O-hexanoyl-2-O-octanoyl-β-D-mannopyranoside (D-xylitol-5-yl 3,4,6-tri-O-hexanoyl-2-O-octanoyl-β-D-mannopyranoside), L-erythritolyl 3,4,6-tri-O-hexanoyl-2-O-octanoyl-β-D-mannopyranoside (D-erythritol-4-yl 3,4,6-tri-O-hexanoyl-2-O-octanoyl-β-D-mannopyranoside), D-erythritol-1-yl 3,4,6-tri-O-hexanoyl-2-O-octanoyl-β-D-mannopyranoside, L-threitolyl 3,4,6-tri-O-hexanoyl-2-O-octanoyl-β-D-mannopyranoside (L-threitol-1-yl 3,4,6-tri-O-hexanoyl-2-O-octanoyl-β-D-mannopyranoside), D-glycerolyl 3,4,6-tri-O-hexanoyl-2-O-octanoyl-β-D-mannopyranoside (D-glycerol-1-yl 3,4,6-tri-O-hexanoyl-2-O-octanoyl-β-D-mannopyranoside), L-glycerolyl 3,4,6-tri-O-hexanoyl-2-O-octanoyl-β-D-mannopyranoside (D-glycerol-3-yl 3,4,6-tri-O-hexanoyl-2-O-octanoyl-β-D-mannopyranoside), Ethylene glycolyl 3,4,6-tri-O-hexanoyl-2-O-octanoyl-β-D-mannopyranoside (2-hydroxyethanol-1-yl 3,4,6-tri-O-hexanoyl-2-O-octanoyl-β-D-mannopyranoside), D-mannitolyl 2,3,4,6-tetra-O-hexanoyl-β-D-mannopyranoside (D-mannitol-1-yl 2,3,4,6-tetra-O-hexanoyl-β-D-mannopyranoside), D-mannitol-1-yl 2,3,4,6-tetra-O-octanoyl-β-D-mannopyranoside, D-mannitol-1-yl 2,3,4,6-tetra-O-propionyl-β-D-mannopyranoside, D-mannitol-1-yl 2,3,4,6-tetra-O-palmitoyl-β-D-mannopyranoside, D-mannitolyl 4,6-di-O-hexanoyl-2,3-di-O-octanoyl-β-D-mannopyranoside (D-mannitol-1-yl 4,6-di-O-hexanoyl-2,3-di-O-octanoyl-β-D-mannopyranoside), D-mannitolyl 4,6-di-O-hexanoyl-2,3-di-O-propionyl-β-D-mannopyranoside (D-mannitol-1-yl 4,6-O-hexanoyl-2,3-di-O-propionyl-β-D-mannopyranoside), D-mannitolyl 4,6-di-O-hexanoyl-2,3-di-O-palmitoyl-β-D-mannopyranoside (D-mannitol-1-yl 4,6-di-O-hexanoyl-2,3-di-O-palmitoyl-β-D-mannopyranoside), D-mannitolyl 3,4,6-tri-O-hexanoyl-2-O-octanoyl-β-D-mannopyranoside (D-mannitol-1-yl 3,4,6-tri-O-hexanoyl-2-O-octanoyl-β-D-mannopyranoside), D-galactitolyl 3,4,6-tri-O-hexanoyl-2-O-octanoyl-β-D-mannopyranoside (D-galactitol-6-yl 3,4,6-tri-O-hexanoyl-2-O-octanoyl-β-D-mannopyranoside), D-glucitol-6-yl 3,4,6-tri-O-hexanoyl-2-O-octanoyl-β-D-mannopyranoside, L-glucitol-1-yl 3,4,6-tri-O-hexanoyl-2-O-octanoyl-β-D-mannopyranoside, L-arabinitol-1-yl 3,4,6-tri-O-hexanoyl-2-O-octanoyl-β-D-mannopyranoside, D-ribitol-5-yl 3,4,6-tri-O-hexanoyl-2-O-octanoyl-β-D-mannopyranoside, D-xylitol-1-yl 3,4,6-tri-O-hexanoyl-2-O-octanoyl-β-D-mannopyranoside, D-threitol-1-yl 3,4,6-tri-O-hexanoyl-2-O-octanoyl-β-D-mannopyranoside, D-glycero-D-galacto-heptitol-1-yl 3,4,6-tri-O-hexanoyl-2-O-octanoyl-β-D-mannopyranoside, L-arabinitol-5-yl 3,4,6-tri-O-hexanoyl-2-O-octanoyl-β-D-mannopyranoside, D-mannitol-1-yl 2,3,4,6-tetra-O-hexanoyl-α-D-mannopyranoside, D-mannitol-1-yl 2,3,4,6-tetra-O-octanoyl-α-D-mannopyranoside, D-mannitol-1-yl 2,3,4,6-tetra-O-propionyl-α-D-mannopyranoside, D-mannitol-1-yl 3,4,6-tri-O-hexanoyl-2-O-octanoyl-α-D-mannopyranoside, D-mannitol-1-yl 2,3,4,6-tetra-O-butanoyl-β-D-mannopyranoside, D-mannitol-1-yl 2,3,4,6-tetra-O-pentanoyl-β-D-mannopyranoside, and D-mannitol-1-yl 2,3,4,6-tetra-O-heptanoyl-β-D-mannopyranoside.

The glycoside compound (1), as shown in Examples, inhibits the proliferation with respect to solid cancer and humoral cancer in human such as renal cancer cells (ACHN), acute lymphoblastic leukemia T-cell (Molt-4), cervical cancer cells (HeLa), gastric cancer cells (MKN45) and bladder cancer cells (T24), at low concentrations.

Antitumor action of the glycoside compound (1) is considered to be due to $Ca^{2+}$ signal antagonism that the glycoside compound (1) has.

By being activated in response to various extracellular stimuli, MAP kinase (mitogen-activated protein kinase: MAPK) signal transduction pathway is involved in the control of various biological phenomena such as cell proliferation, cell differentiation, and apoptosis. In addition, MAPK plays an essential role in the cell proliferation, however, since the excessive activation of MAPK has been reported in many clinical tumors, the development of drugs for inhibiting MAPK signaling is attractive from the point of view of anticancer drug discovery.

Since Pmk1 MAPK pathway in fission yeast exhibits high homology with human ERK1/2 pathway involved in cell proliferation and malignant transformation in higher organisms, Pmk1 MAPK pathway in fission yeast is an important signaling pathway for understanding and analyzing the control mechanism of the cell proliferation signal in higher organisms.

Calcineurin (CN) is a serine/threonine protein phosphatase activated by $Ca^{2+}$/calmodulin (CaM), and a structure thereof is highly conserved in eukaryotes ranging from yeast to human. Ppb1 which is CN in fission yeast is not essential for the cell proliferation, however, it was found that Ppb1 knockout cells exhibit an abnormality of $Cl^-$ homeostasis in addition to defect in cytokinesis. That is, CN knockout cells become lethal in the presence of $MgCl_2$ at low concentrations whereas the wild-type cells can grow. However, if MAPK signal is inhibited, or MAPK is knocked out, CN knockout cells can be grown in the presence of $MgCl_2$.

That is, compounds that can suppress the phenotypes of CN knockout cells, can control MAPK signaling and the cell proliferation, and may therefore serve as inhibitors of cancerous signal transduction pathway, and further proliferation of tumors.

The glycoside compound (1) is a compound that antagonizes calcium CN signal, and has the MAPK signal inhibitory activity. Since these compounds, even in a case of using actual tumor cells, strongly inhibit proliferation of various tumor cells based on the above-described activity, it was found that, as an indicator of $Ca^{2+}$ signal antagonism, glycoside compounds have strong antitumor activity in the invention.

Furthermore, the antitumor effect of a glycolipid glycoside compound or a pharmacologically acceptable salt thereof of the invention is exhibited with respect to any tumors.

Specific examples of the tumors include malignant tumors of the oral cavity, nose, nasal cavity, larynx, pharynx such as tongue cancer, gum cancer, malignant melanoma, upper jaw cancer, nasal cancer, nasal cavity cancer, laryngeal cancer, and pharyngeal cancer; malignant tumors of cranial nerves such as glioma and meningioma, glioma; thyroid cancer such as thyroid papillary carcinoma, follicular thyroid cancer, and medullary thyroid cancer; respiratory cancer such as squamous cell carcinoma, adenocarcinoma, and alveolar epithelial cancer; breast cancer such as breast cancer, Paget's disease of breast, and breast sarcoma; hematologic cancer such as acute myeloid leukemia, acute lymphocytic leukemia, adult T-cell leukemia type, and malignant lymphoma; gastrointestinal cancer such as esophageal cancer, gastric cancer, pancreatic-gallbladder cancer, duodenum cancer, colon cancer, and primary liver cancer; uterine cancer such as cervical carcinoma in situ, cervical adenocarcinoma, uterine sarcoma, malignant uterine chorioepithelioma, uterine malignant melanoma, and ovarian cancer; urological cancer such as kidney cancer, transitional cell cancer of the renal pelvis, prostate cancer, and Wilms' tumor; musculoskeletal cancer such as rhabdomyosarcoma, fibrosarcoma, osteosarcoma, chondrosarcoma, and multiple myeloma; skin cancer such as cutaneous squamous cell carcinoma, basal cell skin cancer, skin Bowen's disease, Paget's disease of the skin, cutaneous malignant melanoma, and metastatic cancer, however, the invention is not limited thereto.

In a glycoside compound (1), as the pharmacologically acceptable salts, inorganic acid salts such as hydrochlorate, hydrobromate, sulfate, nitrate, and phosphate; organic acid salts such as acetate, tartrate, fumarate, maleate, citrate, lactate, methanesulfonate, and benzenesulfonate; alkali metal salts such as sodium salt and potassium salt; alkali earth metal salts such as calcium salt and magnesium salt are exemplified.

The antitumor agent containing a glycoside compound (1) as an active ingredient can be administered orally or parenterally. The dose of a glycoside compound (1) as the antitumor agent is different according to the target type of a tumor, degree of progress of a tumor as a disease, a patient's age, body weight, nutritional condition, sex, method of administration and the like. Generally, the dose may be selected from the range of 0.001 mg to 100 mg per 1 kg of body weight, preferably 0.001 mg to 10 mg and more preferably 0.001 mg to 1 mg.

In the pharmaceutical product field, a glycoside compound (1) may be produced as it is or by mixing with a pharmaceutically acceptable carrier, as solid products such as tablets, powders, granules, capsules, suppositories, and ointments, and products as injections, emulsions, suspensions, syrups, elixirs and lotions by well-known methods which are generally used in pharmaceutical preparation.

As the pharmaceutically acceptable carrier, for example, preparation assistants such as a diluting agent, a lubricant, a binder and a disintegrator in a solid product; or a solvent, a solubilizer, a suspending agent, an isotonizing agent, a buffer and a soothing agent in liquid products are exemplified. Moreover, if necessary, appropriate amount of additives such as a preservative, an antioxidant, a coloring agent, a sweetening agent, an adsorbent and a wetting agent normally used may also be suitably used.

As the diluting agent, for example, lactose, starch, dextrin, white sugar, tragacanth, crystalline cellulose, glucose, lactose, sucrose, corn starch, starch, sorbit, glycine, xylitol, erythritol, maltitol, sorbitol, maltose, trehalose, mannitol, calcium citrate, potassium phosphate, calcium phosphate, calcium hydrogen phosphate, magnesium aluminometasilicate and the like are exemplified.

As the lubricant, for example, magnesium stearate, talc, polyethylene glycol, silica, talc, light silicic acid anhydride, hydrated silicon dioxide, stearic acid alkaline earth metals (for example, magnesium stearate, calcium stearate), sucrose higher fatty acid esters (for example, sucrose stearic acid ester, sucrose behenic acid ester), glycerin higher fatty acid esters (for example, glycerin behenic acid ester) and the like are exemplified.

As the binder, syrup, gum arabic, gelatin, sorbit, tragacanth, polyvinylpyrrolidone, starch, gelatin, hydroxypropyl cellulose, hydroxypropyl methyl cellulose, polyvinyl pyrrolidone, dextrin, ethyl cellulose, cellulose-based binders (for example, hydroxypropyl cellulose), polyvinyl-based binders (for example, polyvinylpyrrolidone) and the like are exemplified.

As the disintegrator, white potato starch, starch, carboxymethyl cellulose, carboxymethyl cellulose calcium, low substituted hydroxypropyl cellulose, corn starch, potato starch, carboxymethyl starch sodium, partly pregelatinized starch, cross-linked carboxymethyl cellulose sodium, cross-linked polyvinyl pyrrolidone, crystalline cellulose and the like are exemplified.

As the solvent, for example, water for injection, alcohol, propylene glycol, macrogol, sesame oil, corn oil, olive oil and the like are exemplified. As the solubilizer, for example, polyethylene glycol, propylene glycol, D-mannitol, benzyl benzoate, ethanol, trisaminomethane, cholesterol, triethanolamine, sodium carbonate, sodium citrate and the like are exemplified.

As the suspending agent, for example, surfactants such as stearyl triethanolamine, sodium lauryl sulfate, lauryl amino propionic acid, lecithin, benzalkonium chloride, benzethonium chloride or glycerin monostearate, hydrophilic macromolecules such as polyvinyl alcohol, polyvinyl pyrrolidone, carboxymethyl cellulose sodium, methyl cellulose, hydroxymethyl cellulose, hydroxyethyl cellulose or hydroxypropyl cellulose and the like are exemplified.

As the isotonizing agent, for example, D-sorbitol, sodium chloride, glycerin, D-mannitol and the like are exemplified.

As the buffer, phosphate, acetate, carbonate, citrate and the like are exemplified.

As the soothing agent, benzyl alcohol and the like are exemplified.

As the preservative, for example, para-hydroxybenzoic acid esters, chlorobutanol, benzyl alcohol, phenethyl alcohol, dehydroacetic acid, sorbic acid and the like are exemplified.

As the antioxidant, for example, sulfite, ascorbic acid, α-tocopherol and the like are exemplified.

As the coloring agent, β-carotene, tar dye, lake dye, caramel, iron oxide, copper chlorophyll, Food Red No. 2, No. 3, Food Yellow No. 4, No. 5, Food Green No. 3, Food Blue No. 1, No. 2, aluminum lake thereof, iron sesquioxide, yellow iron sesquioxide and the like are exemplified. As the sweetening agent, saccharin, aspartame (manufactured by Ajinomoto Co., Ltd., 1-methyl N-L-α-aspartyl-L-phenylalanine), stevia, acesulfame potassium and the like are exemplified.

A glycoside compound (1), by using in combination with other antitumor agents, may synergistically exhibit a high antitumor effect compared to a case of singly using a glycoside compound (1) or the other antitumor agents, respectively.

In the invention, the other antitumor agents are not particularly limited, however, a microtubule depolymerization inhibitor, an antitumor antibiotic and a platinum complex are exemplified.

The microtubule depolymerization inhibitor is a drug represented by taxane-based antitumor agents, and is a drug which stabilizes the state in which microtubules are polymerized, stops the mitosis of cells, and leads to apoptosis. Specifically, paclitaxel, docetaxel and the like are exemplified.

Furthermore, the antitumor antibiotic is a drug which inhibits DNA polymerase and suppresses cell division. Specifically, doxorubicin, epirubicin, daunorubicin, bleomycin and the like are exemplified.

The platinum complex is a drug which suppresses cell division by cross-linking DNA. Specifically, cisplatin, carboplatin, oxaliplatin and the like are exemplified.

In the invention, among them, paclitaxel, doxorubicin and cisplatin are preferable.

One kind of these antitumor agents may be used in combination with a glycoside compound (1), or two or more kinds of the antitumor agents may be used in combination with a glycoside compound (1).

In the invention, "using in combination with" means administrating a glycoside compound (1) and the other antitumor agents so as not to impair respective effect, and though it is not particularly limited, for example, it means administrating two components as a single drug, or administrating at the same time two kinds of drugs obtained by formulating separately, via the same route of administration, further, administrating two kinds of drugs obtained by formulating separately, with a time interval, administrating at the same time two kinds of drugs obtained by formulating separately, via the different route of administration, or administrating two kinds of drugs obtained by formulating separately, via the different route of administration, with a time interval.

As drugs for such a combination, among the drugs, a dosage form may be suitably selected and as a formulation assistant, each of the above-described component may be used.

In the invention, a combination ratio of a glycoside compound (1) and the other antitumor agents may be suitably selected in the range of each dose. Though it is not particularly limited, for example, in any case where two components are singly formulated, or separately formulated, the combination ratio is normally in the range of 1:100 to 100:1, and preferably in the range of 1:10 to 10:1 as a weight ratio.

Furthermore, two or more kinds of other antitumor agents are used in combination, and further the resultant may be used in combination with a glycoside compound (1). In the case, the combination ratio of a glycoside compound (1) and other antitumor agents may be suitably selected in the range of each dose, and though it is not particularly limited, for example, when taxane-based antitumor agents and antitumor antibiotics are used as other antitumor agents, the combination ratio is preferably in the range of 1:100 to 100:1.

A glycoside compound (1) is prepared as follows. By condensation reaction of mannose derivatives represented by Formula (2)

[Chem. 5]

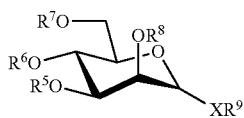

(2)

(in the formula, $R^5$ to $R^8$ are the same as or different from each other and represent an alkanoyl group, a hydrogen atom or a protecting group, and $R^9$ represents a hydrogen atom, a protecting group, or a group capable of being a leaving group together with X, X represents an oxygen atom, a sulfur atom or a nitrogen atom, X and $R^9$ represent that X and R⁹ may be a leaving group represented by XR⁹), and a sugar alcohol residue or a polyol residue represented by Formula (3)

 (3)

(in the formula, AP represents a sugar alcohol residue or a polyol residue in which a hydroxyl group has been protected), Formula (4)

[Chem. 6]

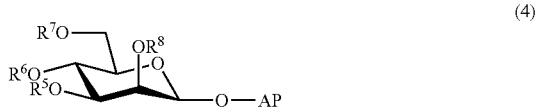 (4)

(in the formula, AP and R⁵ to R⁸ represent the same as described above) is produced.

Subsequently, a protecting group is eliminated from an alcohol represented by Formula (4), and after the elimination, a hydroxyl group is alkanoylated, or after alkanoylating a hydroxyl group of a compound represented by Formula (4), other protecting groups are eliminated.

In Formula (2), as an alkanoyl group, a protecting group in R⁵ to R⁸, and a protecting group in R⁹, the alkanoyl group represented by in R¹ to R⁴, and a protecting group of a hydroxyl group are exemplified.

As the protecting group, for example, ether-based protecting groups such as a benzyl group (Bn), a paramethoxyphenyl group, a paramethoxybenzyl group (PMB) or a tert-butyl group; acetal based-protecting groups such as a methoxy methyl group (MOM), a 2-tetrahydropyranyl group (THP) or an ethoxy ethyl group (EE); acyl-based protecting groups such as an acetyl group (Ac), a pivaloyl (Piv) or a benzoyl group (Bz); silyl ether-based protecting groups such as a trimethylsilyl group, a triethylsilyl group, a tert-butyldimethylsilyl group (TBS), a triisobutylsilyl group or a tert-butyl diphenyl silyl group; and acetal-based protecting groups such as a benzylidene acetal group or an acetonide group are exemplified.

Among them, a benzyl group, a methoxymethyl group, a paramethoxyphenyl group, a tert-butyldimethylsilyl group, a paramethoxybenzyl group, a benzylidene acetal group and an acetonide group are preferable.

Further, in a case where XR⁹ is the leaving group, when the condensation reaction of the mannose derivatives and a sugar alcohol or a polyol are performed, as the leaving group, if it is an eliminable group, anything may be used. As such a leaving group, tosylate, phenyl sulfoxide or trichloroacetimidate is exemplified. Among them, phenyl sulfoxide is preferable.

As the sugar alcohol or the polyol in which a hydroxyl group other than a hydroxyl group of portion glycoside-bonded with the mannose derivatives is protected, the above-described sugar alcohols or the above-described polyols are exemplified, and as the protecting group of a hydroxyl group, the above-described ones are exemplified.

The condensation reaction of the mannose derivatives of formula (2) and the sugar alcohol or the polyol in which a hydroxyl group of formula (3) has been protected may be performed in the presence of a reaction accelerator in an organic solvent under cooling.

As the organic solvent, solvents such as methylene chloride, DMF and dimethyl ether may be used. Moreover, as the reaction accelerator, for example, bases such as trifluoromethanesulfonic anhydride (Tf₂0) and 2,6-di-tert-butyl-4-methyl pyridine (DTBMP) are exemplified.

It is preferable to use 1.1 equivalents to 1.5 equivalents of the sugar alcohol or the polyol in which a hydroxyl group has been protected with respect to the mannose derivatives of formula (2), and it is preferable to use 1.1 equivalents to 1.5 equivalents of the reaction accelerator with respect to the mannose derivatives.

The condensation reaction may be performed at a temperature of about −78° C. to 0° C. under cooling, and is completed in about 0.5 to 1 hour generally. Saturated sodium bicarbonate water is added to the obtained reaction solution, and extracted with an extracting solvent such as methylene chloride. The crude product obtained is purified with a column chromatography, thereby obtaining the compound of formula (4).

Depending on the final objective compound, after eliminating a protecting group of obtained condensates represented by Formula (4) to obtain a hydroxyl group, the hydroxyl group is alkanoylated, or after alkanoylating a hydroxyl group of condensates represented by Formula (4), other protecting groups are eliminated, and thus, a desired glycolipid glycoside compound represented by Formula (1) may be obtained.

An elimination method of the protecting group may be performed by the generally used method in the related art, and for example, in a case where the protecting group is an ether-based protecting group such as a benzyl group (Bn), a paramethoxyphenyl group, a paramethoxybenzyl group (PMB), or a tert-butyl group, condensates of Formula (4) are hydrogenated in the presence of catalysts such as palladium or palladium-carbon, thereby being eliminated. In a case where the protecting group is a tert-butyl group, it is possible to eliminate by treating trifluoroacetic acid with strong acid.

Furthermore, in a case where the protecting group is ether-based protecting group such as a paramethoxybenzyl group (PMB), it is possible to eliminate by treating with 2,3-dichloro-5,6-dicyano-p-benzoquinone (DDQ), ceric ammonium nitrate or the like.

In a case where the protecting group is an ether-based protecting group such as a methoxymethyl group (MOM), a 2-tetrahydropyranyl group (THP) and an ethoxyethyl group (EE), it is possible to eliminate by reacting with water under acidic condition.

In a case where the protecting group is an acyl-based protecting group such as an acetyl group (Ac), a pivaloyl group (Piv) or a benzoyl group (Bz), it is possible to eliminate by treating with potassium carbonate in methanol, under basic conditions or strong basic conditions.

In a case where the protecting group is a silyl ether-based protecting group such as a trimethylsilyl group, a triethylsilyl group, a tert-butyldimethylsilyl group (TBS), a triisobutylsilyl group or a tert-butyldimethylsilyl group, it is possible to eliminate by treating condensates represented by Formula (4) with fluoride under acidic condition.

In a case where the protecting group is an acetal-based protecting group such as a benzylidene acetal group or an acetonide group, it is possible to eliminate by treating with acid.

An alkanoylation of hydroxyl group of the compound of formula (4) may be performed by reacting alkanoyl halide or fatty acid anhydride corresponding to an alkanoyl group with condensates of formula (4) in an inert solvent in the presence of a deoxidizing agent.

As an inert solvent, DMF, THF, N,N-dimethylacetamide and the like are exemplified, and as a deoxidizing agent, triethylamine, pyridine, N,N-dimethylaniline and the like are exemplified. The amount of alkanoyl halide, fatty acid anhydride and a deoxidizing agent used is preferably an equivalent to a slightly excessive equivalent with respect to the compound of formula (4), and alkanoylation is completed in 0.5 to 24 hours at room temperature.

As a typical preparation method of a glycoside compound (1), for example, since $R^5$ to $R^8$ of formula (4) are a protecting group, AP is a compound of the sugar alcohol residue or the polyol residue in which a hydroxyl group has been protected, first, a desired alkanoyl group is introduced to a hydroxyl group in which the protecting group of $R^8$ has been eliminated, and then the protecting group of $R^5$, $R^6$, $R^7$ are eliminated. Next, after introducing the desired alkanoyl group to $R^5$, $R^6$ and $R^7$, by eliminating the protecting group of AP, a desired glycolipid glycoside compound can be obtained.

Raw material compounds used in the invention can all be prepared from known compounds. For example, after protecting, with a TBS group, a 2-position hydroxyl group of known mannose derivative (J. Am. Chem. Soc. 2004, 126, 15081-15086) in which a 1-position hydroxyl group have been substituted, and a 3-position, a 4-position and a 6-position hydroxyl group have been protected, by oxidizing the substituted group of 1-position mannose derivative can be prepared.

Furthermore, the sugar alcohol or the polyol to be condensed with the mannose derivative can be prepared from a known material. After protecting a hydroxyl group with the protecting group of portion to be condensed with the mannose derivative, reduction is performed to be ring-opened, and protection of a hydroxyl group which has not been protected is performed. By eliminating the protecting group of the hydroxyl group of the portion to be condensed, sugar alcohol or polyol can be produced.

Alternatively, after protecting a hydroxyl group of portion to be condensed with the mannose derivative, other hydroxyl groups are protected with the protecting group. Subsequently after reducing, by eliminating the protecting group of portion to be condensed, the sugar alcohol or the polyol can be produced.

As the protecting group of a hydroxyl group of the sugar alcohol to be condensed with the mannose derivative, for example, the protecting group exemplified in a compound represented by Formula (1) can be suitably used. However, adjacent 2 to 6 hydroxyl groups in a case where the sugar alcohol has 6 carbon atoms, and adjacent 2 to 5 hydroxyl groups in a case where the sugar alcohol has 5 carbon atoms are preferably protected with an acetal group.

EXAMPLES

Example 1

Using normal embryonic kidney-derived cells (HEK293F), gastric cancer cells (MKN45), renal cancer cells (ACHN) and cervical cancer cells (HeLa) as tumor cells, an antitumor effect of the glycoside compound (1) was evaluated.
<Test Compound>
As a glycoside compound (1), a compound obtained in Preparation Example 16 (chemical name: D-mannitol-1-yl 3,4,6-tri-O-hexanoyl-2-O-octanoyl-β-D-mannopyranoside) was used.
<Evaluation Method>
For cell culture, RPMI1640 medium (manufactured by Gibco Co., Ltd.) and DMEM medium (manufactured by Gibco Co., Ltd.) were mixed in a ratio of 1:1 and supplied 7% FBS (fetal bovine serum, manufactured by Nichirei Biosciences Inc.) and antibiotic mixture (mixture of penicillin, streptomycin, amphotericin B Mix, 100-fold concentrated solution (Nakarai Co.). Trypsinized cells were diluted to $1\times10^5$ cells/ml and seeded at 400 μl/well in 48-well dishes. Immediately after seeding, the test compound (dissolved in DMSO) was added to a final concentration of 0.5%, cultured for 24 hours in a $CO_2$ incubator under an atmosphere of 5% of $CO_2$, at a temperature of 36° C. to 37° C. After culturing, WST-8 assay was performed. An activity value of DMSO control was set to 100%, and the activities of each cell to which the test compound was added were investigated.
<WST-8 Assay>
To 400 μl of cells culture, 18 μl of Cell Count Reagent SF (manufactured by Nacalai Inc.) was added. After being cultured for 2 to 3 hours (in a case where activity is low, cultured for 19 hours) under an atmosphere of 5% of $CO_2$, at a temperature of 36° C. to 37° C., the broth was stirred, and the amount of formazan produced in the broth was calculated from absorbance at a wavelength of 450 nm. Using a measured value at a wavelength of 600 nm as a control, $OD_{450}$-$OD_{600}$ was set to an activity value.
<Results>
Compared with the normal embryonic kidney-derived cells HEK293F, the test compound exhibited a susceptibility to the gastric cancer cells (MKN45), the renal cancer cells (ACHN) and the cervical cancer cells (HeLa), and $IC_{50}$ was 14.9 μM for the gastric cancer cells (MKN45), 16.7 μM for the cervical cancer cells (HeLa), 17.0 μM for the renal cancer cells (ACHN) with respect to 18.1 μM for HEK293F.

Example 2

$IC_{50}$ was determined in the same manner as in Example 1 except for using a compound obtained in Preparation Example 20 (chemical name: L-arabinitol-1-yl 3,4,6-tri-O-hexanoyl-2-O-octanoyl-β-D-mannopyranoside) as a glycoside compound, gastric cancer cells (MKN45) and renal cancer cells (ACHN) as tumor cells.
<Results>
Compared with normal embryonic kidney-derived cells HEK293F, the test compound exhibited a susceptibility to the gastric cancer cells (MKN45), and the renal cancer cells (ACHN), and $IC_{50}$ was 7.5 μM for the gastric cancer cells (MKN45) and 6.8 μM for the renal cancer cells (ACHN) with respect to 8.9 μM for the HEK293F.

Example 3

$IC_{50}$ was determined in the same manner as in Example 1 except for using a compound obtained in Preparation Example (chemical name: D-glycero-D-galacto-heptitol-1-yl 3,4,6-tri-O-hexanoyl-2-O-octanoyl-β-D-mannopyranoside) as a glycoside compound, acute lymphoblastic leukemia T-cells (Molt-4) and gastric cancer cells (MKN45) as tumor cells.
<Results>
Compared with the normal embryonic kidney-derived cells HEK293F, the test compound exhibited a susceptibility to the acute lymphoblastic leukemia T-cells (Molt-4) and $IC_{50}$ was 8.1 μM for the acute lymphoblastic leukemia T-cells (Molt-4), 16.0 μM for the gastric cancer cells (MKN45) with respect to 21.8 μM for the HEK293F.

Example 4

Using a compound obtained in Preparation Example 24 (chemical name: D-glycero-D-galacto-heptitol-1-yl 3,4,6- tri-O-hexanoyl-2-O-octanoyl-β-D-mannopyranoside) as a glycoside compound, doxorubicin as an antitumor agent and urinary bladder cancer cells (T24) as tumor cells, effect in a case where a glycoside compound (1) and the antitumor agent were used in combination was examined.

<Evaluation Method>

An activity value of a DMSO control was set to 100% and a survival rate of the tumor cells was calculated, in the same manner as in Example 1 except that 12.5 µM of the glycoside compound and 10 µM of doxorubicin were added to a medium immediately after seeding the tumor cells.

<Results>

The survival rate of the tumor cells was 79.0% in a case where a glycoside compound was used alone, that was 57.3% in a case where doxorubicin was used alone, that was 36.9% in a case where a glycoside compound (1) and doxorubicin were used in combination. An antitumor effect of a glycoside compound (1) was further enhanced when they were used in combination.

Example 5

Using a compound obtained in Preparation Example 20 (chemical name: L-arabinitol-1-yl 3,4,6-tri-O-hexanoyl-2-O-octanoyl-β-D-mannopyranoside) as a glycoside compound, paclitaxel as an antitumor agent and renal cancer cells (ACHN) as tumor cells, effect in a case where a glycoside compound (1) and the antitumor agent were used in combination was examined.

<Evaluation Method>

A survival rate of the tumor cells was calculated, in the same manner as in Example 4 except that 5 µM of the glycoside compound and 29 nM of paclitaxel were added to the medium immediately after seeding the tumor cells.

<Results>

The survival rate of the tumor cells was 65.8% in a case where a glycoside compound was used alone, that was 63.8% in a case where paclitaxel was used alone, that was 40.6% in a case where a glycoside compound (1) and paclitaxel were used in combination. An antitumor effect of a glycoside compound (1) was further enhanced when they were used in combination.

Example 6

Using a compound obtained in Preparation Example 24 (chemical name: D-glycero-D-galacto-heptitol-1-yl 3,4,6-tri-O-hexanoyl-2-O-octanoyl-β-D-mannopyranoside) as a glycoside compound, cisplatin as an antitumor agent, and cervical cancer cells (HeLa) as tumor cells, effect in a case where a glycoside compound (1) and the antitumor agent were used in combination was examined.

<Evaluation Method>

<Survival Rate after 2 Hours>

The survival rate of the tumor cells was calculated, in the same manner as in Example 4 except that 15 µM of the glycoside compound and 333 µM of cisplatin were added to the medium immediately after seeding the tumor cells. In WST-8 assay, cell cultures added CCR SF were incubated for 2 hours.

<Survival Rate after 19 Hours>

The survival rate of the tumor cells was calculated, in the same manner as in Example 4 except that 15 µM of the glycoside compound and 42 µM of cisplatin were added to the medium immediately after seeding the tumor cells. In WST-8 assay, cell cultures added CCR SF were incubated for 19 hours.

<Results>

<Survival Rate after 2 Hours>

The survival rate of the tumor cells was 23.5% in a case where a glycoside compound was used alone, that was 58.8% in a case where cisplatin was used alone, that was 0.0% in a case where a glycoside compound (1) and cisplatin were used in combination. An antitumor effect of a glycoside compound (1) was further enhanced when they were used in combination.

<Survival Rate after 19 Hours>

The survival rate of tumor cells was 52.5% in a case where a glycoside compound was used alone, that was 106.8% in a case where cisplatin was used alone, that was 23.4% in a case where a glycoside compound (1) and cisplatin were used in combination. An antitumor effect of a glycoside compound (1) was further enhanced when they were used in combination.

Example 7

<Measurement of MAP Kinase Signal Transduction Inhibitory Action>

After culturing fission yeast calcineurin knockout cells ($h^+$ leu1 ura4-D18 ppb1::ura4$^+$) to a logarithmic proliferation period in YPD liquid medium, calcineurin knockout cells were seeded by $2.0 \times 10^5$ cells/plate onto the YPD agar medium containing 0.11 M of $MgCl_2$. A round filter paper (dia. 3 mm) was placed onto the plate, 5 µL of a test compound which was dissolved in DMSO at a concentration of 100 µM were added to the filter paper. As a control, a DMSO solution was added to a filter paper, and the plate was incubated at 30° C.

After culturing for 3 days, the extent of a cell proliferation was determined. The result thereof is shown in Table 1. A case where a cell proliferation was observed remarkably around the filter paper was indicated as ++, a case where a cell proliferation was observed mildly was indicated as +, and a case where a cell proliferation was observed slightly was indicated as ±. In a case where DMSO solution which does not contain a compound was added, a cell proliferation was not observed around the filter paper (indicated as −).

As clearly understood from the results shown in Table 1, the result shows that the effects of these glycoside compounds obtained in each Preparation Example of the invention exhibited activity to make calcineurin knockout cells grow in the presence of $MgCl_2$ (Calcium signal antagonism in Table 1), indicating that these compounds have MAPK signal transduction inhibitory action.

TABLE 1

| Preparation Example No. | Calcium signal antagonism |
| --- | --- |
| Preparation Example 1 | ++ |
| Preparation Example 2 | ++ |
| Preparation Example 3 | + |
| Preparation Example 4 | + |
| Preparation Example 5 | + |
| Preparation Example 6 | ++ |
| Preparation Example 7(6) | + |
| Preparation Example 7(7) | ++ |
| Preparation Example 8 | ++ |
| Preparation Example 9 | + |
| Preparation Example 10 | + |
| Preparation Example 11 | ± |
| Preparation Example 12 | ++ |
| Preparation Example 13 | ++ |
| Preparation Example 16 | + |
| Preparation Example 17 | ++ |
| Preparation Example 18 | ++ |

TABLE 1-continued

| Preparation Example No. | Calcium signal antagonism |
| --- | --- |
| Preparation Example 19 | ++ |
| Preparation Example 20 | ++ |
| Preparation Example 21 | ++ |
| Preparation Example 22 | ++ |
| Preparation Example 23 | ++ |
| Preparation Example 24 | ++ |
| Preparation Example 25 | + |
| Preparation Example 28 | + |

Preparation Example 1

(1) Under an argon atmosphere, 3.00 g (5.11 mmol) of a mannosyl sulfoxide compound obtained in Reference Example 1 and 2.10 g (10.2 mmol) of 2,6-di-tert-butyl-4-methylpyridine (DTBMP) were dissolved in methylene chloride (50 mL). The solution was cooled to −78° C., 1.32 mL (5.62 mmol) of trifluoromethanesulfonic anhydride (Tf$_2$O) was added thereto, and stirred for 10 minutes. Methylene chloride (60 mL) solution of 2.31 g (6.14 mmol) of an alcohol of a known compound (6-O-tert-butyldimethylsilyl-2,3:4,5-di-O-isopropylidene-D-galactitol) was added dropwise thereto and stirred for 1 hour. After adding saturated sodium bicarbonate water to the reaction solution, the resultant was extracted with methylene chloride. After washing an organic layer with saturated saline solution, the resultant was dried with sodium sulphate. Under reduced pressure, the crude product obtained by distilling off a solvent was purified with silica gel column chromatography (hexane:ethyl acetate=6:1) and 3.41 g of condensates (6-O-tert-butyldimethylsilyl-2,3:4,5-di-O-isopropylidene-D-galactitol-1-yl 3-O-benzyl-4,6-O-benzylidene-2-O-p-methoxybenzyl-β-D-mannopyranoside) was obtained. Yield was 91%.

Physical and spectroscopic constants of the obtained compound were as follows.

$^1$H NMR (700 MHz, CDCl$_3$) δ: 0.081 (s, 3H, SiMe), 0.088 (s, 3H, SiMe), 0.91 (s, 9H, Si$^t$Bu), 1.34 (s, 3H, Me), 1.37 (s, 6H, 2×Me), 1.39 (s, 3H, Me), 3.32 (ddd, J=10.0, 9.6, 4.7 Hz, 1H, OCH), 3.56 (dd, J=10.0, 3.2 Hz, 1H, OCH), 3.73 (dd, J=11.2, 4.3 Hz, 1H, OCH), 3.80 (s, 3H, OMe), 3.86 (dd, J=11.8, 2.6 Hz, 1H, OCH), 3.89 (dd, J=11.2, 2.9 Hz, 1H, OCH), 3.90-3.94 (m, 3H, 3×OCH), 3.96 (d, J=3.2 Hz, 1H, OCH), 4.03-4.07 (m, 1H, OCH), 4.04 (dd, J=11.8, 3.8 Hz, 1H, OCH), 4.11-4.15 (m, 1H, OCH), 4.19 (dd, J=9.6, 9.6 Hz, 1H, OCH), 4.58 (dd, J=10.3, 4.9 Hz, 1H, OCH), 4.57 (d, J=12.6 Hz, 1H, OCHHPh), 4.58 (brs, 1H, OCH), 4.68 (d, J=12.6 Hz, 1H, OCHHPh), 4.81 (d, J=11.8 Hz, 1H, OCHHPh), 4.91 (d, J=11.8 Hz, 1H, OCHHPh), 5.61 (s, 1H, CHPh), 6.83-6.86 (m, 2H, Ar), 7.26-7.31 (m, 4H, Ar), 7.35-7.41 (m, 6H, Ar), 7.48-7.50 (m, 2H, Ar); $^{13}$C NMR (175 MHz, CDCl$_3$) δ: −5.42, −5.25, 18.4, 25.9 (3C), 27.0, 27.1, 27.2, 27.3, 55.2, 63.2, 67.6, 68.6 (2C), 72.3, 74.3, 75.3, 77.6, 77.70, 77.73, 78.6, 79.9, 81.5, 101.4, 102.6, 109.6, 109.8, 113.5 (2C), 126.0 (2C), 127.5 (3C), 128.1 (2C), 128.3 (2C), 128.8, 130.2 (2C), 130.5, 137.6, 138.3, 159.2

(2) 3.43 g (4.10 mmol) of condensate obtained in the above described (1) was dissolved in a mixed solvent of 36 mL of methylene chloride and 1.8 mL of water, and 1.36 g (5.74 mmol) of 2,3-dichloro-5,6-dicyano-p-benzoquinone (DDQ) (96%) was added thereto and stirred for 5 hours. After adding saturated sodium bicarbonate water to the reaction solution, the resultant was extracted with methylene chloride. After washing an organic layer with saturated sodium bicarbonate water and saturated saline solution, the resultant was dried with sodium sulphate. Under reduced pressure, the crude product obtained by distilling off a solvent was purified with silica gel column chromatography (hexane:ethyl acetate=3:1) and 2.41 g of a compound (6-O-tert-butyldimethylsilyl-2,3:4,5-di-O-isopropylidene-D-galactitol-1-yl 3-O-benzyl-4,6-O-benzylidene-β-D-mannopyranoside) was obtained. Yield was 82%.

Physical and spectroscopic constants of the obtained compound were as follows.

$^1$H NMR (400 MHz, CDCl$_3$) δ: 0.08 (s, 6H, 2×SiMe), 0.91 (s, 9H, Si$^t$Bu), 1.37-1.39 (s, 12H, 4×Me), 3.35 (ddd, J=10.0, 9.6, 4.8 Hz, 1H, OCH), 3.63 (dd, J=9.6, 3.2 Hz, 1H, OCH), 3.73 (dd, J=11.2, 4.0 Hz, 1H, OCH), 3.86-3.94 (m, 5H, 5×OCH), 3.99-4.04 (m, 2H, 2×OCH), 4.15 (d, J=3.2 Hz, 1H, OCH), 4.17 (dd, J=9.6, 9.6 Hz, 1H, OCH), 4.14-4.19 (m, 1H, OCH), 4.31 (dd, J=10.4, 4.8 Hz, 1H, OCH), 4.61 (brs, 1H, OCH), 4.78 (d, J=12.8 Hz, 1H, OCHHPh), 4.86 (d, J=12.8 Hz, 1H, OCHHPh), 5.61 (s, 1H, CHPh), 7.26-7.51 (m, 10H, Ar); $^{13}$C NMR (100 MHz, CDCl$_3$) δ: −5.43, −5.26, 18.4, 25.9 (3C), 27.00, 27.01, 27.1, 27.2, 63.1, 67.0, 68.6, 69.0, 69.9, 72.5, 76.5, 77.5, 78.3 (2C), 79.5, 81.4, 100.6, 101.5, 109.7, 109.8, 126.0 (2C), 127.8, 127.9 (2C), 128.2 (2C), 128.4 (2C), 128.9, 137.4, 138.0

(3) 0.5 mL (5.74 mmol) of pyridine was added to 29 mL of methylene chloride solution of 2.40 g (3.35 mmol) of a compound obtained in the above described (2) and 0.77 g (6.32 mmol) of N,N-dimethyl-4-aminopyridine (DMAP), and stirred. 2.5 mL (14.4 mmol) of n-octanoyl chloride was added dropwise and stirred for 24 hours. After adding water to the reaction solution, the resultant was extracted with methylene chloride. After washing an organic layer with saturated sodium bicarbonate water, water and saturated saline solution, the resultant was dried with sodium sulphate. Under reduced pressure, the crude product obtained by distilling off a solvent was purified with silica gel column chromatography (hexane:ethyl acetate=7:1) and 2.85 g of an ester (6-O-tert-butyldimethylsilyl-2,3:4,5-di-O-isopropylidene-D-galactitol-1-yl 3-O-benzyl-4,6-O-benzylidene-2-O-octanoyl-β-D-mannopyranoside) was obtained. Yield was 99%.

Physical and spectroscopic constants of the obtained compound were as follows.

$^1$H NMR (400 MHz, CDCl$_3$) δ: 0.08 (s, 6H, 2×SiMe), 0.87 (t, J=6.0 Hz, 3H, CH$_3$CH$_2$), 0.91 (s, 9H, Si$^t$Bu), 1.24-1.31 (m, 8H, CH$_2$CH$_2$CH$_2$), 1.35 (s, 6H, 2×Me), 1.39 (s, 6H, 2×Me), 1.60-1.70 (m, 2H, CH$_2$CH$_2$CO), 2.42-2.46 (m, 2H, CH$_2$CH$_2$CO), 3.38 (ddd, J=10.8, 10.0, 5.2 Hz, 1H, OCH), 3.70 (dd, J=10.0, 3.6 Hz, 1H, OCH), 3.71 (dd, J=11.2, 4.4 Hz, 1H, OCH), 3.85-3.92 (m, 4H, 4×OCH), 3.89 (dd, J=10.8, 10.8 Hz, 1H, OCH), 3.96-4.08 (m, 3H, 3×OCH), 4.00 (1H, dd, J=10.0, 10.0 Hz, 1H, OCH), 4.31 (1H, dd, J=10.8, 5.2 Hz, 1H, OCH), 4.63 (d, J=12.4 Hz, 1H, OCHHPh), 4.72 (s, 1H, OCH), 4.73 (d, J=12.4 Hz, 1H, OCHHPh), 5.61 (s, 1H, CHPh), 5.71 (d, J=3.6 Hz, 1H, OCH), 7.26-7.51 (m, 10H, Ar); $^{13}$C NMR (100 MHz, CDCl$_3$) δ: −5.43, −5.25, 14.1, 18.4, 22.6, 25.0, 25.9 (3C), 26.9, 27.0, 27.1 (2C), 28.9, 29.0, 31.7, 34.1, 63.1, 67.2, 68.4, 68.5, 68.6, 71.6, 75.5, 76.7, 77.6, 78.0, 79.9, 81.5, 100.1, 101.5, 109.7, 109.7, 126.1 (2C), 127.7, 127.8 (2C), 128.2 (2C), 128.3 (2C), 128.9, 137.4, 137.7, 173.1

(4) 282 mg of 10% palladium-carbon (Pd—C) was added to 34 mL of ethyl acetate solution of 2.82 g (3.35 mmol) of a compound obtained in the above described (3), hydrogenation was performed and stirred for 28 hours at room temperature. The reaction solution was filtered with a glass filter. Under reduced pressure, the crude product obtained by distilling off a solvent was purified with silica gel column chromatography (chloroform:methanol=20:1) and 1.70 g of a compound (6-O-tert-butyldimethylsilyl-2,3:4,5-di-O-isopropylidene-D-galactitol-1-yl 2-O-octanoyl-β-D-mannopyranoside) was obtained. Yield was 76%.

Physical and spectroscopic constants of the obtained compound were as follows.

$^1$H NMR (400 MHz, CDCl$_3$) δ: 0.07 (s, 6H, 2×SiMe), 0.88 (s, 9H, Si$^t$Bu), 0.90 (t, J=6.8 Hz, 3H, CH$_3$CH$_2$), 1.27-1.32 (m, 8H, CH$_2$CH$_2$CH$_2$), 1.36 (s, 6H, 2×Me), 1.39 (s, 6H, 2×Me), 1.60-1.67 (m, 2H, CH$_2$CH$_2$CO), 2.39-2.42 (m, 2H, CH$_2$CH$_2$CO), 3.33-3.38 (m, 1H, OCH), 3.69-3.77 (m, 2H, OCH), 3.71 (dd, J=10.8, 4.4 Hz, 1H, OCH), 3.82-3.96 (m, 7H, 7×OCH), 3.86 (dd, J=10.8, 2.8 Hz, 1H, OCH), 4.04 (ddd, J=6.4, 4.4, 4.0 Hz, 1H, OCH), 4.09 (ddd, J=6.8, 3.6, 3.6 Hz, 1H, OCH), 4.74 (s, 1H, OCH), 5.42 (d, J=2.4 Hz, 1H, OCH); $^{13}$C NMR (100 MHz, CDCl$_3$) δ: −5.43, −5.27, 14.1, 18.4, 22.6, 24.9, 25.9 (3C), 26.9, 27.03, 27.06, 27.1, 28.9, 29.0, 31.6, 34.2, 62.5, 63.1, 68.6, 69.0, 70.9, 73.1, 75.7, 77.5, 77.6, 79.8, 81.3, 99.4, 109.8 (2C), 174.2.

(5) 0.8 mL (10.2 mmol) of pyridine was added to 25 mL of methylene chloride solution of 1.69 g (2.54 mmol) of a compound obtained in the above described (4) and 0.93 g (7.61 mmol) of N,N-dimethyl-4-aminopyridine (DMAP), and stirred. 2.4 mL (10.2 mmol) of hexanoic anhydride was added dropwise thereto and stirred for 30 minutes. After adding water to the reaction solution, the resultant was extracted with methylene chloride. After washing an organic layer with saturated sodium bicarbonate water, water and saturated saline solution, the resultant was dried with sodium sulphate. Under reduced pressure, the crude product obtained by distilling off a solvent was purified with silica gel column chromatography (hexane:ethyl acetate=6:1) and 2.69 g of an ester (6-O-tert-butyldimethylsilyl-2,3:4,5-di-O-isopropylidene-D-galactitol-1-yl 3,4,6-tri-O-hexanoyl-2-O-octanoyl-β-D-mannopyranoside) was obtained. Yield was 76%.

Physical and spectroscopic constants of the obtained compound were as follows.

$^1$H NMR (400 MHz, CDCl$_3$) δ: 0.07 (s, 6H, 2×SiMe), 0.86-0.93 (m, 12H, 4×CH$_3$CH$_2$), 1.22-1.35 (m, 20H, 10×CH$_2$CH$_2$CH$_2$), 1.33 (s, 3H, Me), 1.34 (s, 3H, Me), 1.38 (s, 3H, Me), 1.39 (s, 3H, Me), 1.50-1.66 (m, 8H, 4×CH$_2$CH$_2$CO), 2.13-2.45 (m, 8H, 4×CH$_2$CH$_2$CO), 3.66 (ddd, J=10.4, 5.6, 2.4 Hz, 1H, OCH), 3.70 (dd, J=11.2, 2.8 Hz, 1H, OCH), 3.87-3.88 (m, 2H, 2×OCH), 3.90 (dd, J=11.2, 2.8 Hz, 1H, OCH), 3.99 (dd, J=12.0, 5.6 Hz, 1H, OCH), 4.01-4.06 (m, 2H, 2×OCH), 4.16 (dd, J=12.0, 2.4 Hz, 1H, OCH), 4.25 (dd, J=12.0, 5.6 Hz, 1H, OCH), 4.81 (d, J=0.8 Hz, 1H, OCH), 5.05 (dd, J=10.4, 3.2 Hz, 1H, OCH), 5.27 (dd, J=10.4, 10.4 Hz, 1H, OCH), 5.54 (dd, J=3.2, 0.8 Hz, 1H, OCH); $^{13}$C NMR (100 MHz, CDCl$_3$) δ: −5.45, −5.27, 13.8 (2C), 13.9, 14.3, 18.4, 22.2 (2C), 22.3, 22.6, 24.3, 24.4, 24.5, 25.0, 25.9 (3C), 26.8, 27.02, 27.04, 27.1, 28.9, 29.0, 31.2 (2C), 31.3, 31.7, 32.9, 34.0 (2C), 34.1, 62.4, 63.1, 65.8, 68.2, 68.4, 71.0, 72.5, 77.3, 77.6, 79.9, 81.5, 99.1, 109.7, 109.8, 172.2, 172.6, 172.9, 173.4

(6) 1.00 g (1.04 mmol) of a compound obtained in the above described (5) was stirred in 10 mL of 90% TFA aqueous solution for 40 minutes under ice-cooling. Under reduced pressure, a solvent of the reaction solution was distilled off, further, methanol was added, and was distilled azeotropically several times. The obtained crude product was purified with silica gel column chromatography (chloroform:methanol=10:1) and 568 mg of D-galactitol-1-yl 3,4,6-tri-O-hexanoyl-2-O-octanoyl-β-D-mannopyranoside) was obtained. Yield was 71%.

Physical and spectroscopic constants of the obtained compound were as follows.

$^1$H NMR (700 MHz, CD$_3$OD) δ: 0.89-0.91 (m, 12H, 4×CH$_3$CH$_2$), 1.30-1.32 (m, 20H, 10×CH$_2$CH$_3$CH$_2$), 1.56-1.65 (m, 8H, 4×CH$_2$CH$_2$CO), 2.19-2.36 (m, 8H, 4×CH$_2$CH$_2$CO), 3.61-3.64 (m, 3H, 3×OCH), 3.66 (dd, J=8.8, 1.6 Hz, 1H, OCH), 3.73 (dd, J=10.2, 6.3 Hz, 1H, OCH), 3.83 (ddd, J=10.2, 4.2, 2.2 Hz, 1H, OCH), 3.90 (dd, J=10.2, 6.3 Hz, 1H, OCH), 3.89-3.91 (m, 1H, OCH), 4.43 (ddd, J=6.3, 6.3, 1.4 Hz, 1H, OCH), 4.16 (dd, J=10.2, 2.2 Hz, 1H, OCH), 4.28 (dd, J=12.3, 4.2 Hz, 1H, OCH), 4.90 (d, J=0.8 Hz, 1H, OCH), 5.16 (dd, J=10.2, 3.2 Hz, 1H, OCH), 5.30 (dd, J=10.2, 10.2 Hz, 1H, OCH), 5.47 (dd, J=3.2, 0.8 Hz, 1H, OCH); $^{13}$C NMR (175 MHz, CD$_3$OD) δ: 14.2 (2C), 14.3, 14.5, 23.4, 23.9, 23.4, 23.8, 25.5, 25.59, 25.62, 26.3, 30.2, 30.3, 32.3, 32.4, 32.5, 33.0, 34.8, 34.9, 35.0, 35.2, 63.0, 65.0, 66.8, 69.6, 70.5, 71.2, 71.3, 71.9, 72.67, 72.69, 73.4, 100.0, 173.7, 173.8, 174.7, 175.0

Preparation Example 2

(1) Treatment in the same manner as Preparation Example 1 (1) was performed using 1.14 g of a mannosyl sulfoxide compound of Reference Example 1 and 0.88 g of an alcohol (6-O-tert-butyldimethylsilyl-2,3:4,5-di-O-isopropylidene-D-glucitol) of Reference Example 3 and 0.40 g of a compound (4-O-tert-butyldimethylsilyl-2,3:5,6-di-O-isopropylidene-D-glucitol-1-yl 4,6-O-benzylidene-2-O-p-methoxybenzyl-β-D-mannopyranoside) was obtained. Yield was 65%.

Physical and spectroscopic constants of the obtained compound were as follows.

$^1$H-NMR (400 MHz, CDCl$_3$) δ: 0.09 (3H, s), 0.13 (3H, s), 0.90 (9H, s), 1.32 (3H, s), 1.34 (3H, s), 1.39 (6H, s), 3.32 (1H, ddd, J=10.3, 9.6, 4.9), 3.56 (1H, dd, J=9.6, 3.2), 3.80 (3H, s), 3.81 (1H, dd, J=11.8, 2.8), 3.84 (1H, dd, J=4.9, 4.5), 3.88 (1H, dd, J=8.2, 7.8), 3.92 (1H, dd, J=10.3, 10.3), 3.97 (1H, dd, J=3.2, 0.8), 4.02 (1H, dd, J=8.2, 6.4), 4.03 (1H, dd, J=11.8, 2.8), 4.08 (1H, dd, J=8.4, 4.5), 4.10 (1H, ddd, J=7.8, 6.4, 4.9), 4.15 (1H, ddd, J=8.4, 2.8, 2.8), 4.18 (1H, dd, J=9.6, 9.6), 4.29 (1H, dd, J=10.3, 4.9), 4.55 (1H, d, J=0.8), 4.56 (1H, d, J=12.4), 4.67 (1H, d, J=12.4), 4.80 (1H, d, J=11.6), 4.90 (1H, d, J=11.6), 5.61 (1H, s), 6.85 (2H, d, J=8.8), 7.25-7.32 (5H, m), 7.34-7.41 (3H, m), 7.39 (2H, d, J=8.8), 7.48-7.51 (2H, m); $^{13}$C-NMR (100 MHz, CDCl$_3$) δ: −4.17, −3.89, 18.3, 25.3, 26.0 (3C), 26.5, 27.0, 27.2, 55.2, 66.5, 67.7, 68.2, 68.6, 72.3, 72.8, 74.5, 75.5, 75.9, 76.7, 77.8, 78.6, 78.7, 101.4, 102.8, 108.6, 108.7, 113.6 (2C), 126.0 (2C), 127.5 (2C), 128.2 (2C), 128.3 (2C), 128.8, 130.1, 130.2 (2C), 130.5, 137.6, 138.3, 159.2.

(2) A compound obtained in the above-described (1) was treated in the same manner as Preparation Example 1 (2) to obtain a compound (4-O-tert-butyldimethylsilyl-2,3:5,6-di-O-isopropylidene-D-glucitol-1-yl 3-O-benzyl-4,6-O-benzylidene-β-D-mannopyranoside).

(3) A compound obtained in the above-described (2) was treated in the same manner as Preparation Example 1 (3) to obtain 0.41 g of a compound (4-O-tert-butyldimethylsilyl-2,3:5,6-di-O-isopropylidene-D-glucitol-1-yl 3-O-benzyl-4,6-O-benzylidene-2-O-octanoyl-β-D-mannopyranoside).

Physical and spectroscopic constants of the obtained compound were as follows.

$^1$H-NMR (400 MHz, CDCl$_3$) δ: 0.08 (3H, s), 0.12 (3H, s), 0.87 (3H, t, J=6.8), 0.90 (9H, s), 1.24-1.31 (8H, m), 1.32 (3H, s), 1.36 (3H, s), 1.38 (3H, s), 1.41 (3H, s), 1.62-1.70

(2H, m), 2.40-2.50 (2H, m), 3.38 (1H, ddd, J=9.6, 9.6, 4.8), 3.70 (1H, dd, J=9.8, 3.4), 3.78-3.92 (4H, m), 3.95-4.02 (4H, m), 4.06-4.15 (2H, m), 4.31 (1H, dd, J=10.4, 4.8), 4.63 (1H, d, J=12.4), 4.68 (1H, d, J=1.2), 4.73 (1H, d, J=12.4), 5.61 (1H, s), 5.70 (1H, dd, J=3.4, 1.2), 7.28-7.42 (8H, m), 7.48-7.52 (2H, m); $^{13}$C-NMR (100 MHz, CDCl$_3$) δ: −4.23, −4.00, 14.1, 18.3, 22.6, 25.0, 25.3, 26.0 (3C), 26.5, 26.8, 27.0, 28.96, 29.04, 31.7, 34.1, 66.3, 67.3, 68.3, 68.5, 68.6, 71.6, 72.5, 75.6, 75.7, 76.7, 77.9, 78.7, 100.2, 101.5, 108.6, 108.8, 126.1 (2C), 127.71, 127.75 (2C), 128.2 (2C), 128.3 (2C), 129.0, 137.3, 137.6, 173.0.

(4) In the same manner as Preparation Example 1 (4) was treated 0.27 g of a compound obtained in the above-described (3) to obtain 0.17 g of a compound (4-O-tert-butyldimethylsilyl-2,3:5,6-di-O-isopropylidene-D-glucitol-1-yl 2-O-octanoyl-β-D-mannopyranoside).

Physical and spectroscopic constants of the obtained compound were as follows.

$^1$H-NMR (400 MHz, CDCl$_3$) δ: 0.08 (3H, s), 0.12 (3H, s), 0.88 (3H, t, J=7.2), 0.90 (9H, s), 1.27-1.32 (8H, m), 1.33 (3H, s), 1.35 (3H, s), 1.38 (3H, s), 1.40 (3H, s), 1.59-1.68 (2H, m), 2.36-2.45 (2H, m), 3.30-3.34 (1H, m), 3.72-3.97 (9H, m), 4.01-4.10 (3H, m), 4.69 (1H, d, J=0.8), 5.41 (1H, dd, J=2.8, 0.8); $^{13}$C-NMR (100 MHz, CDCl$_3$) δ: −4.23, −4.07, 14.1, 18.3, 22.6, 24.9, 25.4, 26.0 (3C), 26.5, 26.7, 27.0, 28.9, 29.1, 31.7, 34.1, 62.2, 65.9, 68.1, 68.5, 70.8, 72.3, 72.9, 75.8, 76.2, 76.9, 78.5, 99.3, 108.7 (2C), 173.9.

(5) In the same manner as Preparation Example 1 (5) was treated 0.15 g of a compound obtained in the above-described (4) to obtain 198 mg of a compound (4-O-tert-butyldimethylsilyl-2,3:5,6-di-O-isopropylidene-D-glucitol-1-yl 3,4,6-tri-O-hexanoyl-2-O-octanoyl-β-D-mannopyranoside).

Physical and spectroscopic constants of the obtained compound were as follows.

$^1$H-NMR (400 MHz, CDCl$_3$) δ: 0.05 (3H, s), 0.11 (3H, s), 0.75-0.79 (12H, m), 0.78 (9H, s), 1.11-1.19 (20H, m), 1.20 (3H, s), 1.24 (3H, s), 1.26 (3H, s), 1.28 (3H, s), 1.39-1.54 (8H, m), 2.06-2.36 (8H, m), 3.54 (1H, ddd, J=10.0, 5.6, 2.6), 3.67-3.78 (3H, m), 3.82-3.89 (3H, m), 3.94-4.02 (2H, m), 4.06 (1H, dd, J=12.0, 2.6), 4.12 (1H, dd, J=12.0, 5.6), 4.66 (1H, d, J=1.0), 4.93 (1H, dd, J=10.0, 3.2), 5.15 (1H, dd, J=10.0, 10.0), 5.41 (1H, dd, J=3.2, 1.0); $^{13}$C-NMR (100 MHz, CDCl$_3$) δ: −4.25, −4.04, 13.8 (2C), 13.9, 14.0, 18.3, 22.2 (2C), 22.3, 22.6, 24.2, 24.4, 24.5, 25.0, 25.2, 26.0 (3C), 26.4, 26.8, 27.0, 28.96, 29.03, 31.2 (2C), 31.3, 31.7, 33.9, 34.0 (2C), 34.1, 62.4, 65.7, 66.2, 68.31, 68.33, 71.0, 72.4, 72.6, 75.7, 76.7, 78.7, 99.2, 108.5, 108.8, 172.3, 172.6, 172.8, 173.4.

(6) In the same manner as Preparation Example 1 (6) was treated 0.20 g of a compound obtained in the above-described (5) to obtain 0.04 g of D-glucitolyl 3,4,6-tri-O-hexanoyl-2-O-octanoyl-β-D-mannopyranoside (D-glucitol-1-yl 3,4,6-tri-O-hexanoyl-2-O-octanoyl-β-D-mannopyranoside).

Physical and spectroscopic constants of the obtained compound were as follows.

$^1$H-NMR (700 MHz, CD$_3$OD) δ: 0.90 (6H, t, J=7.3), 0.91 (3H, t, J=7.2), 0.93 (3H, t, J=7.2) 1.24-1.45 (20H, m), 1.52-1.59 (4H, m), 1.63-1.70 (4H, m), 2.19 (1H, dt, J=15.4, 7.7), 2.21 (1H, dt, J=15.4, 7.8), 2.27 (1H, dt, J=15.8, 7.4), 2.32 (1H, dt, J=15.8, 7.4), 2.36 (1H, dt, J=14.2, 7.5), 2.37 (1H, dt, J=14.2, 7.5), 2.40 (1H, dt, J=15.5, 7.5), 2.48 (1H, dt, J=15.5, 7.2), 3.60 (1H, dd, J=11.2, 6.0), 3.63 (1H, dd, J=7.8, 2.0), 3.69 (1H, ddd, J=7.8, 6.0, 3.6), 3.77 (1H, dd, J=11.2, 3.6), 3.76 (1H, dd, J=11.3, 7.3), 3.83 (1H, dd, J=4.2, 2.0), 3.84 (1H, ddd, J=10.0, 4.3, 2.2), 3.88 (1H, ddd, J=7.3, 5.6, 4.2), 3.89 (1H, dd, J=11.3, 5.6), 4.15 (1H, dd, J=12.3, 2.2), 4.28 (1H, dd, J=12.3, 4.3), 4.91 (1H, d, J=1.0), 5.17 (1H, dd, J=10.0, 3.2), 5.29 (1H, dd, J=10.0, 10.0), 5.48 (1H, dd, J=3.2, 1.0); $^{13}$C-NMR (175 MHz, CD$_3$OD) δ: 14.2 (2C), 14.3, 14.5, 23.35, 23.37, 23.4, 23.8, 25.5, 25.58, 25.61, 26.3, 30.2, 30.3, 32.33, 32.35, 32.4, 33.0, 34.8, 34.9, 35.0, 35.2, 63.0, 64.9, 66.8, 70.4, 70.8, 72.1, 72.6, 73.0, 73.2, 73.5, 73.7, 100.0, 173.7, 173.8, 174.7, 175.0.

Preparation Example 3

(1) Treatment in the same manner as Preparation Example 1 (1) was performed using 1.00 g of a mannosyl sulfoxide compound of Reference Example 1 and 476 mg of an alcohol (2,3:4,5-di-O-isopropylidene-D-lyxitol)(1,2:3,4-di-O-isopropylidene-D-arabinitol) to obtain 615 mg of a compound (2,3:4,5-di-O-isopropylidene-D-lyxitolyl 3-O-benzyl-4,6-O-benzylidene-2-O-p-methoxybenzyl-β-D-mannopyranoside) (1,2:3,4-di-O-isopropylidene-D-arabinitol-5-yl 3-O-benzyl-4,6-O-benzylidene-2-O-p-methoxybenzyl-β-D-mannopyranoside). Yield was 52%.

Physical and spectroscopic constants of the obtained compound were as follows.

$^{13}$C-NMR (175 MHz, CDCl$_3$) δ: −0.012 25.3 25.5 26.6 27.6 29.7 55.2 66.3 67.6 72.5 74.275.5 77.7 101.4 101.9 109.2 109.6 113.5 126.0 127.5 128.2 128.3 130.2 137.5 138.3 159.2)

(2) In the same manner as Preparation Example 1 (2) was treated 596 mg of a compound obtained in the above-described (1) to obtain 453 mg of a compound (2,3:4,5-di-O-isopropylidene-D-lixitolyl 3-O-benzyl-4,6-O-benzylidene-β-D-mannopyranoside) (1,2:3,4-di-O-isopropylidene-D-arabinitol-5-yl 3-O-benzyl-4,6-O-benzylidene-β-D-mannopyranoside).

Physical and spectroscopic constants of the obtained compound were as follows.

$^{13}$C NMR (100 MHz, CDCl$_3$) δ: 25.2 25.4 26.6 27.7 66.3 67.0 28.0 68.6 69.7 72.5 74.1 75.4 77.9 78.3 100.5 101.6 109.3 109.7 126.0 (2C) 127.8 127.9 (2C) 128.2 (2C) 128.5 (2C) 129.0 137.3 137.8)

(3) In the same manner as Preparation Example 1 (3) was treated 417 mg of a compound obtained in the above-described (2) to obtain 509 mg of a compound (2,3:4,5-di-O-isopropylidene-D-lyxitolyl 3-O-benzyl-4,6-O-benzylidene-2-O-octanoyl-β-D-mannopyranoside) (1,2:3,4-di-O-isopropylidene-D-arabinitol-5-yl 3-O-benzyl-4,6-O-benzylidene-2-O-octanoylβ-D-mannopyranoside).

$^{13}$C NMR (100 MHz, CDCl$_3$) δ: 14.1 22.6 24.9 25.2 25.4 26.6 27.8 28.96 29.00 31.7 34.2 66.4 67.4 67.8 68.4 68.5 71.6 74.1 74.9 75.6 77.9 78.4 99.6 101.6 109.2 109.5 126.1 (2C) 127.7 (2C) 128.2 (2C) 128.3 (2C) 129.0 137.3 137.6 173.1)

(4) In the same manner as Preparation Example 1 (4) was treated 454 mg of a compound obtained in the above-described (3) to obtain 294 mg of a compound (2,3:4,5-di-O-isopropylidene-D-lyxitolyl 2-O-octanoyl-β-D-mannopyranoside) (1,2:3,4-di-O-isopropylidene-D-arabinitol-5-yl 2-O-octanoyl-β-D-mannopyranoside).

Physical and spectroscopic constants of the obtained compound were as follows.

$^{13}$C NMR (100 MHz, CDCl$_3$) δ: 14.0 22.6 24.9 25.426.6 27.7 28.9 29.0 31.7 34.2 62.3 66.4 67.8 68.2 70.9 73.0 74.3 75.0 75.7 78.2 98.8 109.2 109.6 174.2)

(5) In the same manner as Preparation Example 1 (5) was treated 286 mg of a compound obtained in the above-described (4) to obtain 351 mg of a compound (2,3:4,5-di-O-isopropylidene-D-lyxitolyl 3,4,6-tri-O-hexanoyl-2-O-octanoyl-β-D-mannopyranoside) (1,2:3,4-di-O-isopropylidene-D-arabinitol-5-yl 3,4,6-tri-O-hexanoyl-2-O-octanoyl-β-D-mannopyranoside).

Physical and spectroscopic constants of the obtained compound were as follows.

$^{13}$C NMR (100 MHz, CDCl$_3$) δ: 13.8 (2C) 13.9 14.1 22.2 (2C) 22.3 22.6 24.2 24.4 24.5 24.98 24.99 25.4 26.6 27.8 28.98 29.03 31.2 (2C) 31.3 31.7 33.91 33.95 34.0 34.1 62.3 65.6 66.4 67.7 68.4 71.0 72.7 74.1 74.9 78.5 98.5 109.2 109.5 172.2 172.6 172.9 173.4)

(6) In the same manner as Preparation Example 1 (6) was treated 31 mg of a compound obtained in the above-described (5) to obtain 195 mg of D-lyxitolyl 3,4,6-tri-O-hexanoyl-2-O-octanoyl-β-D-mannopyranoside (D-arabinitol-5-yl 3,4,6-tri-O-hexanoyl-2-O-octanoyl-β-D-mannopyranoside).

Physical and spectroscopic constants of the obtained compound were as follows.

$^{13}$C NMR (175 MHz, CD$_3$OD) δ: 14.2 (2C) 14.3 14.5 23.38 (2C) 23.41 23.8 25.5 25.60 25.62 26.3 30.2 30.3 32.3 32.4 32.5 33.0 34.8 34.9 35.0 35.2 63.1 64.8 66.8 70.5 71.67 71.69 72.1 72.7 73.48 73.50 100.6 173.77 173.84 174.8 175.0)

Preparation Example 4

(1) Treatment in the same manner as Preparation Example 1 (1) was performed using 500 mg of a mannosyl sulfoxide compound of Reference Example 1 and 218 mg of an alcohol (2,3:4,5-di-O-isopropylidene-D-arabinitol) to obtain 425 mg of a compound (2,3:4,5-di-O-isopropylidene-D-arabinitol-1-yl 3-O-benzyl-4,6-O-benzylidene-2-O-p-methoxybenzyl-β-D-mannopyranoside). Yield was 72%.

Physical and spectroscopic constants of the obtained compound were as follows.

$^1$H NMR (400 MHz, CDCl$_3$) δ: 1.33 (s, 3H, CH$_3$), 1.36 (s, 3H, CH$_3$), 1.40 (s, 3H, CH$_3$), 1.41 (s, 3H, CH$_3$), 3.32 (ddd, J=9.6, 9.6, 4.8 Hz, 1H, OCH), 3.57 (dd, J=10.0, 3.2 Hz, 1H, OCH), 3.60 (dd, J=12.0, 8.4 Hz, 1H, OCH), 3.64 (dd, J=8.0, 8.0 Hz, 1H, OCH), 3.80 (s, 3H, OMe), 3.93 (dd, J=8.4, 5.2 Hz, 1H, OCH), 3.94 (dd, J=10.4, 9.6 Hz, 1H, OCH), 4.00 (d, J=3.2 Hz, 1H, OCH), 4.07 (ddd, J=8.0, 6.0, 5.2 Hz, 1H, OCH), 4.13 (dd, J=8.4, 6.0 Hz, 1H, OCH), 4.15-4.22 (m, 1H, OCH), 4.189 (dd, J=12.0, 5.6 Hz, 1H, OCH), 4.194 (dd, J=10.0, 9.6 Hz, 1H, OCH), 4.30 (dd, J=10.4, 4.8 Hz, 1H, OCH), 4.56 (d, J=12.4 Hz, 1H, OCHHPh), 4.58 (s, 1H, OCH), 4.66 (d, J=12.4 Hz, 1H, OCHHPh), 4.84 (d, J=12.0 Hz, 1H, OCHHAr), 4.93 (d, J=12.0 Hz, 1H, OCHHAr), 5.62 (s, 1H, OCHPh), 6.85 (d, J=8.4 Hz, 2H, Ar), 7.25-7.31 (m, 5H, Ar), 7.35-7.42 (m, 5H, Ar), 7.50 (dd, J=8.0, 2.0 Hz, 2H, Ar); $^{13}$C NMR (125 MHz, CDCl$_3$) δ: 25.2, 26.7, 27.0, 27.2, 55.2, 67.57, 67.62, 68.6, 70.6, 72.2, 74.3, 75.0, 76.9, 77.7, 77.9, 78.6, 79.9, 101.4, 102.3, 109.6, 109.8, 113.5 (2C), 126.0 (2C), 127.45 (2C), 127.48, 128.1 (2C), 128.2 (2C), 128.8, 130.3 (2C), 130.5, 137.6, 138.3, 159.1

(2) In the same manner as Preparation Example 1 (2) was treated 352 mg of a compound obtained in the above-described (1) to obtain 291 mg of a compound (2,3:4,5-di-O-isopropylidene-D-arabinitol-1-yl 3-O-benzyl-4,6-O-benzylidene-β-D-mannopyranoside).

Physical and spectroscopic constants of the obtained compound were as follows.

$^1$H NMR (400 MHz, CDCl$_3$) δ: 1.33 (s, 3H, CH$_3$), 1.38 (s, 6H, 2×CH$_3$), 1.39 (s, 3H, CH$_3$), 3.35 (ddd, J=10.0, 10.0, 4.8 Hz, 1H, OCH), 3.61 (dd, J=8.0, 8.0 Hz, 1H, OCH), 3.65 (dd, J=10.0, 3.2 Hz, 1H, OCH), 3.67 (dd, J=11.6, 6.4 Hz, 1H, OCH), 3.90 (dd, J=10.0, 10.0 Hz, 1H, OCH), 3.93 (dd, J=8.4, 5.2 Hz, 1H, OCH), 4.06 (ddd, J=8.0, 6.0, 5.2 Hz, 1H, OCH), 4.13 (dd, J=8.4, 6.0 Hz, 1H, OCH), 4.150 (dd, J=11.6, 5.2 Hz, 1H, OCH), 4.154 (ddd, J=8.0, 6.8, 5.2 Hz, 1H, OCH), 4.17 (dd, J=10.0, 10.0 Hz, 1H, OCH), 4.20 (dd, J=3.2, 0.8 Hz, 1H, OCH), 4.32 (dd, J=10.0, 4.8 Hz, 1H, OCH), 4.64 (d, J=0.8 Hz, 1H, OCH), 4.79 (d, J=12.4 Hz, 1H, OCHHPh), 4.86 (d, J=12.4 Hz, 1H, OCHHPh), 5.61 (s, 1H, OCHPh), 7.29-7.42 (m, 8H, Ar), 7.50 (dd, J=7.6, 2.0 Hz, 2H, Ar); $^{13}$C NMR (100 MHz, CDCl$_3$) δ: 25.1, 26.6, 27.0, 27.1, 67.0, 67.6, 68.6, 69.7, 70.2, 72.4, 76.5, 76.9, 78.4, 78.4, 79.6, 100.3, 101.5, 109.7, 109.9, 126.0 (2C), 127.76, 127.84 (2C), 128.2 (2C), 128.4 (2C), 128.9, 137.4, 138.0

(3) In the same manner as Preparation Example 1 (3) was treated 268 mg of a compound obtained in the above-described (2) to obtain 326 mg of a compound (2,3:4,5-di-O-isopropylidene-D-arabinitol-1-yl 3-O-benzyl-4,6-O-benzylidene-2-O-octanoyl-β-D-mannopyranoside).

Physical and spectroscopic constants of the obtained compound were as follows.

$^1$H NMR (400 MHz, CDCl$_3$) δ: 0.87 (t, J=7.2 Hz, 3H, CH$_3$), 1.25-1.39 (m, 8H, 4×CH$_2$), 1.33 (s, 3H, CH$_3$), 1.367 (s, 3H, CH$_3$), 1.374 (s, 6H, 2×CH$_3$), 1.66 (tt, J=7.6, 7.6 Hz, 2H, CH$_2$), 2.04 (t, J=7.6 Hz, 2H, COCH$_2$), 3.39 (ddd, J=10.0, 10.0, 4.8 Hz, 1H, OCH), 3.66 (dd, J=7.6, 7.6 Hz, 1H, OCH), 3.69 (dd, J=11.6, 7.2 Hz, 1H, OCH), 3.73 (dd, J=10.0, 3.2 Hz, 1H, OCH), 3.91 (dd, J=10.0, 10.0 Hz, 1H, OCH), 3.92 (dd, J=8.4, 4.8 Hz, 1H, OCH), 3.99 (dd, J=10.0, 10.0 Hz, 1H, OCH), 4.04 (ddd, J=7.6, 6.4, 4.8 Hz, 1H, OCH), 4.068 (dd, J=11.6, 5.2 Hz, 1H, OCH), 4.075 (ddd, J=7.6, 7.2, 5.2 Hz, 1H, OCH), 4.12 (dd, J=8.4, 6.4 Hz, 1H, OCH), 4.33 (dd, J=10.0, 4.8 Hz, 1H, OCH), 4.63 (d, J=12.8 Hz, 1H, OCHHPh), 4.74 (d, J=12.8 Hz, 1H, OCHHPh), 4.75 (s, 1H, OCH), 5.61 (s, 1H, OCHPh), 5.71 (d, J=3.2 Hz, 1H, OCH), 7.24-7.33 (m, 3H, Ar), 7.35-7.40 (m, 5H, Ar), 7.50 (dd, J=7.6, 2.0 Hz, 2H, Ar); $^{13}$C NMR (100 MHz, CDCl$_3$) δ: 14.0, 22.6, 24.9, 25.2, 26.6, 26.9, 27.0, 28.91, 28.95, 31.6, 34.1, 67.3, 67.5, 68.3, 68.5, 70.0, 71.5, 75.7, 76.8, 77.7, 78.0, 79.7, 99.7, 101.5, 109.6, 109.8, 126.0 (2C), 127.6, 127.7 (2C), 128.1 (2C), 128.3 (2C), 128.9, 137.3, 137.7, 173.1

(4) In the same manner as Preparation Example 1 (4) was treated 316 mg of a compound obtained in the above-described (3) to obtain 171 mg of a compound (2,3:4,5-di-O-isopropylidene-D-arabinitol-1-yl 2-O-octanoyl-β-D-mannopyranoside).

Physical and spectroscopic constants of the obtained compound were as follows.

$^1$H NMR (400 MHz, CD$_3$OD) δ: 0.81 (t, J=6.8 Hz, 3H, CH$_3$), 1.18-1.26 (m, 8H, 4×CH$_2$), 1.23 (s, 3H, CH$_3$), 1.25 (s, 6H, 2×CH$_3$), 1.29 (s, 3H, CH$_3$), 1.53 (tdd, J=7.6, 7.6, 7.6 Hz, 2H, CH$_2$), 2.26 (dt, J=15.6, 7.6 Hz, 1H, COCHHCH$_2$), 2.31 (dt, J=15.6, 7.6 Hz, 1H, COCHHCH$_2$), 3.16 (ddd, J=9.6, 6.4, 2.8 Hz, 1H, OCH), 3.43 (dd, J=9.6, 9.6 Hz, 1H, OCH), 3.54 (dd, J=9.6, 3.2 Hz, 1H, OCH), 3.59 (dd, J=10.8, 5.2 Hz, 1H, OCH), 3.62 (dd, J=12.0, 6.4 Hz, 1H, OCH), 3.71 (dd, J=8.0, 7.2 Hz, 1H, OCH), 3.80 (dd, J=12.0, 2.8 Hz, 1H, OCH), 3.79-3.83 (m, 1H, OCH), 3.92 (ddd, J=8.0, 5.2, 3.2 Hz, 1H, OCH), 3.99 (dd, J=10.8, 3.2 Hz, 1H, OCH), 3.98-4.03 (m, 2H, 2×OCH), 4.61 (s, 1H, OCH), 5.26 (d, J=3.2 Hz, 1H, OCH); $^{13}$C NMR (100 MHz, CD$_3$OD) δ: 14.4, 23.7, 25.5, 26.0, 26.9, 27.3 (2C), 30.13, 30.15, 32.9, 35.1, 62.9, 68.0, 68.9, 70.7, 72.8, 73.5, 78.1, 78.6, 78.8, 80.6, 100.6, 110.76, 110.80, 175.0

(5) In the same manner as Preparation Example 1 (5) was treated 161 mg of a compound obtained in the above-described (4) to obtain 252 mg of a compound (2,3:4,5-di-O-isopropylidene-D-arabinitol-1-yl 3,4,6-tri-O-hexanoyl-2-O-octanoyl-β-D-mannopyranoside).

Physical and spectroscopic constants of the obtained compound were as follows.

$^1$H NMR (400 MHz, CDCl$_3$) δ: 0.88 (t, J=6.8 Hz, 9H, 3×CH$_3$), 0.90 (t, J=6.8 Hz, 3H, CH$_3$), 1.24-1.39 (m, 20H, 10×CH$_2$), 1.33 (s, 3H, CH$_3$), 1.37 (s, 6H, 2×CH$_3$), 1.39 (s, 3H, CH$_3$), 1.53-1.67 (m, 8H, 4×CH$_2$), 2.17 (dt, J=16.0, 7.6 Hz, 1H, COCHHCH$_2$), 2.22 (dt, J=16.0, 7.6 Hz, 1H, COCHHCH$_2$), 2.23 (dt, J=15.6, 7.6 Hz, 1H, COCHHCH$_2$), 2.28 (dt, J=15.6, 7.6 Hz, 1H, COCHHCH$_2$), 2.33 (t, J=7.6 Hz, 2H, COCH$_2$), 2.41 (dt, J=15.6, 7.6 Hz, 1H, COCHHCH$_2$), 2.45 (dt, J=15.6, 7.6 Hz, 1H, COCHHCH$_2$), 3.61 (dd, J=7.6, 7.6 Hz, 1H, OCH), 3.64-3.68 (m, 1H, OCH), 3.67 (dd, J=12.0, 7.6 Hz, 1H, OCH), 3.92 (dd, J=8.4, 5.2 Hz, 1H, OCH), 4.03 (ddd, J=7.6, 6.4, 5.2 Hz, 1H, OCH), 4.05-4.11 (m, 1H, OCH), 4.08 (dd, J=12.0, 6.4 Hz, 1H, OCH), 4.11 (dd, J=8.4, 6.4 Hz, 1H, OCH), 4.18 (dd, J=12.0, 2.4 Hz, 1H, OCH), 4.25 (dd, J=12.0, 5.6 Hz, 1H, OCH), 4.84 (s, 1H, OCH), 5.07 (dd, J=10.0, 3.2 Hz, 1H, OCH), 5.27 (dd, J=10.0, 10.0 Hz, 1H, OCH), 5.53 (d, J=3.2 Hz, 1H, OCH); $^{13}$C NMR (100 MHz, CDCl$_3$) δ: 13.79, 13.81, 13.9, 14.0, 22.2 (2C), 22.3, 22.6, 24.2, 24.4, 24.5, 25.0, 25.2, 26.6, 27.0 (2C), 28.9, 29.0, 31.2 (2C), 31.3, 31.7, 33.9, 33.98, 34.00, 34.1, 62.4, 65.9, 67.5, 68.5, 69.9, 71.0, 72.6, 76.9, 77.8, 79.8, 98.5, 109.6, 109.9, 172.2, 172.7, 173.0, 173.4

(6) In the same manner as Preparation Example 1 (6) was treated 180 mg of a compound obtained in the above-described (5) to obtain 142 mg of D-arabinitol-1-yl 3,4,6-tri-O-hexanoyl-2-O-octanoyl-β-D-mannopyranoside.

Physical and spectroscopic constants of the obtained compound were as follows.

$^1$H NMR (500 MHz, CDCl$_3$) δ: 0.89 (t, J=6.8 Hz, 6H, 2×CH$_3$), 0.91 (t, J=6.8 Hz, 3H, CH$_3$), 0.92 (t, J=6.8 Hz, 3H, CH$_3$), 1.24-1.42 (m, 20H, 10×CH$_2$), 1.50-1.60 (m, 4H, 2×CH$_2$), 1.61-1.70 (m, 4H, 2×CH$_2$), 2.210 (dt, J=15.2, 7.4 Hz, 1H, COCHH), 2.212 (dt, J=15.2, 7.4 Hz, 1H, COCHH), 2.26 (dt, J=14.6, 7.4 Hz, 1H, COCHH), 2.31 (dt, J=14.6, 7.4 Hz, 1H, COCHH), 2.34 (dt, J=14.9, 7.4 Hz, 1H, COCHH), 2.37 (dt, J=14.9, 7.4 Hz, 1H, COCHH), 2.39 (dt, J=14.6, 7.4 Hz, 1H, COCHH), 2.46 (dt, J=14.6, 7.4 Hz, 1H, COCHH), 3.45 (dd, J=8.3, 1.7 Hz, 1H, OCH), 3.59 (dd, J=11.1, 5.7 Hz, 1H, OCH), 3.67 (ddd, J=8.3, 5.7, 3.4 Hz, 1H, OCH), 3.68 (dd, J=10.4, 7.4 Hz, 1H, OCH), 3.78 (dd, J=11.1, 3.4 Hz, 1H, OCH), 3.83 (ddd, J=10.0, 4.0, 2.3 Hz, 1H, OCH), 3.90 (dd, J=10.4, 5.2 Hz, 1H, OCH), 4.01 (ddd, J=7.4, 5.2, 1.7 Hz, 1H, OCH), 4.14 (dd, J=12.3, 2.3 Hz, 1H, OCH), 4.28 (dd, J=12.3, 4.0 Hz, 1H, OCH), 4.93 (d, J=0.8 Hz, 1H, OCH), 5.16 (dd, J=10.0, 3.2 Hz, 1H, OCH), 5.29 (dd, J=10.0, 10.0 Hz, 1H, OCH), 5.48 (dd, J=3.2, 0.8 Hz, 1H, OCH); $^{13}$C NMR (125 MHz, CDCl$_3$) δ: 14.2 (2C), 14.3, 14.5, 23.36, 23.39, 23.40, 23.8, 25.4, 25.57, 25.61, 26.3, 30.2, 30.3, 32.33, 32.35, 32.4, 33.0, 34.8, 34.9, 35.0, 35.2, 63.0, 65.0, 66.8, 70.1, 70.5, 72.3, 72.66, 72.72, 72.9, 73.4, 100.2, 173.75, 173.84, 174.7, 175.0)

Preparation Example 5

(1) Treatment in the same manner as Preparation Example 1 (1) was performed using 500 mg of a mannosyl sulfoxide compound of Reference Example 1 and 218 mg of an alcohol (2,3:4,5-di-O-isopropylidene-D-ribitol) to obtain 442 mg of a compound (2,3:4,5-di-O-isopropylidene-D-ribitol-1-yl 3-O-benzyl-4,6-benzylidene-2-O-p-methoxybenzyl-β-D-mannopyranoside). Yield was 75%.

Physical and spectroscopic constants of the obtained compound were as follows.

$^1$H NMR (700 MHz, CDCl$_3$) δ: 1.29 (s, 3H, CH$_3$), 1.33 (s, 3H, CH$_3$), 1.36 (s, 3H, CH$_3$), 1.42 (s, 3H, CH$_3$), 3.32 (ddd, J=9.8, 9.8, 4.8 Hz, 1H, OCH), 3.55 (dd, J=9.8, 3.2 Hz, 1H, OCH), 3.75 (dd, J=10.8, 4.8 Hz, 1H, OCH), 3.80 (s, 3H, OMe), 3.91 (dd, J=3.2, 0.6 Hz, 1H, OCH), 3.92 (dd, J=8.6, 5.6 Hz, 1H, OCH), 3.93 (dd, J=10.4, 9.8 Hz, 1H, OCH), 4.02 (dd, J=9.2, 6.0 Hz, 1H, OCH), 4.07 (dd, J=8.6, 6.0 Hz, 1H, OCH), 4.13 (dd, J=10.8, 5.2 Hz, 1H, OCH), 4.18 (ddd, J=9.2, 6.0, 5.6 Hz, 1H, OCH), 4.20 (dd, J=9.8, 9.8 Hz, 1H, OCH), 4.30 (dd, J=10.4, 4.8 Hz, 1H, OCH), 4.36 (ddd, J=6.0, 5.2, 4.8 Hz, 1H, OCH), 4.50 (d, J=0.6 Hz, 1H, OCH), 4.58 (d, J=12.4 Hz, 1H, OCHHPh), 4.69 (d, J=12.4 Hz, 1H, OCHHPh), 4.81 (d, J=11.6 Hz, 1H, OCHHAr), 4.90 (d, J=11.6 Hz, 1H, OCHHAr), 5.61 (s, 1H, OCHPh), 6.85 (d, J=8.6 Hz, 2H, Ar), 7.25-7.30 (m, 5H, Ar), 7.34-7.38 (m, 3H, Ar), 7.40 (d, J=8.6 Hz, 2H, Ar), 7.49-7.51 (m, 2H, Ar); $^{13}$C NMR (175 MHz, CDCl$_3$) δ: 25.3, 25.6, 26.9, 27.7, 55.3, 67.6, 67.9, 68.1, 68.6, 72.3, 73.3, 74.3, 75.4, 76.2, 77.7, 78.0, 78.6, 101.4, 102.5, 108.8, 109.6, 113.5 (2C), 126.0 (2C), 127.5 (2C), 128.2 (2C), 128.3 (2C), 128.8 (2C), 130.2 (2C), 130.6, 137.6, 138.4, 159.2

(2) In the same manner as Preparation Example 1 (2) was treated 309 mg of a compound obtained in the above-described (1) to obtain 216 mg of a compound (2,3:4,5-di-O-isopropylidene-D-ribitol-1-yl 3-O-benzyl-4,6-O-benzylidene-β-D-mannopyranoside). Yield was 84%.

Physical and spectroscopic constants of the obtained compound were as follows.

$^1$H NMR (400 MHz, CDCl$_3$) δ: 1.34 (s, 6H, 2×CH$_3$), 1.39 (s, 3H, CH$_3$), 1.40 (s, 3H, CH$_3$), 3.35 (ddd, J=10.4, 9.6, 4.8 Hz, 1H, OCH), 3.62 (dd, J=9.6, 3.2 Hz, 1H, OCH), 3.85 (dd, J=10.8, 6.0 Hz, 1H, OCH), 3.87 (dd, J=10.4, 10.4 Hz, 1H, OCH), 3.93 (dd, J=8.4, 4.8 Hz, 1H, OCH), 3.99 (dd, J=10.8, 6.0 Hz, 1H, OCH), 4.03 (dd, J=9.2, 6.0 Hz, 1H, OCH), 4.11 (dd, J=3.2, 1.2 Hz, 1H, OCH), 4.12 (dd, J=8.4, 6.0 Hz, 1H, OCH), 4.15 (ddd, J=9.2, 6.0, 4.8 Hz, 1H, OCH), 4.19 (dd, J=9.6, 9.6 Hz, 1H, OCH), 4.32 (dd, J=10.4, 4.8 Hz, 1H, OCH), 4.39 (ddd, J=6.0, 6.0, 6.0 Hz, 1H, OCH), 4.56 (d, J=1.2 Hz, 1H, OCH), 4.79 (d, J=12.4 Hz, 1H, OCHHPh), 4.87 (d, J=12.4 Hz, 1H, OCHHPh), 5.61 (s, 1H, OCHPh), 7.28-7.42 (m, 8H, Ar), 7.50 (dd, J=8.0, 2.0 Hz, 2H, Ar); $^{13}$C NMR (100 MHz, CDCl$_3$) δ: 25.39, 25.41, 26.8, 27.8, 67.0, 67.4, 68.0, 68.6, 69.9, 72.4, 73.2, 76.0, 76.4, 78.0, 78.3, 100.5, 101.5, 108.8, 109.8, 126.0 (2C), 127.7, 127.9 (2C), 128.2 (2C), 128.4 (2C), 128.9, 137.5, 138.1)

(3) In the same manner as Preparation Example 1 (3) was treated 195 mg of a compound obtained in the above-described (2) to obtain 238 mg of a compound (2,3:4,5-di-O-isopropylidene-D-ribitol-1-yl 3-O-benzyl-4,6-O-benzylidene-2-O-octanoyl-β-D-mannopyranoside).

Physical and spectroscopic constants of the obtained compound were as follows.

$^1$H NMR (400 MHz, CDCl$_3$) δ: 0.87 (t, J=6.8 Hz, 3H, CH$_3$), 1.23-1.36 (m, 8H, 4×CH$_2$), 1.315 (s, 3H, CH$_3$), 1.319 (s, 3H, CH$_3$), 1.39 (s, 3H, CH$_3$), 1.40 (s, 3H, CH$_3$), 1.67 (tt, J=7.6, 7.6 Hz, 2H, CH$_2$), 2.36 (t, J=7.6 Hz, 2H, COCH$_2$), 3.39 (ddd, J=10.4, 9.6, 5.2 Hz, 1H, OCH), 3.71 (dd, J=9.6, 3.2 Hz, 1H, OCH), 3.87 (dd, J=10.8, 4.0 Hz, 1H, OCH), 3.899 (dd, J=8.4, 5.2 Hz, 1H, OCH), 3.903 (dd, J=10.4, 10.4 Hz, 1H, OCH), 4.005 (dd, J=9.6, 9.6 Hz, 1H, OCH), 4.005 (dd, J=8.8, 6.0 Hz, 1H, OCH), 4.06 (dd, J=10.8, 6.0 Hz, 1H, OCH), 4.09 (dd, J=8.4, 6.0 Hz, 1H, OCH), 4.14 (ddd, J=8.8, 6.0, 5.2 Hz, 1H, OCH), 4.319 (ddd, J=6.0, 6.0, 4.0 Hz, 1H, OCH), 4.324 (dd, J=10.4, 5.2 Hz, 1H, OCH), 4.63 (d, J=12.4 Hz, 1H, OCHHPh), 4.67 (d, J=1.2 Hz, 1H, OCH), 4.74 (d, J=12.4 Hz, 1H, OCHHPh), 5.61 (s, 1H, OCHPh), 5.67 (dd, J=3.2, 1.2 Hz, 1H, OCH), 7.28-7.33 (m, 3H, Ar), 7.35-7.42 (m, 5H, Ar), 7.49-7.52 (m, 2H, Ar); $^{13}$C NMR (100 MHz, CDCl$_3$) δ: 14.1, 22.6, 25.0, 25.2, 25.5, 26.8, 27.5, 28.9, 29.0, 31.6, 34.1, 67.3, 67.9, 68.1, 68.4, 68.5, 71.5, 73.4, 75.5, 76.2, 77.8, 77.9, 99.8, 101.5, 108.8, 109.6, 126.0 (2C), 127.69, 127.73 (2C), 128.17 (2C), 128.3 (2C), 128.9, 137.3, 137.7, 173.2

(4) In the same manner as Preparation Example 1 (4) was treated 231 mg of a compound obtained in the above-described (1) to obtain 89.8 mg of a compound (2,3:4,5-di-O-isopropylidene-D-ribitol-1-yl 2-O-octanoyl-β-D-mannopyranoside). Yield was 52%.

Physical and spectroscopic constants of the obtained compound were as follows.

$^1$H NMR (400 MHz, CD$_3$OD) δ: 0.90 (t, J=7.2 Hz, 3H, CH$_3$), 1.30-1.35 (m, 8H, 4×CH$_2$), 1.30 (s, 3H, CH$_3$), 1.32 (s, 3H, CH$_3$), 1.37 (s, 3H, CH$_3$), 1.38 (s, 3H, CH$_3$), 1.63 (tt, J=7.2, 7.2 Hz, 2H, CH$_2$), 2.35 (dt, J=16.0, 7.2 Hz, 1H, COCHH), 2.39 (dt, J=16.0, 7.2 Hz, 1H, COCHH), 3.26 (ddd, J=9.6, 6.4, 2.4 Hz, 1H, OCH), 3.50 (dd, J=9.6, 9.6 Hz, 1H, OCH), 3.63 (dd, J=9.6, 3.6 Hz, 1H, OCH), 3.70 (dd, J=12.0, 6.4 Hz, 1H, OCH), 3.82 (dd, J=11.2, 4.4 Hz, 1H, OCH), 3.87 (dd, J=8.4, 6.4 Hz, 1H, OCH), 3.90 (dd, J=12.0, 2.4 Hz, 1H, OCH), 4.03 (dd, J=11.2, 5.6 Hz, 1H, OCH), 4.049 (dd, J=8.4, 6.4 Hz, 1H, OCH), 4.054 (dd, J=8.4, 6.0 Hz, 1H, OCH), 4.22 (ddd, J=8.4, 6.4, 6.0 Hz, 1H, OCH), 4.31 (ddd, J=6.0, 5.6, 4.4 Hz, 1H, OCH), 4.69 (d, J=0.8 Hz, 1H, OCH), 5.35 (dd, J=3.6, 0.8 Hz, 1H, OCH); $^{13}$C NMR (100 MHz, CD$_3$OD) δ: 14.4, 23.7, 25.4, 25.7, 26.0, 27.1, 27.8, 30.2 (2C), 32.9, 35.1, 62.9, 68.5, 68.8, 68.9, 72.8, 73.6, 74.8, 77.6, 78.5, 79.2, 100.6, 109.9, 110.7, 175.1

(5) In the same manner as Preparation Example 1 (5) was treated 79.2 mg of a compound obtained in the above-described (4) to obtain 124 mg of a compound (2,3:4,5-di-O-isopropylidene-D-ribitol-1-yl 3,4,6-tri-O-hexanoyl-2-O-octanoyl-β-D-mannopyranoside). Yield was 76%.

Physical and spectroscopic constants of the obtained compound were as follows.

$^1$H NMR (400 MHz, CDCl$_3$) δ: 0.86-0.92 (m, 12H, 4×CH$_3$), 1.20-1.36 (m, 20H, 10×CH$_2$), 1.31 (s, 3H, CH$_3$), 1.34 (s, 3H, CH$_3$), 1.389 (s, 3H, CH$_3$), 1.393 (s, 3H, CH$_3$), 1.50-1.69 (m, 8H, 4×CH$_2$), 2.17-2.45 (m, 8H, 4×COCH$_2$), 3.67 (ddd, J=10.0, 5.6, 2.4 Hz, 1H, OCH), 3.84 (dd, J=10.8, 4.8 Hz, 1H, OCH), 3.89 (dd, J=8.4, 6.0 Hz, 1H, OCH), 4.00 (dd, J=8.4, 6.0 Hz, 1H, OCH), 4.08 (dd, J=8.4, 6.0 Hz, 1H, OCH), 4.09 (dd, J=10.8, 4.8 Hz, 1H, OCH), 4.12 (ddd, J=8.4, 6.0, 6.0 Hz, 1H, OCH), 4.17 (dd, J=12.0, 2.4 Hz, 1H, OCH), 4.26 (dd, J=12.0, 5.6 Hz, 1H, OCH), 4.31 (ddd, J=6.0, 4.8, 4.8 Hz, 1H, OCH), 4.74 (s, 1H, OCH), 5.04 (dd, J=10.0, 3.2 Hz, 1H, OCH), 5.28 (dd, J=10.0, 10.0 Hz, 1H, OCH), 5.50 (d, J=3.2 Hz, 1H, OCH); $^{13}$C NMR (100 MHz, CDCl$_3$) δ: 13.8 (2C), 13.9, 14.0, 22.2 (2C), 22.3, 22.6, 24.3, 24.4, 24.5, 25.0, 25.3, 25.5, 26.7, 27.5, 28.96, 29.01, 31.2 (2C), 31.3, 31.7, 33.9, 34.0 (2C), 34.1, 62.5, 65.8, 67.90, 67.92, 68.4, 71.0, 72.5, 73.3, 76.0, 78.0, 98.9, 108.8, 109.7, 172.2, 172.7, 173.0, 173.4

(6) In the same manner as Preparation Example 1 (6) was treated 111 mg of a compound obtained in the above-described (5) to obtain 90.2 mg of D-ribitol-1-yl 3,4,6-tri-O-hexanoyl-2-O-octanoyl-β-D-mannopyranoside. Yield was 90%.

Physical and spectroscopic constants of the obtained compound were as follows.

$^1$H NMR (700 MHz, CD$_3$OD) δ: 0.90 (t, J=7.2 Hz, 6H, 2×CH$_3$), 0.91 (t, J=7.2 Hz, 3H, CH$_3$), 0.93 (t, J=7.2 Hz, 3H, CH$_3$), 1.23-1.44 (m, 20H, 10×CH$_2$), 1.51-1.59 (m, 4H, 2×CH$_2$), 1.62-1.69 (m, 4H, 2×CH$_2$), 2.19 (dt, J=15.3, 7.4 Hz, 1H, COCHH), 2.21 (dt, J=15.3, 7.4 Hz, 1H, COCHH), 2.28 (dt, J=15.8, 7.4 Hz, 1H, COCHH), 2.31 (dt, J=15.8, 7.4 Hz, 1H, COCHH), 2.35 (q, J=7.4 Hz, 2H, COCH$_2$), 2.40 (dt, J=15.4, 7.2 Hz, 1H, COCHH), 2.48 (dt, J=15.4, 7.2 Hz, 1H, COCHH), 3.58 (dd, J=6.2, 6.4 Hz, 1H, OCH), 3.61 (dd, J=11.2, 6.2 Hz, 1H, OCH), 3.71 (ddd, J=6.2, 6.2, 3.4 Hz, 1H, OCH), 3.75 (dd, J=11.2, 3.4 Hz, 1H, OCH), 3.84 (ddd, J=10.2, 4.2, 2.2 Hz, 1H, OCH), 3.86 (ddd, J=6.4, 5.6, 3.4 Hz, 1H, OCH), 3.87 (dd, J=10.2, 3.4 Hz, 1H, OCH), 3.92 (dd, J=10.2, 5.6 Hz, 1H, OCH), 4.14 (dd, J=12.3, 2.2 Hz, 1H, OCH), 4.28 (dd, J=12.3, 4.2 Hz, 1H, OCH), 4.93 (d, J=1.0 Hz, 1H, OCH), 5.17 (dd, J=10.2, 3.2 Hz, 1H, OCH), 5.29 (dd, J=10.2, 10.2 Hz, 1H, OCH), 5.48 (dd, J=3.2, 1.0 Hz, 1H, OCH); $^{13}$C NMR (175 MHz, CD$_3$OD) δ: 14.2 (2C), 14.3, 14.5, 23.35, 23.37, 23.40, 23.8, 25.5, 25.58, 25.62, 26.3, 30.2, 30.3, 32.3, 32.36, 32.44, 33.0, 34.8, 34.9, 35.0, 35.2, 63.0, 64.5, 66.8, 70.5, 72.50, 72.53, 72.6, 73.5, 73.6, 74.1, 100.0, 173.75, 173.84, 174.7, 175.0

Preparation Example 6

(1) Treatment in the same manner as Preparation Example 1 (1) was performed using 0.50 g of a mannosyl sulfoxide compound of Reference Example 1 and 0.24 g of an alcohol (1,2:3,4-di-O-isopropylidene-D-xylitol) to obtain 0.41 g of a compound (2,3:4,5-di-O-isopropylidene-L-xylitolyl 3-O-benzyl-4,6-O-benzylidene-2-O-p-methoxybenzyl-β-D-mannopyranoside) (1,2:3,4-di-O-isopropylidene-D-xylitol-5-yl 3-O-benzyl-4,6-O-benzylidene-2-O-p-methoxybenzyl-β-D-mannopyranoside). Yield was 58%.

Physical and spectroscopic constants of the obtained compound were as follows.

$^1$H-NMR (700 MHz, CDCl$_3$) δ: 1.38 (s, 3H, CH$_3$), 1.39 (s, 3H, CH$_3$), 1.432 (s, 3H, CH$_3$), 1.434 (s, 3H, CH$_3$), 3.32 (ddd, J=10.0, 9.6, 4.8 Hz, 1H, H-5), 3.57 (dd, J=9.9, 3.2 Hz, 1H, H-3), 3.78 (dd, J=11.6, 3.6 Hz, 1H, H-1'a), 3.80 (s, 3H, OCH$_3$), 3.88 (dd, J=8.2, 7.0 Hz, 1H, H-5'a) 3.93 (dd, J=10.0, 4.8 Hz, 1H, H-6a), 3.97 (d, J=3.2 Hz, 1H, H-2), 3.98 (dd, J=11.6, 3.6 Hz, 1H, H-1'b), 4.02 (dd, J=8.2, 7.0 Hz, 1H, H-5'b), 4.05 (dd, J=8.0, 4.2 Hz, 1H, H-3'), 4.10 (ddd, J=8.0, 3.6, 3.6 Hz, 1H, H-2'), 4.16 (ddd, J=7.0, 7.0, 4.2 Hz, 1H, H-4'), 4.19 (dd, J=9.9, 9.6 Hz, 1H, H-4), 4.29 (dd, J=10.0, 4.8 Hz, 1H, H-6b), 4.54 (s, 1H, H-1), 4.58 (d, J=12.4 Hz, 1H, OCHHPh), 4.69 (d, J=12.4 Hz, 1H, OCHHPh), 4.80 (d, J=11.6 Hz, 1H, OCHHPhOMe), 4.87 (d, J=11.6 Hz, 1H, OCHHPhOMe), 5.61 (s, 1H, H-7), 6.84-6.86 (m, 2H, Ar), 7.26-7.31 (m, 6H, Ar), 7.34-7.39 (m, 4H, Ar), 7.49-7.50 (m, 2H, Ar); $^{13}$C NMR (175 MHz, CDCl$_3$) δ: −0.01 1.01 25.56 25.60 26.2 27.0 27.2 29.7 55.3 65.68 65.73 67.7 68.2 68.5 72.5 74.5 75.0 75.1 75.6 76.26 76.32 77.9 78.6 101.4 102.6 109.4 109.7 113.5 113.6 126.0 127.51 127.55 127.58 128.2 128.3 128.9 129.4 130.1 130.2 130.4

(2) In the same manner as Preparation Example 1 (2) was treated 0.339 mg of a compound obtained in the above-described (1) to obtain a compound (2,3:4,5-di-O-isopropylidene-L-xylitolyl 3-O-benzyl-4,6-O-benzylidene-β-D-mannopyranoside) (1,2:3,4-di-O-isopropylidene-D-xylitol-5-yl 3-O-benzyl-4,6-O-benzylidene-β-D-mannopyranoside). Yield was 61%. Physical and spectroscopic constants of the obtained compound were as follows.

$^1$H NMR (400 MHz, CDCl$_3$) δ: 1.37 (s, 3H, CH$_3$), 1.41 (s, 3H, CH$_3$), 1.43 (s, 6H, CH$_3$), 2.60 (brS, 1H, OH), 3.35 (ddd, J=10.4, 10.0, 4.8 Hz, 1H, H-5), 3.65 (dd, J=9.6, 3.2 Hz, 1H, H-3), 3.71 (dd, J=10.8, 6.8 Hz, 1H, H-1'a), 3.83 (dd, J=10.4, 4.8 Hz, 1H, H-6a), 3.87 (dd, J=8.8, 7.6 Hz, 1H, H-5'a) 3.91 (d, J=3.2 Hz, 1H, H-2), 3.98 (dd, J=10.8, 4.4 Hz, 1H, H-1'b), 4.04 (dd, J=8.4, 6.8 Hz, 1H, H-3'), 4.11-4.22 (m, 1H, H-5'b), 4.11-4.22 (m, 1H, H-2'), 4.11-4.22 (m, 1H, H-4'), 4.11-4.22 (m, 1H, H-4), 4.32 (dd, J=10.4, 4.8 Hz, 1H, H-6b), 4.61 (s, 1H, H-1), 4.78 (d, J=12.4 Hz, 1H, OCHHPh), 4.85 (d, J=12.4 Hz, 1H, OCHHPh), 5.61 (s, 1H, H-7), 7.29-7.42 (m, 8H, Ar), 7.49-7.51 (m, 2H, Ar); $^{13}$C NMR (100 MHz, CDCl$_3$) δ: 25.4 26.2 27.0 27.1 65.6 67.0 68.5 69.7 70.5 72.5 75.3 76.3 76.5 78.3 78.4 100.3 101.6 109.8 110.2 126.0 (2C) 127.8 127.9 (2C) 128.2 (2C) 128.4 (2C) 129.0 137.4 137.9

(3) In the same manner as Preparation Example 1 (3) was treated 0.157 g of a compound obtained in the above-described (2) to obtain 0.189 g of a compound (2,3:4,5-di-O-isopropylidene-L-xylitolyl 3-O-benzyl-4,6-O-benzylidene-2-O-octanoyl-β-D-mannopyranoside) (1,2:3,4-di-O-isopropylidene-D-xylitol-5-yl 3-O-benzyl-4,6-O-benzylidene-2-O-octanoyl-β-D-mannopyranoside). Yield was 98%.

Physical and spectroscopic constants of the obtained compound were as follows.

$^1$H NMR (400 MHz, CDCl$_3$) δ: 0.87 (t, J=6.4 Hz, 3H, CH$_3$), 1.24-1.35 (m, 8H, CH$_2$), 1.38 (s, 3H, CH$_3$), 1.39 (s, 3H, CH$_3$), 1.43 (s, 6H, CH$_3$), 1.66 (dt, J=7.2, 7.2 Hz, 2H, CH$_2$CH$_2$CO), 2.40 (t, J=7.6 Hz, 2H, CH$_2$CH$_2$CO), 3.39 (ddd, J=9.6, 9.6, 4.8 Hz, 1H, H-5), 3.71 (dd, J=10.4, 4.8 Hz, 1H, H-1'a), 3.72 (dd, J=9.6, 3.2 Hz, 1H, H-3), 3.87 (dd, J=8.8, 7.6 Hz, 1H, H-5'a), 3.86 (dd, J=8.0, 4.4 Hz, 1H, H-3'), 3.90 (dd, J=10.0, 10.0 Hz, 1H, H-6a), 3.92 (dd, J=10.4, 4.8 Hz, 1H, H-1'b), 3.99 (dd, J=9.6, 9.6 Hz, 1H, H-4), 3.997 (dd, J=8.4, 6.8 Hz, 1H, H-5'b), 4.09 (ddd, J=7.2, 7.2, 5.2 Hz, 1H, H-4'), 4.16 (dt, J=7.2, 5.2 Hz, 1H, H-2'), 4.33 (dd, J=10.4, 4.8 Hz, 1H, H-6b), 4.62 (d, J=12.8 Hz, 1H, OCHHPh), 4.69 (s, 1H, H-1), 4.73 (d, J=12.8 Hz, 1H, OCHHPh), 5.61 (s, 1H, H-7), 5.69 (d, J=2.8 Hz, 1H, H-2), 7.28-7.42 (m, 8H, Ar), 7.49-7.51 (m, 2H, Ar); $^{13}$C NMR (100 MHz, CDCl$_3$) δ: 14.1 22.6 24.9 25.4 26.2 26.97 27.02 28.9 29.0 31.7 34.1 65.6 67.4 68.2 68.4 70.3 71.6 75.4 75.6 76.0 77.9 78.7 99.7 101.5 109.7 109.9 126.0 (2C) 127.7 (3C) 128.2 (2C) 128.3 (2C) 129.0 137.3 137.6 173.1

(4) In the same manner as Preparation Example 1 (4) was treated 0.169 g of a compound obtained in the above-described (3) to obtain 0.094 g of a compound (2,3:4,5-di-O-isopropylidene-L-xylitolyl 2-O-octanoyl-β-D-mannopyranoside) (1,2:3,4-di-O-isopropylidene-D-xylitol-5-yl 2-O-octanoyl-β-D-mannopyranoside). Yield was 78%.

Physical and spectroscopic constants of the obtained compound were as follows.

$^1$H NMR (400 MHz, CD$_3$OD) δ: 0.90 (t, J=6.8 Hz, 3H, CH$_3$), 1.30-1.33 (m, 8H, CH$_2$), 1.35 (s, 6H, CH$_3$), 1.38 (s, 3H, CH$_3$), 1.39 (s, 3H, CH$_3$), 1.62 (dt, J=14.4, 7.6 Hz, 2H, CH$_2$CH$_2$CO), 2.38 (ddd, J=7.2, 7.2, 5.6 Hz, 2H, CH$_2$CH$_2$CO), 3.28 (ddd, J=9.6, 6.4, 2.8 Hz, 1H, H-5), 3.50 (dd, J=9.6, 9.6 Hz, 1H, H-4), 3.64 (dd, J=9.6, 3.2 Hz, 1H, H-3), 3.70 (dd, J=12.0, 6.4 Hz, 1H, H-6a), 3.71 (dd, J=10.4, 4.8 Hz, 1H, H-1'a), 3.85 (dd, J=8.0, 7.6 Hz, 1H, H-5'a), 3.89 (dd, J=8.0, 4.4 Hz, 1H, H-3'), 3.91 (dd, J=12.0, 2.4 Hz, 1H, H-6b), 3.96 (dd, J=10.4, 5.2 Hz, 1H, H-1'b), 4.01 (dd, J=8.4, 6.8 Hz, 1H, H-5'b), 4.10 (dt, J=8.0, 5.2 Hz, 1H, H-4'), 4.18 (ddd, J=8.0, 6.8, 4.0 Hz, 1H, H-2'), 4.70 (d, J=0.8 Hz, 1H, H-1), 5.35 (dd, J=3.2, 0.8 Hz, 1H, H-2); $^{13}$C NMR (100 MHz, CD$_3$OD) δ: 14.4 23.7 25.9 26.0 26.6 27.3 27.5 30.16 30.17 32.9 35.1 62.9 66.8 68.9 70.8 72.8 73.5 76.5 77.3 78.7 79.7 100.5 110.68 110.72 175.0

(5) In the same manner as Preparation Example 1 (5) was treated 0.074 g of a compound obtained in the above-described (4) to obtain 0.105 g of a compound (2,3:4,5-di-O-isopropylidene-L-xylitolyl 3,4,6-tri-O-hexanoyl-2-O-octanoyl-β-D-mannopyranoside) (1,2:3,4-di-O-isopropylidene-D-xylitol-5-yl 3,4,6-tri-O-hexanoyl-2-O-octanoyl-β-D-mannopyranoside). Yield was 76%.

Physical and spectroscopic constants of the obtained compound were as follows.

$^1$H NMR (400 MHz, CDCl$_3$) δ: 0.86 (s, 3H, CH$_3$), 0.88 (s, 3H, CH$_3$), 0.90 (s, 3H, CH$_3$), 0.92 (s, 3H, CH$_3$), 1.23-1.33 (m, 20H, CH$_2$), 1.37 (s, 3H, CH$_3$), 1.39 (s, 6H, CH$_3$), 1.418 (s, 3H, CH$_3$), 1.423 (s, 3H, CH$_3$), 1.50-1.67 (m, 8H, CH$_2$CH$_2$CO), 2.20 (ddd, J=7.6, 7.6, 4.0 Hz, 2H, CH$_2$CH$_2$CO), 2.26 (ddd, J=7.6, 7.6, 5.2 Hz, 2H, CH$_2$CH$_2$CO), 2.34 (ddd, J=16.8, 7.6, 5.2 Hz, 2H, CH$_2$CH$_2$CO), 2.42 (ddd, J=7.6, 7.6, 3.6 Hz, 2H, CH$_2$CH$_2$CO), 3.66 (ddd, J=10.0, 5.6, 2.8 Hz, 1H, H-5), 3.72 (dd, J=10.4, 5.6 Hz, 1H, H-5'b), 3.83 (dd, J=11.2, 8.0 Hz, 1H, H-1'a), 3.83 (ddd, J=8.0, 8.0, 6.4 Hz, 1H, H-2'), 3.90 (dd, J=10.4, 5.6 Hz, 1H, H-5'a), 3.89 (dd, J=8.0, 6.4 Hz, 1H, H-3'), 4.08 (dt, J=8.0, 5.6 Hz, 1H, H-4'), 4.14 (dd, J=11.2, 6.4 Hz, 1H, H-1'b), 4.17 (dd, J=12.0, 2.8 Hz, 1H, H-6a), 4.24 (dd, J=12.0, 5.6 Hz, 1H, H-6b), 4.77 (s, 1H, H-1), 5.06 (dd, J=10.0, 3.6 Hz, 1H, H-3), 5.26 (dd, J=10.0, 10.0 Hz, 1H, H-4), 5.52 (d, J=2.8 Hz, 1H, H-2); $^{13}$C NMR (100 MHz, CDCl$_3$) δ: 13.8 (2C) 13.9 14.1 22.2 (2C) 22.3 22.6 24.3 24.45 24.48 25.0 25.4 26.2 26.95 27.03 28.97 29.01 31.2 (2C) 31.3 31.7 33.9 34.0 (2C) 34.1 62.4 65.6 65.7 68.3 70.2 70.9 72.7 75.4 76.0 78.8 98.5 109.7 110.0 172.3 172.6 173.0 173.4)

(6) In the same manner as Preparation Example 1 (6) was treated 0.085 g of a compound obtained in the above-described (5) to obtain 0.061 g of L-xylitolyl 3,4,6-tri-O-hexanoyl-2-O-octanoyl-β-D-mannopyranoside (D-xylitol-5-yl 3,4,6-tri-O-hexanoyl-2-O-octanoyl-β-D-mannopyranoside). Yield was 90%.

Physical and spectroscopic constants of the obtained compound were as follows.

$^1$H NMR (700 MHz, CD$_3$OD) δ: 0.89-0.93 (m, 12H, CH$_3$), 1.23-1.42 (m, 20H, CH$_2$), 1.51-1.59 (m, 4H, CH$_2$), 1.62-1.69 (m, 4H, CH$_2$), 2.18-2.48 (m, 8H, COCH$_2$), 3.56 (dd, J=7.8, 4.1 Hz, 1H, H-3'), 3.58 (dd, J=11.2, 4.8 Hz, 1H, H-5'b), 3.63 (dd, J=11.2, 4.8 Hz, 1H, H-5'a), 3.67 (dd, J=10.4, 7.0 Hz, 1H, H-1'a), 3.71 (dt, J=4.8, 4.1 Hz, 1H, H-4'), 3.82 (ddd, J=10.0, 4.2, 2.2 Hz, 1H, H-5), 3.86 (ddd, J=7.8, 7.0, 4.2 Hz, 1H, H-2'), 3.95 (dd, J=10.4, 4.2 Hz, 1H, H-1'b), 4.14 (dd, J=12.3, 2.2 Hz, 1H, H-6a), 4.28 (dd, J=12.3, 4.2 Hz, 1H, H-6b), 4.91 (d, J=0.98 Hz, 1H, H-1), 5.16 (dd, J=10.2, 3.2 Hz, 1H, H-3), 5.29 (dd, J=10.2, 10.0 Hz, 1H, H-4), 5.48 (dd, J=3.2, 0.98 Hz, 1H, H-2); $^{13}$C NMR (175 MHz, CD$_3$OD) δ: 14.2 (2C) 14.3 14.5 23.36 23.38 23.41 23.8 25.46 25.59 25.62 26.3 30.2 30.3 32.3 32.36 32.44 33.0 34.8 34.92 34.96 35.2 63.0 64.3 66.8 70.5 72.1 72.3 72.7 72.8 73.5 73.9 100.3 173.7 173.8 174.7 175.0

Preparation Example 7

(1) Treatment in the same manner as Preparation Example 1 (1) was performed using 1.75 g of a mannosyl sulfoxide compound of Reference Example 1 and 0.99 g of an alcohol of racemic form (1-O-tert-butyldimethylsilyl-2,3-O-isopropylidene-erythritol) of Reference Example 4 to obtain 1.32 g of a compound (a) and a compound (b) (1-O-tert-butyldimethylsilyl-2,3-O-isopropylidene-erythritolyl 3-O-benzyl-4,6-benzylidene-2-O-p-methoxybenzyl-β-D-mannopyranoside). Yield was 60%.

Physical and spectroscopic constants of the obtained compound were as follows.

(Physical constants of the compound (a): $^1$H-NMR (700 MHz, CDCl$_3$) δ: 0.039 (3H, s), 0.042 (3H, s), 0.87 (9H, s), 1.38 (3H, s), 1.45 (3H, s), 3.31 (1H, ddd, J=10.4, 9.6, 4.8), 3.57 (1H, dd, J=9.6, 3.2), 3.57 (1H, dd, J=10.1, 4.4), 3.60 (1H, dd, 11.0, 2.4), 3.62 (1H, dd, J=10.1, 7.0), 3.80 (3H, s), 3.92 (1H, dd, J=10.4, 10.4), 4.01 (1H, dd, J=3.2, 0.6), 4.13 (1H, ddd, J=7.0, 6.2, 4.4), 4.19 (1H, dd, J=9.6, 9.6), 4.27 (1H, dd, J=10.4, 4.8), 4.29 (1H, dd, J=11.0, 2.6), 4.44 (1H, ddd, J=6.2, 2.6, 2.4), 4.55 (1H, d, J=0.6), 4.58 (1H, d, J=12.6), 4.66 (1H, d, J=12.6), 4.85 (1H, d, J=11.9), 4.91 (1H, d, J=11.9), 5.62 (1H, s), 6.85 (2H, d, J=8.5), 7.25-7.33 (5H, m), 7.33-7.39 (3H, m), 7.41 (2H, d, J=8.5), 7.48-7.51 (2H, m). $^{13}$C-NMR (175 MHz, CDCl$_3$) δ: −5.56, −5.52, 18.1, 25.4, 25.8 (3C), 28.0, 55.2, 61.6, 67.6, 68.56, 68.58, 72.2, 72.3, 74.9, 76.7, 77.7, 78.6, 79.3, 101.4, 102.2, 108.6, 113.5 (2C), 126.0 (2C), 127.51 (2C), 127.53, 128.2 (2C), 128.3 (2C), 128.8, 130.3, 130.5 (2C), 137.6, 138.3, 159.2.)

(Physical constants of the compound (b): $^{1}$H-NMR (700 MHz, CDCl$_3$) δ: 0.041 (3H, s), 0.046 (3H, s), 0.87 (9H, s), 1.37 (3H, s), 1.44 (3H, s), 3.31 (1H, ddd, J=10.3, 9.5, 4.8), 3.56 (1H, dd, J=9.5, 3.2), 3.65 (1H, dd, J=10.8, 5.1), 3.74 (1H, dd, 10.8, 6.1), 3.76 (1H, dd, J=10.7, 4.9), 3.80 (3H, s), 3.91 (1H, dd, J=3.2, 0.6), 3.93 (1H, dd, J=10.3, 10.3), 4.02 (1H, dd, J=10.7, 6.1), 4.17 (1H, ddd, J=6.1, 6.1, 5.1), 4.19 (1H, dd, J=9.5, 9.5), 4.28 (1H, dd, J=10.3, 4.8), 4.34 (1H, ddd, J=6.1, 6.1, 4.9), 4.47 (1H, d, J=0.6), 4.58 (1H, d, J=12.6), 4.68 (1H, d, J=12.6), 4.81 (1H, d, J=11.8), 4.90 (1H, d, J=11.8), 5.61 (1H, s), 6.85 (2H, d, J=8.7), 7.25-7.32 (5H, m), 7.34-7.41 (3H, m), 7.39 (2H, d, J=8.7), 7.48-7.51 (2H, m). $^{13}$C-NMR (175 MHz, CDCl$_3$) δ: −5.43, −5.39, 18.2, 25.3, 25.9 (3C), 27.8, 55.2, 61.8, 67.7, 68.3, 68.6, 72.3, 74.3, 75.2, 75.8, 77.2, 77.8, 78.6, 101.4, 102.4, 108.5, 113.5 (2C), 126.0 (2C), 127.5 (3C), 128.2 (2C), 128.3 (2C), 128.8, 130.3 (2C), 130.5, 137.6, 138.3, 159.2.

(2) The compound (a) obtained in the above-described (1) was treated in the same manner as Preparation Example 1 (2) to obtain a compound (1-O-tert-butyldimethylsilyl-2,3-O-isopropylidene-L-erythritolyl 3-O-benzyl-4,6-O-benzylidene-2-hydroxy-β-D-mannopyranoside). Yield was 84%.

(3) A compound obtained in the above-described (2) was treated in the same manner as Preparation Example 1 (3) to obtain 0.58 g of a compound (1-O-tert-butyldimethylsilyl-2,3-O-isopropylidene-L-erythritolyl 3-O-benzyl-4,6-O-benzylidene-2-O-octanoyl-β-D-mannopyranoside).

Physical and spectroscopic constants of the obtained compound were as follows.

$^{1}$H-NMR (400 MHz, CDCl$_3$) δ: 0.047 (3H, s), 0.048 (3H, s), 0.87 (3H, J=7.4), 0.88 (9H, s), 1.21-1.32 (8H, m), 1.35 (3H, s), 1.42 (3H, s), 1.64-1.69 (2H, m), 2.46 (2H, t, J=7.6), 3.38 (1H, ddd, J=10.3, 9.7, 4.8), 3.57 (1H, dd, J=10.7, 4.7), 3.62 (1H, dd, J=10.7, 7.3), 3.70 (1H, dd, J=11.3, 8.1), 3.73 (1H, dd, J=9.7, 3.3), 3.89 (1H, dd, J=10.3, 10.3), 3.98 (1H, dd, J=9.7, 9.7), 4.11 (1H, ddd, J=7.3, 6.3, 4.7), 4.14 (1H, dd, J=11.3, 3.0), 4.31 (1H, dd, J=10.3, 4.8), 4.34 (1H, ddd, J=8.1, 6.3, 3.0), 4.63 (1H, d, J=12.4), 4.74 (1H, d, J=12.4), 4.74 (1H, d, J=1.2), 5.61 (1H, s), 5.72 (1H, dd, J=3.3, 1.2), 7.25-7.32 (5H, m), 7.35-7.41 (3H, m), 7.49-7.52 (2H, m). $^{13}$C-NMR (100 MHz, CDCl$_3$) δ: −5.52, −5.49, 14.0, 18.1, 22.6, 25.0, 25.3 (3C), 25.8, 27.9, 28.9, 29.0, 31.7, 34.2, 61.6, 67.3, 68.4, 68.49, 68.52, 71.5, 75.7, 76.78, 76.82, 78.0, 99.7, 101.5, 108.7, 126.1 (2C), 127.67, 127.72 (2C), 128.2 (2C), 128.3 (2C), 128.9, 137.4, 137.7, 173.2.)

(4) In the same manner as Preparation Example 1 (4) was treated 100 mg of a compound obtained in the above-described (3) to obtain 55.9 mg of a compound (1-O-tert-butyldimethylsilyl-2,3-O-isopropylidene-L-erythritolyl 2-O-octanoyl-β-D-mannopyranoside). Yield was 74%.

Physical and spectroscopic constants of the obtained compound were as follows.

$^{1}$H-NMR (400 MHz, CD$_3$OD) δ: 0.041 (6H, s), 0.80-0.82 (3H, m), 0.82 (9H, s), 1.20-1.31 (8H, m), 1.23 (3H, s), 1.32 (3H, s), 1.50-1.55 (2H, m), 2.25-2.31 (2H, m), 3.15 (1H, ddd, J=9.6, 6.8, 4.9), 3.43 (1H, t, J=9.6, 9.6), 3.54 (1H, dd, J=9.6, 3.6), 3.56 (1H, dd, J=11.4, 6.6), 3.58 (1H, dd, J=11.2, 6.8), 3.64 (1H, dd, J=10.8, 6.0), 3.66 (1H, dd, J=11.2, 4.9), 3.80 (1H, dd, J=11.4, 2.4), 3.93 (1H, dd, J=10.8, 4.8), 4.07 (1H, ddd, J=6.6, 6.0, 2.4), 4.20 (1H, ddd, J=6.0, 6.0, 4.8), (1H, dd, J=6.0, 6.0, 4.8), 4.61 (1H, d, J=0.8), 5.62 (1H, dd, J=3.6, 0.8). $^{13}$C-NMR (100 MHz, CD$_3$OD) δ: 14.4, 19.2, 23.7, 25.6, 26.0, 26.4 (3C), 28.1, 30.1 (2C), 33.0, 35.1, 62.9, 63.2, 68.96, 69.02, 72.9, 73.6, 77.5, 78.5, 79.0, 100.4, 109.8, 175.0.

(5) In the same manner as Preparation Example 1 (5) was treated 40.0 g of a compound obtained in the above-described (4) to obtain 0.06 g of a compound (1-O-tert-butyldimethylsilyl-2,3-O-isopropylidene-L-erythritolyl 3,4,6-tri-O-hexanoyl-2-O-octanoyl-β-D-mannopyranoside. Yield was 96%.

Physical and spectroscopic constants of the obtained compound were as follows.

$^{1}$H-NMR (400 MHz, CDCl$_3$) δ: 0.050 (3H, s), 0.052 (3H, s), 0.87 (12H, t, J=7.2), 0.88 (9H, s), 1.24-1.36 (20H, m), 1.34 (3H, s), 1.43 (3H, s), 1.50-1.70 (8H, m), 2.15-2.50 (8H, m), 3.58 (1H, dd, J=11.6, 6.4), 3.63 (1H, dd, J=11.6, 5.2), 3.64 (1H, ddd, J=10.0, 5.0, 2.4), 3.72 (1H, dd, J=11.6, 8.0), 4.10 (1H, dd, J=11.6, 4.4), 4.11 (1H, ddd, J=5.2, 4.4, 2.8), 4.15 (1H, dd, J=12.2, 2.4), 4.26 (1H, dd, J=12.2, 5.0), 4.33 (1H, ddd, J=8.0, 6.4, 2.8), 4.83 (1H, d, J=0.4), 5.07 (1H, dd, J=10.0, 3.2), 5.29 (1H, dd, J=10.0, 10.0), 5.53 (1H, dd, J=3.2, 0.4). $^{13}$C-NMR (100 MHz, CDCl$_3$) δ: 13.8 (2C), 13.9, 14.1, 18.2, 22.2 (2C), 22.3, 22.6, 24.3, 24.4, 24.5, 25.0, 25.3, 25.9 (3C), 27.9, 28.96, 29.00, 31.2 (2C), 31.3, 31.7, 33.95 (2C), 34.02, 34.2, 61.6, 62.3, 65.7, 68.4, 68.7, 71.1, 72.6, 76.9 (2C), 98.7, 108.7, 172.2, 172.7, 173.0, 173.5.

(6) In the same manner as Preparation Example 1 (6) was treated 0.05 g of a compound obtained in the above-described (5) to obtain 0.03 g of L-erythritolyl 3,4,6-tri-O-hexanoyl-2-O-octanoyl-β-D-mannopyranoside. Yield was 75%.

Physical and spectroscopic constants of the obtained compound were as follows.

$^{1}$H-NMR (CD$_3$OD) δ: 0.90 (6H, t, J=7.2), 0.916 (3H, t, J=6.8), 0.923 (3H, t, J=7.0), 1.23-1.43 (20H, m), 1.51-1.59 (4H, m), 1.62-1.71 (4H, m), 2.19 (1H, dt, J=15.2, 7.2), 2.21 (1H, dt, J=15.1, 7.2), 2.27 (1H, dt, J=15.8, 7.2), 2.31 (1H, dt, J=15.8, 7.2), 2.34 (1H, dt, J=15.8, 7.4), 2.37 (1H, dt, J=15.8, 7.6), 2.40 (1H, dt, J=15.4, 7.2), 2.46 (1H, dt, J=15.2, 7.2), 3.52 (1H, ddd, J=6.2, 6.2, 3.6), 3.57 (1H, dd, J=11.4, 6.2), 3.64 (1H, dd, J=10.0, 3.2), 3.66 (1H, ddd, J=6.2, 3.2, 2.3), 3.70 (1H, dd, J=11.4, 3.6), 3.82 (1H, ddd, J=10.0, 4.4, 2.4), 4.05 (1H, dd, J=10.0, 2.3), 4.14 (1H, dd, J=12.4, 2.4), 4.28 (1H, dd, J=12.4, 4.4), 4.90 (1H, d, J=0.9), 5.16 (1H, dd, J=10.0, 3.3), 5.29 (1H, dd, J=10.0, 10.0), 5.50 (1H, dd, J=3.3, 0.9). $^{13}$C-NMR (CD$_3$OD) δ: 14.2 (2C), 14.3, 14.5, 23.36, 23.38, 23.4, 23.8, 25.5, 25.60, 25.62, 26.4, 30.2, 30.3, 32.34, 32.36, 32.5, 33.0, 34.8, 34.9, 35.0, 35.2, 63.1, 64.6, 66.8, 70.5, 72.4, 72.7, 73.1, 73.5, 73.6, 100.5, 173.78, 173.84, 174.7, 175.0.

(7) Furthermore, treatment in the entirely same manner as described above was performed using the compound (b) obtained in the above-described (1) to obtain 0.02 g of D-erythritolyl 3,4,6-tri-O-hexanoyl-2-O-octanoyl-β-D-mannopyranoside (erythritol-1-yl 3,4,6-tri-O-hexanoyl-2-O-octanoyl-β-D-mannopyranoside). Yield was 75%.

Physical and spectroscopic constants of the obtained compound were as follows.

$^{1}$H-NMR (CD$_3$OD) δ: 0.90 (6H, t, J=7.2), 0.92 (3H, t, J=7.0), 0.94 (3H, t, J=7.6), 1.24-1.46 (20H, m), 1.51-1.60 (4H, m), 1.61-1.71 (4H, m), 2.19 (1H, dt, J=15.0, 7.2), 2.21

(1H, dt, J=14.8, 7.8), 2.27 (1H, dt, J=15.8, 7.4), 2.31 (1H, dt, J=15.8, 7.4), 2.36 (1H, dt, J=15.1, 7.4), 2.37 (1H, dt, J=15.8, 7.6), 2.40 (1H, dt, J=15.5, 7.2), 2.47 (1H, dt, J=15.4, 7.2), 3.56 (1H, ddd, J=6.2, 5.8, 3.0), 3.58 (1H, dd, J=10.8, 6.2), 3.67 (1H, dd, J=5.8, 5.8, 3.6), 3.71 (1H, dd, J=10.8, 3.0), 3.83 (1H, dd, J=10.8, 3.6), 3.83 (1H, ddd, J=10.0, 4.6, 2.2), 3.90 (1H, dd, J=10.8, 5.8), 4.14 (1H, dd, J=12.4, 2.2), 4.28 (1H, dd, J=12.4, 4.6), 4.91 (1H, d, J=1.0), 5.16 (1H, dd, J=10.0, 3.2), 5.29 (1H, dd, J=10.0, 10.0), 5.48 (1H, dd, J=3.2, 1.0). $^{13}$C-NMR (CD$_3$OD) δ: 14.2 (2C), 14.3, 14.5, 23.37 (2C), 23.40, 23.8, 25.5, 25.58, 25.62, 26.3, 30.2, 30.3, 32.34, 32.36, 32.4, 33.0, 34.8, 34.9, 35.0, 35.2, 63.0, 64.6, 66.8, 69.1, 70.4, 72.1, 72.6, 73.4, 73.5, 100.0, 173.76, 173.83, 174.7, 174.9.

Preparation Example 8

(1) Treatment in the same manner as Preparation Example 1 (1) was performed using 0.50 g of a mannosyl sulfoxide compound of Reference Example 1 and 0.28 g of an alcohol (4-O-tert-butyldimethylsilyl-2,3-O-isopropylidene-L-threitol) to obtain 0.37 g of a compound (4-O-tert-butyldimethylsilyl-2,3-O-isopropylidene-L-threitolyl 3-O-benzyl-4,6-O-benzylidene-2-O-p-methoxybenzyl-β-D-mannopyranoside). Yield was 59%.

Physical and spectroscopic constants of the obtained compound were as follows.

$^1$H NMR (700 MHz, CDCl$_3$) δ: 0.06 (s, 3H, SiCH$_3$), 0.07 (s, 3H, SiCH$_3$), 0.89 (s, 9H, C(CH$_3$)$_3$), 1.37 (s, 3H, CH$_3$), 1.40 (s, 3H, CH$_3$), 3.32 (ddd, J=10.4, 9.6, 5.0 Hz, 1H, H-5), 3.56 (dd, J=10.0, 3.2 Hz, 1H, H-3), 3.74 (dd, J=10.8, 5.3 Hz, 1H, H-1'a), 3.78 (dd, J=10.8, 4.0 Hz, 1H, H-1'b), 3.80 (s, 3H, OCH$_3$), 3.82 (dd, J=11.6, 3.2 Hz, 1H, H-4'a), 3.92 (dd, J=10.4, 10.4 Hz, 1H, H-6a), 3.96 (dd, J=3.2, 0.6 Hz, 1H, H-2), 3.99 (dd, J=11.6, 3.2 Hz, 1H, H-4'b), 4.04 (ddd, J=8.0, 5.3, 4.0 Hz, 1H, H-2'), 4.08 (ddd, J=8.0, 3.2, 3.2 Hz, 1H, H-3'), 4.18 (dd, J=10.0, 9.6 Hz, 1H, H-4), 4.29 (dd, J=10.4, 5.0 Hz, 1H, H-6b), 4.558 (d, J=12.4 Hz, 1H, OCHHPh), 4.560 (d, J=0.6 Hz, 1H, H-1), 4.66 (d, J=12.4 Hz, 1H, OCHHPh), 4.80 (d, J=11.8 Hz, 1H, OCHHPhOMe), 4.90 (d, J=11.8 Hz, 1H, OCHHPhOMe), 5.61 (s, 1H, OCHPh), 6.84-6.86 (m, 2H, Ar), 7.25-7.39 (m, 10H, Ar), 7.49-7.51 (m, 2H, Ar); $^{13}$C NMR (175 MHz, CDCl$_3$) δ: −5.43, −5.38, 18.3, 25.9 (3C), 27.0, 27.2, 55.2, 63.3, 67.6, 68.5, 68.6, 72.3, 74.4, 75.3, 77.0, 77.5, 77.7, 78.6, 101.4, 102.6, 109.0, 113.5 (2C), 126.0 (2C), 127.5 (3C), 128.2 (2C), 128.3 (2C), 128.8, 130.2 (2C), 130.5, 137.6, 138.3, 159.2

(2) In the same manner as Preparation Example 1 (2) was treated 373 mg of a compound in the above-described (1) to obtain 196 mg of a compound (4-O-tert-butyldimethylsilyl-2,3-di-O-isopropylidene-L-threitol-1-yl 3-O-benzyl-4,6-O-benzylidene-2-O-p-methoxybenzyl-β-D-mannopyranoside). Yield was 63%.

Physical and spectroscopic constants of the obtained compound were as follows.

$^1$H NMR (400 MHz, CDCl$_3$) δ: 0.07 (s, 6H, SiCH$_3$), 0.89 (s, 9H, C(CH$_3$)$_3$), 1.389 (s, 3H, CH$_3$), 1.392 (s, 3H, CH$_3$), 3.34 (ddd, J=10.0, 9.6, 4.4 Hz, 1H, H-5), 3.63 (dd, J=9.6, 3.2 Hz, 1H, H-3), 3.71 (dd, J=10.8, 5.6 Hz, 1H, H-1'a), 3.79 (dd, J=10.8, 4.4 Hz, 1H, H-1'b), 3.86 (dd, J=11.2, 3.2 Hz, 1H, H-4'a), 3.88 (dd, J=10.8, 10.0 Hz, 1H, H-6a), 3.95 (ddd, J=5.6, 4.4, 3.2 Hz, 1H, H-2'), 3.97 (dd, J=11.2, 4.4 Hz, 1H, H-4'b), 4.09 (ddd, J=8.0, 4.4, 3.2 Hz, 1H, H-3'), 4.16 (dd, J=2.0, 0.6 Hz, 1H, H-2), 4.16 (dd, J=9.6, 9.6 Hz, 1H, H-4), 4.32 (dd, J=10.8, 5.2 Hz, 1H, H-6b), 4.60 (d, J=0.6 Hz, 1H, H-1), 4.78 (d, J=12.4 Hz, 1H, OCHHPh), 4.87 (d, J=12.4 Hz, 1H, OCHHPh), 5.61 (s, 1H, OCHPh), 7.29-7.42 (m, 8H, Ar), 7.49-7.51 (m, 2H, Ar); $^{13}$C NMR (100 MHz, CDCl$_3$) δ: −5.44, −5.39, 18.3, 25.9 (3C), 27.00, 27.03, 63.5, 67.0, 68.6, 69.0 70.0, 72.5, 76.6, 77.0, 77.7, 78.4, 100.6, 101.5, 109.4, 126.0 (2C), 127.8, 127.9 (2C), 128.2 (2C), 128.4 (2C), 128.9, 137.4, 138.0

(3) In the same manner as Preparation Example 1 (3) was treated 196 mg of a compound obtained in the above-described (2) to obtain 190 mg of a compound (4-O-tert-butyldimethylsilyl-2,3-O-isopropylidene-L-threitol-1-yl 3-O-benzyl-4,6-O-benzylidene-2-O-octanoyl-β-D-mannopyranoside). Yield was 81%.

Physical and spectroscopic constants of the obtained compound were as follows.

$^1$H NMR (400 MHz, CDCl$_3$) δ: 0.062 (s, 3H, SiCH$_3$), 0.065 (s, 3H, SiCH$_3$), 0.87 (t, J=7.2 Hz, 3H, CH$_3$), 0.89 (s, 9H, C(CH$_3$)$_3$), 1.26-1.40 (m, 8H, CH$_2$), 1.38 (s, 3H, CH$_3$), 1.39 (s, 3H, CH$_3$), 1.66 (tt, J=7.2, 7.2 Hz, 2H, CH$_2$CH$_2$CO), 2.45 (t, J=7.2 Hz, 2H, CH$_2$CH$_2$CO), 3.34 (ddd, J=10.4, 9.6, 4.8 Hz, 1H, H-5), 3.71 (dd, J=9.6, 3.2 Hz, 1H, H-3), 3.74 (dd, J=10.4, 3.6 Hz, 1H, H-1'a), 3.77 (dd, J=10.4, 3.6 Hz, 1H, H-1'b), 3.82 (dd, J=11.6, 3.6 Hz, 1H, H-4'a), 3.89 (dd, J=10.4, 10.4 Hz, 1H, H-6a), 3.94 (dd, J=11.6, 3.6 Hz, 1H, H-4'b), 3.97 (ddd, J=10.0, 3.6, 3.6 Hz, 1H, H-2'), 3.99 (dd, J=9.6, 9.6 Hz, 1H, H-4), 4.02 (ddd, J=10.0, 3.6, 3.6 Hz, 1H, H-3'), 4.31 (dd, J=10.4, 4.8 Hz, 1H, H-6b), 4.63 (d, J=12.4 Hz, 1H, OCHHPh), 4.70 (d, J=1.2 Hz, 1H, H-1), 4.73 (d, J=12.4 Hz, 1H, OCHHPh), 5.61 (s, 1H, OCHPh), 5.70 (dd, J=3.2, 1.2 Hz, 1H, H-2), 7.24-7.43 (m, 8H, Ar), 7.49-7.51 (m, 2H, Ar); $^{13}$C NMR (100 MHz, CDCl$_3$) δ: −5.43, −5.39, 14.1, 18.3, 22.6, 25.0, 25.9 (3C), 26.9, 27.0, 29.0, 31.7, 34.1, 63.3, 67.3, 68.3, 68.5, 68.9, 71.6, 75.6, 77.5, 78.0, 100.1, 101.5, 109.2, 126.1 (2C), 127.70 (2C), 127.74 (2C), 128.2 (2C), 128.3, 128.9, 137.4, 137.7, 173.0

(4) In the same manner as Preparation Example 1 (4) was treated 198 mg of a compound obtained in the above-described (3) to obtain 57 mg of a compound (4-O-tert-butyldimethylsilyl-2,3-O-isopropylidene-L-threitol-1-yl 2-O-octanoyl-β-D-mannopyranoside). Yield was 38%.

Physical and spectroscopic constants of the obtained compound were as follows.

$^1$H NMR (400 MHz, CDCl$_3$) δ: 0.065 (s, 3H, SiCH$_3$), 0.068 (s, 3H, SiCH$_3$), 0.88 (t, J=6.8 Hz, 3H, CH$_3$), 0.89 (s, 9H, C(CH$_3$)$_3$), 1.24-1.40 (m, 8H, CH$_2$), 1.38 (s, 3H, CH$_3$), 1.39 (s, 3H, CH$_3$), 1.63 (tt, J=7.6, 7.6 Hz, 2H, CH$_2$CH$_2$CO), 2.40 (t, J=7.6 Hz, 2H, CH$_2$CH$_2$CO), 3.35 (ddd, J=8.0, 4.0, 4.0 Hz, 1H, H-5), 3.71 (dd, J=10.0, 5.2 Hz, 1H, H-1'a), 3.74 (dd, J=9.6, 3.2 Hz, 1H, H-3), 3.75 (dd, J=10.0, 4.4 Hz, 1H, H-1'b), 3.82 (dd, J=11.6, 3.6 Hz, 1H, H-4'a), 3.89 (dd, J=10.4, 10.4 Hz, 1H, H-6a), 3.94 (dd, J=11.6, 3.6 Hz, 1H, H-4'b), 3.97 (ddd, J=10.0, 3.6, 3.6 Hz, 1H, H-2'), 3.99 (dd, J=9.6, 9.6 Hz, 1H, H-4), 4.02 (ddd, J=10.0, 3.6, 3.6 Hz, 1H, H-3'), 4.31 (dd, J=10.4, 4.8 Hz, 1H, H-6b), 4.63 (d, J=12.4 Hz, 1H, OCHHPh), 4.70 (d, J=1.2 Hz, 1H, H-1), 4.73 (d, J=12.4 Hz, 1H, OCHHPh), 5.61 (s, 1H, OCHPh), 5.70 (dd, J=3.2, 1.2 Hz, 1H, H-2), 7.24-7.43 (m, 8H, Ar), 7.49-7.51 (m, 2H, Ar); $^{13}$C NMR (100 MHz, CDCl$_3$) δ: −5.43, −5.39, 14.1, 18.3, 22.6, 25.0, 25.9 (3C), 26.9, 27.0, 29.0, 31.7, 34.1, 63.3, 67.3, 68.3, 68.5, 68.9, 71.6, 75.6, 77.5, 78.0, 100.1, 101.5, 109.2, 126.1 (2C), 127.70 (2C), 127.74 (2C), 128.2 (2C), 128.3, 128.9, 137.4, 137.7, 173.0

(5) In the same manner as Preparation Example 1 (5) was treated 44 mg of a compound obtained in the above-described (4) to obtain 64 mg of a compound (4-O-tert-butyldimethylsilyl-2,3-O-isopropylidene-L-threitol-1-yl 3,4,6-tri-O-hexanoyl-2-O-octanoyl-β-D-mannopyranoside). Yield was 85%.

Physical and spectroscopic constants of the obtained compound were as follows.

$^1$H NMR (400 MHz, CDCl$_3$) δ: 0.049 (s, 3H, SiCH$_3$), 0.056 (s, 3H, SiCH$_3$), 0.85-0.92 (m, 12H, CH$_3$), 0.88 (s, 9H, C(CH$_3$)$_3$), 1.22-1.41 (m, 20H, CH$_2$), 1.38 (s, 3H, CH$_3$), 1.39 (s, 3H, CH$_3$), 1.50-1.66 (m, 8H, CH$_2$CH$_2$CO), 2.17-2.43 (m, 8H CH$_2$CH$_2$CO), 3.66 (ddd, J=10.0, 5.6, 2.4 Hz, 1H, H-5), 3.71 (dd, J=10.8, 4.8 Hz, 1H, H-1'a), 3.74 (dd, J=10.8, 4.0 Hz, 1H, H-1'b), 3.81 (dd, J=11.2, 3.2 Hz, 1H, H-4'a), 3.95 (dd, J=11.2, 3.6 Hz, 1H, H-4'b), 3.96 (ddd, J=8.0, 4.8, 4.0 Hz, 1H, H-2'), 4.02 (ddd, J=8.0, 3.6, 3.2 Hz, 1H, H-3'), 4.16 (dd, J=12.4, 2.4 Hz, 1H, H-6a), 4.24 (dd, J=12.4, 5.6 Hz, 1H, H-6b), 4.78 (d, J=1.2 Hz, 1H, H-1), 5.05 (dd, J=10.0, 3.2 Hz, 1H, H-3), 5.27 (dd, J=10.0, 10.0 Hz, 1H, H-4), 5.53 (dd, J=3.2, 1.2 Hz, 1H, H-2); $^{13}$C NMR (100 MHz, CDCl$_3$) δ: −5.44, −5.39, 13.8, 13.9, 14.0, 18.3, 22.2, 22.6, 24.3, 24.5, 25.0, 25.9 (3C), 26.8, 27.0, 28.97, 29.03, 31.2, 31.3, 31.7, 33.9, 34.0, 34.1, 62.5 63.2, 65.8, 68.7, 71.0, 72.6, 77.1, 77.2, 99.2, 109.2, 172.3, 172.6, 172.8, 173.4

(6) Treatment was performed in the same manner as Preparation Example 3 (6) except that 90% trifluoroacetic acid solution obtained in Preparation Example 1 (6) was substituted with 80% acetic acid solution using 57 mg of a compound obtained in the above-described (5) to obtain 25 mg of L-threitol-1-yl 3,4,6-tri-O-hexanoyl-2-O-octanoyl-β-D-mannopyranoside. Yield was 53%.

Physical and spectroscopic constants of the obtained compound were as follows.

$^1$H NMR (700 MHz, CDCl$_3$) δ: 0.87-0.95 (m, 12H, CH$_3$), 1.23-1.42 (m, 20H, CH$_2$), 1.51-1.59 (m, 4H, CH$_2$), 1.62-1.70 (m, 4H, CH$_2$), 2.16-2.48 (m, 8H, COCH$_2$), 3.57 (dd, J=12.6, 8.6 Hz, 1H, H-4'a), 3.619 (ddd, J=8.2, 4.6, 3.0 Hz, 1H, H-3'), 3.623 (dd, J=12.6, 4.6 Hz, 1H, H-4'b), 3.72 (dd, J=10.0, 5.8 Hz, 1H, H-1'a), 3.76 (ddd, J=6.4, 5.8, 3.0 Hz, 1H, H-2'), 3.83 (ddd, J=10.2, 4.4, 2.2 Hz, 1H, H-5), 3.86 (dd, J=10.0, 6.4 Hz, 1H, H-1'b), 4.15 (dd, J=12.3, 4.4 Hz, 1H, H-6a), 4.27 (dd, J=12.3, 4.4 Hz, 1H, H-6b), 4.89 (d, J=0.8 Hz, 1H, H-1), 5.16 (dd, J=10.2, 3.2 Hz, 1H, H-3), 5.29 (dd, J=10.2, 10.2 Hz, 1H, H-4), 5.47 (dd, J=3.2, 0.8 Hz, 1H, H-2); $^{13}$C NMR (175 MHz, CDCl$_3$) δ: 14.2 (2C), 14.3, 14.5, 23.36, 23.38, 23.41, 23.8, 25.5, 25.60, 25.62, 26.3, 30.2, 30.3, 32.4 (2C), 32.5, 33.0, 34.86, 34.92, 35.0, 35.2, 63.1, 64.3, 66.8, 70.4, 71.0, 72.1, 72.6, 72.9, 73.5, 100.0, 173.8, 173.9, 174.6, 175.0

Preparation Example 9

(1) Treatment in the same manner as Preparation Example 1 (1) was performed using 1.15 g of a mannosyl sulfoxide compound of Reference Example 1 and 0.31 g of an alcohol (2,3-O-isopropylidene-D-glycerol) to obtain 0.62 g of a compound (2,3-O-isopropylidene-D-glycerol-1-yl 3-O-benzyl-4,6-O-benzylidene-2-O-p-methoxybenzyl-β-D-mannopyranoside). Yield was 53%.

Physical and spectroscopic constants of the obtained compound were as follows.

$^1$H-NMR (CDCl$_3$) δ: 1.37 (3H, s), 1.40 (3H, s), 3.32 (1H, ddd, J=9.6, 7.3, 4.9), 3.56 (1H, dd, J=9.6, 3.2), 3.59 (1H, dd, J=10.5, 5.9), 3.80 (3H, s), 3.89 (1H, dd, J=8.3, 6.1), 3.93 (1H, dd, J=10.3, 7.3), 3.93 (1H, dd, J=3.2, 0.8), 3.96 (1H, dd, J=10.5, 3.7), 4.04 (1H, dd, J=8.3, 6.4), 4.19 (1H, dd, J=9.6, 9.6), 4.29 (1H, dddd, J=6.4, 6.1, 5.9, 3.7), 4.29 (1H, dd, J=10.3, 4.9), 4.51 (1H, d, J=0.8), 4.57 (1H, d, J=12.4), 4.68 (1H, d, J=12.4), 4.78 (1H, d, J=11.9), 4.89 (1H, d, J=11.9), 5.61 (1H, s), 6.85 (2H, d, J=8.6), 7.25-7.31 (5H, m), 7.34-7.39 (3H, m), 7.38 (2H, d, J=8.6), 7.48-7.51 (2H, m). $^{13}$C-NMR (CDCl$_3$) δ: 25.3, 26.8, 55.3, 66.4, 67.6, 68.5, 69.5, 72.4, 74.3 (2C), 75.1, 77.8, 78.6, 101.4, 102.6, 109.2, 113.5 (2C), 126.0 (2C), 127.50, 127.55 (2C), 128.2 (2C), 128.3 (2C), 128.8, 130.3, 130.4 (2C), 137.5, 138.3, 159.2

(2) In the same manner as Preparation Example 1 (2) was treated 0.61 g of a compound obtained in the above-described (1) to obtain 0.45 g of a compound (2,3-O-isopropylidene-D-glycerol-1-yl 3-O-benzyl-4,6-O-benzylidene-β-D-mannopyranoside). Yield was 93%.

Physical and spectroscopic constants of the obtained compound were as follows.

$^1$H-NMR (CDCl$_3$) δ: 1.35 (3H, s), 1.40 (3H, s), 3.35 (1H, ddd, J=9.6, 9.6, 4.8), 3.64 (1H, dd, J=9.6, 3.2), 3.64 (1H, dd, J=10.6, 5.8), 3.87 (1H, dd, J=8.4, 5.6), 3.89 (1H, dd, J=10.4, 9.6), 3.93 (1H, dd, J=10.6, 4.2), 4.05 (1H, dd, J=8.4, 6.4), 4.13 (1H, dd, J=3.2, 0.8), 4.14 (1H, dd, J=9.6, 9.6), 4.30 (1H, dddd, J=6.4, 5.8, 5.6, 4.2), 4.32 (1H, dd, J=10.4, 4.8), 4.57 (1H, d, J=0.8), 4.76 (1H, d, J=12.4), 4.85 (1H, d, J=12.4), 5.60 (1H, s), 7.29-7.41 (5H, m), 7.29-7.41 (3H, m), 7.48-7.51 (2H, m). $^{13}$C-NMR (CDCl$_3$) δ: 25.3, 26.7, 66.4, 66.6, 67.0, 68.5, 69.7, 69.8, 72.45, 72.54, 74.3, 74.7, 76.6, 76.7, 78.3, 100.4, 100.8, 101.5, 109.4, 126.0, 127.8, 127.9, 128.2, 128.4, 128.4, 137.4, 137.8.)

(3) In the same manner as Preparation Example 1 (3) was treated 0.44 g of a compound obtained in the above-described (1) to obtain 0.47 g of a compound (2,3-O-isopropylidene-D-glycerol-1-yl 3-O-benzyl-4,6-O-benzylidene-2-O-octanoyl-β-D-mannopyranoside). Yield was 83%.

Physical and spectroscopic constants of the obtained compound were as follows.

$^1$H-NMR (CDCl$_3$) δ: 0.87 (3H, t, J=7.2), 1.20-1.34 (8H, m), 1.35 (3H, s), 1.40 (3H, s), 1.60-1.70 (2H, m), 2.45 (2H, t, J=7.6), 3.38 (1H, ddd, J=9.8, 4.8, 4.0), 3.63 (1H, dd, J=9.8, 5.8), 3.71 (1H, dd, J=10.0, 3.6), 3.83 (1H, dd, J=8.4, 6.4), 3.89 (1H, dd, J=10.4, 4.0), 3.90 (1H, dd, J=10.0, 5.2), 3.99 (1H, dd, J=9.8, 9.8), 4.00 (1H, dd, J=8.4, 6.4), 4.22 (1H, dddd, J=6.4, 6.4, 5.2, 3.6), 4.32 (1H, dd, J=10.4, 4.8), 4.63 (1H, d, J=12.0), 4.65 (1H, d, J=0.8), 4.73 (1H, d, J=12.0), 5.61 (1H, s), 5.67 (1H, dd, J=3.2, 0.8), 7.27-7.42 (5H, m), 7.27-7.42 (3H, m), 7.48-7.52 (2H, m). $^{13}$C-NMR (CDCl$_3$) δ: 14.0, 22.6, 25.0, 25.5, 26.6, 28.9, 31.7, 34.1, 66.3, 67.3, 68.3, 68.4, 69.5, 71.6, 74.3, 75.5, 77.9, 99.6, 100.0, 101.5, 109.3, 126.0 (2C), 127.7 (2C), 128.2 (2C), 128.3 (2C), 128.9, 137.3, 137.7, 173.2.

(4) In the same manner as Preparation Example 1 (4) was treated 0.45 g of a compound obtained in the above-described (3) to obtain 0.13 g of a compound (2,3-O-isopropylidene-D-glycerol-1-yl 2-O-octanoyl-β-D-mannopyranoside). Yield was 40%.

Physical and spectroscopic constants of the obtained compound were as follows.

$^1$H-NMR (CDCl$_3$) δ: 0.88 (3H, t, J=6.8), 1.25-1.32 (8H, m), 1.35 (3H, s), 1.40 (3H, s), 1.59-1.66 (2H, m), 2.41 (2H, t, J=7.6), 3.32 (1H, ddd, J=10.8, 6.4, 4.4), 3.63 (1H, dd, J=10.8, 5.2), 3.78 (1H, dd, J=8.6, 6.4), 3.85 (1H, dd, J=12.0, 5.6), 3.86 (1H, dd, J=10.8, 4.4), 3.88 (1H, dd, J=10.8, 10.8), 3.89 (1H, dd, J=10.8, 6.4), 3.91 (1H, dd, J=12.0, 3.2), 4.01 (1H, dd, J=8.6, 6.4), 4.23 (1H, dddd, J=6.4, 6.4, 5.6, 3.2), 4.67 (1H, d, J=0.8), 5.39 (1H, dd, J=5.2, 0.8). $^{13}$C-NMR (CDCl$_3$) δ: 14.0, 22.6, 24.9, 25.4, 26.6, 28.9, 29.0, 31.7, 34.1, 62.3, 66.3, 68.1, 69.8, 70.8, 72.7, 74.5, 75.8, 99.3, 109.5, 174.1.

(5) In the same manner as Preparation Example 1 (5) was treated 0.113 g of a compound obtained in the above-described (4) to obtain 0.158 g of a compound (2,3-O-isopropylidene-D-glycerol-1-yl 3,4,6-tri-O-hexanoyl-2-O-octanoyl-β-D-mannopyranoside). Yield was 82%.

Physical and spectroscopic constants of the obtained compound were as follows.

$^1$H-NMR (CDCl$_3$) δ: 0.86-0.92 (12H, m), 1.20-1.35 (20H, m), 1.35 (3H, s), 1.39 (3H, s) 1.50-1.68 (8H, m), 2.17-2.44 (8H, m), 3.63 (1H, dd, J=10.6, 6.2), 3.66 (1H, ddd, J=10.0, 5.4, 2.4), 3.81 (1H, dd, J=8.4, 6.4), 3.89 (1H, dd, J=10.6, 3.8), 3.99 (1H, dd, J=8.4, 6.0), 4.17 (1H, dd, J=12.0, 2.4), 4.22 (1H, dddd, J=6.4, 6.2, 6.0, 3.8), 4.24 (1H, dd, J=12.0, 5.4), 4.72 (1H, d, J=0.8), 5.05 (1H, dd, J=10.0, 3.2), 5.26 (1H, dd, J=10.0, 10.0), 5.50 (1H, dd, J=3.2, 0.8). $^{13}$C-NMR (CDCl$_3$) δ: 13.8 (2C), 13.9, 14.0, 22.2 (2C), 22.3, 22.6, 24.3, 24.5 (2C), 25.0, 25.5, 26.6, 28.9, 29.0, 31.1, 31.3, 31.7, 33.9, 34.0 (2C), 34.1, 62.4, 65.8, 66.3, 68.3, 69.5, 70.9, 72.6, 74.2, 99.1, 109.3, 172.2, 172.6, 172.9, 173.4.

(6) In the same manner as Preparation Example 1 (6) was treated 0.15 g of a compound obtained in the above-described (5) to obtain 0.10 g of D-glycerol-1-yl 3,4,6-tri-O-hexanoyl-2-O-octanoyl-β-D-mannopyranoside. Yield was 53%.

Physical and spectroscopic constants of the obtained compound were as follows.

$^1$H-NMR (CD$_3$OD) δ: 0.900 (6H, t, J=7.4), 0.91 (3H, t, J=7.0), 0.92 (3H, t, J=7.0), 1.23-1.46 (20H, m), 1.52-1.61 (4H, m), 1.62-1.71 (4H, m), 2.19 (1H, dt, J=15.6, 7.6), 2.21 (1H, dt, J=15.6, 7.7), 2.27 (1H, dt, J=15.8, 7.4), 2.31 (1H, dt, J=15.8, 7.4), 2.34 (1H, dt, J=15.8, 7.4), 2.37 (1H, dt, J=15.8, 7.6), 2.37 (1H, dt, J=15.8, 7.6), 2.39 (1H, dt, J=15.4, 7.2), 2.45 (1H, dt, J=15.4, 7.2), 3.50 (1H, dd, J=11.4, 5.8), 3.55 (1H, dd, J=11.4, 4.9), 3.65 (1H, dd, J=10.2, 5.3), 3.74 (1H, dddd, J=5.8, 5.4, 5.3, 4.9), 3.81 (1H, dd, J=10.2, 5.4), 3.82 (1H, ddd, J=10.0, 4.4, 2.2), 4.15 (1H, dd, J=12.4, 2.2), 4.27 (1H, dd, J=12.4, 4.4), 4.89 (1H, d, J=0.8), 5.16 (1H, dd, J=10.0, 3.3), 5.28 (1H, dd, J=10.0, 10.0), 5.47 (1H, dd, J=3.3, 0.8). $^{13}$C-NMR (CD$_3$OD) δ: 14.2 (2C), 14.3, 14.5, 23.35, 23.37, 23.4, 23.8, 25.5, 25.60, 25.62, 26.3, 30.16, 30.25, 30.7, 32.3, 32.4, 32.9, 34.85, 34.93, 34.86, 34.93, 35.0, 35.2, 63.1, 64.3, 66.9, 70.4, 71.8, 72.0, 72.6, 73.4, 100.1, 173.8, 173.9, 174.6, 175.0.

Preparation Example 10

(1) Treatment in the same manner as Preparation Example 1 (1) was performed using 1.76 g of a mannosyl sulfoxide compound of Reference Example 1 and 0.48 g of (R)-(–)-2,2-dimethyl-1,3-dioxolane-4-methanol to obtain 0.69 g of a compound (2,3-O-isopropylidene-L-glycerolyl 3-O-benzyl-4,6-O-benzylidene-2-O-p-methoxybenzyl-β-D-mannopyranoside) (1,2-O-isopropylidene-D-glycerol-3-yl 3-O-benzyl-4,6-O-benzylidene-2-O-p-methoxybenzyl-β-D-mannopyranoside). Yield was 40%.

Physical and spectroscopic constants of the obtained compound were as follows.

$^1$H-NMR (CDCl$_3$) δ: 1.38 (3H, s), 1.42 (3H, s), 3.32 (1H, ddd, J=10.2, 9.6, 4.8), 3.57 (1H, dd, J=9.6, 3.2), 3.59 (1H, dd, J=10.1, 6.3), 3.75 (1H, dd, J=8.4, 6.3), 3.80 (3H, s), 3.88 (1H, dd, J=10.1, 5.7), 3.93 (1H, dd, J=10.2, 10.2), 3.96 (1H, dd, J=3.2, 0.8), 4.09 (1H, dd, J=8.4, 6.3), 4.19 (1H, dd, J=9.6, 9.6), 4.29 (1H, dddd, J=6.3, 6.3, 6.3, 5.7), 4.30 (1H, dd, J=10.2, 4.8), 4.52 (1H, d, J=0.8), 4.58 (1H, d, J=12.5), 4.68 (1H, d, J=12.5), 4.81 (1H, d, J=11.9), 4.88 (1H, d, J=11.9), 5.61 (1H, s), 6.85 (2H, d, J=8.6), 7.26-7.31 (5H, m), 7.34-7.39 (3H, m), 7.38 (2H, d, J=8.6), 7.48-7.51 (2H, m). $^{13}$C-NMR (CDCl$_3$) δ: 25.4, 26.8, 55.3, 67.0, 67.7, 68.5, 70.9, 72.4, 74.3, 74.7, 75.1, 77.8, 78.6, 101.4, 102.2, 109.6, 113.5 (2C), 126.0 (2C), 127.52 (2C), 127.55, 128.2 (2C), 128.3 (2C), 128.8, 130.2 (2C), 130.5, 137.5, 138.3, 159.2.

(2) In the same manner as Preparation Example 1 (2) was treated 0.12 g of a compound obtained in the above-described (1) to obtain a compound (2,3-O-isopropylidene-L-glycerolyl 3-O-benzyl-4,6-O-benzylidene-β-D-mannopyranoside) (1,2-O-isopropylidene-D-glycerol-3-yl 3-O-benzyl-4,6-O-benzylidene-β-D-mannopyranoside).

(3) A compound obtained in the above-described (2) was treated in the same manner as Preparation Example 1 (3) to obtain 0.11 g of a compound (2,3-O-isopropylidene-L-glycerolyl 3-O-benzyl-4,6-O-benzylidene-2-O-octanoyl-β-D-mannopyranoside) (1,2-O-isopropylidene-D-glycerol-3-yl 3-O-benzyl-4,6-O-benzylidene-2-O-octanoyl-β-D-mannopyranoside). Yield was 91% (Total yield of the previous two steps).

Physical and spectroscopic constants of the obtained compound were as follows.

$^1$H-NMR (CDCl$_3$) δ: 0.87 (3H, t, J=7.2), 1.25-1.34 (8H, m), 1.35 (3H, s), 1.40 (3H, s), 1.60-1.70 (2H, m), 2.45 (2H, t, J=7.4), 3.38 (1H, ddd, J=9.6, 6.0, 4.8), 3.67 (1H, dd, J=10.4, 6.0), 3.71 (1H, dd, J=8.4, 6.0), 3.72 (1H, dd, J=9.6, 3.6), 3.78 (1H, dd, J=10.8, 6.0), 3.90 (1H, dd, J=10.8, 6.0), 3.99 (1H, dd, J=9.6, 9.6), 4.03 (1H, dd, J=8.4, 6.0), 4.25 (1H, dddd, J=6.0, 6.0, 6.0, 6.0), 4.33 (1H, dd, J=10.4, 4.8), 4.63 (1H, d, J=12.4), 4.70 (1H, d, J=1.2), 4.74 (1H, d, J=12.4), 5.61 (1H, s), 5.67 (1H, dd, J=3.6, 1.2), 7.28-7.42 (5H, m), 7.28-7.42 (3H, m), 7.49-7.51 (2H, m). $^{13}$C-NMR (CDCl$_3$) δ: 14.1, 22.6, 25.0, 26.8, 28.93, 28.98, 31.7, 34.1, 66.8, 67.3, 68.3, 68.5, 70.5, 71.6, 74.5, 75.6, 77.9, 99.6, 101.5, 109.6, 126.0 (2C), 127.7 (3C), 128.2 (2C), 128.3 (2C), 129.0, 137.3, 137.7, 173.2.

(4) In the same manner as Preparation Example 1 (4) was treated 0.12 g of a compound obtained in the above-described (3) to obtain 0.056 g of a compound (2,3-O-isopropylidene-L-glycerolyl 2-O-octanoyl-β-D-mannopyranoside) (1,2-O-isopropylidene-D-glycerol-3-yl 2-O-octanoyl-β-D-mannopyranoside). Yield was 74%.

Physical and spectroscopic constants of the obtained compound were as follows.

$^1$H-NMR (CDCl$_3$) δ: 0.88 (3H, t, J=7.2), 1.25-1.33 (8H, m), 1.35 (3H, s), 1.40 (3H, s), 1.59-1.67 (2H, m), 2.41 (2H, t, J=7.2), 3.34 (1H, ddd, J=9.0, 4.8, 3.2), 3.64 (1H, dd, J=10.2, 6.0), 3.74 (1H, dd, J=9.0, 9.0), 3.73 (1H, dd, J=8.0, 6.0), 3.74 (1H, dd, J=9.0, 3.0), 3.81 (1H, dd, J=10.2, 6.0), 3.86 (1H, dd, J=12.0, 4.8), 3.94 (1H, dd, J=12.0, 3.2), 4.02 (1H, dd, J=8.0, 6.0), 4.25 (1H, dddd, J=6.0, 6.0, 6.0, 6.0), 4.71 (1H, d, J=0.8), 5.39 (1H, dd, J=3.0, 0.8). $^{13}$C-NMR (CDCl$_3$) δ: 14.0, 22.6, 24.9, 25.4, 26.7, 28.9, 29.0, 31.7, 34.2, 62.4, 66.6, 68.4, 70.2, 70.9, 72.9, 74.5, 75.7, 98.9, 109.6, 174.2.

(5) In the same manner as Preparation Example 1 (5) was treated 0.046 g of a compound obtained in the above-described (4) to obtain 0.077 g of a compound (2,3-O-isopropylidene-L-glycerolyl 3,4,6-tri-O-hexanoyl-2-O-octanoyl-β-D-mannopyranoside) (1,2-O-isopropylidene-D-glycerol-3-yl 3,4,6-tri-O-hexanoyl-2-O-octanoyl-β-D-mannopyranoside).

Physical and spectroscopic constants of the obtained compound were as follows.

$^1$H-NMR (CDCl$_3$) δ: 0.86-0.92 (12H, m), 1.24-1.34 (20H, m), 1.35 (3H, s), 1.40 (3H, s) 1.50-1.68 (8H, m), 2.19-2.44 (8H, m), 3.66 (1H, dd, J=10.4, 6.0), 3.67 (1H, ddd, J=10.0, 2.4, 2.4), 3.69 (1H, dd, J=8.6, 6.2), 3.78 (1H, dd, J=10.4, 5.6), 4.02 (1H, dd, J=8.6, 6.2), 4.17 (1H, dd, J=12.2, 2.4), 4.23 (1H, dd, J=12.2, 2.4), 4.24 (1H, dddd, J=6.2, 6.2, 6.0, 5.6), 4.77 (1H, d, J=1.0), 5.06 (1H, dd, J=10.0, 3.2), 5.26 (1H, dd, J=10.0, 10.0), 5.50 (1H, dd, J=3.2, 1.0). $^{13}$C-NMR (CDCl$_3$) δ: 13.8, 13.9, 14.0, 22.2 (2C), 22.3, 22.6, 24.3, 24.4, 24.5, 25.0, 25.3, 26.8, 28.9, 29.0, 31.1, 31.2, 31.7, 33.9, 34.0 (2C), 34.1, 62.4, 65.8, 66.7, 68.4, 70.4, 70.9, 72.6, 74.6, 98.5, 109.6, 172.2, 172.6, 173.0, 173.4)

(6) In the same manner as Preparation Example 1 (6) was treated 0.03 g of a compound obtained in the above-described (5) to obtain 0.020 g of a compound (L-glycerolyl 3,4,6-tri-O-hexanoyl-2-O-octanoyl-β-D-mannopyranoside) (D-glycerol-3-yl 3,4,6-tri-O-hexanoyl-2-O-octanoyl-β-D-mannopyranoside). Yield was 72%.

Physical and spectroscopic constants of the obtained compound were as follows.

$^1$H-NMR (CD$_3$OD) δ: 0.900 (3H, t, J=7.4), 0.902 (3H, t, J=7.4), 0.91 (3H, t, J=7.1), 0.93 (3H, t, J=7.2), 1.24-1.44 (20H, m), 1.52-1.60 (4H, m), 1.63-1.76 (4H, m), 2.19 (1H, dt, J=14.8, 7.6), 2.21 (1H, dt, J=14.8, 7.4), 2.27 (1H, dt, J=14.9, 7.4), 2.32 (1H, dt, J=14.9, 7.4), 2.34 (1H, dt, J=15.8, 7.4), 2.37 (1H, dt, J=15.8, 7.4), 2.40 (1H, dt, J=15.4, 7.2), 2.46 (1H, dt, J=15.4, 7.2), 3.48 (1H, dd, J=11.4, 5.8), 3.53 (1H, dd, J=11.4, 5.4), 3.57 (1H, dd, J=10.4, 6.6), 3.75 (1H, dddd, J=6.6, 5.8, 5.4, 4.4), 3.83 (1H, ddd, J=10.0, 4.4, 2.2), 3.88 (1H, dd, J=10.4, 4.4), 4.15 (1H, dd, J=12.4, 2.2), 4.27 (1H, dd, J=12.4, 4.4), 4.90 (1H, d, J=1.0), 5.16 (1H, dd, J=10.0, 3.5), 5.29 (1H, dd, J=10.0, 10.0), 5.48 (1H, dd, J=3.5, 1.0). $^{13}$C-NMR (CD$_3$OD) δ: 14.2 (2C), 14.3, 14.5, 23.36, 23.38, 23.4, 23.8, 25.5, 25.60, 25.62, 26.4, 30.2, 30.3, 32.3, 32.35, 32.44, 33.0, 34.86, 34.92, 32.96, 35.2, 63.1, 64.3, 66.9, 70.4, 72.2, 72.6, 72.7, 73.5, 100.3, 173.8, 173.9, 174.7, 175.0.

Preparation Example 11

(1) Treatment in the same manner as Preparation Example 1 (1) was performed using 500 mg of a mannosyl sulfoxide compound of Reference Example 1 and 165 mg of 1-tert-butyldimethylsilyl-ethanediol to obtain 397 mg of a compound (2-O-tert-butyldimethylsilyl ethylene glycol-3-O-benzyl-4,6-O-benzylidene-2-O-p-methoxybenzyl-β-D-mannopyranoside). Yield was 73%.

(2) In the same manner as Preparation Example 1 (2) was treated 368 mg of a compound obtained in the above-described (1) to obtain 216 mg of a compound (2-O-tert-butyldimethylsilylethylene glycolyl 3-O-benzyl-4,6-O-benzylidene-β-D-mannopyranoside). Yield was 72%.

Physical and spectroscopic constants of the obtained compound were as follows.

$^1$H NMR (400 MHz, CDCl$_3$) δ: 0.05 (s, 3H, SiCH$_3$), 0.06 (s, 3H, SiCH$_3$), 0.88 (s, 9H, C(CH$_3$)$_3$), 3.34 (ddd, J=9.6, 9.6, 4.8 Hz, 1H, OCH), 3.63 (dd, J=9.6, 3.2 Hz, 1H, OCH), 3.68-3.94 (m, 5H, 5×OCH), 4.14 (dd, J=3.2, 0.8 Hz, 1H, OCH), 4.15 (dd, J=9.6, 9.6 Hz, 1H, OCH), 4.33 (dd, J=10.4, 4.8 Hz, 1H, OCH), 4.63 (d, J=0.8 Hz, 1H, OCH), 4.78 (d, J=12.0 Hz, 1H, OCHHPh), 4.87 (d, J=12.0 Hz, 1H, OCHHPh), 5.61 (s, 1H, OCHPh), 7.27-7.41 (m, 8H, Ar), 7.50 (dd, J=8.0, 2.0 Hz, 2H, Ar); $^{13}$C NMR (100 MHz, CDCl$_3$) δ: −5.4, −5.3, 18.2, 25.8 (3C), 62.6, 66.9, 68.6, 70.0, 70.8, 72.5, 76.7, 78.4, 100.7, 101.5, 126.0 (2C), 127.8, 127.9 (2C), 128.2 (2C), 128.4 (2C), 128.9, 137.4, 137.9

(3) In the same manner as Preparation Example 1 (3) was treated 216 mg of a compound obtained in the above-described (2) to obtain 207 mg of a compound (2-O-tert-butyldimethylsilylethylene glycol 3-O-benzyl-4,6-O-benzylidene-2-O-octanoyl-β-D-mannopyranoside). Yield was 77%.

Physical and spectroscopic constants of the obtained compound were as follows.

$^1$H NMR (400 MHz, CDCl$_3$) δ: 0.05 (s, 3H, SiCH$_3$), 0.06 (s, 3H, SiCH$_3$), 0.87 (t, J=7.2 Hz, 3H, CH$_3$), 0.88 (s, 9H, C(CH$_3$)$_3$), 1.25-1.33 (m, 8H, 4×CH$_2$), 1.66 (tt, J=7.6, 7.6 Hz, 2H, CH$_2$), 2.46 (t, J=7.6 Hz, 2H, COCH$_2$), 3.38 (ddd, J=10.0, 10.0, 4.8 Hz, 1H, OCH), 3.67 (dd, J=10.0, 3.6 Hz, 1H, OCH), 3.69 (ddd, J=10.0, 4.0, 4.0 Hz, 1H, OCH), 3.73 (ddd, J=8.0, 4.0, 4.0 Hz, 1H, OCH), 3.78 (ddd, J=8.0, 4.0, 4.0 Hz, 1H, OCH), 3.86 (ddd, J=10.0, 4.0, 4.0 Hz, 1H, OCH), 3.90 (dd, J=10.0, 10.0 Hz, 1H, OCH), 3.99 (dd, J=10.0, 10.0 Hz, 1H, OCH), 4.33 (dd, J=10.0, 4.8 Hz, 1H, OCH), 4.62 (d, J=12.4 Hz, 1H, OCHHPh), 4.73 (d, J=1.2 Hz, 1H, OCH), 4.74 (d, J=12.4 Hz, 1H, OCHHPh), 5.61 (s, 1H, OCHPh), 5.69 (dd, J=3.6, 1.2 Hz, 1H, OCH), 7.24-7.40 (m, 8H, Ar), 7.49-7.52 (m, 2H, Ar); $^{13}$C NMR (100 MHz, CDCl$_3$) δ: −5.4, −5.3, 14.1, 18.3, 22.6, 25.0, 25.9 (3C), 28.95, 28.99, 31.7, 34.1, 62.7, 67.3, 68.47, 68.53, 71.2, 71.6, 75.8, 78.0, 100.1, 101.5, 126.1 (2C), 127.7, 127.8 (2C), 128.2 (2C), 128.3 (2C), 128.9, 137.4, 137.7, 173.1

(4) In the same manner as Preparation Example 1 (4) was treated 216 mg of a compound obtained in the above-described (3) to obtain 116 mg of a compound (2-O-tert-butyldimethylsilylethylene glycolyl 2-O-octanoyl-β-D-mannopyranoside). Yield was 78%.

Physical and spectroscopic constants of the obtained compound were as follows.

$^{13}$C NMR (100 MHz, CD$_3$OD) δ: −5.2, −5.1, 14.4, 19.2, 23.7, 26.0, 26.4 (3C), 30.1, 30.2, 32.9, 35.1, 62.9, 63.9, 68.9, 71.9, 72.9, 73.7, 78.6, 100.7, 175.0

(5) In the same manner as Preparation Example 1 (5) was treated 103 mg of a compound obtained in the above-described (4) to obtain 134 mg of a compound (2-O-tert-butyldimethylsilylethylene glycolyl 3,4,6-tri-O-hexanoyl-2-O-octanoyl-β-D-mannopyranoside). Yield was 80%.

Physical and spectroscopic constants of the obtained compound were as follows.

$^1$H NMR (400 MHz, CDCl$_3$) δ: 0.045 (s, 3H, SiCH$_3$), 0.049 (s, 3H, SiCH$_3$), 0.86-0.91 (m, 12H, 4×CH$_3$), 0.89 (s, 9H, C(CH$_3$)$_3$), 1.22-1.36 (m, 20H, 10×CH$_2$), 1.50-1.67 (m, 8H, 4×CH$_2$), 2.15-2.45 (m, 8H, 4×CH$_2$), 3.65 (ddd, J=10.0, 5.6, 2.4 Hz, 1H, OCH), 3.63-3.68 (m, 1H, OCH), 3.70-3.81 (m, 2H, 2×OCH), 3.87 (ddd, J=10.0, 4.0, 4.0 Hz, 1H, OCH), 4.17 (dd, J=12.0, 2.4 Hz, 1H, OCH), 4.25 (dd, J=12.0, 5.6 Hz, 1H, OCH), 4.77 (s, 1H, OCH), 5.05 (dd, J=10.0, 3.6 Hz, 1H, OCH), 5.26 (dd, J=10.0, 10.0 Hz, 1H, OCH), 5.50 (d, J=3.6 Hz, 1H, OCH); $^{13}$C NMR (100 MHz, CDCl$_3$) δ: −5.4, −5.3, 13.8 (2C), 13.9, 14.0, 18.3, 22.2 (2C), 22.3, 22.6, 24.2, 24.4, 24.5, 25.0, 25.8 (3C), 28.95, 28.99, 31.2 (2C), 31.3, 31.7, 33.9, 34.0 (2C), 34.1, 62.45, 62.53, 65.8, 68.6, 71.0, 71.1, 72.5, 99.1, 172.3, 172.6, 173.0, 173.5

(6) In the same manner as Preparation Example 1 (6) was treated 114 mg of a compound obtained in the above-described (5) to obtain 97 mg of ethylene glycol 3,4,6-tri-O-hexanoyl-2-O-octanoyl-β-D-mannopyranoside (2-hydroxyethanol-1-yl 3,4,6-tri-O-hexanoyl-2-O-octanoyl-β-D-mannopyranoside). Yield was 72%.

Physical and spectroscopic constants of the obtained compound were as follows.

$^1$H NMR (700 MHz, CDCl$_3$) δ: 0.882 (t, J=7.2 Hz, 3H, CH$_3$), 0.885 (t, J=7.2 Hz, 6H, 2×CH$_3$), 0.90 (t, J=7.2 Hz, 3H, CH$_3$), 1.22-1.38 (m, 20H, 10×CH$_2$), 1.53 (dtt, J=10.8, 7.6, 7.6 Hz, 1H, CH$_2$), 1.55 (dtt, J=10.8, 7.6, 7.6 Hz, 1H, CH$_2$), 1.57 (tt, J=7.6, 7.6 Hz, 2H, CH$_2$), 1.63 (tt, J=7.6, 7.6 Hz, 2H, CH$_2$), 1.66 (tt, J=7.6, 7.6 Hz, 2H, CH$_2$), 2.20 (dt, J=15.6, 7.6 Hz, 1H, COCHH), 2.21 (dt, J=15.6, 7.6 Hz, 1H, COCHH), 2.26 (dt, J=15.6, 7.6 Hz, 1H, COCHH), 2.29 (dt, J=15.6, 7.6

Hz, 1H, COCHH), 2.34 (dt, J=15.6, 7.6 Hz, 1H, COCHH), 2.36 (dt, J=15.6, 7.6 Hz, 1H, COCHH), 2.344 (t, J=7.6 Hz, 2H, COCH$_2$), 3.69 (ddd, J=12.6, 5.8, 2.8 Hz, 1H, OCH), 3.71 (ddd, J=10.0, 6.2, 2.8 Hz, 1H, OCH), 3.72 (ddd, J=12.6, 5.8, 2.8 Hz, 1H, OCH), 3.83 (ddd, J=11.2, 5.8, 2.8 Hz, 1H, OCH), 3.87 (ddd, J=11.2, 5.8, 2.8 Hz, 1H, OCH), 4.19 (dd, J=12.3, 6.2 Hz, 1H, OCH), 4.22 (dd, J=12.3, 2.8 Hz, 1H, OCH), 4.70 (d, J=1.0 Hz, 1H, OCH), 5.08 (dd, J=10.0, 3.2 Hz, 1H, OCH), 5.26 (dd, J=10.0, 10.0 Hz, 1H, OCH), 5.52 (dd, J=3.2, 1.0 Hz, 1H, OCH); $^{13}$C NMR (175 MHz, CDCl$_3$) d: 13.8 (2C), 13.9, 14.0, 22.2 (2C), 22.3, 22.6, 24.3, 24.4, 24.5, 25.0, 28.9, 29.0, 31.1 (2C), 31.2, 31.7, 33.88, 33.91, 34.0, 34.1, 61.9, 62.4, 65.7, 68.6, 70.7, 72.6, 73.3, 99.4, 172.3, 172.6, 173.4, 173.4

Preparation Example 12

(1) Treatment in the same manner as Preparation Example 1 (1) was performed using 1.24 g of a mannosyl sulfoxide compound (2,3-di-O-benzyl-4,6-O-benzylidene-1-thio-u-D-mannopyranoside S-oxide) and 1.00 g of an alcohol (6-O-tert-butyldimethylsilyl-2,3:4,5-di-O-isopropylidene-D-mannitol) to obtain 974 mg of a compound (6-O-tert-butyldimethylsilyl-2,3:4,5-di-O-isopropylidene-D-mannitol-1-yl 2,3-di-O-benzyl-4,6-O-benzylidene-β-D-mannopyranoside). Yield was 71%.

Physical and spectroscopic constants of the obtained compound were as follows.

$^1$H NMR (700 MHz, CDCl$_3$) δ: 0.05 (3H, s), 0.07 (3H, s), 0.88 (9H, s), 1.33 (3H, s), 1.37 (3H, s), 1.46 (3H, s), 1.47 (3H, s), 3.51 (1H, dd, J=10.3, 5.2), 3.57 (1H, dd, J=10.3, 4.0), 3.71 (1H, dd, J=10.3, 6.0), 3.73 (1H, dd, J=10.3, 8.6), 3.82 (1H, dd, J=3.2, 1.5), 3.87 (1H, ddd, J=10.0, 10.0, 5.4), 3.88 (1H, dd, J=10.4, 10.0), 3.97 (1H, dd, J=10.0, 3.2), 4.07 (1H, ddd, J=8.6, 5.7, 4.0), 4.22 (1H, dd, J=7.5, 5.7), 4.25 (1H, dd, J=10.0, 10.0), 4.26 (1H, dd, J=10.4, 5.4), 4.33 (1H, ddd, J=6.3, 6.0, 5.2), 4.39 (1H, dd, J=7.5, 6.3), 4.63 (1H, d, J=12.3), 4.72 (1H, d, J=12.0), 4.80 (1H, d, J=12.0), 4.82 (1H, d, J=1.5), 4.84 (1H, d, J=12.3), 5.64 (1H, s), 7.25-7.39 (13H, m), 7.49 (2H, dd, J=7.8, 2.0); $^{13}$C NMR (175 MHz, CDCl$_3$) δ: −5.5, −5.4, 18.3, 25.4, 25.5, 25.9 (3C), 27.6, 27.8, 62.0, 64.3, 66.9, 68.8, 73.3, 73.6, 75.1, 75.2, 75.5, 76.3, 76.6, 77.0, 79.1, 99.7, 101.5, 108.6, 108.8, 126.1 (2C), 127.35 (2C), 127.44, 127.8, 128.0 (2C), 128.1 (2C), 128.3 (2C), 128.4 (2C), 128.8, 137.6, 138.0, 138.7

(2) In the same manner as Preparation Example 1 (4) was treated 636 mg of a compound obtained in the above-described (1) to obtain 273 mg of a compound (6-O-tert-butyldimethylsilyl-2,3:4,5-di-O-isopropylidene-D-mannitol-1-yl β-D-mannopyranoside). Yield was 69%.

Physical and spectroscopic constants of the obtained compound were as follows.

$^1$H NMR (400 MHz, CD$_3$OD) δ: −0.004 (3H, s), −0.000 (3H, s), 0.82 (9H, s), 1.24 (3H, s), 1.25 (3H, s), 1.34 (3H, s), 1.35 (3H, s), 3.11 (1H, ddd, J=9.6, 6.0, 2.4), 3.34 (1H, dd, J=9.6, 3.2), 3.45 (1H, dd, J=10.4, 6.0), 3.54 (1H, dd, J=10.4, 6.0), 3.61 (1H, dd, J=12.0, 6.0) 3.62 (1H, dd, J=10.8, 4.4), 3.74 (1H, dd, J=10.8, 5.6), 3.76 (1H, d, J=3.2), 3.78 (1H, dd, J=12.0, 2.4), 3.95 (1H, dd, J=10.4, 6.0), 4.23-4.28 (2H, m), 4.31 (1H, ddd, J=6.0, 6.0, 5.6), 4.36 (1H, dd, J=5.6, 5.6), 4.46 (1H, s); $^{13}$C NMR (100 MHz, CD$_3$OD) δ: −5.3, −5.2, 19.2, 25.5, 25.9, 26.4 (3C), 27.7, 27.9, 62.9, 63.9, 68.5, 69.3, 72.3, 75.2, 76.2, 76.4, 77.2, 78.4, 78.7, 101.9, 109.5, 109.7)

(3) In the same manner as Preparation Example 1 (5) was treated 167 mg of a compound obtained in the above-described (2) to obtain 226 mg of a compound (6-O-tert-butyldimethylsilyl-2,3:4,5-di-O-isopropylidene-D-mannitol-1-yl 2,3,4,6-tetra-O-hexanoyl-β-D-mannopyranoside). Yield was 95%.

Physical and spectroscopic constants of the obtained compound were as follows.

$^1$H-NMR (400 MHz, CDCl$_3$) δ: 0.06 (3H, s), 0.07 (3H, s), 0.88 (6H, t, J=7.2), 0.89 (9H, s), 0.90 (3H, t, J=8.0), 0.91 (3H, t, J=8.0), 1.24-1.37 (16H, m), 1.35 (3H, s), 1.37 (3H, s), 1.45 (3H, s), 1.47 (3H, s), 1.50-1.68 (8H, m), 2.19 (1H, dt, J=7.6, 4.4), 2.20 (1H, dt, J=7.6, 4.4), 2.26 (2H, td, J=7.6, 5.6), 2.32 (2H, td, J=7.6, 2.0), 2.39 (1H, dt, J=16.0, 8.0), 2.45 (1H, dt, J=16.0, 8.0), 3.54 (1H, dd, J=10.4, 4.0), 3.58 (1H, dd, J=10.4, 5.6), 3.65 (1H, ddd, J=9.6, 5.6, 2.4), 3.72 (1H, dd, J=10.4, 8.0), 4.13 (1H, ddd, J=8.0, 7.6, 4.0), 4.17 (1H, dd, J=12.4, 2.4), 4.23 (1H, dd, J=12.4, 5.6), 4.26 (1H, dd, J=7.6, 5.6), 4.36 (1H, dt, J=5.6, 5.6), 4.41 (1H, dd, J=7.6, 5.6), 4.77 (1H, s), 5.05 (1H, dd, J=10.0, 3.2), 5.25 (1H, dd, J=10.0, 9.6), 5.49 (1H, d, J=3.2). $^{13}$C-NMR (CDCl$_3$) δ: −5.62, −5.47, 13.8, 13.9 (2C), 18.3, 22.2 (3C), 22.27, 22.32, 24.2, 24.4, 24.5, 24.6, 25.3, 25.5, 25.9 (4C), 27.6, 28.0, 31.2 (4C), 31.3, 33.9, 33.95, 33.98, 34.0, 62.2, 62.4, 65.7, 68.2, 68.5, 71.0, 72.6, 75.0, 75.2, 75.7, 76.8, 98.4, 108.4, 108.8, 172.2, 172.6, 172.8, 173.4

(4) In the same manner as Preparation Example 1 (6) was treated 931 mg of a compound obtained in the above-described (3) to obtain 142 mg of D-mannitol-1-yl 2,3,4,6-tetra-O-hexanoyl-β-D-mannopyranoside. Yield was 72%.

Physical and spectroscopic constants of the obtained compound were as follows.

$^1$H-NMR (700 MHz, CD$_3$OD) δ: 0.89 (6H, t, J=7.2), 0.92 (3H, t, J=7.2), 0.93 (3H, t, J=7.2) 1.23-1.41 (16H, m), 1.54 (1H, tt, J=7.4, 7.4), 1.54 (1H, tt, J=7.4, 7.4), 1.57 (2H, tt, J=7.4, 7.4), 1.64 (2H, tt, J=7.4, 7.4), 1.68 (2H, tt, J=7.4, 7.4), 2.20 (1H, t, J=7.4), 2.27 (1H, dt, J=15.8, 7.4), 2.31 (1H, dt, J=15.8, 7.4), 2.34 (1H, dt, J=14.8, 7.4), 2.37 (1H, dt, J=14.8, 7.4), 2.40 (1H, dt, J=15.0, 7.4), 2.47 (1H, dt, J=15.0, 7.4), 3.61 (1H, dd, J=11.0, 5.6), 3.66 (1H, ddd, J=8.4, 5.6, 3.6), 3.69 (1H, dd, J=10.8, 6.6), 3.72 (1H, dd, J=8.4, 1.0), 3.75 (1H, dd, J=8.4, 1.0), 3.78 (1H, ddd, J=8.4, 6.6, 2.6), 3.79 (1H, dd, J=11.0, 3.6), 3.83 (1H, ddd, J=10.0, 4.2, 2.2), 4.13 (1H, dd, J=10.8, 2.6), 4.15 (1H, dd, J=12.2, 2.2), 4.28 (1H, dd, J=12.2, 4.2), 4.92 (1H, d, J=1.0), 5.16 (1H, dd, J=10.0, 3.2), 5.29 (1H, dd, J=10.0, 10.0), 5.51 (1H, dd, J=3.2, 1.0); $^{13}$C-NMR (CD$_3$OD) δ: 14.2 (2C), 14.3 (2C), 23.4 (3C), 23.5, 25.4, 25.6 (2C), 26.0, 32.3 (3C), 32.4, 34.9 (2C), 35.0, 35.1, 63.1, 65.2 (2C), 66.9, 70.5, 71.1, 71.2, 71.7, 72.7, 73.0, 73.5, 73.7, 173.8, 173.9, 174.8, 175.0)

Furthermore, treatment was performed in the same manner as described above except that hexanoic anhydride used in Preparation Example 1 (3) was substituted with octanoyl chloride, propionyl chloride and palmitoyl chloride, respectively, to obtain a compound A (D-mannitolyl 2,3,4,6-tetra-O-octanoyl-β-D-mannopyranoside) (D-mannitol-1-yl 2,3,4,6-tetra-O-octanoyl-β-D-mannopyranoside), a compound B (D-mannitolyl 2,3,4,6-tetra-O-propionyl-β-D-mannopyranoside) (D-mannitol-1-yl 2,3,4,6-tetra-O-propionyl-β-D-mannopyranoside) and a compound C (D-mannitolyl 2,3,4,6-tetra-O-palmitoyl-β-D-mannopyranoside) (D-mannitol-1-yl 2,3,4,6-tetra-O-palmitoyl-β-D-mannopyranoside).

Physical and spectroscopic constants of the compounds A to C obtained were as follows.

Physical and spectroscopic constants of the compound A:
$^1$H NMR (700 MHz, CD$_3$OD) δ: 1.05 (3H, dd, J=7.6, 7.6), 1.08 (3H, dd, J=7.6, 7.6), 1.14 (3H, dd, J=7.6, 7.6), 1.17 (3H, t, J=7.6), 2.21 (1H, dq, J=16.6, 7.6), 2.24 (1H, dq, J=16.6, 7.6), 2.30 (1H, dq, J=16.6, 7.6), 2.34 (1H, dq, J=16.6, 7.6), 2.36 (1H, dq, J=16.6, 7.6), 2.39 (1H, dq, J=16.6, 7.6), 2.46

(2H, q, J=7.6 Hz), 3.62 (1H, dd, J=11.2, 6.0 Hz), 3.67 (1H, dd, J=8.2, 6.0, 3.6), 3.71 (1H, dd, J=10.6, 6.4), 3.73 (1H, dd, J=8.6, 1.0), 3.76 (1H, dd, J=8.2, 1.0), 3.79 (1H, ddd, J=8.6, 6.4, 2.6), 3.80 (1H, dd, J=11.2, 3.6), 3.84 (1H, ddd, J=10.0, 4.6, 2.2), 4.13 (1H, dd, J=10.6, 2.6), 4.15 (1H, dd, J=12.2, 2.2), 4.31 (1H, dd, J=12.2, 4.6), 4.93 (1H, d, J=1.0), 5.17 (1H, dd, J=10.0, 3.2), 5.27 (1H, dd, J=10.0, 10.0), 5.52 (1H, dd, J=3.2, 1.0); $^{13}$C NMR (175 MHz, CD$_3$OD) δ: 9.2, 9.3, 9.4, 9.6, 23.20, 28.23, 28.26, 38.34, 63.1, 65.2, 67.0, 70.5, 71.0, 71.2, 71.7, 72.7, 73.0, 73.5, 73.7, 100.5, 174.6, 174.8, 175.6, 175.7

Physical and spectroscopic constants of the compound B: $^1$H NMR (700 MHz, CD$_3$OD) δ: 0.88-0.92 (m, 12H, 4×CH$_3$), 1.25-1.42 (m, 32H, 16×CH$_2$), 1.51-1.58 (m, 4H, 2×CH$_2$), 1.62-1.70 (m, 4H, 2×CH$_2$), 2.19-2.50 (m, 8H, 4×COCH$_2$), 3.61 (dd, J=11.0, 6.0 Hz, 1H, OCH), 3.66 (dd, J=8.4, 6.0, 3.6 Hz, 1H, OCH), 3.69 (dd, J=10.6, 6.4 Hz, 1H, OCH), 3.72 (dd, J=8.4, 1.0 Hz, 1H, OCH), 3.75 (dd, J=8.2, 1.0 Hz, 1H, OCH), 3.78 (ddd, J=8.2, 6.4, 2.6 Hz, 1H, OCH), 3.79 (dd, J=11.0, 3.6 Hz, 1H, OCH), 3.83 (ddd, J=10.0, 4.2, 2.2 Hz, 1H, OCH), 4.13 (dd, J=10.6, 2.6 Hz, 1H, OCH), 4.14 (dd, J=12.2, 2.2 Hz, 1H, OCH), 4.29 (dd, J=12.2, 4.2 Hz, 1H, OCH), 4.92 (d, J=0.8 Hz, 1H, OCH), 5.16 (dd, J=10.0, 3.2 Hz, 1H, OCH), 5.31 (dd, J=10.0, 10.0 Hz, 1H, OCH), 5.51 (dd, J=3.2, 0.8 Hz, 1H, OCH); $^{13}$C NMR (175 MHz, CD$_3$OD) δ: 14.4 (2C), 14.45, 14.50, 23.7 (3C), 23.8, 25.8, 25.9, 26.0, 26.4, 30.10, 31.14 (3C), 30.19, 30.22, 30.25, 30.30, 32.85 (2C), 32.91, 33.0, 34.9, 35.0, 35.1, 35.2, 63.0, 65.2, 66.8, 70.5, 71.1, 71.2, 71.7, 72.8, 73.0, 73.5, 73.7, 100.6, 173.7, 173.8, 174.8, 175.0

Physical and spectroscopic constants of the compound C: $^1$H-NMR (700 MHz, CDCl$_3$) δ: 0.88 (12H, t, J=7.0), 1.26-1.32 (96H, m), 1.52 (2H, ddt, J=14.0, 7.0, 7.0), 1.56 (2H, ddt, J=14.0, 7.0, 7.0), 1.62 (2H, ddt, J=14.0, 7.6, 7.6), 1.64 (2H, ddt, J=14.8, 7.4, 7.4), 2.19 (1H, dt, J=22.7, 7.6), 2.21 (1H, dt, J=22.7, 7.0), 2.26 (1H, dt, J=22.7, 7.0), 2.28 (1H, dt, J=22.7, 7.4), 2.34 (1H, dt, J=18.3, 7.6), 2.36 (1H, dt, J=18.3, 7.6), 2.42 (1H, dt, J=21.6, 8.1), 2.45 (1H, dt, J=21.6, 8.1), 3.69 (1H, ddd, J=10.0, 4.0, 4.0), 3.77-3.87 (7H, m), 4.05 (1H, dd, J=10.3, 3.5), 4.22 (2H, d, J=4.0), 4.73 (1H, d, J=0.6), 5.06 (1H, dd, J=10.0, 3.2), 5.28 (1H, dd, J=10.0, 10.0), 5.50 (1H, dd, J=3.2, 0.6), $^{13}$C-NMR (CD$_3$OD) δ: 14.1 (4C), 22.7 (4C), 24.7, 24.8, 24.9, 25.1, 29.1 (2C), 29.2, 29.3 (2C), 39.3, 29.4 (4C), 29.5 (2C), 29.6 (2C), 29.7 (16C), 31.9 (4C), 34.0, 34.1 (2C), 62.1, 63.8, 65.5, 68.7, 70.5, 70.7, 70.8, 71.2, 72.2 (2C), 72.7, 77.2, 172.2, 172.7, 173.6, 173.7

Preparation Example 13

(1) Treatment in the same manner as Preparation Example 1 (1) was performed using 1.82 g of a mannosyl sulfoxide compound (4,6-O-benzylidene-2,3-di-O-p-methoxybenzyl-1-thio-α-D-mannopyranoside S-oxide) and 1.23 g of an alcohol (6-O-tert-butyldimethylsilyl-2,3:4,5-di-O-isopropylidene-D-mannitol) to obtain 1.98 g of a compound (6-O-tert-butyldimethylsilyl-2,3:4,5-di-O-isopropylidene-D-mannitol-1-yl 4,6-O-benzylidene-2,3-di-O-p-methoxybenzyl-β-D-mannopyranoside). Yield was 77%.

Physical and spectroscopic constants of the obtained compound were as follows.

$^1$H NMR (700 MHz, CDCl$_3$) δ: 0.07 (s, 3H, SiMe), 0.08 (s, 3H, SiMe), 0.90 (s, 9H, Si$^t$Bu), 1.36 (s, 3H, CH$_3$), 1.39 (s, 3H, CH$_3$), 1.46 (s, 3H, CH$_3$), 1.50 (s, 3H, CH$_3$), 3.30 (ddd, J=10.1, 10.1, 4.8 Hz, 1H, OCH), 3.54 (dd, J=9.9, 3.2 Hz, 1H, OCH), 3.60 (dd, J=10.4, 4.0 Hz, 1H, OCH), 3.64 (dd, J=10.4, 7.0 Hz, 1H, OCH), 3.76 (dd, J=10.4, 8.0 Hz, 1H, OCH), 3.797 (s, 3H, OMe), 3.801 (s, 3H, OMe), 3.89 (dd, J=10.4, 10.1 Hz, 1H, OCH), 3.93 (dd, J=3.2, 0.8 Hz, 1H, OCH), 4.00 (dd, J=10.4, 4.6 Hz, 1H, OCH), 4.15 (dd, J=10.1, 9.9 Hz, 1H, OCH), 4.22-4.27 (m, 2H, 4×OCH), 4.30 (dd, J=10.4, 4.8 Hz, 1H, OCH), 4.43-4.45 (m, 2H, 4×OCH), 4.49 (d, J=12.0 Hz, 1H, OCHHAr), 4.568 (d, J=0.8 Hz, 1H, OCH), 4.572 (d, J=12.0 Hz, 1H, OCHHAr), 4.78 (d, J=11.8 Hz, 1H, OCHHAr), 4.85 (d, J=11.8 Hz, 1H, OCHHAr), 5.60 (s, 1H, OCH), 6.82 (d, J=8.8 Hz, 1H, Ar), 6.84 (d, J=8.8 Hz, 1H, Ar), 7.17 (d, J=8.8 Hz, 1H, Ar), 7.37 (d, J=8.8 Hz, 1H, Ar), 7.35-7.39 (m, 3H, Ar), 7.49-7.50 (m, 2H, Ar); $^{13}$C NMR (175 MHz, CDCl$_3$) δ: −5.5, −5.4, 18.4, 25.45, 25.52, 25.9 (3C), 27.6, 27.8, 55.2 (2C), 62.3, 67.7, 68.6, 68.7, 71.9, 74.4, 74.9, 75.1, 75.5, 76.2, 76.9, 77.4, 78.6, 101.4, 102.1, 108.5, 108.8, 113.5 (2C), 113.7 (2C), 126.0 (2C), 128.2 (2C), 128.8, 129.1 (2C), 130.1 (2C), 130.4, 130.6, 137.6, 159.1 (2C))

(2) In the same manner as Preparation Example 1 (2) was treated 1.64 g of a compound obtained in the above-described (1) to obtain 816 mg of a compound (6-O-tert-butyldimethylsilyl-2,3:4,5-di-O-isopropylidene-D-mannitol-1-yl 4,6-O-benzylidene-β-D-mannopyranoside). Yield was 69%.

Physical and spectroscopic constants of the obtained compound were as follows.

$^{13}$C NMR (175 MHz, CDCl$_3$) δ: −5.5, −5.4, 18.4, 25.3, 25.4, 25.9 (3C), 27.6, 27.8, 62.6, 66.7, 68.5, 70.7, 70.8, 75.1, 75.2, 75.8, 77.1, 77.2, 78.7, 100.6, 102.1, 108.6, 108.9, 126.2 (2C), 128.3 (2C), 129.1, 137.1

(3) In the same manner as Preparation Example 1 (3) was treated 704 mg of a compound obtained in the above-described (2) to obtain 919 mg of a compound (6-O-tert-butyldimethylsilyl-2,3:4,5-di-O-isopropylidene-D-mannitol-1-yl 4,6-O-benzylidene-2,3-di-O-octanoyl-β-D-mannopyranoside). Yield was 93%.

Physical and spectroscopic constants of the obtained compound were as follows.

$^{13}$C NMR (100 MHz, CDCl$_3$) δ: −5.6, −5.5, 14.0, 14.1, 18.3, 22.58, 22.64, 24.6, 25.0, 25.4, 25.5, 25.9, 27.7, 27.9, 28.9, 29.0, 29.1, 31.6, 31.8, 34.01, 34.03, 34.04, 62.2, 67.4, 68.47, 68.52, 69.0, 70.0, 75.07, 75.15, 75.7, 75.9, 76.8, 77.2, 99.2, 101.7, 108.4, 108.8, 126.1 (2C), 128.2 (2C), 129.1, 137.0, 172.7)

(4) In the same manner as Preparation Example 1 (4) was treated 71.6 mg of a compound obtained in the above-described (3) to obtain 51.9 mg of a compound (6-O-tert-butyldimethylsilyl-2,3:4,5-di-O-isopropylidene-D-mannitol-1-yl 2,3-di-O-octanoyl-β-D-mannopyranoside). Yield was 81%.

Physical and spectroscopic constants of the obtained compound were as follows.

$^{13}$C NMR (100 MHz, CDCl$_3$) δ: −5.6, −5.5, 14.0, 18.3, 22.59, 22.61, 25.6, 25.0, 25.45, 25.52, 25.9, 27.7, 27.9, 28.9, 28.97, 29.01, 29.05, 31.6, 31.7, 34.0, 34.1, 62.1, 62.2, 66.0, 68.4, 68.6, 73.9, 75.1, 75.2, 75.6, 75.8, 76.7, 98.5, 108.5, 108.8, 172.6, 173.4

(5) In the same manner as Preparation Example 1 (5) was treated 42.1 mg of a compound obtained in the above-described (4) to obtain 48.9 mg of a compound (6-O-tert-butyldimethylsilyl-2,3:4,5-di-O-isopropylidene-D-mannitol-1-yl 4,6-O-hexanoyl-2,3-di-O-octanoyl-β-D-mannopyranoside).

Physical and spectroscopic constants of the obtained compound were as follows.

$^{13}$C NMR (100 MHz, CDCl$_3$) δ: −5.6, −5.5, 13.8, 13.9, 14.02, 14.05, 18.3, 22.2, 22.3, 22.6, 24.4, 24.5, 24.6, 25.0, 25.3, 25.5, 25.9, 27.6, 28.0, 28.9, 29.00, 29.03, 29.1, 31.2, 31.3, 31.6, 31.7, 33.97, 34.01, 62.2, 62.5, 65.8, 68.2, 68.5, 71.1, 72.6, 75.1, 75.2, 75.7, 76.7, 77.2, 98.5, 108.4, 108.8, 172.2, 172.6, 172.8, 173.4

(6) In the same manner as Preparation Example 1 (6) was treated 35.4 mg of a compound obtained in the above-described (5) to obtain 19.5 mg of D-mannitol-1-yl 4,6-di-O-hexanoyl-2,3-di-O-octanoyl-β-D-mannopyranoside. Yield was 72%.

Physical and spectroscopic constants of the obtained compound were as follows.

$^1$H NMR (700 MHz, CD$_3$OD) δ: 0.88-0.93 (m, 12H, 4×CH$_3$), 1.25-1.42 (m, 24H, 12×CH$_2$), 1.51-1.59 (m, 4H, 2×CH$_2$), 1.62-1.69 (m, 4H, 2×CH$_2$), 2.19-2.49 (m, 8H, 4×CH$_2$), 3.61 (dd, J=11.2, 6.0 Hz, 1H, OCH), 3.66 (ddd, J=8.2, 6.0, 3.6 Hz, 1H, OCH), 3.69 (dd, J=10.6, 6.4 Hz, 1H, OCH), 3.72 (dd, J=8.6, 1.0 Hz, 1H, OCH), 3.75 (dd, J=8.2, 1.0 Hz, 1H, OCH), 3.78 (ddd, J=8.6, 6.4, 2.6 Hz, 1H, OCH), 3.79 (dd, J=11.2, 3.6 Hz, 1H, OCH), 3.83 (ddd, J=10.0, 4.2, 2.2 Hz, 1H, OCH), 4.13 (dd, J=10.6, 2.6 Hz, 1H, OCH), 4.14 (dd, J=12.4, 2.2 Hz, 1H, OCH), 4.28 (dd, J=12.4, 4.2 Hz, 1H, OCH), 4.92 (d, J=0.8 Hz, 1H, OCH), 5.16 (dd, J=10.0, 3.2 Hz, 1H, OCH), 5.30 (dd, J=10.0, 10.0 Hz, 1H, OCH), 5.51 (dd, J=3.2, 0.8 Hz, 1H, OCH); $^{13}$C NMR (175 MHz, CD$_3$OD) δ: 14.4, 14.3, 14.4, 14.5, 23.4 (2C), 23.7, 23.8, 25.58, 25.62, 25.8, 26.4, 30.1, 30.15, 30.20, 30.3, 32.3, 32.4, 32.8, 33.0, 34.8, 34.9, 35.0, 35.2, 63.0, 65.2, 66.8, 70.5, 71.1, 71.2, 71.7, 72.7, 73.0, 73.5, 73.7, 173.7, 173.8, 174.8, 175.0

Preparation Example 14

(1) 200 mg of the compound obtained in Preparation Example 13 (2) was treated in the same manner as described above except that n-octanoyl chloride in Preparation Example 1 (3) was substituted with propionyl chloride to obtain 171 mg of a compound (6-O-tert-butyldimethylsilyl-2,3:4,5-di-O-isopropylidene-D-mannitol-1-yl 4,6-O-benzylidene-2,3-di-O-propionyl-β-D-mannopyranoside). Yield was 96%.

Physical and spectroscopic constants of the obtained compound were as follows.

$^{13}$C NMR (100 MHz, CDCl$_3$) δ: −5.6, −5.5, 8.8, 9.3, 18.3, 25.4, 25.5, 25.9, 27.28,
27.33, 27.7, 27.9, 62.2, 67.3, 68.5, 69.1, 70.2, 75.0, 75.2, 75.6, 75.8, 76.8, 99.1, 101.8, 108.4, 108.8, 126.1 (2C), 128.3 (2C), 129.2, 136.9, 173.3, 173.5

(2) In the same manner as Preparation Example 1 (4) was treated 149 mg of a compound obtained in the above-described (1) to obtain 123 mg of a compound (6-O-tert-butyldimethylsilyl-2,3:4,5-di-O-isopropylidene-D-mannitol-1-yl 2,3-di-O-propionyl-β-D-mannopyranoside). Yield was 81%.

Physical and spectroscopic constants of the obtained compound were as follows.

$^{13}$C NMR (100 MHz, CDCl$_3$) δ: −5.6, −5.5, 8.8, 9.2, 18.3, 25.48, 25.52, 25.9, 27.36, 27.39, 27.8, 27.9, 62.1, 62.2, 65.9, 68.4, 68.7, 74.0, 75.1, 75.2, 75.6, 75.8, 76.9, 98.5, 108.5, 108.8, 173.4, 174.0

(3) In the same manner as Preparation Example 1 (5) was treated 97.2 mg of a compound obtained in the above-described (2) to obtain 126 mg of a compound (6-O-tert-butyldimethylsilyl-2,3:4,5-di-O-isopropylidene-D-mannitol-1-yl 4,6-di-O-hexanoyl-2,3-di-O-propioyl-β-D-mannopyranoside).

Physical and spectroscopic constants of the obtained compound were as follows.

$^{13}$C NMR (100 MHz, CDCl$_3$) δ: −5.6, −5.5, 8.7, 9.2, 13.8, 13.9, 18.3, 22.2, 22.3, 24.4, 24.5, 25.3, 25.5, 25.9, 27.3, 27.4, 27.6, 28.0, 31.1, 31.3, 33.95, 34.01, 62.2, 62.4, 65.7, 68.2, 68.5, 71.2, 72.6, 75.0, 75.2, 75.6, 76.8, 98.4, 108.4, 108.8, 172.4, 173.2, 173.4, 173.6

(4) In the same manner as Preparation Example 1 (6) was treated 103 mg of a compound obtained in the above-described (3) to obtain 48.6 mg of D-mannitol-1-yl 4,6-di-O-hexanoyl-2,3-di-O-propionyl-β-D-mannopyranoside. Yield was 61%.

Physical and spectroscopic constants of the obtained compound were as follows.

$^1$H NMR (700 MHz, CD$_3$OD) δ: 0.90 (t, J=7.2 Hz, 3H, CH$_3$), 0.93 (t, J=7.2 Hz, 3H, CH$_3$), 1.05 (t, J=7.6 Hz, 3H, CH$_3$), 1.17 (t, J=7.6 Hz, 3H, CH$_3$), 1.25-1.39 (m, 8H, 4×CH$_2$), 1.57 (ddt, J=7.4, 7.4, 7.4 Hz, 2H, CH$_2$), 1.64 (ddt, J=7.4, 7.4, 7.4 Hz, 2H, CH$_2$), 2.22 (q, J=7.6 Hz, 2H, COCH$_2$), 2.29 (dt, J=15.8, 7.4 Hz, 1H, CHH), 2.32 (dt, J=15.8, 7.4 Hz, 1H, CHH), 2.34 (dt, J=15.8, 7.4 Hz, 1H, CHH), 2.37 (dt, J=15.8, 7.4 Hz, 1H, CHH), 2.49 (q, J=7.6 Hz, 2H, COCH$_2$), 3.61 (dd, J=11.2, 6.0 Hz, 1H, OCH), 3.67 (ddd, J=8.2, 6.0, 3.6 Hz, 1H, OCH), 3.70 (dd, J=10.6, 6.4 Hz, 1H, OCH), 3.73 (dd, J=8.6, 1.2 Hz, 1H, OCH), 3.76 (dd, J=8.2, 1.2 Hz, 1H, OCH), 3.78 (ddd, J=8.6, 6.4, 2.6 Hz, 1H, OCH), 3.80 (dd, J=11.2, 3.6 Hz, 1H, OCH), 3.84 (ddd, J=10.0, 4.6, 2.4 Hz, 1H, OCH), 4.13 (dd, J=10.6, 2.6 Hz, 1H, OCH), 4.15 (dd, J=12.4, 2.4 Hz, 1H, OCH), 4.27 (dd, J=12.4, 4.6 Hz, 1H, OCH), 4.93 (d, J=1.0 Hz, 1H, OCH), 5.17 (dd, J=10.0, 3.2 Hz, 1H, OCH), 5.27 (dd, J=10.0, 10.0 Hz, 1H, OCH), 5.52 (dd, J=3.2, 1.0 Hz, 1H, OCH); $^{13}$C NMR (175 MHz, CD$_3$OD) δ: 9.2, 9.6, 14.2, 14.3, 23.3, 23.4, 25.6, 25.7, 28.2, 28.4, 32.3, 32.4, 34.9 (2C), 63.1, 65.2, 66.9, 70.5, 71.0, 71.2, 71.7, 72.8, 73.0, 73.4, 73.7, 100.5, 174.0, 174.5, 175.0, 175.6

Preparation Example 15

(1) 200 mg of the compound obtained in Preparation Example 13 (2) was treated in the same manner as described above except that n-octanoyl chloride in Preparation Example 1 (3) was substituted with palmitic acid chloride to obtain 313 mg of a compound (6-O-tert-butyldimethylsilyl-2,3:4,5-di-O-isopropylidene-D-mannitol-1-yl 4,6-O-benzylidene-2,3-di-O-palmitoyl-β-D-mannopyranoside). Yield was 89%.

(2) In the same manner as Preparation Example 1 (4) was treated 242 mg of a compound obtained in the above-described (1) to obtain 200 mg of a compound (6-O-tert-butyldimethylsilyl-2,3:4,5-di-O-isopropylidene-D-mannitol-1-yl 2,3-di-O-palmitoyl-β-D-mannopyranoside). Yield was 90%.

Physical and spectroscopic constants of the obtained compound were as follows.

$^{13}$C NMR (100 MHz, CDCl$_3$) δ: −5.6, −5.5, 14.1 (2C), 18.3, 22.7 (2C), 24.6, 25.1,
25.47, 25.54, 25.9 (3C), 27.7, 27.9, 29.10, 29.14, 29.3, 29.4 (2C), 29.5, 29.59, 29.64, 29.66 (4C), 29.70 (8C), 31.9 (2C), 34.05, 34.09, 62.1, 62.3, 66.0, 68.4, 68.6, 73.9, 75.1, 75.2, 75.7, 75.8, 76.9, 98.5, 108.5, 108.8, 172.7, 173.4

(3) In the same manner as Preparation Example 1 (5) was treated 157 mg of a compound obtained in the above-described (2) to obtain 187 mg of a compound (6-O-tert-butyldimethylsilyl-2,3:4,5-di-O-isopropylidene-D-mannitol-1-yl 4,6-di-O-hexanoyl-2,3-di-O-palmitoyl-β-D-mannopyranoside).

Physical and spectroscopic constants of the obtained compound were as follows.

$^{13}$C NMR (100 MHz, CDCl$_3$) δ: −5.6, −5.5, 13.8, 13.9, 14.1 (2C), 18.3, 22.26, 22.29, 22.7 (2C), 24.4, 24.5, 24.6, 25.0, 25.3, 25.5, 25.9 (3C), 27.6, 28.0, 29.11, 29.14, 29.3, 29.37 (2C), 29.39, 29.5, 29.6, 29.66 (2C), 29.68 (2C), 29.70 (4C), 29.73 (4C), 31.2, 31.3, 31.9 (2C), 33.96, 33.99, 34.02, 34.03, 62.1, 62.3, 66.0, 68.4, 68.6, 73.9, 75.1, 75.2, 75.7, 75.8, 76.9, 98.5, 108.5, 108.8, 172.4, 173.2, 173.4, 173.6

(4) In the same manner as Preparation Example 1 (6) was treated 162 mg of a compound obtained in the above-described (3) to obtain 111 mg of D-mannitol-1-yl 4,6-di-O-hexanoyl-2,3-di-O-palmitoyl-β-D-mannopyranoside. Yield was 82%.

Physical and spectroscopic constants of the obtained compound were as follows.

$^1$H NMR (700 MHz, CD$_3$OD) δ: 0.89-0.94 (m, 12H, 4×CH$_3$), 0.90 (t, J=7.2 Hz, 6H, 2×CH$_3$), 0.91 (t, J=7.2 Hz, 3H, CH$_3$), 0.93 (t, J=7.2 Hz, 3H, CH$_3$), 1.29-1.43 (m, 56H, 28×CH$_2$), 1.51-1.60 (m, 4H, 2×CH$_2$), 1.63-1.72 (m, 4H, 2×CH$_2$), 2.17-1.52 (m, 8H, 4×COCH$_2$), 2.19 (dt, J=15.2, 7.2 Hz, 1H, COCHH), 2.22 (dt, J=15.2, 7.2 Hz, 1H, COCHH), 2.27 (dt, J=15.8, 7.4 Hz, 1H, COCHH), 2.31 (dt, J=15.8, 7.4 Hz, 1H, COCHH), 2.34 (dt, J=15.8, 7.6 Hz, 1H, COCHH), 2.37 (dt, J=15.8, 7.6 Hz, 1H, COCHH), 2.39 (dt, J=15.2, 7.4 Hz, 1H, COCHH), 2.49 (dt, J=15.2, 7.4 Hz, 1H, COCHH), 3.61 (dd, J=11.0, 6.0 Hz, 1H, OCH), 3.66 (ddd, J=8.2, 6.0, 3.6 Hz, 1H, OCH), 3.70 (dd, J=10.6, 6.5 Hz, 1H, OCH), 3.72 (dd, J=8.6, 1.0 Hz, 1H, OCH), 3.76 (dd, J=8.2, 1.0 Hz, 1H, OCH), 3.79 (ddd, J=8.6, 6.5, 2.6 Hz, 1H, OCH), 3.80 (dd, J=11.0, 3.6 Hz, 1H, OCH), 3.83 (ddd, J=10.0, 4.2, 2.2 Hz, 1H, OCH), 4.137 (dd, J=10.6, 2.6 Hz, 1H, OCH), 4.142 (dd, J=12.4, 2.2 Hz, 1H, OCH), 4.30 (dd, J=12.4, 4.2 Hz, 1H, OCH), 4.93 (d, J=0.8 Hz, 1H, OCH), 5.16 (dd, J=10.0, 3.2 Hz, 1H, OCH), 5.32 (dd, J=10.0, 10.0 Hz, 1H, OCH), 5.51 (dd, J=3.2, 0.8 Hz, 1H, OCH); $^{13}$C NMR (125 MHz, CD$_3$OD) δ: 14.3, 14.4, 14.5 (2C), 23.5 (2C), 23.8 (2C), 25.6, 25.7, 25.8, 26.5, 30.2, 30.3, 30.4, 30.51, 30.53, 30.6, 30.75, 30.80, 30.84 (7C), 30.89, 30.92 (2C), 31.0 (2C), 32.4, 32.5, 33.1 (2C), 34.8, 34.9, 35.1, 35.3, 63.0, 65.2, 66.7, 70.5, 71.0, 71.1, 71.6, 72.8, 73.0, 73.5, 73.7, 100.6, 173.6, 173.8, 174.7, 175.0

Preparation Example 16

(1) Treatment in the same manner as Preparation Example 1 (1) was performed using 799 mg of a mannosyl sulfoxide compound (4,6-O-benzylidene-3-O-p-methoxybenzyl-2-O-tert-butyldimethylsilyl-α-D-mannopyranoside S-oxide) and 591 mg of D-mannitol derivative of Reference Example 2 to obtain 679 mg of (6-O-benzyl-2,3:4,5-di-O-isopropylidene-D-mannitol-1-yl 4,6-O-benzylidene-3-O-p-methoxybenzyl-2-O-tert-butyldimethylsilyl-β-D-mannopyranoside). Yield was 62%.

Physical and spectroscopic constants of the obtained compound were as follows.

$^{13}$C NMR (175 MHz, CDCl$_3$) δ: −4.6, −4.4, 18.5, 25.4, 25.5, 26.0 (3C), 27.4, 27.5, 55.2, 67.6, 67.8, 68.8, 69.3, 71.3, 71.9, 73.5, 74.7, 74.8, 75.58, 75.60, 77.1, 77.2, 78.8, 101.1, 101.4, 108.7, 108.9, 113.6 (2C), 126.1 (2C), 127.9, 128.0 (2C), 128.1 (2C), 128.5 (2C), 128.8, 129.4 (2C), 130.5, 137.69, 137.75, 159.1

(2) 435 mg of a compound obtained in the above-described (1) was treated in tetrahydrofuran using tetra-n-butylammonium fluoride (TBAF) at 40° C. for 5 hours to obtain 340 mg of an alcohol 6-O-benzyl-2,3:4,5-di-O-isopropylidene-D-mannitol-1-yl 4,6-O-benzylidene-3-O-p-methoxybenzyl-β-D-mannopyranoside. Yield was 90%.

Physical and spectroscopic constants of the obtained compound were as follows.

$^1$H NMR (400 MHz, CDCl$_3$) δ: 1.35 (s, 3H, CH$_3$), 1.37 (s, 3H, CH$_3$), 1.46 (s, 3H, CH$_3$), 1.56 (s, 3H, CH$_3$), 2.64 (brs, 1H, OH), 3.27 (ddd, J=10.0, 10.0, 4.8 Hz, 1H, OCH), 3.48 (dd, J=10.0, 4.8 Hz, 1H, OCH), 3.57 (dd, J=9.6, 3.2 Hz, 1H, OCH), 3.58 (dd, J=9.6, 6.0 Hz, 1H, OCH), 3.60 (dd, J=9.2, 9.2 Hz, 1H, OCH), 3.80 (s, 3H, OMe), 3.85 (dd, J=10.0, 10.0 Hz, 1H, OCH), 3.96 (dd, J=10.0, 6.0 Hz, 1H, OCH), 4.05 (d, J=3.2 Hz, 1H, OCH), 4.10 (dd, J=9.6, 9.6 Hz, 1H, OCH), 4.12-4.35 (m, 5H, OCH), 4.48 (d, J=12.0 Hz, 1H, OCHHPh), 4.49 (s, 1H, OCH), 4.56 (d, J=2.0 Hz, 1H, OCHHPh), 4.69 (d, J=12.0 Hz, 1H, OCHHPh), 4.77 (d, J=12.0 Hz, 1H, OCHHPh), 5.59 (s, 1H, OCH), 6.86 (d, J=8.4 Hz, 2H, Ar), 7.27-7.41 (m, 10H, Ar), 7.50 (dd, J=8.0, 1.2 Hz, 2H, Ar).

(3) In the same manner as Preparation Example 1 (3) was treated 340 mg of a compound obtained in the above-described (2) to obtain 354 mg of a compound (6-O-benzyl-2,3:4,5-di-O-isopropylidene-D-mannitol-1-yl 4,6-O-benzylidene-3-O-p-methoxybenzyl-2-O-octanoyl-β-D-mannopyranoside). Yield was 89%.

$^1$H NMR (400 MHz, CDCl$_3$) δ: 0.86 (t, J=7.2 Hz, 3H, CH$_3$), 1.24-1.31 (m, 8H, 4×CH$_2$), 1.34 (s, 3H, CH$_3$), 1.38 (s, 3H, CH$_3$), 1.44 (s, 3H, CH$_3$), 1.46 (s, 3H, CH$_3$), 1.64 (tt, J=7.6, 7.2 Hz, 2H, CH$_2$), 2.44 (t, J=7.6 Hz, 2H, COCH$_2$), 3.29 (ddd, J=9.6, 9.6, 4.8 Hz, 1H, OCH), 3.44 (dd, J=9.6, 4.8 Hz, 1H, OCH), 3.57 (dd, J=10.4, 5.2 Hz, 1H, OCH), 3.58 (dd, J=10.4, 3.6 Hz, 1H, OCH), 3.63 (dd, J=10.4, 3.6 Hz, 1H, OCH), 3.79 (s, 3H, OMe), 3.84 (dd, J=10.4, 9.6 Hz, 1H, OCH), 3.90 (dd, J=10.4, 7.6 Hz, 1H, OCH), 3.92 (dd, J=9.6, 9.6 Hz, 1H, OCH), 4.21-4.32 (m, 4H, 4×OCH), 4.38 (ddd, J=7.6, 5.2, 5.2 Hz, 1H, OCH), 4.48 (d, J=12.0 Hz, 1H, OCHHAr), 4.53 (d, J=12.0 Hz, 1H, OCHHAr), 4.54 (d, J=12.0 Hz, 1H, OCHHAr), 4.57 (s, 1H, OCH), 4.66 (d, J=12.0 Hz, 1H, OCHHAr), 5.59 (s, 1H, OCHPh), 5.62 (d, J=4.8 Hz, 1H, OCH), 6.84 (d, J=8.4 Hz, 2H, Ar), 7.27-7.41 (m, 10H, Ar), 7.50 (dd, J=8.0, 2.4 Hz, 2H, Ar); $^{13}$C NMR (175 MHz, CDCl$_3$) δ: 14.1, 22.6, 25.0, 25.5, 25.6, 27.7, 27.9, 29.0 (2C), 31.7, 34.1, 55.2, 67.3, 67.8, 68.4, 68.5, 69.1, 71.3, 73.6, 75.0, 75.18 (2C), 75.25, 75.3, 77.9, 99.2, 101.5, 108.6, 108.7, 113.7 (2C), 126.1 (2C), 127.87, 127.94 (2C), 128.2 (2C), 128.5 (2C), 128.9, 129.4 (2C), 129.8, 137.3, 137.7, 159.3, 173.1

(4) 342 mg of a compound obtained in the above-described (3) was treated with trifluoro acetic acid (TFA) in methylene chloride to obtain 36.2 mg of a compound (6-O-benzyl-2,3:4,5-di-O-isopropylidene-D-mannitol-1-yl 2-O-octanoyl-β-D-mannopyranoside). Yield was 89%.

Physical and spectroscopic constants of the obtained compound were as follows.

$^{13}$C NMR (100 MHz, CDCl$_3$) δ: 14.0, 22.6, 24.8, 25.5, 25.6, 27.8, 27.9, 28.9, 29.0, 31.7, 34.1, 62.2, 68.0, 68.1, 68.9, 70.9, 73.0, 73.59, 73.60, 75.16, 75.25 (2C), 75.7, 98.5, 108.7, 108.8, 127.9, 128.0 (2C), 128.5 (2C), 137.5, 174.3

(5) In the same manner as Preparation Example 1 (5) was treated 36.2 mg of a compound obtained in the above-described (4) to obtain 41.2 mg of a compound (6-O-benzyl-2,3:4,5-di-O-isopropylidene-D-mannitol-1-yl 3,4,6-tri-O-hexanoyl-2-O-octanoyl-β-D-mannopyranoside). Yield was 78%.

$^{13}$C NMR (100 MHz, CDCl$_3$) δ: 13.80, 13.82, 13.9, 14.0, 22.2 (2C), 22.3, 22.6, 24.2, 24.4, 24.5, 25.0, 25.3, 25.6, 27.7, 27.9, 28.99, 29.02, 31.2 (2C), 31.3, 31.7, 33.93, 33.94, 34.00, 34.02, 62.4, 65.7, 67.8, 68.4, 69.0, 71.0, 72.6, 73.5, 75.0, 75.2 (2C), 75.3, 98.2, 108.6, 108.7, 127.8, 128.0 (2C), 128.5 (2C), 137.7, 172.2, 172.6, 173.0, 173.4

(6) In the same manner as Preparation Example 1 (6) was treated 18.5 mg of a compound obtained in the above-described (5) to obtain 18.5 mg of a compound (6-O-benzyl-D-mannitol-1-yl 3,4,6-tri-O-hexanoyl-2-O-octanoyl-β-D-mannopyranoside). Yield was 49%.

Physical and spectroscopic constants of the obtained compound were as follows.

$^{13}$C NMR (100 MHz, CDCl$_3$) δ: 13.8 (2C), 13.9, 14.1, 22.2 (2C), 22.3, 22.6, 24.3, 24.4, 24.5, 25.0, 28.9, 29.0, 31.1, 31.3, 31.7, 33.9, 33.9, 34.0, 34.1, 62.1, 65.6, 68.6, 70.6, 70.7, 71.0, 71.1, 71.2, 71.6, 72.5, 72.7, 99.3, 127.8 (2C), 127.9, 128.5, 137.6, 172.2, 172.6, 173.4, 173.5

(7) 18.5 mg of a compound obtained in the above-described (6) was reduced in methanol in the presence of acetic acid and palladium-carbon catalyst, the catalyst was filtered and the filtrate was concentrated to obtain 9.8 mg of D-mannitol-1-yl 3,4,6-tri-O-hexanoyl-2-O-octanoyl-β-D-mannopyranoside). Yield was 59%.

Physical and spectroscopic constants of the compound: colorless amorphous material; $[α]^{25}_D$ −31.1 (c 0.97, MeOH); IR (neat) cm$^{-1}$: 3368 (OH), 1744 (C=O); $^1$H NMR (700 MHz, CD$_3$OD) δ: 0.90 (t, J=7.2 Hz, 6H, 2×CH$_3$), 0.91 (t, J=7.2 Hz, 3H, CH$_3$), 0.92 (t, J=7.2 Hz, 3H, CH$_3$), 1.25-1.42 (m, 20H, 10×CH$_2$), 1.53-1.59 (m, 4H, 2 CH$_2$), 1.62-1.70 (m, 4H, 2×CH$_2$), 2.19 (dt, J=15.3, 7.4 Hz, 1H, COCHH), 2.21 (dt, J=15.3, 7.4 Hz, 1H, COCHH), 2.27 (dt, J=15.8, 7.4 Hz, 1H, COCHH), 2.31 (dt, J=15.8, 7.4 Hz, 1H, COCHH), 2.34 (dt, J=15.6, 7.4 Hz, 1H, COCHH), 2.37 (dt, J=15.6, 7.4 Hz, 1H, COCHH), 2.40 (dt, J=15.4, 7.4 Hz, 1H, COCHH), 2.47 (dt, J=15.4, 7.4 Hz, 1H, COCHH), 3.61 (dd, J=11.2, 6.0 Hz, 1H, OCH), 3.66 (ddd, J=8.2, 6.0, 3.6 Hz, 1H, OCH), 3.69 (dd, J=10.6, 6.6 Hz, 1H, OCH), 3.72 (dd, J=8.6, 1.0 Hz, 1H, OCH), 3.75 (dd, J=8.2, 1.0 Hz, 1H, OCH), 3.78 (ddd, J=8.6, 6.6, 2.4 Hz, 1H, OCH), 3.79 (dd, J=11.2, 3.6 Hz, 1H, OCH), 3.83 (ddd, J=10.0, 4.2, 2.2 Hz, 1H, OCH), 4.13 (dd, J=10.6, 2.4 Hz, 1H, OCH), 4.15 (dd, J=12.2, 2.2 Hz, 1H, OCH), 4.28 (dd, J=12.2, 4.2 Hz, 1H, OCH), 4.92 (d, J=0.8 Hz, 1H, OCH), 5.16 (dd, J=10.0, 3.2 Hz, 1H, OCH), 5.30 (dd, J=10.0, 10.0 Hz, 1H, OCH), 5.51 (dd, J=3.2, 0.8 Hz, 1H, OCH); $^{13}$C NMR (175 MHz, CD$_3$OD) δ: 14.2 (2C), 14.3, 14.5, 23.35, 23.37, 23.4, 23.8, 25.5, 23.59, 23.62, 26.3, 30.2, 30.3, 32.3, 32.4, 32.5, 33.0, 34.85, 34.93, 35.0, 35.2, 63.0, 65.2, 66.8, 70.5, 71.1, 71.2, 71.7, 72.7, 73.0, 73.5, 73.7, 100.6, 173.8, 173.9, 174.8, 175.0;

Preparation Example 17

(1) Treatment in the same manner as Preparation Example 1 (1) was performed using a mannosyl sulfoxide compound and an alcohol of a known compound (1,2:3,4-di-O-isopropylidene-D-galactopyranose) to obtain a compound (1,2:3,4-di-O-isopropylidene-D-galactopyranosyl 4,6-O-benzylidene-2-O-tert-butyldimethylsilyl-3-O-p-methoxybenzyl-β-D-mannopyranoside) as a yield of 89%. Physical constants of the compound: $^1$H NMR (700 MHz, CDCl$_3$) δ: 0.12 (s, 6H, 2×SiMe), 0.92 (s, 9H, Si$^t$Bu), 1.32 (s, 3H, Me), 1.34 (s, 3H, Me), 1.44 (s, 3H, Me), 1.51 (s, 3H, Me), 3.29 (ddd, J=10.0, 10.0, 4.8 Hz, 1H, OCH), 3.48 (dd, J=10.0, 2.4 Hz, 1H, OCH), 3.64 (dd, J=11.2, 8.0 Hz, 1H, OCH), 3.81 (s, 3H, OMe), 3.85 (dd, J=10.4, 10.0 Hz, 1H, OCH), 3.99 (ddd, J=8.0, 2.0, 2.0 Hz, 1H, OCH), 4.07 (dd, J=11.2, 2.0 Hz, 1H, OCH), 4.11 (dd, J=10.0, 10.0 Hz, 1H, OCH), 4.15 (d, J=2.4 Hz, 1H, OCH), 4.19 (dd, J=8.0, 2.0 Hz, 1H, OCH), 4.28 (dd, J=10.4, 4.8 Hz, 1H, OCH), 4.32 (dd, J=4.4, 2.0 Hz, 1H, OCH), 4.40 (brs, 1H, OCH), 4.59 (dd, J=8.0, 2.0 Hz, 1H, OCH), 4.65 (s, 2H, OCH$_2$Ph), 5.56 (d, J=4.4 Hz, 1H, OCH), 5.59 (s, 1H, CHPh), 6.83-6.85 (2H, m), 7.22-7.53 (7H, m); $^{13}$C NMR (175 MHz, CD$_3$OD) δ: −4.88, −3.78, 18.5, 24.3, 24.9, 25.96, 26.0 (2C), 26.1, 55.2, 67.4, 67.6, 68.9, 69.9, 70.2, 70.7, 71.0, 71.5, 71.6, 77.1, 78.7, 96.4, 101.4, 102.5, 108.5, 109.3, 113.6 (2C), 126.1 (2C), 128.1 (2C), 128.8, 129.4 (2C), 130.5, 137.7, 159.1

(2) a compound obtained in the above-described (1) was treated in the same manner as Preparation Example 16 (2) and Preparation Example 1 (3) to obtain a compound (1,2:3,4-di-O-isopropylidene-D-galactopyranosyl 4,6-O-benzylidene-3-O-p-methoxybenzyl-2-O-octanoyl-β-D-mannopyranoside).

(3) A compound obtained in the above-described (2) was treated in the same manner as Preparation Example 16 (4) to obtain 55 mg of a compound (1,2:3,4-di-O-isopropylidene-D-galactopyranosyl 2-octanoyl-β-D-mannopyranoside). Yield was 72%.

$^1$H NMR (400 MHz, CDCl$_3$) δ: 0.88 (t, J=6.8 Hz, 3H, CH$_3$CH$_2$) 1.27-1.30 (m, 8H, CH$_2$CH$_2$CH$_2$), 1.33 (s, 6H, 2×Me), 1.44 (s, 3H, Me), 1.52 (s, 3H, Me), 1.56-1.67 (m, 2H, CH$_2$CH$_2$CO), 2.39-2.43 (m, 2H, CH$_2$CH$_2$CO), 3.38 (ddd, J=9.2, 5.6, 3.6 Hz, 1H, OCH), 3.70 (dd, J=9.2, 9.2 Hz, 1H, OCH), 3.72-3.78 (m, 2H, 2×OCH), 3.83 (dd, J=11.2, 5.6 Hz, 1H, OCH), 3.95 (dd, J=12.0, 5.2 Hz, 1H, OCH), 3.96 (dd, J=12.0, 2.0 Hz, 1H, OCH), 4.00 (dd, J=11.2, 3.6 Hz, 1H, OCH), 4.21 (dd, J=8.0, 2.0 Hz, 1H, OCH), 4.30 (dd, J=5.2, 2.4 Hz, 1H, OCH), 4.58 (dd, J=8.0, 2.4 Hz, 1H, OCH), 4.80 (d, J=1.2 Hz, 1H, OCH), 5.40 (dd, J=3.2, 1.2 Hz, 1H, OCH), 5.51 (d, J=5.2 Hz, 1H, OCH); $^{13}$C NMR (100 MHz, CDCl$_3$) δ: 14.0, 22.6, 24.3, 25.0 (2C), 25.9, 26.0, 28.9, 29.0, 31.7, 34.2, 62.7, 68.1, 68.8 (2C), 70.5, 70.7, 71.2, 71.3, 73.3, 75.6, 96.2, 99.1, 108.8, 109.5, 174.3

(4) A compound obtained in the above-described (3) was treated in the same manner as Preparation Example 1 (5) to obtain a compound (1,2:3,4-di-O-isopropylidene-D-galactopyranosyl 3,4,6-tri-O-hexanoyl-2-O-octanoyl-β-D-mannopyranoside).

Physical and spectroscopic constants of the obtained compound were as follows.

$^1$H-NMR (CDCl$_3$) δ: 0.86-0.91 (12H, m), 1.20-1.35 (20H, m), 1.31 (3H, s), 1.32 (3H, s), 1.44 (3H, s), 1.51 (3H, s), 1.52-1.68 (8H, m), 2.15-2.44 (8H, m), 3.67 (1H, ddd, J=2.4, 5.2, 10.0), 3.75 (1H, ddd, J=2.4, 9.6, 10.0), 3.94-4.00 (2H, m), 4.16 (1H, dd, J=2.4, 12.0), 4.18 (1H, dd, J=2.4, 8.0), 4.26 (1H, dd, J=5.2, 12.0), 4.28 (1H, dd, J=2.8, 4.8), 4.58 (1H, dd, J=2.8, 8.0), 4.85 (1H, brs), 5.08 (1H, dd, J=3.2, 10.0), 5.26 (1H, dd, J=10.0, 10.0), 5.49 (1H, d, J=4.8), 5.50 (1H, d, J=3.2). $^{13}$C-NMR (CDCl$_3$) δ: 13.80, 13.82, 13.9, 14.4, 22.2 (2C), 22.3, 22.6, 22.3, 24.3, 24.4, 24.5, 25.00, 25.02, 25.9, 26.0, 28.9, 29.0, 31.2 (2C), 31.3, 31.7, 33.9, 34.0 (2C), 34.1, 62.5, 66.0, 68.1, 68.8, 69.1, 70.5, 70.7, 71.0, 71.3, 72.4, 96.2, 98.8, 108.8, 109.4, 172.3, 172.5, 172.8, 173.5.

(5) A compound obtained in the above-described (4) was treated in the same manner as Preparation Example 1 (6), via a compound (D-galactopyranosyl 3,4,6-tri-O-hexanoyl-2-O-octanoyl-β-D-mannopyranoside), was treated with sodium borohydride in methanol and reduced to obtain D-galactitol-6-yl 3,4,6-tri-O-hexanoyl-2-O-octanoyl-β-D-mannopyranoside. Yield was 40%.

Physical and spectroscopic constants of the obtained compound were as follows.

$^1$H NMR (700 MHz, CD$_3$OD) δ: 0.88-0.94 (m, 12H, 4×CH$_3$CH$_2$), 1.25-1.48 (m, 20H, 10×CH$_2$CH$_3$CH$_2$), 1.51-1.78 (m, 8H, 4×CH$_2$CH$_2$CO), 2.24-2.48 (m, 8H, 4×CH$_2$CH$_2$CO), 3.59 (dd, J=9.0, 1.5 Hz, 1H, OCH), 3.70 (dd, J=10.4, 7.6 Hz, 1H, OCH), 3.83 (ddd, J=10.0, 4.3, 2.2 Hz, 1H, OCH), 3.89 (ddd, J=6.2, 4.9, 1.6 Hz, 1H, OCH), 3.92 (dd, J=10.4, 5.0 Hz, 1H, OCH), 4.04 (ddd, J=7.6, 5.0, 1.5 Hz, 1H, OCH), 4.15 (dd, J=12.3, 2.2 Hz, 1H, OCH), 4.28 (dd, J=12.3, 4.3 Hz, 1H, OCH), 4.94 (d, J=0.7 Hz, 1H, OCH), 5.16 (dd, J=10.0, 3.2 Hz, 1H, OCH), 5.30 (dd, J=10.0, 10.0 Hz, 1H, OCH), 5.49 (dd, J=3.2, 0.7 Hz, 1H, OCH); $^{13}$C NMR (175 MHz, CD$_3$OD) δ: 14.2, 14.3, 14.4, 14.5, 23.36, 23.38, 23.4, 23.8, 25.5, 25.60, 26.62, 26.35, 30.2, 30.3, 32.3, 32.4, 32.5, 33.0, 34.8, 34.9, 35.0, 35.2, 63.0, 65.0, 66.8, 70.2, 70.5, 71.30, 71.33, 71.8, 72.7, 73.2, 73.5, 100.3, 173.80, 173.84, 174.7, 175.0

Preparation Example 18

(1) Treatment in the same manner as Preparation Example 1 (1) was performed using 0.500 g of a mannosyl sulfoxide compound of Reference Example 1 and 0.320 g of an alcohol (1,2:3,4-di-O-isopropylidene-5-O-methoxymethyl-D-glucitol) to obtain 0.360 g of a compound (1,2:3,4-di-O-isopropylidene-5-O-methoxymethyl-D-glucitol-6-yl 3-O-benzyl-4,6-O-benzylidene-2-O-p-methoxybenzyl-β-D-mannopyranoside). Yield was 56%.

Physical and spectroscopic constants of the obtained compound were as follows.

$[α]^{25}{}_D$ −46.4 (c 0.88, CHCl$_3$); IR (neat) cm$^{-1}$: 1250; $^1$H NMR (700 MHz, CDCl$_3$) δ. 1.37 (s), 1.41 (s), 1.44 (s), 3.31 (s), 3.33 (ddd, J=9.8, 9.8, 4.8 Hz), 3.57 (dd, J=9.8, 3.0 Hz), 3.63 (dd, J=10.8, 6.0 Hz), 3.80 (s, 3H), 3.84 (ddd, J=6.8, 6.0, 2.8 Hz), 3.91 (dd, J=10.4, 9.8 Hz), 3.92 (dd, J=8.4, 3.0 Hz), 3.95 (dd, J=3.0, 0.6 Hz), 4.01 (dd, J=8.4, 6.6 Hz), 4.05 (dd, J=6.8, 4.2 Hz), 4.08 (ddd, J=6.6, 6.6, 3.0 Hz) 4.18 (dd, J=6.6, 4.2 Hz), 4.18 (dd, J=9.8, 9.8 Hz), 4.20 (dd, J=10.8, 2.8 Hz), 4.23 (dd, J=10.4, 4.8 Hz), 4.49 (d, J=0.6 Hz), 4.56 (d, J=12.4 Hz), 4.66 (d, J=6.9 Hz), 4.68 (d, J=12.4 Hz), 4.79 (d, J=11.8 Hz), 4.83 (d, J=6.9 Hz), 4.89 (d, J=11.8 Hz), 5.61 (s), 6.83-6.85 (m), 7.26-7.31 (m), 7.35-7.39 (m), 7.49-7.50 (m); $^{13}$C NMR (175 MHz, CDCl$_3$) δ: 25.7, 26.3, 27.2, 27.4, 55.2, 56.0, 60.4, 65.9, 67.7, 68.6, 69.8, 72.4, 74.4, 75.4, 76.2, 76.6, 77.2, 77.9, 78.6, 79.1, 101.4, 102.7, 109.6, 110.2, 113.6, 113.8, 126.0, 126.1, 127.5, 127.6, 128.2, 128.3, 128.9, 129.7, 130.2, 130.5, 137.6, 138.3, 159.2. MS (FAB) m/z (%): 789 (M+Na$^+$, 8), 121 (100); HRMS (FAB) calcd for C$_{42}$H$_{54}$O$_{13}$Na (M+Na$^+$): 789.3462. found: 789.3468.

(2) In the same manner as Preparation Example 1 (2) was treated 0.340 g of a compound obtained in the above-described (1) to obtain 0.266 g of a compound (1,2:3,4-di-O-isopropylidene-5-O-methoxymethyl-D-glucitol-6-yl 3-O-benzyl-4,6-O-benzylidene-β-D-mannopyranoside). Yield was 92%.

Physical and spectroscopic constants of the obtained compound were as follows.

$[α]^{25}{}_D$ +12.3 (c 1.10, CHCl$_3$); IR (neat) cm$^{-1}$: 3480, 1250; $^1$H NMR (700 MHz, CDCl$_3$) δ. 1.40 (s), 1.43 (s), 1.44 (s), 2.86 (brs), 3.35 (ddd, J=10.2, 9.8, 4.8 Hz), 3.39 (s), 3.63 (dd, J=9.5, 3.2 Hz), 3.69 (dd, J=10.9, 6.4 Hz), 3.87 (dd, J=10.2, 9.8 Hz), 3.88 (ddd, J=6.4, 6.0, 3.2 Hz), 3.92 (dd, J=8.2, 7.0 Hz), 4.03 (dd, J=7.0, 5.4 Hz), 4.04 (dd, J=5.4, 4.0 Hz), 4.06 (dd, J=7.0, 6.0 Hz), 4.14 (dd, J=10.9, 3.2 Hz), 4.14 (dd, J=3.2, 1.0 Hz), 4.16 (dd, J=10.2, 9.5 Hz), 4.19 (ddd, J=8.2, 7.0, 4.0 Hz), 4.31 (dd, J=10.2, 4.8 Hz), 4.55 (d, J=1.0 Hz), 4.71 (d, J=6.8 Hz), 4.79 (d, J=12.4 Hz), 4.80 (d, J=6.8 Hz), 4.86 (d, J=12.4 Hz), 5.60 (s), 7.26-7.40 (m), 7.49-7.51 (m); $^{13}$C NMR (175 MHz, CDCl$_3$) δ: 25.6, 26.3, 27.1, 27.3, 56.0, 65.9, 67.0, 68.6, 69.4, 69.8, 72.5, 75.9, 76.5, 76.6, 77.2, 78.4, 78.7, 96.7, 100.9, 101.6 109.7, 110.0 126.0, 127.8, 127.9, 128.2, 128.4, 128.9, 137.4, 138.0. MS (FAB) m/z (%): 669 (M+Na$^+$, 57), 91 (100); HRMS (FAB) calcd for C$_{34}$H$_{46}$O$_{12}$Na (M+Na$^+$): 669.2887. found: 669.2866.

(3) In the same manner as Preparation Example 1 (3) was treated 0.247 g of a compound obtained in the above-described (2) to obtain 0.250 g of a compound (1,2:3,4-di-O-isopropylidene-5-O-methoxymethyl-D-glucitol-6-yl 3-O-benzyl-4,6-O-benzylidene-2-O-octanoyl-β-D-mannopyranoside). Yield was 84%.

Physical and spectroscopic constants of the obtained compound were as follows.

$[α]^{25}{}_D$ −29.7 (c 1.14, CHCl$_3$); IR (neat) cm$^{-1}$: 1744, 1250; $^1$H NMR (400 MHz, CDCl$_3$) δ. 0.87 (t, J=6.4 Hz), 1.24-1.33 (m), 1.386 (s), 1.392 (s), 1.43 (s), 1.44 (s), 1.66 (tt, J=7.6, 7.6 Hz), 2.44 (t, J=7.6 Hz), 3.37 (s), 3.38 (ddd, J=10.0, 8.0, 5.2 Hz), 3.62 (dd, J=10.0, 6.8 Hz), 3.72 (dd, J=9.6, 3.2 Hz), 3.81 (ddd, J=6.8, 6.8, 2.8 Hz), 3.87 (dd, J=7.6, 6.4 Hz), 3.89 (dd, J=10.4, 8.0 Hz), 3.98 (dd, J=10.0, 2.8 Hz), 4.02 (dd, J=8.8, 6.4 Hz), 4.03 (dd, J=8.8, 2.4 Hz), 4.11 (dd, J=7.6, 6.8 Hz), 4.16 (ddd, J=6.4, 6.4, 2.4 Hz), 4.15-4.20 (m), 4.32 (dd, J=10.4, 5.2 Hz), 4.62 (s), 4.63 (d, J=12.4 Hz), 4.65 (d, J=6.8 Hz), 4.73 (d, J=12.4 Hz), 4.78 (d, J=6.8 Hz), 5.61 (s), 5.67 (d, J=3.2 Hz), 7.28-7.41 (m), 7.49-7.51 (m); $^{13}$C NMR (100 MHz, CDCl$_3$) δ: 14.0, 22.6, 25.0, 25.7, 26.3, 27.2, 27.4, 28.95, 29.02, 31.7, 34.1, 56.0, 65.9, 67.3, 68.4, 68.5, 70.8, 71.7, 75.6, 76.2, 76.7 78.0, 79.1, 96.8, 100.2, 101.6, 109.6, 110.2, 126.1, 127.7, 128.2, 128.3, 129.0, 137.3, 137.7, 173.1. MS (FAB) m/z (%): 795 (M+Na$^+$, 14), 91 (100); HRMS (FAB) calcd for C$_{42}$H$_{60}$O$_{13}$Na (M+Na$^+$): 795.3932. found: 795.3943.

(4) In the same manner as Preparation Example 1 (4) was treated 0.219 g of a compound obtained in the above-described (3) to obtain 0.150 g of a compound (1,2:3,4-di-O-isopropylidene-5-O-methoxymethyl-D-glucitol-6-yl 2-O-octanoyl-β-D-mannopyranoside). Yield was 90%.

Physical and spectroscopic constants of the obtained compound were as follows.

$[α]^{25}{}_D$ −6.52 (c 1.00, CHCl$_3$); IR (neat) cm$^{-1}$: 3418, 1744, 1250; $^1$H NMR (400 MHz, CD$_3$OD) δ. 0.83 (t, J=6.8 Hz), 1.22-1.26 (m), 1.28 (s), 1.31 (s), 1.32 (s), 1.33 (s), 1.56 (tt, J=7.6, 7.2 Hz), 2.31 (t, J=7.2 Hz), 3.21 (ddd, J=9.2, 6.4, 2.4 Hz), 3.30 (s), 3.44 (dd, J=9.2, 9.2 Hz), 3.55 (dd, J=10.4, 6.4 Hz), 3.58 (dd, J=9.2, 3.6 Hz), 3.63 (dd, J=11.6, 6.4 Hz), 3.75 (ddd, J=6.4, 6.0, 3.2 Hz), 3.82 (dd, J=7.2, 7.2 Hz), 3.84 (dd, J=11.6, 2.4 Hz), 3.96 (dd, J=7.2, 2.4 Hz), 3.98 (dd, J=7.6, 6.8 Hz), 3.98 (dd, J=6.8, 6.0 Hz), 4.19 (dd, J=10.4, 3.2 Hz), 4.16 (ddd, J=7.6, 7.2, 2.4 Hz), 4.57 (d, J=6.8 Hz), 4.60 (d, J=0.8 Hz), 4.75 (d, J=6.8 Hz), 5.28 (dd, J=3.6, 0.8 Hz); $^{13}$C NMR (100 MHz, CD$_3$OD) δ: 14.4, 23.7, 26.0, 26.1, 26.6, 27.5, 27.7, 30.2, 32.9, 35.1, 56.4, 63.0, 67.0, 69.0, 71.1, 72.9, 73.5, 77.0, 77.9, 78.0, 78.5, 79.6, 97.8, 100.8, 110.6, 111.0, 175.1. MS (FAB) m/z (%): 617 (M+Na$^+$, 33), 55 (100); HRMS (FAB) calcd for C$_{28}$H$_{50}$O$_{13}$Na (M+Na$^+$): 617.3149. found: 617.3171.

(5) In the same manner as Preparation Example 1 (5) was treated 130 mg of a compound obtained in the above-described (4) to obtain 101 mg of a compound (1,2:3,4-di-O-isopropylidene-5-O-methoxymethyl-D-glucitol-6-yl 3,4, 6-tri-O-hexanoyl-2-O-octanoyl-β-D-mannopyranoside). Yield was 51%.

Physical and spectroscopic constants of the obtained compound were as follows.

$[α]^{25}{}_D$ −4.47 (c 0.96, CHCl$_3$); IR (neat) cm$^{-1}$: 1748, 1246; $^1$H NMR (400 MHz, CDCl$_3$) δ. 0.86-0.92 (m, 12H, CH$_3$), 1.23-1.32 (m, 20H, CH$_2$), 1.38 (s), 1.39 (s), 1.42 (s), 1.43 (s), 1.50-1.67 (m), 2.18 (dt, J=15.2, 7.6 Hz), 2.22 (dt, J=15.2, 7.6 Hz), 2.23 (dt, J=15.6, 7.6 Hz), 2.29 (dt, J=15.6, 7.6 Hz), 2.33 (t, J=7.6 Hz), 2.40 (dt, J=16.0, 8.0 Hz), 2.44 (dt, J=16.0, 8.0 Hz), 3.36 (s), 3.62 (dd, J=10.4, 6.8 Hz), 3.66 (ddd, J=9.6, 5.6, 2.4 Hz), 3.80 (ddd, J=6.8, 6.8, 3.2 Hz), 3.88 (dd, J=7.6, 7.6 Hz), 3.96 (dd, J=7.6, 6.4 Hz), 4.01 (dd, J=8.4, 6.8 Hz), 4.01 (dd, J=8.4, 4.8 Hz), 4.14-4.20 (m), 4.24 (dd, J=12.4, 5.6 Hz), 4.64 (d, J=6.8 Hz), 4.68 (s), 4.75 (d, J=6.8 Hz), 5.06

(dd, J=10.4, 2.8 Hz), 5.27 (dd, J=12.4, 9.6 Hz), 5.51 (d, J=2.8 Hz); $^{13}$C NMR (100 MHz, CDCl$_3$) δ: 13.8, 13.9, 14.0, 22.2, 22.3, 22.6, 24.3, 24.43, 24.48, 25.0, 25.6, 26.3, 27.1, 27.4, 28.98, 29.03, 31.2, 31.3, 31.7, 33.94, 33.97, 34.0, 34.1, 55.9, 62.4 65.78, 65.84, 68.4, 70.5, 70.9, 72.6, 76.1, 76.6, 77.3, 78.9, 96.7, 99.2, 109.6, 110.2, 172.3, 172.7, 172.9, 173.4. MS (FAB) m/z (%): 911 (M+Na$^+$, 19), 99 (100); HRMS (FAB) calcd for C$_{46}$H$_{80}$O$_{16}$Na (M+Na$^+$): 911.5344. found: 911.5341.

(6) In the same manner as Preparation Example 1 (6) was treated 83 mg of a compound obtained in the above-described (5) to obtain 47 mg of a compound (D-glucitol-6-yl 3,4,6-tri-O-hexanoyl-2-O-octanoyl-β-D-mannopyranoside). Yield was 67%.

Physical and spectroscopic constants of the obtained compound were as follows.

$[α]^{25}_D$ −4.85 (c 1.01, CHCl$_3$); IR (neat) cm$^{-1}$: 3391, 1748, 1246; $^1$H NMR (700 MHz, CD$_3$OD) δ. 0.89-0.93 (m), 1.24-1.42 (m), 1.52-1.59 (m), 1.62-1.70 (m), 2.19 (dt, J=14.4, 7.6 Hz), 2.21 (dt, J=14.4, 7.6 Hz), 2.27 (dt, J=15.8, 7.4 Hz), 2.31 (dt, J=15.8, 7.4 Hz), 2.34 (dt, J=15.6, 8.1 Hz), 2.37 (dt, J=15.6, 8.1 Hz), 2.40 (dt, J=15.4, 7.2 Hz), 2.47 (dt, J=15.4, 7.2 Hz), 3.57 (dd, J=8.8, 2.0 Hz), 3.58 (dd, J=11.8, 6.0 Hz), 3.66 (dd, J=10.6, 2.8 Hz), 3.67 (dd, J=11.8, 6.0 Hz), 3.74 (dd, J=6.0, 6.0, 4.8 Hz), 3.80 (ddd, J=8.8, 6.4, 2.8 Hz), 3.82 (ddd, J=9.8, 4.2, 2.2 Hz), 3.83 (dd, J=4.8, 2.0 Hz), 4.10 (dd, J=10.6, 6.4 Hz), 4.14 (dd, J=12.2, 2.2 Hz), 4.28 (dd, J=12.2, 4.2 Hz), 4.91 (d, J=0.8 Hz), 5.16 (dd, J=10.0, 3.2 Hz), 5.29 (dd, J=10.0, 9.8 Hz), 5.50 (dd, J=3.2, 0.8 Hz); $^{13}$C NMR (175 MHz, CD$_3$OD) δ: 14.2, 14.3, 14.5, 23.36, 23.38, 23.42, 23.8, 25.5, 25.60, 25.62, 26.4, 30.2, 30.3, 32.3, 32.4 32.5, 33.0, 34.8, 34.9, 35.0, 35.2, 63.1, 64.2, 66.8, 70.5, 70.6, 71.7, 72.7, 73.37, 73.39, 73.5, 75.1, 100.6, 173.77, 173.84, 174.8, 175.0. MS (FAB) m/z (%): 787 (M+Na$^+$, 4), 99 (100); HRMS (FAB) calcd for C$_{38}$H$_{68}$O$_{15}$Na (M+Na$^+$): 787.4456. found: 787.4442.

Preparation Example 19

(1) Treatment in the same manner as Preparation Example 1 (1) was performed using 0.500 g of a mannosyl sulfoxide compound of Reference Example 1 and 0.384 g of an alcohol (4-O-tert-butyldimethylsilyl-2,3:5,6-di-O-isopropylidene-L-glucitol) to obtain 0.424 g of a compound (4-O-tert-butyldimethylsilyl-2,3:5,6-di-O-isopropylidene-L-glucitol-1-yl 3-O-benzyl-4,6-O-benzylidene-2-O-p-methoxybenzyl-β-D-mannopyranoside). Yield was 59%.

Physical and spectroscopic constants of the obtained compound were as follows.

$[α]^{25}_D$ −54.8 (c 1.13, CHCl$_3$); IR (neat) cm$^{-1}$: 1250; $^1$H NMR (500 MHz, CDCl$_3$) δ. 0.12 (s), 0.13 (s), 0.91 (s), 1.33 (s), 1.38 (s), 1.41 (s), 1.42 (s), 3.32 (ddd, J=10.3, 9.7, 4.9 Hz), 3.58 (dd, J=9.7, 3.5 Hz), 3.62 (dd, J=10.9, 7.2 Hz), 3.78 (dd, J=8.1, 4.0 Hz), 3.80 (s), 3.90 (dd, J=8.1, 8.0 Hz), 3.91 (dd, J=8.6, 4.0 Hz), 3.92 (dd, J=10.3, 10.3 Hz), 3.99 (d, J=3.5 Hz), 4.00 (dd, J=8.1, 4.9 Hz), 4.07 (dd, J=10.9, 2.9 Hz), 4.12 (ddd, J=8.6, 8.0, 4.9 Hz), 4.19 (dd, J=9.7, 9.7 Hz), 4.23 (ddd, J=8.1, 7.2, 2.9 Hz), 4.29 (dd, J=10.3, 4.9 Hz), 4.57 (s), 4.57 (d, J=12.6 Hz), 4.67 (d, J=12.6 Hz), 4.81 (d, J=11.8 Hz), 4.91 (d, J=11.8 Hz), 5.61 (s), 6.83-6.86 (m), 7.25-7.32 (m), 7.33-7.40 (m), 7.49-7.51 (m); $^{13}$C NMR (125 MHz, CDCl$_3$) δ: −4.12, −3.92, 18.3, 25.1, 26.0, 26.5, 26.9, 27.3, 55.2, 66.1, 67.7, 68.5, 70.9, 72.22, 72.24, 74.3, 75.3, 76.3, 76.7, 77.7, 78.6, 79.8, 101.4, 102.4, 108.5, 109.3, 113.5, 126.0, 127.50, 127.52, 128.2, 128.3, 128.8, 130.1, 130.6, 137.5, 138.3, 159.1. MS (FAB) m/z (%): 859 (M+Na$^+$, 10), 73 (100); HRMS (FAB) calcd for C$_{46}$H$_{64}$O$_{12}$SiNa (M+Na$^+$): 859.4065. found: 859.4092.

(2) In the same manner as Preparation Example 1 (2) was treated 402 mg of a compound obtained in the above-described (1) to obtain 295 mg of a compound (4-O-tert-butyldimethylsilyl-2,3:5,6-di-O-isopropylidene-L-glucitol-1-yl 3-O-benzyl-4,6-O-benzylidene-β-D-mannopyranoside). Yield was 86%.

Physical and spectroscopic constants of the obtained compound were as follows.

$[α]^{25}_D$ −12.8 (c 1.07, CHCl$_3$); IR (neat) cm$^{-1}$: 3483, 1254; $^1$H NMR (400 MHz, CDCl$_3$) δ. 0.10 (s), 0.13 (s), 0.90 (s), 1.32 (s), 1.38 (s), 1.39 (s), 1.42 (s), 2.55 (brs), 3.34 (ddd, J=10.0, 9.6, 4.8 Hz), 3.64 (dd, J=9.6, 3.2 Hz), 3.68 (dd, J=10.4, 7.2 Hz), 3.71 (dd, J=8.0, 4.0 Hz), 3.88 (dd, J=10.0, 7.6 Hz), 3.88 (dd, J=10.0, 10.0 Hz), 3.90 (dd, J=7.6, 4.0 Hz), 4.31 (dd, J=10.0, 4.8 Hz), 4.04 (dd, J=10.4, 3.6 Hz), 4.10 (ddd, J=7.6, 7.6, 4.8 Hz), 4.16 (dd, J=9.6, 9.6 Hz), 4.18 (dd, J=3.2, 0.9 Hz), 4.21 (ddd, J=8.0, 7.2, 3.6 Hz), 4.31 (dd, J=10.0, 4.8 Hz), 4.61 (d, J=0.9 Hz), 4.78 (d, J=12.4 Hz), 4.86 (d, J=12.4 Hz), 5.61 (s), 7.24-7.41 (m), 7.49-7.51 (m); $^{13}$C NMR (100 MHz, CDCl$_3$) δ: −4.27, −3.99, 18.3, 25.1, 26.0, 26.4, 26.9, 27.1, 66.1, 67.0, 68.6, 69.7, 70.7, 72.4, 76.0, 76.5, 78.4, 80.1, 100.4, 101.5, 108.6, 109.3, 126.0, 127.8, 127.9, 128.2, 128.4, 128.9, 137.4, 138.0. MS (FAB) m/z (%): 739 (M+Na$^+$, 100), 73 (100); HRMS (FAB) calcd for C$_{38}$H$_{56}$O$_{11}$SiNa (M+Na$^+$): 739.3490. found: 739.3505.

(3) In the same manner as Preparation Example 1 (3) was treated 275 mg of a compound obtained in the above-described (2) to obtain 313 mg of a compound (4-O-tert-butyldimethylsilyl-2,3:5,6-di-O-isopropylidene-L-glucitol-1-yl 3-O-benzyl-4,6-O-benzylidene-2-O-octanoyl-β-D-mannopyranoside). Yield was 97%.

Physical and spectroscopic constants of the obtained compound were as follows.

$[α]^{25}_D$ −43.8 (c 0.97, CHCl$_3$); IR (neat) cm$^{-1}$: 1744, 1254; $^1$H NMR (400 MHz, CDCl$_3$) δ. 0.09 (s), 0.13 (s), 0.87 (t, J=6.8 Hz), 0.90 (s), 1.24-1.29 (m), 1.32 (s), 1.34 (s), 1.39 (s), 1.41 (s), 1.16 (tt, J=7.6, 7.6 Hz), 2.44 (t, J=7.6 Hz), 3.38 (ddd, J=9.6, 9.6, 4.8 Hz), 3.68 (dd, J=10.4, 5.6 Hz), 3.72 (dd, J=9.6, 3.2 Hz), 3.79 (dd, J=9.2, 6.0 Hz), 3.86 (dd, J=8.4, 6.0 Hz), 3.89 (dd, J=6.0, 6.0 Hz), 3.89 (dd, J=10.4, 9.6 Hz), 3.96 (dd, J=8.4, 4.4 Hz), 3.97 (dd, J=9.6, 9.6 Hz), 3.98 (dd, J=10.4, 9.2 Hz), 4.10 (ddd, J=6.0, 6.0, 4.4 Hz), 4.12 (ddd, J=9.2, 9.2, 5.6 Hz), 4.32 (dd, J=10.4, 4.8 Hz), 4.63 (d, J=12.4 Hz), 4.71 (s), 4.74 (d, J=12.4 Hz), 5.61 (s), 5.70 (dd, J=3.2 Hz), 7.27-7.41 (m), 7.49-7.52 (m); $^{13}$C NMR (100 MHz, CDCl$_3$) δ: −4.18, −4.03, 14.1, 18.3, 22.6, 24.9, 25.1, 26.0, 26.5, 26.9, 27.0, 28.96, 29.03, 31.7, 34.1, 66.0, 67.4, 68.3, 68.5, 70.4, 71.5, 72.1, 75.7, 75.9, 76.8, 77.9, 79.9, 99.7, 101.5, 108.4, 109.2, 126.1, 127.67, 127.71, 128.2, 128.3, 128.9, 137.3, 137.7, 173.0. MS (FAB) m/z (%): 865 (M+Na$^+$, 12), 57 (100); HRMS (FAB) calcd for C$_{46}$H$_{70}$O$_{12}$SiNa (M+Na$^+$): 865.4534. found: 865.4508.

(4) In the same manner as Preparation Example 1 (4) was treated 278 mg of a compound obtained in the above-described (3) to obtain 142 mg of a compound (4-O-tert-butyldimethylsilyl-2,3:5,6-di-O-isopropylidene-L-glucitol-1-yl 2-O-octanoyl-β-D-mannopyranoside).

Physical and spectroscopic constants of the obtained compound were as follows.

$[α]^{25}_D$ −25.4 (c 1.04, CHCl$_3$); IR (neat) cm$^{-1}$: 3402, 1743, 1254; $^1$H NMR (400 MHz, CD$_3$OD) δ. 0.10 (s), 0.13 (s), 0.89 (t, J=8.0 Hz), 0.91 (s), 1.30-1.38 (m), 1.297 (s), 1.303 (s), 1.34 (s), 1.38 (s), 1.62 (ddt, J=7.6, 7.6, 7.2 Hz), 2.34 (t, J=16.0, 7.6 Hz), 2.39 (t, J=16.0, 7.6 Hz), 3.25 (ddd, J=9.6, 5.6, 2.4 Hz), 3.48 (dd, J=9.6, 9.6 Hz), 3.62 (dd, J=9.6, 3.2 Hz), 3.68 (dd, J=12.8, 5.6 Hz), 3.69 (dd, J=10.8, 5.6 Hz), 3.86-3.95 (m), 4.10-4.17 (m), 3.98 (dd, J=10.8, 4.8 Hz), 4.10-4.17 (m), 4.68 (s), 5.34 (dd, J=3.2 Hz); $^{13}$C NMR (100 MHz, CD$_3$OD) δ: -3.66, -3.53, 14.4, 19.2, 23.7, 25.3, 26.0, 26.6, 26.9, 27.4, 27.4, 30.21, 30.23, 32.9, 35.1, 62.9, 66.6, 69.0, 70.9, 72.6, 72.7, 73.6, 76.7, 78.6, 78.7, 81.4, 100.5, 109.5, 110.3, 174.8. MS (FAB) m/z (%): 687 (M+Na$^+$, 100), 687 (100); HRMS (FAB) calcd for C$_{32}$H$_{60}$O$_{12}$SiNa (M+Na$^+$): 687.3752. found: 687.3741.

(5) In the same manner as Preparation Example 1 (5) was treated 122 mg of a compound obtained in the above-described (4) to obtain 170 mg of a compound (4-O-tert-butyldimethylsilyl-2,3:5,6-di-O-isopropylidene-L-glucitol-1-yl 3,4,6-tri-O-hexanoyl-2-O-octanoyl-β-D-mannopyranoside).

Physical and spectroscopic constants of the obtained compound were as follows.

$[α]^{25}{}_D$ -23.5 (c 1.08, CHCl$_3$); IR (neat) cm$^{-1}$: 1748, 1250; $^1$H NMR (400 MHz, CDCl$_3$) δ. 0.07 (s), 0.11 (s), 0.86-0.92 (m), 0.89 (s), 1.24-1.33 (m), 1.31 (s), 1.38 (s), 1.40 (s), 1.51-1.68 (m), 2.17 (dt), 2.22 (dt, J=16.0, 7.6 Hz), 2.23 (dt, J=15.6, 8.0 Hz), 2.28 (dt, J=15.6, 8.0 Hz), 2.33 (dt, J=14.0, 7.2 Hz), 2.34 (dt, J=14.0, 7.2 Hz), 2.39 (dt, J=16.0, 7.6 Hz), 2.44 (dt, J=16.0, 7.6 Hz), 3.65 (ddd, J=10.0, 5.6, 2.4 Hz), 3.62 (dd, J=11.2, 6.0 Hz), 3.77 (dd, J=8.0, 4.0 Hz), 3.83 (dd, J=6.4, 4.4 Hz), 3.88 (dd, J=7.2, 6.4 Hz), 3.95 (dd, J=11.2, 4.8 Hz), 3.98 (dd, J=8.0, 6.4 Hz), 4.08 (ddd, J=7.2, 6.0, 4.8 Hz), 4.14 (ddd, J=6.4, 4.4, 4.0 Hz), 4.17 (dd, J=12.0, 2.4 Hz), 4.24 (dd, J=12.0, 5.6 Hz), 4.79 (d, J=0.8 Hz), 5.06 (dd, J=10.0, 3.6 Hz), 5.26 (dd, J=10.0, 10.0 Hz), 5.52 (dd, J=3.6, 0.8 Hz); $^{13}$C NMR (100 MHz, CDCl$_3$) δ: -4.21, -4.03, 13.8, 13.9, 14.1, 18.3, 22.2, 22.3, 22.6, 24.2, 24.4, 24.5, 25.0, 25.1, 26.0, 26.4, 26.9, 27.0, 28.98, 29.04, 31.2, 31.3, 31.7, 33.9, 34.0, 62.4, 65.8, 66.1, 68.4, 70.3, 71.0, 72.2, 72.6, 75.8, 76.8, 80.1, 98.5, 108.5, 109.3, 172.7, 172.9, 173.4. MS (FAB) m/z (%): 981 (M+Na$^+$, 3), 99 (100); HRMS (FAB) calcd for C$_{50}$H$_{90}$O$_{15}$SiNa (M+Na$^+$): 981.5947. found: 981.5958.

(6) In the same manner as Preparation Example 1 (6) was treated 112 mg of a compound obtained in the above-described (5) to obtain 63.0 mg of L-glycitol-1-yl 3,4,6-tri-O-hexanoyl-2-O-octanoyl-β-D-mannopyranoside. Yield was 71%.

Physical and spectroscopic constants of the obtained compound were as follows.

$[α]^{25}{}_D$ -15.5 (c 0.55, CHCl$_3$); IR (neat) cm$^{-1}$: 3418, 1744, 1246; $^1$H NMR (500 MHz, CD$_3$OD) δ. 0.890 (t), 0.895 (t), 0.91 (t), 0.92 (t), 1.22-1.40 (m), 1.51-1.60 (m), 1.61-1.70 (m), 2.18 (dt, J=14.9, 7.5 Hz), 2.11 (dt, J=14.9, 7.5 Hz), 2.26 (dt, J=15.8, 7.4 Hz), 2.31 (dt, J=15.8, 7.4 Hz), 2.33 (dt, J=15.5, 7.5 Hz), 2.37 (dt, J=15.5, 7.5 Hz), 2.39 (dt, J=15.5, 7.2 Hz), 2.47 (dt, J=15.5, 7.2 Hz), 3.60 (dd, J=6.0, 2.1 Hz), 3.63 (dd, J=11.2, 8.1 Hz), 3.66 (dd, J=10.6, 6.6 Hz), 3.67 (ddd, J=8.1, 6.0, 3.5 Hz), 3.76 (dd, J=11.2, 3.5 Hz), 3.78 (dd, J=4.6, 2.1 Hz), 3.82 (ddd, J=10.0, 4.3, 2.0 Hz), 3.89 (ddd, J=6.6, 4.6, 4.6 Hz), 3.97 (dd, J=10.6, 4.6 Hz), 4.14 (dd, J=12.4, 2.0 Hz), 4.28 (dd, J=12.4, 4.3 Hz), 4.91 (d, J=0.9 Hz), 5.16 (dd, J=10.1, 3.2 Hz), 5.29 (dd, J=10.1, 10.0 Hz), 5.49 (dd, J=3.2, 0.9 Hz); $^{13}$C NMR (125 MHz, CD$_3$OD) δ: 14.2, 14.3, 14.5, 23.37, 23.39, 23.43, 23.8, 25.5, 25.58, 25.62, 26.4, 30.2, 30.3, 32.3, 32.4, 32.5, 33.0, 34.8, 34.9, 35.0, 35.2, 63.0, 64.8, 66.8, 70.5, 71.0, 72.66, 72.68, 73.0, 73.4, 73.57, 73.65, 100.3, 173.7, 173.8, 174.7, 175.0.

MS (FAB) m/z (%): 787 (M+Na$^+$, 100), 787 (100); HRMS (FAB) calcd for C$_{38}$H$_{68}$O$_{15}$Na (M+Na$^+$): 787.4456. found: 787.4432.

Preparation Example 20

(1) Treatment in the same manner as Preparation Example 1 (1) was performed using 0.529 g of a mannosyl sulfoxide compound of Reference Example 1 and 0.252 g of an alcohol (2,3:4,5-di-O-isopropylidene-L-arabinitol) to obtain 0.380 g of a compound (2,3:4,5-di-O-isopropylidene-L-arabinitol-1-yl 3-O-benzyl-4,6-O-benzylidene-2-O-p-methoxybenzyl-β-D-mannopyranoside). Yield was 61%.

Physical and spectroscopic constants of the obtained compound were as follows.

$[α]^{25}{}_D$ -50.8 (c 0.88, CHCl$_3$); IR (neat) cm$^{-1}$: 1250; $^1$H NMR (500 MHz, CDCl$_3$) δ. 1.32 (s), 1.33 (s), 1.37 (s), 1.42 (s), 3.32 (ddd, J=10.3, 9.5, 4.9 Hz), 3.56 (dd, J=9.8, 2.9 Hz), 3.80 (s), 3.878 (dd, J=9.2, 2.6 Hz), 3.880 (dd, J=13.2, 4.1 Hz), 3.92 (dd, J=10.4, 10.3 Hz), 3.95 (d, J=2.9 Hz), 3.98 (dd, J=8.3, 4.3 Hz) 4.04 (dd, J=13.2, 3.5 Hz), 4.06 (ddd, J=4.1, 3.5, 2.6 Hz), 4.08 (ddd, J=9.2, 6.0, 4.3 Hz), 4.13 (dd, J=8.3, 6.0 Hz), 4.19 (dd, J=9.8, 9.5 Hz), 4.28 (dd, J=10.4, 4.9 Hz), 4.57 (s), 4.59 (d, J=12.6 Hz), 4.69 (d, J=12.6 Hz), 4.81 (d, J=11.7 Hz), 4.91 (d, J=11.7 Hz), 5.61 (s), 6.85-6.87 (m), 7.25-7.31 (m), 7.33-7.40 (m), 7.48-7.50 (m); $^{13}$C NMR (125 MHz, CDCl$_3$) δ: 25.2, 26.8, 26.97, 27.05, 29.3, 55.2, 67.5, 67.6, 68.4, 68.6, 72.4, 74.3, 75.3, 77.8, 78.6, 79.5, 101.4, 102.6, 109.3, 109.7, 113.5, 126.0, 127.5, 128.2, 128.3, 128.8, 130.1, 130.5, 137.6, 138.3, 159.2. MS (FAB) m/z (%): 715 (M+Na$^+$, 22), 121 (100); HRMS (FAB) calcd for C$_{39}$H$_{48}$O$_{11}$Na (M+Na$^+$): 715.3094. found: 715.3091.

(2) In the same manner as Preparation Example 1 (2) was treated 356 mg of a compound obtained in the above-described (1) to obtain 259 mg of a compound (2,3:4,5-di-O-isopropylidene-L-arabinitol-1-yl 3-O-benzyl-4,6-O-benzylidene-β-D-mannopyranoside). Yield was 86%.

Physical and spectroscopic constants of the obtained compound were as follows.

$[α]^{25}{}_D$ -19.8 (c 1.11, CHCl$_3$); IR (neat) cm$^{-1}$: 3480, 1246 (C—O); $^1$H NMR (400 MHz, CDCl$_3$) δ. 1.33 (s), 1.37 (s), 1.41 (s), 2.26 (brs), 3.35 (ddd, J=10.0, 9.2, 4.8 Hz), 3.62 (dd, J=9.6, 3.2 Hz), 3.81 (dd, J=8.0, 8.0 Hz), 3.88 (dd, J=10.4, 10.0 Hz), 3.89 (dd, J=11.6, 3.2 Hz), 3.96 (dd, J=8.4, 4.8 Hz), 4.01 (dd, J=11.6, 4.0 Hz), 4.07 (ddd, J=8.0, 8.0, 4.8 Hz), 4.11 (dd, J=8.4, 8.0 Hz), 4.14 (ddd, J=8.0, 4.0, 3.2 Hz), 4.15 (d, J=3.2 Hz), 4.16 (dd, J=9.6, 9.2 Hz), 4.31 (dd, J=10.4, 4.8 Hz), 4.61 (s), 4.78 (d, J=12.8 Hz), 4.86 (d, J=12.8 Hz), 5.60 (s), 7.28-7.41 (m), 7.48-7.51 (m); $^{13}$C NMR (100 MHz, CDCl$_3$) δ: 25.2, 26.7, 26.96, 26.99, 67.0, 67.6, 68.6, 68.9, 69.9, 72.5, 76.5, 77.1, 77.6, 78.4, 79.3, 100.6, 101.5, 109.7, 109.8, 126.0, 127.8, 127.9, 128.2, 128.4, 128.9, 137.5, 138.0. MS (FAB) m/z (%): 595 (M+Na$^+$, 7), 73 (100); HRMS (FAB) calcd for C$_{31}$H$_{40}$O$_{10}$Na (M+Na$^+$): 595.2519. found: 595.2548.

(3) In the same manner as Preparation Example 1 (3) was treated 232 mg of a compound obtained in the above-described (2) to obtain 285 mg of a compound (2,3:4,5-di-O-isopropylidene-L-arabinitol-1-yl 3-O-benzyl-4,6-O-benzylidene-2-O-octanoyl-β-D-mannopyranoside).

Physical and spectroscopic constants of the obtained compound were as follows.

$[α]^{25}{}_D$ -43.7 (c 1.25, CHCl$_3$); IR (neat) cm$^{-1}$: 1744, 1250; $^1$H NMR (400 MHz, CDCl$_3$) δ. 0.87 (t, J=6.4 Hz), 1.24-1.31 (m), 1.33 (s), 1.37 (s), 1.386 (s), 1.389 (s), 1.66 (tdd, J=7.2, 6.8, 6.8 Hz), 2.44 (t, J=6.8 Hz), 2.45 (t, J=6.8 Hz), 3.37 (ddd, J=10.6, 9.6, 4.8 Hz), 3.70 (dd, J=10.0, 3.2 Hz), 3.85 (dd, J=8.0, 8.0 Hz), 3.88 (dd, J=10.4, 10.0 Hz), 3.89 (dd, J=11.2, 4.0 Hz), 3.96 (dd, J=8.4, 4.4 Hz), 3.98 (dd, J=11.2, 4.4 Hz), 4.01 (dt, J=8.0, 4.4, 4.0 Hz), 4.05 (ddd, J=8.0, 6.0, 4.4 Hz), 4.11 (dd, J=8.4, 6.0 Hz), 4.13 (dd, J=10.0, 9.6 Hz), 4.31 (dd, J=10.4, 4.8 Hz), 4.63 (d, J=12.4 Hz), 4.71 (s), 4.73 (d, J=12.4 Hz), 5.61 (s), 5.70 (d, J=3.2 Hz), 7.27-7.41 (m), 7.49-7.51 (m); $^{13}$C NMR (100 MHz, CDCl$_3$) δ: 14.1, 22.6, 25.0, 25.3, 26.6, 26.8, 27.0, 28.95, 29.03, 31.7, 34.1, 67.2, 67.5, 68.4, 68.5, 71.6, 75.5, 76.5, 77.1, 78.0, 79.4, 100.0, 101.5, 109.5, 109.6, 126.1, 127.71, 127.75, 128.2, 128.3, 128.9, 137.4, 137.7, 173.1. MS (FAB) m/z (%): 721 (M+Na$^+$, 3), 91 (100); HRMS (FAB) calcd for C$_{39}$H$_{54}$O$_{11}$Na (M+Na$^+$): 721.3564. found: 721.3592.

(4) In the same manner as Preparation Example 1 (4) was treated 253 mg of a compound obtained in the above-described (3) to obtain 169 mg of a compound (2,3:4,5-di-O-isopropylidene-L-arabinitol-1-yl 2-O-octanoyl-β-D-mannopyranoside).

Physical and spectroscopic constants of the obtained compound were as follows.

$[α]^{25}_D$ −36.9 (c 1.04, CHCl$_3$); IR (neat) cm$^{-1}$: 3437, 1744, 1250; $^1$H NMR (400 MHz, CD$_3$OD) δ. 0.90 (t, J=7.2 Hz), 1.31-1.38 (m), 1.31 (s), 1.34 (s), 1.36 (s), 1.38 (s), 1.62 (ddt, J=7.6, 7.2, 6.4 Hz), 2.35 (dt, J=16.0, 7.2 Hz), 2.40 (dt, J=16.0, 7.6 Hz), 3.25 (ddd, J=8.8, 6.4, 2.4 Hz), 3.49 (dd, J=9.6, 8.8 Hz), 3.64 (dd, J=9.6, 3.6 Hz), 3.69 (dd, J=11.6, 6.4 Hz), 3.83 (dd, J=12.4, 4.4 Hz), 3.90 (dd, J=7.6, 4.8 Hz), 3.90 (dd, J=11.6, 2.4 Hz), 3.90 (dd, J=7.6, 6.4 Hz), 3.97 (dd, J=12.4, 3.6 Hz), 3.97 (ddd, J=7.6, 4.4, 3.6 Hz), 4.06 (dd, J=7.6, 6.4 Hz), 4.10 (ddd, J=6.4, 6.4, 4.8 Hz), 4.71 (d, J=1.2 Hz), 5.38 (dd, J=3.6, 1.2 Hz); $^{13}$C NMR (100 MHz, CD$_3$OD) δ: 14.4, 23.7, 25.5, 26.0, 27.1, 27.32, 27.35, 30.17, 30.20, 32.9, 35.1, 63.0, 67.9, 69.0, 69.6, 72.8, 73.5, 78.2, 78.6, 80.5, 100.8, 110.6, 110.8, 175.0. MS (FAB) m/z (%): 543 (M+Na$^+$, 100), 543 (100); HRMS (FAB) calcd for C$_{25}$H$_{44}$O$_{11}$Na (M+Na$^+$): 543.2781. found: 543.2805.

(5) In the same manner as Preparation Example 1 (5) was treated 147 mg of a compound obtained in the above-described (4) to obtain 220 mg of a compound (2,3:4,5-di-O-isopropylidene-L-arabinitol-1-yl 3,4,6-tri-O-hexanoyl-2-O-octanoyl-β-D-mannopyranoside).

Physical and spectroscopic constants of the obtained compound were as follows.

$[α]^{25}_D$ −35.8 (c 1.27, CHCl$_3$); IR (neat) cm$^{-1}$: 1748, 1246; $^1$H NMR (400 MHz, CDCl$_3$) δ. 0.877 (t, J=7.2 Hz), 0.882 (t, J=7.2 Hz), 0.885 (t, J=7.2 Hz), 0.90 (t, J=7.2 Hz), 1.20-1.30 (m), 1.31 (s), 1.32 (s), 1.37 (s), 1.38 (s), 1.50-1.69 (m), 2.17 (dt, J=15.6, 7.6 Hz), 2.22 (dt, J=15.6, 7.6 Hz), 2.23 (dt, J=14.8, 7.6 Hz), 2.28 (dt, J=14.8, 7.6 Hz), 2.34 (t, J=15.8, 6.8 Hz), 2.40 (dt, J=15.6, 8.4 Hz), 2.44 (dt, J=15.6, 8.0 Hz), 3.66 (ddd, J=10.0, 5.6, 2.4 Hz), 3.85 (dd, J=8.4, 8.0 Hz), 3.88 (dd, J=12.4, 3.6 Hz), 3.95 (dd, J=8.0, 4.0 Hz), 3.99 (dd, J=12.4, 6.0 Hz), 4.01 (ddd, J=8.0, 6.0, 3.6 Hz), 4.04 (ddd, J=8.0, 6.0, 4.0 Hz), 4.10 (dd, J=8.4, 6.0 Hz), 4.15 (dd, J=12.0, 2.4 Hz), 4.23 (dd, J=12.0, 5.6 Hz), 4.80 (d, J=0.8 Hz), 5.05 (dd, J=10.4, 3.2 Hz), 5.26 (dd, J=10.4, 10.0 Hz), 5.54 (dd, J=3.2, 0.8 Hz); $^{13}$C NMR (100 MHz, CDCl$_3$) δ: 13.8, 13.9, 14.1, 22.2, 22.3, 22.6, 24.3, 24.45, 24.48, 25.0, 25.3, 26.6, 26.7, 27.0, 28.95, 29.03, 31.2, 31.3, 31.7, 33.9, 34.0, 34.1, 62.5, 65.8, 67.4, 68.2, 68.4, 71.0, 72.5, 76.4, 77.01, 79.4, 99.0, 109.5, 109.6, 172.3, 172.6, 172.9, 173.4. MS (FAB) m/z (%): 837 (M+Na$^+$, 8), 99 (100); HRMS (FAB) calcd for C$_{43}$H$_{74}$O$_{14}$Na (M+Na$^+$): 837.4976. found: 837.4995.

(6) In the same manner as Preparation Example 1 (6) was treated 192 mg of a compound obtained in the above-described (5) to obtain 148 mg of L-arabinitol-1-yl 3,4,6-tri-O-hexanoyl-2-O-octanoyl-β-D-mannopyranoside. Yield was 85%.

Physical and spectroscopic constants of the obtained compound were as follows.

$[α]^{25}_D$ −28.1 (c 1.15, CHCl$_3$); IR (neat) cm$^{-1}$: 3418, 1748, 1246; $^1$H NMR (500 MHz, CD$_3$OD) δ. 0.90 (t, J=7.2 Hz), 0.91 (t, J=7.2 Hz), 0.92 (t, J=6.9 Hz), 1.22-1.40 (m), 1.50-1.60 (m), 1.62-1.70 (m), 2.18 (dt, J=15.2, 7.5 Hz), 2.21 (dt, J=15.2, 7.5 Hz), 2.26 (dt, J=15.8, 8.3 Hz), 2.31 (dt, J=15.8, 7.2 Hz), 2.34 (dt, J=16.0, 7.5 Hz), 2.37 (dt, J=16.0, 7.2 Hz), 2.39 (dt, J=15.2, 7.2 Hz), 2.46 (dt, J=15.2, 7.2 Hz), 3.49 (dd, J=8.0, 1.8 Hz), 3.60 (dd, J=11.2, 6.0 Hz), 3.68 (ddd, J=8.0, 6.0, 3.5 Hz), 3.72 (dd, J=10.1, 6.3 Hz), 3.78 (dd, J=11.2, 3.5 Hz), 3.83 (ddd, J=10.0, 4.3, 2.3 Hz), 3.88 (dd, J=10.21, 6.3 Hz), 4.00 (ddd, J=6.3, 6.3, 1.8 Hz), 4.16 (dd, J=12.3, 2.3 Hz), 4.27 (dd, J=12.3, 4.3 Hz), 4.89 (d, J=0.9 Hz), 5.16 (dd, J=10.0, 3.2 Hz), 5.29 (dd, J=10.0, 10.0 Hz), 5.46 (dd, J=3.2, 0.9 Hz); $^{13}$C NMR (125 MHz, CD$_3$OD) δ: 14.2, 14.3, 14.5, 23.37, 23.39, 23.42, 23.8, 25.5, 25.60, 25.63, 26.3, 30.2, 30.3, 32.3, 32.5, 33.0, 34.8, 34.9, 35.0, 35.2, 63.0, 65.0, 66.8, 69.6, 70.4, 72.2, 72.4, 72.7, 72.9, 73.5, 100.0, 173.77, 173.84, 174.7, 175.0. MS (FAB) m/z (%): 757 (M+Na$^+$, 100), 757 (100); HRMS (FAB) calcd for C$_{37}$H$_{66}$O$_{14}$Na (M+Na$^+$): 757.4350. found: 757.4342.

Preparation Example 21

(1) Treatment in the same manner as Preparation Example 1 (1) was performed using 0.700 g of a mannosyl sulfoxide compound of Reference Example 1 and 0.252 g of an alcohol (1,2:3,4-di-O-isopropylidene-ribitol) to obtain 0.395 g of a compound (1,2:3,4-di-O-isopropylidene-ribitol-5-yl 3-O-benzyl-4,6-O-benzylidene-2-O-p-methoxybenzyl-β-D-mannopyranoside). Yield was 48%.

Physical and spectroscopic constants of the obtained compound were as follows.

$[α]^{25}_D$ −23.4 (c 1.18, CHCl$_3$); IR (neat) cm$^{-1}$: 1246; $^1$H NMR (500 MHz, CDCl$_3$) δ. 1.29 (s), 1.30 (s), 1.34 (s), 1.35 (s), 1.38 (s), 1.41 (s), 1.43 (s), 1.47 (s), 3.31 (ddd, J=10.1, 10.1, 4.9 Hz), 3.32 (ddd, J=10.1, 9.5, 5.2 Hz), 3.56 (dd, J=9.8, 3.2 Hz), 3.57 (dd, J=9.8, 3.2 Hz), 3.67 (dd, J=11.5, 8.1 Hz), 3.77 (dd, J=10.9, 4.9 Hz), 3.79 (s$_3$), 3.89 (dd, J=8.6, 6.3 Hz), 3.899 (dd, J=8.1, 4.9 Hz), 3.91 (dd, J=3.2, 0.9 Hz), 3.91 (dd, J=10.1, 10.1 Hz), 3.91 (dd, J=10.6, 10.1 Hz), 3.98 (d, J=3.2 Hz), 3.99 (dd, J=6.3, 5.8 Hz), 4.01 (dd, J=9.5, 4.6 Hz), 4.03 (ddd, J=6.3, 6.3, 5.5 Hz), 4.04 (ddd, J=9.5, 5.7, 4.9 Hz), 4.06 (dd, J=8.6, 5.5 Hz), 4.07 (dd, J=8.1, 5.7 Hz), 4.11 (dd, J=10.9, 5.2 Hz), 4.18 (dd, J=9.8, 9.5 Hz), 4.18 (dd, J=10.1, 9.8 Hz), 4.24 (dd, J=11.5, 2.9 Hz), 4.29 (dd, J=10.1, 4.9 Hz), 4.30 (dd, J=10.6, 5.2 Hz), 4.34 (ddd, J=5.8, 5.2, 4.9 Hz), 4.41 (ddd, J=8.1, 4.6, 2.9 Hz), 4.50 (d, J=0.9 Hz), 4.58 (d, J=12.3 Hz), 5.598 (s), 4.60 (d, J=12.3 Hz), 4.90 (d, J=12.3 Hz), 4.72 (d, J=12.3 Hz), 4.78 (d, J=11.7 Hz), 4.82 (d, J=11.8 Hz), 4.88 (d, J=11.7 Hz), 4.90 (d, J=11.8 Hz), 5.59 (s), 5.599 (s), 6.81-6.84 (m), 7.23-7.28 (m), 7.31-7.40 (m), 7.47-7.49 (m); $^{13}$C NMR (125 MHz, CDCl$_3$) δ: 25.3, 25.42, 25.46, 25.53, 26.8, 27.8, 28.0, 67.6, 67.6, 67.8, 67.9, 68.1, 68.2, 68.6, 72.2, 72.3, 73.32, 73.38, 74.2, 74.3, 74.9, 75.4, 76.2, 77.5, 77.7, 78.0, 78.6, 101.4, 102.3, 102.5, 108.8, 108.9, 109.8, 113.5, 126.0, 127.5, 127.5, 128.2, 128.26, 128.28, 128.8, 130.2, 130.3, 130.5, 130.6, 159.2. MS (FAB) m/z (%): 716 (M+Na$^+$, 19), 91 (100); HRMS (FAB) calcd for C$_{39}$H$_{48}$O$_{11}$Na (M+Na$^+$): 715.3094. found: 715.3085.

(2) In the same manner as Preparation Example 1 (2) was treated 373 mg of a compound obtained in the above-described (1) to obtain 258 mg of a compound (1,2:3,4-di-O-isopropylidene-ribitol-5-yl 3-O-benzyl-4,6-O-benzylidene-β-D-mannopyranoside). Yield was 84%.

Physical and spectroscopic constants of the obtained compound were as follows.

[α]$^{25}_D$ −5.93 (c 1.03, CHCl$_3$); IR (neat) cm$^{-1}$: 3480, 1246; $^1$H NMR (500 MHz, CDCl$_3$) δ. 1.336 (s), 1.342 (s), 1.39 (s), 1.40 (s), 1.41 (s), 2.94 (brs), 3.350 (ddd, J=9.7, 9.7, 4.9 Hz), 3.351 (ddd, J=9.7, 8.0, 4.9 Hz), 3.62 (dd, J=8.1, 3.5 Hz), 3.63 (dd, J=9.5, 3.2 Hz), 3.64 (dd, J=10.6, 7.5 Hz), 3.85 (dd, J=10.6, 4.9 Hz), 3.89 (dd, J=10.3, 8.0 Hz), 3.90 (dd, J=10.3, 9.7 Hz), 3.94 (dd, J=10.1, 6.9 Hz), 3.95 (dd, J=8.0, 8.0 Hz), 3.99 (dd, J=10.6, 8.9 Hz), 4.00 (dd, J=10.6, 6.9 Hz), 4.03 (dd, J=9.2, 5.2 Hz), 4.10 (dd, J=10.1, 5.2 Hz), 4.11 (ddd, J=6.9, 6.9, 5.2 Hz), 4.11 (dd, J=3.5, 0.9 Hz), 4.23 (ddd, J=8.0, 5.2, 4.0 Hz), 4.14 (dd, J=8.0, 4.0 Hz), 4.17 (dd, J=3.2, 0.9 Hz), 4.17 (dd, J=9.7, 9.5 Hz), 4.18 (dd, J=10.6, 4.9 Hz), 4.19 (dd, J=9.7, 8.1 Hz), 4.325 (dd, J=10.3, 4.9 Hz), 4.338 (dd, J=10.3, 4.9 Hz), 4.39 (ddd, J=9.2, 8.9, 4.9 Hz), 4.40 (ddd, J=10.6, 7.5, 4.9 Hz), 4.56 (d, J=0.9 Hz), 4.62 (d, J=0.9 Hz), 4.79 (d, J=12.6 Hz), 4.80 (d, J=12.4 Hz), 4.86 (d, J=12.4 Hz), 4.87 (d, J=12.6 Hz), 5.61 (s), 7.26-7.41 (m), 7.50-7.51 (m); $^{13}$C NMR (125 MHz, CDCl$_3$) δ: 25.35, 25.38, 25.41, 25.45, 26.79, 26.81, 27.8, 28.0, 66.9, 67.0, 67.2, 67.4, 67.9, 68.0, 68.60, 68.63, 69.9, 72.35, 72.41, 73.1, 73.2, 76.0, 76.4, 76.5, 77.8, 78.0, 78.33, 78.35, 100.1, 100.5, 101.5, 108.8, 108.9, 109.75, 109.81, 126.0, 127.7, 127.86, 127.89, 128.2, 128.4, 128.9, 137.5, 138.1. MS (FAB) m/z (%): 595 (M+Na$^+$, 70), 91 (100); HRMS (FAB) calcd for C$_{31}$H$_{40}$O$_{10}$Na (M+Na$^+$): 595.2519. found: 595.2530.

(3) In the same manner as Preparation Example 1 (3) was treated 222 mg of a compound obtained in the above-described (2) to obtain 279 mg of a compound (1,2:3,4-di-O-isopropylidene-ribitol-5-yl 3-O-benzyl-4,6-O-benzylidene-2-O-octanoyl-β-D-mannopyranoside).

Physical and spectroscopic constants of the obtained compound were as follows.

[α]$^{25}_D$ −47.7 (c 1.13, CHCl$_3$); IR (neat) cm$^{-1}$: 1744, 1246; $^1$H NMR (500 MHz, CDCl$_3$) δ. 0.87 (t, J=6.4 Hz), 1.25-1.30 (m), 1.315 (s), 1.320 (s), 1.34 (s), 1.37 (s), 1.39 (s), 1.40 (s), 1.41 (s), 1.67 (dt, J=14.6, 7.5 Hz), 2.45 (t, J=7.5 Hz), 2.46 (t, J=7.5 Hz), 3.39 (ddd, J=8.6, 8.0, 4.9 Hz), 3.40 (ddd, J=10.3, 9.7, 4.9 Hz), 3.71 (dd, J=10.0, 3.2 Hz), 3.73 (dd, J=9.8, 3.2 Hz), 3.78 (dd, J=11.7, 7.7 Hz), 3.87 (dd, J=10.9, 2.7 Hz), 3.90 (dd, J=12.6, 10.3 Hz), 3.91 (dd, J=8.0, 8.0 Hz), 3.97 (dd, J=9.2, 6.0 Hz), 3.98 (dd, J=10.9, 4.0 Hz), 4.00 (dd, J=10.4, 5.5 Hz), 4.01 (dd, J=10.3, 6.1 Hz), 4.04 (dd, J=8.6, 4.0 Hz), 4.04 (dd, J=9.8, 9.7 Hz), 4.05-4.11 (m), 4.07 (dd, J=10.0, 8.6 Hz), 4.09-4.15 (m), 4.16 (dd, J=11.7, 2.6 Hz), 4.31 (dd, J=8.0, 4.9 Hz), 4.33 (dd, J=12.6, 4.9 Hz), 4.34 (ddd, J=8.6, 7.7, 2.6 Hz), 4.36 (ddd, J=10.3, 4.0, 2.7 Hz), 4.63 (d, J=12.3 Hz), 4.67 (d, J=1.2 Hz), 4.74 (d, J=12.3 Hz), 4.75 (d, J=12.3 Hz), 4.80 (d, J=1.2 Hz), 5.61 (s), 5.61 (s), 5.67 (dd, J=3.5, 1.2 Hz), 5.72 (dd, J=3.2, 1.2 Hz), 7.25-7.41 (m), 7.50-7.52 (m); $^{13}$C NMR (125 MHz, CDCl$_3$) δ: 14.1, 22.6, 25.0, 25.2, 25.42, 25.45, 25.51, 26.8, 27.5, 27.9, 28.95, 28.98, 29.01, 31.7, 34.1, 34.2, 67.3, 67.8, 67.9, 68.0, 68.1, 68.4, 68.48, 68.54, 71.5, 71.6, 73.4, 75.5, 75.6, 76.2, 77.6, 77.8, 77.9, 80.0, 99.6, 99.8, 101.50, 101.53, 108.9, 109.1, 109.59, 109.64, 126.1, 127.67, 127.70, 127.8, 128.2, 128.3, 128.9, 137.3, 137.65, 137.73, 173.2. MS (FAB) m/z (%): 721 (M+Na$^+$, 4), 91 (100); HRMS (FAB) calcd for C$_{39}$H$_{54}$O$_{11}$Na (M+Na$^+$): 721.3564. found: 721.3564.

(4) In the same manner as Preparation Example 1 (4) was treated 261 mg of a compound obtained in the above-described (3) to obtain 115 mg of a compound (1,2:3,4-di-O-isopropylidene-ribitol-5-yl 2-O-octanoyl-β-D-mannopyranoside). Yield was 59%.

Physical and spectroscopic constants of the obtained compound were as follows.

[α]$^{25}_D$ −30.2 (c 0.81, CHCl$_3$); IR (neat) cm$^{-1}$: 3379, 1732, 1258; $^1$H NMR (500 MHz, CD$_3$OD) δ. 0.90 (t, J=6.9 Hz), 1.31-1.40 (m), 1.31 (s), 1.32 (s), 1.366 (s), 1.375 (s), 1.382 (s), 1.40 (s), 1.63 (dt, J=14.4, 7.4 Hz), 2.360 (dt, J=14.9, 7.5 Hz), 2.363 (dt, J=14.9, 7.5 Hz), 2.390 (dt, J=14.9, 7.5 Hz), 2.392 (dt, J=14.9, 7.5 Hz), 3.25 (ddd, J=9.5, 6.3, 2.3 Hz), 3.27 (ddd, J=9.5, 6.3, 2.3 Hz), 3.50 (dd, J=9.5, 9.5 Hz), 3.51 (dd, J=10.0, 9.5 Hz), 3.634 (dd, J=9.5, 3.5 Hz), 3.636 (dd, J=10.0, 3.5 Hz), 3.70 (dd, J=12.1, 6.3 Hz), 3.75 (dd, J=11.5, 6.9 Hz), 3.82 (dd, J=10.9, 4.3 Hz), 3.86 (dd, J=8.6, 5.6 Hz), 3.87 (dd, J=8.6, 5.8 Hz), 3.90 (dd, J=12.1, 2.3 Hz), 4.01-4.09 (m), 4.01-4.09 (m), 4.03 (dd, J=8.6, 5.6 Hz), 4.06 (dd, J=12.3, 6.3 Hz), 4.10 (dd, J=11.5, 3.2 Hz), 4.18 (ddd J=8.6, 5.6, 5.6 Hz), 4.22 (ddd, J=8.6, 6.3 Hz), 4.32 (ddd, J=12.3, 5.2, 3.2 Hz), 4.33 (ddd, J=9.5, 6.9, 3.2 Hz), 4.70 (d, J=1.2 Hz), 4.74 (d, J=1.2 Hz), 5.36 (dd, J=3.5, 1.2 Hz), 5.37 (dd, J=3.5, 1.2 Hz); $^{13}$C NMR (125 MHz, CD$_3$OD) δ: 25.4, 25.5, 25.69, 25.71, 26.01, 26.03, 27.04, 27.06, 27.8, 28.0, 30.1, 30.2, 32.9, 35.1, 68.5, 68.8, 68.9, 69.0, 72.8, 72.9, 73.6, 74.8, 77.7, 78.2, 78.5, 78.6, 79.1, 79.2, 100.5, 100.6, 109.9, 110.1, 110.71, 110.73, 175.07, 175.12. MS (FAB) m/z (%): 543 (M+Na$^+$, 12), 55 (100); HRMS (FAB) calcd for C$_{25}$H$_{44}$O$_{11}$Na (M+Na$^+$): 543.2781. found: 543.2754.

(5) In the same manner as Preparation Example 1 (5) was treated 94.0 mg of a compound obtained in the above-described (4) to obtain 141 mg of a compound (1,2:3,4-di-O-isopropylidene-ribitol-5-yl 3,4,6-tri-O-hexanoyl-2-O-octanoyl-β-D-mannopyranoside). Yield was 95%.

Physical and spectroscopic constants of the obtained compound were as follows.

[α]$^{25}_D$ −25.3 (c 1.15, CHCl$_3$); IR (neat) cm$^{-1}$: 1748 (COOR), 1246 (C—O); $^1$H NMR (500 MHz, CDCl$_3$) δ. 0.878 (t, J=7.5 Hz), 0.883 (t, J=7.2 Hz), 0.898 (t, J=7.2 Hz), 1.21-1.33 (m), 1.31 (s), 1.33 (s), 1.335 (s), 1.37 (s), 1.389 (s), 1.394 (s), 1.42 (s), 1.51-1.69 (m), 2.19 (dt, J=15.8, 8.3 Hz), 2.21 (dt, J=15.8, 8.1 Hz), 2.25 (dt, J=15.2, 7.5 Hz), 2.27 (dt, J=15.5, 8.0 Hz), 2.32 (dt, J=12.5, 7.7 Hz), 2.34 (dt, J=12.5, 6.6 Hz), 2.423 (dt, J=15.5, 7.7 Hz), 2.433 (dt, J=15.7, 8.3 Hz), 3.671 (ddd, J=10.1, 5.5, 2.3 Hz), 3.674 (ddd, J=10.1, 5.5, 2.3 Hz), 3.75 (dd, J=11.8, 8.0 Hz), 3.84 (dd, J=10.9, 4.6 Hz), 3.892 (dd, J=10.6, 3.2 Hz), 3.984 (dd, J=8.6, 5.2 Hz), 3.96 (dd, J=9.2, 5.7 Hz), 4.00 (ddd, J=9.2, 5.5, 5.2 Hz), 4.01 (dd, J=8.9, 6.0 Hz), 4.08 (dd, J=8.6, 5.5 Hz), 4.09 (dd, J=10.6, 5.8 Hz), 4.12 (ddd, J=6.0, 5.8, 3.2 Hz), 4.168 (dd, J=10.9, 2.3 Hz), 4.170 (dd, J=11.8, 2.9 Hz), 4.18 (dd, J=12.3, 2.3 Hz), 4.25 (dd, J=12.3, 5.5 Hz), 4.31 (ddd, J=8.9, 4.6, 2.3 Hz), 4.35 (ddd, J=8.0, 5.7, 2.9 Hz), 4.74 (d, J=1.2 Hz), 4.86 (d, J=1.5 Hz), 5.05 (dd, J=10.1, 3.2 Hz), 5.07 (dd, J=10.1, 3.8 Hz), 5.277 (dd, J=10.1, 10.1 Hz), 5.279 (dd, J=10.1, 10.1 Hz), 5.50 (dd, J=3.2, 1.2 Hz), 5.54 (d, J=3.8, 1.5 Hz); $^{13}$C NMR (125 MHz, CDCl$_3$) δ: 13.8, 13.9, 14.0, 22.2, 22.3, 22.6, 24.3, 24.41, 24.43, 24.5, 24.98, 24.01, 25.2, 25.36, 25.39, 25.5, 26.7, 26.8, 27.5, 27.9, 28.96, 28.99, 31.2, 31.3, 31.7, 33.93, 33.96, 34.00, 34.08, 34.13, 62.4, 62.5, 65.8, 67.8, 67.9, 68.4, 68.6, 71.00, 71.04, 72.47, 72.51, 73.3, 76.0, 77.6, 78.0, 98.5, 98.9, 108.8, 109.1, 109.6, 172.2, 172.7, 173.00, 173.04, 173.5. MS (FAB) m/z (%): 837 (M+Na$^+$, 8), 99 (100); HRMS (FAB) calcd for C$_{74}$H$_{44}$O$_{14}$Na (M+Na$^+$): 837.4976. found: 837.4968.

(6) In the same manner as Preparation Example 1 (6) was treated 129 mg of a compound obtained in the above-described (5) to obtain 76.0 mg of ribitol-5-yl 3,4,6-tri-O-hexanoyl-2-O-octanoyl-β-D-mannopyranoside. Yield was 66%.

Physical and spectroscopic constants of the obtained compound were as follows.

$[\alpha]^{25}_D$ −23.7 (c 0.79, CHCl$_3$); IR (neat) cm$^{-1}$: 3399, 1748, 1246; $^1$H NMR (500 MHz, CD$_3$OD) δ. 0.89 (t, J=7.2 Hz), 0.90 (t, J=6.6 Hz), 0.91 (t, J=6.3 Hz), 0.92 (t, J=7.2 Hz), 1.22-1.40 (m), 1.51-1.60 (m), 1.61-1.71 (m), 2.18 (dt, J=15.5, 7.5 Hz), 2.21 (dt, J=15.5, 7.8 Hz), 2.26 (dt, J=16.1, 8.1 Hz), 2.31 (dt, J=16.1, 7.5 Hz), 2.35 (dt, J=16.0, 8.9 Hz), 2.36 (dt, J=16.0, 7.7 Hz), 2.397 (dt, J=14.6, 7.2 Hz), 2.402 (dt, J=15.2, 7.2 Hz), 2.469 (dt, J=14.6, 7.2 Hz), 2.275 (dt, J=15.2, 7.2 Hz), 3.55 (dd, J=6.3, 6.3 Hz), 3.58 (dd, J=6.3, 6.0 Hz), 3.61 (dd, J=11.2, 6.1 Hz), 3.61 (dd, J=10.9, 5.7 Hz), 3.67 (dd, J=10.9, 7.2 Hz), 3.69 (ddd, J=6.3, 6.1, 3.4 Hz), 3.70 (ddd, J=6.0, 5.7, 3.8 Hz), 3.74 (dd, J=11.2, 3.4 Hz), 3.75 (dd, J=10.9, 3.8 Hz), 3.82 (ddd, J=10.0, 4.3, 2.3 Hz), 3.85 (ddd, J=7.2, 6.3, 2.9 Hz), 3.87 (ddd, J=7.2, 6.9, 6.3 Hz), 3.91 (dd, J=10.9, 6.9 Hz), 4.07 (dd, J=10.9, 2.9 Hz), 4.14 (dd, J=12.4, 2.3 Hz), 4.278 (dd, J=12.4, 4.3 Hz), 4.280 (dd, J=12.4, 4.3 Hz), 4.91 (d, J=0.9 Hz), 4.92 (d, J=1.2 Hz), 5.16 (dd, J=10.0, 3.2 Hz), 5.17 (dd, J=10.0, 3.2 Hz), 5.29 (dd, J=10.0, 10.0 Hz), 5.48 (dd, J=3.2, 1.2 Hz) 5.50 (dd, J=3.2, 0.9 Hz); $^{13}$C NMR (125 MHz, CD$_3$OD) δ: 14.2, 14.3, 14.5, 23.37, 23.39, 23.42, 23.8, 25.5, 25.59, 25.63, 26.4, 30.2, 30.3, 32.3, 32.4, 32.5, 33.0, 34.8, 34.9, 35.0, 35.2, 63.00, 63.05, 64.5, 66.76, 66.81, 70.5, 72.50, 72.52, 72.6, 72.7, 72.9, 73.0, 73.47, 73.48, 73.6, 73.9, 74.0, 74.1, 100.0, 100.5, 173.76, 173.84, 174.7, 174.8, 175.0. MS (FAB) m/z (%): 757 (M+Na$^+$, 85), 99 (100); HRMS (FAB) calcd for C$_{37}$H$_{66}$O$_{14}$Na (M+Na$^+$): 757.4350. found: 757.4359.

Preparation Example 22

(1) Treatment in the same manner as Preparation Example 1 (1) was performed using 0.500 g of a mannosyl sulfoxide compound of Reference Example 1 and 0.237 g of an alcohol (2,3:4,5-di-O-isopropylidene-D-xylitol) to obtain 0.389 g of a compound (2,3:4,5-di-O-isopropylidene-D-xylitol-1-yl 3-O-benzyl-4,6-O-benzylidene-2-O-p-methoxybenzyl-β-D-mannopyranoside). Yield was 66%.

Physical and spectroscopic constants of the obtained compound were as follows.

$[\alpha]^{25}_D$ −58.8 (c 1.10, CHCl$_3$); IR (neat) cm$^{-1}$: 1250; $^1$H NMR (700 MHz, CDCl$_3$) δ. 1.38 (s), 1.39 (s), 1.432 (s), 1.434 (s), 3.32 (ddd, J=10.0, 10.0, 5.0 Hz), 3.57 (dd, J=10.0, 3.2 Hz), 3.78 (dd, J=11.6, 3.4 Hz), 3.80 (s), 3.88 (dd, J=8.2, 7.4 Hz), 3.92 (dd, J=10.4, 10.0 Hz), 3.96 (dd, J=3.2, 0.8 Hz), 3.98 (dd, J=11.6, 3.4 Hz), 4.02 (dd, J=8.2, 6.7 Hz), 4.05 (dd, J=8.2, 4.2 Hz), 4.10 (ddd, J=8.2, 3.4, 3.4 Hz), 4.16 (ddd, J=7.4, 6.7, 4.2 Hz), 4.19 (dd, J=10.0, 10.0 Hz), 4.29 (dd, J=10.4, 5.0 Hz), 4.54 (d, J=0.8 Hz), 4.58 (d, J=12.4 Hz), 4.69 (d, J=12.4 Hz), 4.80 (d, J=11.6 Hz), 4.87 (d, J=11.6 Hz), 5.61 (s), 6.84-6.86 (m), 7.26-7.31 (m), 7.34-7.39 (m), 7.49-7.50 (m); $^{13}$C NMR (175 MHz, CDCl$_3$) δ: 25.6, 26.2, 27.0, 27.2, 55.2, 65.7, 67.7, 68.2, 68.5, 72.5, 74.5, 75.0, 75.6, 76.3, 76.8, 77.9, 78.6, 101.4, 102.6, 109.4, 109.7, 113.6, 126.0, 127.5, 127.6, 128.2, 128.3, 128.9, 130.1, 130.4, 137.5, 138.3, 159.2. MS (FAB) m/z (%): 715 (M+Na$^+$, 13), 55 (100); HRMS (FAB) calcd for C$_{39}$H$_{48}$O$_{11}$Na (M+Na$^+$): 715.3094. found: 715.3069.

(2) In the same manner as Preparation Example 1 (2) was treated 360 mg of a compound obtained in the above-described (1) to obtain 265 mg of a compound (2,3:4,5-di-O-isopropylidene-D-xylitol-1-yl 3-O-benzyl-4,6-O-benzylidene-β-D-mannopyranoside). Yield was 88%.

Physical and spectroscopic constants of the obtained compound were as follows.

$[\alpha]^{25}_D$ −19.3 (c 0.90, CHCl$_3$); IR (neat) cm$^{-1}$: 3488, 1250; $^1$H NMR (400 MHz, CDCl$_3$) δ. 1.38 (s), 1.40 (s), 1.429 (s), 1.434 (s), 2.57 (brs), 3.35 (ddd, J=10.0, 10.0, 5.2 Hz), 3.64 (dd, J=9.6, 3.2 Hz), 3.81 (dd, J=11.6, 4.4 Hz), 3.87 (dd, J=7.2, 4.8 Hz), 3.91 (d, J=3.2 Hz), 3.98 (dd, J=11.6, 4.0 Hz), 4.03 (dd, J=7.2, 4.4 Hz), 4.05 (dd, J=8.0, 7.2 Hz), 4.09-4.13 (m), 4.11 (ddd, J=8.0, 4.4, 4.0 Hz), 4.14 (dd, J=10.0, 9.6 Hz), 4.18 (ddd, J=7.2, 4.8, 4.4 Hz), 4.32 (dd, J=10.8, 5.2 Hz), 4.61 (s), 4.77 (d, J=12.4 Hz), 4.86 (d, J=12.4 Hz), 5.60 (s), 7.29-7.39 (m), 7.49-7.51 (m); $^{13}$C NMR (100 MHz, CDCl$_3$) δ: 25.5, 26.2, 26.96, 27.03, 65.7, 67.0, 68.5, 68.6, 69.8, 72.6, 75.2, 76.2, 76.6, 77.4, 78.4, 100.8, 101.6, 109.7, 126.0, 127.88, 127.90, 128.2, 128.4, 129.0, 137.4, 137.8. MS (FAB) m/z (%): 595 (M+Na$^+$, 5), 73 (100); HRMS (FAB) calcd for C$_{31}$H$_{40}$O$_{10}$Na (M+Na$^+$): 595.2519. found: 595.2502.

(3) In the same manner as Preparation Example 1 (3) was treated 244 mg of a compound obtained in the above-described (2) to obtain 265 mg of a compound (2,3:4,5-di-O-isopropylidene-D-xylitol-1-yl 3-O-benzyl-4,6-O-benzylidene-2-O-octanoyl-β-D-mannopyranoside). Yield was 88%.

Physical and spectroscopic constants of the obtained compound were as follows.

$[\alpha]^{25}_D$ −54.8 (c 1.00, CHCl$_3$); IR (neat) cm$^{-1}$: 1250, 1744; $^1$H NMR (400 MHz, CDCl$_3$) δ. 0.87 (t, J=6.4 Hz), 1.24-1.35 (m), 1.38 (s), 1.40 (s), 1.42 (s), 1.43 (s), 1.66 (tt, J=7.6, 7.2 Hz), 2.45 (t, J=7.6 Hz), 3.38 (ddd, J=10.0, 10.0, 4.8 Hz), 3.71 (dd, J=9.6, 3.6 Hz), 3.77 (dd, J=11.2, 4.4 Hz), 3.84 (dd, J=8.0, 7.6 Hz), 3.89 (dd, J=10.0, 10.0 Hz), 3.93 (dd, J=11.2, 3.2 Hz), 3.99 (dd, J=8.0, 4.4 Hz), 3.99 (dd, J=10.0, 9.6 Hz), 4.03 (dd, J=8.0, 6.8 Hz), 4.05 (dd, J=8.0, 4.4, 3.2 Hz), 4.14 (ddd, J=7.6, 6.8, 4.4 Hz), 4.32 (dd, J=10.0, 4.8 Hz), 4.63 (d, J=12.4 Hz), 4.68 (s), 4.73 (d, J=12.4 Hz), 5.61 (s), 5.69 (d, J=3.6 Hz), 7.28-7.42 (m), 7.49-7.51 (m); $^{13}$C NMR (100 MHz, CDCl$_3$) δ: 14.1, 22.6, 25.0, 25.6, 26.2, 26.9, 27.0, 28.9, 29.0, 31.7, 34.1, 65.7, 67.3, 68.3, 68.4, 69.0, 71.7, 75.2, 75.5, 76.1, 77.5, 77.9, 100.2, 101.5, 109.7, 126.1, 127.7, 128.2, 128.3, 129.0, 137.3, 137.6, 173.0. MS (FAB) m/z (%): 721 (M+Na$^+$, 7), 73 (100); HRMS (FAB) calcd for C$_{39}$H$_{54}$O$_{11}$Na (M+Na$^+$): 721.3564. found: 721.3592.

(4) In the same manner as Preparation Example 1 (4) was treated 234 mg of a compound obtained in the above-described (3) to obtain 161 mg of a compound (2,3:4,5-di-O-isopropylidene-D-xylitol-1-yl 2-O-octanoyl-β-D-mannopyranoside). Yield was 93%.

Physical and spectroscopic constants of the obtained compound were as follows.

$[\alpha]^{25}_D$ −28.7 (c 1.10, CHCl$_3$); IR (neat) cm$^{-1}$: 3437, 1740, 1254; $^1$H NMR (400 MHz, CD$_3$OD) δ. 0.90 (t, J=7.2 Hz), 1.29-1.33 (m), 1.38 (s), 1.36 (s), 1.37 (s), 1.38 (s), 1.62 (ddt, J=7.6, 7.6, 7.2 Hz), 2.35 (dt, J=15.0, 7.6 Hz), 2.39 (dt, J=15.0, 7.6 Hz), 3.25 (ddd, J=9.6, 6.4, 2.0 Hz), 3.49 (dd, J=9.6, 9.6 Hz), 3.63 (dd, J=9.6, 3.2 Hz), 3.69 (dd, J=11.6, 6.4 Hz), 3.71 (dd, J=11.2, 5.2 Hz), 3.85 (dd, J=8.4, 5.2 Hz), 3.90 (dd, J=11.6, 2.0 Hz), 3.95 (dd, J=7.2, 3.6 Hz), 3.97 (dd, J=11.2, 4.0 Hz), 4.04 (dd, J=8.8, 8.4 Hz), 4.09 (ddd, J=8.8, 5.2, 3.6 Hz), 4.20 (ddd, J=7.2, 5.2, 4.0 Hz), 4.69 (d, J=1.2 Hz), 5.35 (dd, J=3.2, 1.2 Hz); $^{13}$C NMR (100 MHz, CD$_3$OD) δ: 14.4, 23.7, 25.9, 26.1, 26.6, 27.3, 27.4, 30.2, 32.9, 35.2, 62.9, 66.9, 69.0, 70.2, 72.8, 73.5, 76.3, 77.3, 78.5, 79.2, 100.8, 110.6, 110.7, 175.0. MS (FAB) m/z (%): 543 (M+Na+, 7), 73 (100); HRMS (FAB) calcd for $C_{25}H_{44}O_{11}Na$ (M+Na+): 543.2781. found: 543.2789.

(5) In the same manner as Preparation Example 1 (5) was treated 141 mg of a compound obtained in the above-described (4) to obtain 192 mg of a compound (2,3:4,5-di-O-isopropylidene-D-xylitol-1-yl 3,4,6-tri-O-hexanoyl-2-O-octanoyl-β-D-mannopyranoside). Yield was 87%.

Physical and spectroscopic constants of the obtained compound were as follows.

$[\alpha]^{25}_D$ –28.7 (c 1.30, $CHCl_3$); IR (neat) cm$^{-1}$: 1748, 1246; $^1$H NMR (400 MHz, $CDCl_3$) δ. 0.86 (s), 0.88 (s), 0.90 (s), 0.92 (s), 1.22-1.33 (m), 1.37 (s), 1.39 (s), 1.41 (s), 1.42 (s), 1.50-1.66 (m), 2.17 (dt, J=15.2, 7.6 Hz), 2.22 (dt, J=15.2, 7.6 Hz), 2.23 (dt, J=15.2, 7.6 Hz), 2.29 (dt, J=15.2, 7.6 Hz), 2.34 (t, J=6.4 Hz), 2.40 (dt, J=15.2, 7.6 Hz), 2.45 (dt, J=15.2, 7.6 Hz), 3.66 (ddd, J=9.6, 5.6, 2.4 Hz), 3.78 (dd, J=11.2, 4.8 Hz), 3.82 (dd, J=8.0, 6.8 Hz), 3.92 (dd, J=11.2, 3.2 Hz), 3.98 (ddd, J=8.4, 4.8, 3.2 Hz), 4.01 (dd, J=8.4, 6.4 Hz), 4.05 (ddd, J=6.8, 6.8, 6.4 Hz), 4.11 (dd, J=8.0, 6.8 Hz), 4.17 (dd, J=12.0, 2.4 Hz), 4.24 (dd, J=12.0, 5.6 Hz), 4.75 (s 5.05 (dd, J=10.0, 3.2 Hz), 5.26 (dd, J=10.0, 9.6 Hz), 5.52 (d, J=3.2 Hz); $^{13}$C NMR (100 MHz, $CDCl_3$) δ: 13.8, 13.9, 14.0, 22.2, 22.3, 22.6, 24.3, 24.45, 24.46, 25.0, 25.6, 26.2, 26.9, 27.0, 28.95, 29.01, 31.2, 31.3, 31.7, 33.91, 33.99, 34.04, 62.3, 65.7, 68.3, 69.0, 70.9, 72.6, 75.3, 76.0, 77.8, 99.2, 109.6, 109.7, 172.3, 172.6, 172.8, 173.4. MS (FAB) m/z (%): 837 (M+Na+, 7), (100); HRMS (FAB) calcd for $C_{43}H_{74}O_{14}Na$ (M+Na+): 837.4976. found: 837.4968.

(6) In the same manner as Preparation Example 1 (6) was treated 169 mg of a compound obtained in the above-described (5) to obtain 112 mg of D-xylitol-1-yl 3,4,6-tri-O-hexanoyl-2-O-octanoyl-β-D-mannopyranoside. Yield was 79%.

Physical and spectroscopic constants of the obtained compound were as follows.

$[\alpha]^{25}_D$ –32.6 (c 0.80, $CHCl_3$); IR (neat) cm$^{-1}$: 3422, 1748, 1246; $^1$H NMR (700 MHz, $CD_3OD$) δ. 0.88 (s), 0.90 (s), 0.91 (s), 1.23-1.41 (m), 1.51-1.59 (m), 1.62-1.69 (m), 2.18 (dt, J=14.8, 7.6 Hz), 2.21 (dt, J=14.8, 7.6 Hz), 2.27 (dt, J=15.8, 7.2 Hz), 2.31 (dt, J=15.8, 7.2 Hz), 2.35 (dt, J=15.0, 7.6 Hz), 2.36 (dt, J=15.0, 7.6 Hz), 2.39 (dt, J=15.4, 7.2 Hz), 2.46 (dt, J=15.4, 7.2 Hz), 3.58 (dd, J=11.3, 6.2 Hz), 3.59 (dd, J=5.0, 3.9 Hz), 3.63 (dd, J=11.3, 5.0 Hz), 3.74 (ddd, J=6.2, 5.0, 5.0 Hz), 3.75 (dd, J=10.2, 5.2 Hz), 3.83 (ddd, J=10.0, 4.4, 2.2 Hz), 3.85 (ddd, J=5.6, 5.2, 3.9 Hz), 3.88 (dd, J=10.2, 5.6 Hz), 4.15 (dd, J=12.3, 2.2 Hz), 4.27 (dd, J=12.3, 4.4 Hz), 4.90 (d, J=1.0 Hz), 5.16 (dd, J=10.0, 3.4 Hz), 5.28 (dd, J=10.0, 10.0 Hz), 5.47 (dd, J=3.4, 1.0 Hz); $^{13}$C NMR (175 MHz, $CD_3OD$) δ: 14.3, 14.5, 23.36, 23.38, 23.41, 23.8, 25.5, 25.59, 25.62, 26.3, 30.2, 30.3, 32.3, 32.36, 32.45, 33.0, 34.8, 34.92, 34.96, 35.2, 63.1, 64.4, 66.8, 70.4, 71.9, 72.06, 72.13, 72.6, 73.5, 73.8, 100.1, 173.77, 173.87, 174.6, 175.0. MS (FAB) m/z (%): 757 (M+Na+, 63), 99 (100); HRMS (FAB) calcd for $C_{37}H_{66}O_{14}Na$ (M+Na+): 757.4350. found: 757.4359.

Preparation Example 23

(1) Treatment in the same manner as Preparation Example 1 (1) was performed using 1.60 g of a mannosyl sulfoxide compound of Reference Example 1 and 0.850 g of an alcohol (4-O-tert-butyldimethylsilyl-2,3-O-isopropylidene-D-threitol) to obtain 1.12 g of a compound (4-O-tert-butyldimethylsilyl-2,3-O-isopropylidene-D-threitol-1-yl 3-O-benzyl-4,6-O-benzylidene-2-O-p-methoxybenzyl-β-D-mannopyranoside). Yield was 70%.

Physical and spectroscopic constants of the obtained compound were as follows.

$^1$H NMR (700 MHz, $CDCl_3$) δ. 0.06 (s), 0.07 (s), 0.89 (s), 1.41 (s), 1.42 (s), 3.32 (ddd, J=10.0, 9.6, 4.8 Hz), 3.57 (dd, J=9.9, 3.2 Hz), 3.63 (dd, J=10.6, 7.0 Hz), 3.72 (dd, J=10.0, 4.0 Hz), 3.77 (ddd, J=7.2, 4.0, 4.0 Hz), 3.79 (dd, J=10.0, 4.0 Hz), 3.80 (s), 3.93 (dd, J=10.2, 10.0 Hz), 3.99 (dd, J=3.2, 0.8 Hz), 4.09 (dd, J=10.6, 3.2 Hz), 4.15 (ddd, J=7.2, 7.0, 3.2 Hz), 4.18 (dd, J=9.9, 9.6 Hz), 4.29 (dd, J=10.2, 4.8 Hz), 4.56 (d, J=0.8 Hz), 4.57 (d, J=12.4 Hz), 4.67 (d, J=12.4 Hz), 4.82 (d, J=11.8 Hz), 4.91 (d, J=11.8 Hz), 5.61 (s), 6.83-6.86 (m), 7.25-7.31 (m), 7.34-7.41 (m), 7.48-7.51 (m); $^{13}$C NMR (175 MHz, $CDCl_3$) δ: –5.43, –5.34, 18.3, 25.9, 27.0, 27.3, 55.2, 63.6, 67.7, 68.6, 70.8, 72.3, 74.4, 75.2, 77.8, 78.1, 78.2, 78.6, 101.4, 102.2, 109.5, 113.5, 126.0, 127.5, 128.2, 128.3, 128.8, 130.2, 130.6, 137.6, 138.4, 159.2.

(2) In the same manner as Preparation Example 1 (2) was treated 1.25 g of a compound obtained in the above-described (1) to obtain 990 mg of a compound (4-O-tert-butyldimethylsilyl-2,3-O-isopropylidene-D-threitol-1-yl 3-O-benzyl-4,6-O-benzylidene-β-D-mannopyranoside). Yield was 94%.

Physical and spectroscopic constants of the obtained compound were as follows.

$^{13}$C NMR (100 MHz, $CDCl_3$) δ: –5.83, –5.39, 18.3, 25.8, 25.9, 27.0, 27.2, 63.6, 67.0, 68.6, 69.7, 70.7, 72.4, 76.6, 78.1, 78.3, 100.3, 101.5, 109.7, 126.0, 127.8, 127.9, 128.2, 128.4, 128.9, 137.4, 138.0.

(3) In the same manner as Preparation Example 1 (3) was treated 931 mg of a compound obtained in the above-described (2) to obtain 1.02 g of a compound (4-O-tert-butyldimethylsilyl-2,3-O-isopropylidene-D-threitol-1-yl 3-O-benzyl-4,6-O-benzylidene-2-O-octanoyl-β-D-mannopyranoside). Yield was 91%.

Physical and spectroscopic constants of the obtained compound were as follows.

$^{13}$C NMR (100 MHz, $CDCl_3$) δ: –5.44, –5.39, 14.1, 18.3, 22.6, 25.0, 25.9, 27.0, 28.9, 29.0, 31.7, 34.1, 63.5, 67.3, 68.3, 68.5, 70.4, 71.5, 75.7, 77.9, 78.0, 78.1, 99.6, 101.5, 109.5, 126.1, 127.7, 128.2, 128.3, 128.9, 137.3, 137.7, 173.1.

(4) In the same manner as Preparation Example 1 (4) was treated 1.05 g of a compound obtained in the above-described (3) to obtain 582 mg of a compound (4-O-tert-butyldimethylsilyl-2,3-O-isopropylidene-D-threitol-1-yl 2-O-octanoyl-β-D-mannopyranoside).

Physical and spectroscopic constants of the obtained compound were as follows.

$^1$H NMR (400 MHz, $CD_3OD$) δ. 0.088 (s), 0.90 (t, J=7.2 Hz), 0.91 (s), 1.29-1.36 (m), 1.34 (s), 1.36 (s), 1.62 (tt, J=7.2, 7.2 Hz), 2.40 (dt, J=7.2, 5.6 Hz), 3.35 (ddd, J=9.2, 6.0, 2.4 Hz), 3.51 (dd, J=9.2, 9.2 Hz), 3.63 (dd, J=9.2, 3.6 Hz), 3.69 (dd, J=11.2, 8.0 Hz), 3.70 (dd, J=12.0, 6.0 Hz), 3.74 (dd, J=9.6, 4.0 Hz), 3.77 (dd, J=11.2, 4.0 Hz), 3.88 (ddd, J=8.0, 4.0, 4.0 Hz), 3.89 (dd, J=12.0, 2.8 Hz), 3.97 (dd, J=9.6, 4.4 Hz), 4.01 (dd, J=8.0, 4.4, 4.0 Hz), 4.69 (d, J=0.8 Hz), 5.35 (dd, J=3.6, 0.8 Hz); $^{13}$C NMR (100 MHz, $CD_3OD$) δ: –5.13, 14.4, 19.2, 23.7, 26.0, 26.5, 27.36, 27.42, 30.2, 32.9, 35.1, 62.9, 64.5, 68.9, 70.9, 72.8, 73.6, 77.9, 78.6, 80.2, 100.5, 110.5, 174.9.

(5) In the same manner as Preparation Example 1 (5) was treated 530 mg of a compound obtained in the above-described (4) to obtain 743 mg of a compound (4-O-tert-butyldimethylsilyl-2,3-O-isopropylidene-D-threitol-1-yl 3,4,6-tri-O-hexanoyl-2-O-octanoyl-β-D-mannopyranoside).

Physical and spectroscopic constants of the obtained compound were as follows.

$^1$H NMR (400 MHz, CDCl$_3$) δ. 0.059 (s), 0.85-0.92 (m, 12H, CH$_3$), 0.89 (s)$_3$), 1.22-1.35 (m, 20H, CH$_2$), 1.38 (s), 1.39 (s), 1.50-1.69 (m), 2.18 (dt, J=16.0, 7.6 Hz), 2.22 (dt, J=16.0, 7.6 Hz), 2.23 (dt, J=16.0, 7.6 Hz), 2.28 (dt, J=16.0, 7.6 Hz), 2.32 (dt, J=16.0, 7.6 Hz), 2.37 (dt, J=16.0, 7.6 Hz), 2.39 (dt, J=16.0, 7.6 Hz), 2.44 (dt, J=16.0, 7.6 Hz), 3.65 (ddd, J=9.6, 5.6, 1.6 Hz), 3.69 (dd, J=11.2, 6.0 Hz), 3.70 (dd, J=11.2, 3.6 Hz), 3.75 (dd, J=11.2, 2.4 Hz), 3.76 (ddd, J=6.8, 3.6, 2.4 Hz), 3.97 (dd, J=11.2, 3.2 Hz), 4.06 (ddd, J=6.8, 6.0, 3.2 Hz), 4.17 (dd, J=12.0, 1.6 Hz), 4.24 (dd, J=12.0, 5.6 Hz), 4.82 (s), 5.07 (dd, J=10.0, 3.2 Hz), 5.27 (dd, J=10.0, 9.6 Hz), 5.53 (d, J=3.2 Hz); $^{13}$C NMR (100 MHz, CDCl$_3$) δ: −5.47, −5.42, 13.79, 13.81, 13.9, 14.0, 18.3, 22.2, 22.3, 22.6, 24.3, 24.4, 24.5, 25.0, 25.9, 26.95, 27.01, 28.95, 29.00, 31.2, 31.3, 31.7, 33.9, 34.0, 34.1, 62.4, 63.5, 65.8, 68.5, 70.2, 71.0, 72.6, 77.9, 78.1, 98.5, 109.6, 172.2, 172.6, 172.9, 173.4.

(6) In the same manner as Preparation Example 1 (6) was treated 737 mg of a compound obtained in the above-described (5) to obtain 414 mg of D-threitol-1-yl 3,4,6-tri-O-hexanoyl-2-O-octanoyl-β-D-mannopyranoside. Yield was 68%.

Physical and spectroscopic constants of the obtained compound were as follows.

$^1$H NMR (800 MHz, CD$_3$OD) δ: 0.88-0.93 (m, 12H, CH$_3$), 1.23-1.42 (m, 20H, CH$_2$), 1.51-1.59 (m), 1.62-1.70 (m), 2.18 (dt, J=15.8, 7.6 Hz), 2.21 (dt, J=15.8, 7.6 Hz), 2.27 (dt, J=15.8, 7.6 Hz), 2.31 (dt, J=15.8, 7.6 Hz), 2.34 (dt, J=15.8, 7.6 Hz), 2.37 (dt, J=15.8, 7.6 Hz), 2.39 (dt, J=15.8, 7.6 Hz), 2.46 (dt, J=15.8, 7.6 Hz), 3.55 (dd, J=12.6, 8.6 Hz), 3.57 (ddd, J=8.6, 4.6, 3.0 Hz), 3.62 (dd, J=12.6, 4.6 Hz), 3.64 (dd, J=10.0, 5.8 Hz), 3.76 (ddd, J=6.4, 5.8, 3.0 Hz), 3.83 (ddd, J=10.2, 4.4, 2.2 Hz), 3.92 (dd, J=10.0, 6.4 Hz), 4.14 (dd, J=12.3, 2.2 Hz), 4.28 (dd, J=12.3, 4.4 Hz), 4.91 (d, J=0.8 Hz), 5.16 (dd, J=10.2, 3.2 Hz), 5.29 (dd, J=10.2, 10.2 Hz), 5.48 (dd, J=3.2, 0.8 Hz); $^{13}$C NMR (200 MHz, CD$_3$OD) δ: 14.2, 14.3, 14.5, 23.38, 23.39, 23.41, 23.8, 25.5, 26.00, 25.63, 26.4, 30.2, 30.3, 32.3, 32.4, 32.5, 33.0, 34.8, 34.9, 35.0, 35.2, 63.0, 64.2, 66.8, 70.5, 71.4, 72.67, 72.70, 73.2, 73.5, 100.3, 173.77, 173.83, 174.7, 175.0.

Preparation Example 24

(1) Treatment in the same manner as Preparation Example 1 (1) was performed using 0.441 g of a mannosyl sulfoxide compound of Reference Example 1 and 0.300 g of an alcohol (2,3:4,5:6,7-tri-O-isopropylidene-D-glycero-D-galactoheptitol) to obtain 0.250 g of a compound (2,3:4,5:6, 7-tri-O-isopropylidene-D-glycero-D-galactoheptitol-1-yl 3-O-benzyl-4,6-O-benzylidene-2-O-p-methoxybenzyl-β-D-mannopyranoside). Yield was 42%.

Physical and spectroscopic constants of the obtained compound were as follows.

$^{13}$C NMR (175 MHz, CDCl$_3$) δ: 25.3, 26.5, 26.9, 27.1, 27.6, 27.7, 55.2, 66.1, 67.6, 68.4, 68.5, 72.3, 74.4, 75.3, 76.2, 77.0, 77.7, 78.6, 78.8, 79.7, 79.8, 101.4, 102.6, 109.5, 109.6, 110.5, 113.5, 126.0, 127.5, 128.2, 128.3, 128.8, 130.1, 130.5, 137.6, 138.3, 159.2.

(2) In the same manner as Preparation Example 1 (2) was treated 229 mg of a compound obtained in the above-described (1) to obtain 165 mg of a compound (2,3:4,5:6, 7-tri-O-isopropylidene-D-glycero-D-galactoheptitol-1-yl 3-O-benzyl-4,6-O-benzylidene-β-D-mannopyranoside). Yield was 85%.

Physical and spectroscopic constants of the obtained compound were as follows.

$^{13}$C NMR (100 MHz, CDCl$_3$) δ: 25.3, 26.4, 27.0, 27.1, 27.5, 66.2, 67.0, 68.6, 69.0, 69.9, 72.5, 76.2, 76.5, 77.9, 78.0, 78.4, 79.4, 79.6, 100.6, 101.5, 109.7, 110.4, 126.0, 127.8, 127.9, 128.2, 128.4, 128.9, 137.4, 138.0.

(3) In the same manner as Preparation Example 1 (3) was treated 150 mg of a compound obtained in the above-described (2) to obtain 160 mg of a compound (2,3:4,5:6, 7-tri-O-isopropylidene-D-glycero-D-galactoheptitol-1-yl 3-O-benzyl-4,6-O-benzylidene-2-O-octanoyl-β-D-mannopyranoside). Yield was 90%.

Physical and spectroscopic constants of the obtained compound were as follows.

$^{13}$C NMR (100 MHz, CDCl$_3$) δ: 14.1, 22.6, 24.9, 25.3, 26.5, 26.9, 27.0, 27.5, 27.6, 28.9, 29.0, 31.7, 34.1, 66.0, 67.3, 68.3, 68.4, 68.5, 71.6, 75.5, 76.1, 78.0, 78.9, 79.6, 79.7, 100.1, 101.6, 109.5, 109.6, 110.4, 126.1, 127.7, 127.8, 128.2, 128.3, 128.9, 137.3, 137.7, 173.0.

(4) In the same manner as Preparation Example 1 (4) was treated 150 mg of a compound obtained in the above-described (3) to obtain 81.0 mg of a compound (2,3:4,5:6, 7-tri-O-isopropylidene-D-glycero-D-galactoheptitol-1-yl 2-O-octanoyl-β-D-mannopyranoside).

Physical and spectroscopic constants of the obtained compound were as follows.

$^{13}$C NMR (100 MHz, CD$_3$OD) δ: 14.4, 23.7, 25.5, 26.0, 26.9, 27.4, 27.8, 27.9, 30.19, 30.22, 32.9, 35.1, 63.0, 67.2, 69.0, 69.6, 72.8, 73.6, 77.7, 78.5, 78.6, 79.6, 80.6, 81.0, 100.7, 110.7, 110.8, 111.4, 174.9.

(5) In the same manner as Preparation Example 1 (5) was treated 70.0 mg of a compound obtained in the above-described (4) to obtain 95.0 mg of a compound (2,3:4,5:6, 7-tri-O-isopropylidene-D-glycero-D-galactoheptitol-1-yl 3,4,6-tri-O-hexanoyl-2-O-octanoyl-β-D-mannopyranoside).

Physical and spectroscopic constants of the obtained compound were as follows.

$^{13}$C NMR (100 MHz, CDCl$_3$) δ: 13.8, 13.9, 14.0, 22.2, 22.3, 22.6, 24.3, 24.4, 24.5, 25.0, 25.3, 26.4, 26.8, 27.0, 27.47, 27.55, 28.95, 29.0, 31.2, 31.3, 31.7, 33.9, 34.00, 34.04, 62.4, 65.8, 66.0, 68.0, 68.4, 70.9, 72.5, 76.1, 76.5, 79.1, 79.6, 79.8, 99.1, 109.5, 109.6, 110.4, 172.2, 172.6, 172.8, 173.4.

(6) In the same manner as Preparation Example 1 (6) was treated 74.0 mg of a compound obtained in the above-described (5) to obtain 62.0 mg of D-glycero-D-galactoheptitol-1-yl 3,4,6-tri-O-hexanoyl-2-O-octanoyl-β-D-mannopyranoside. Yield was 97%.

Physical and spectroscopic constants of the obtained compound were as follows.

$^{13}$C NMR (100 MHz, CDOD$_3$) δ: 14.2, 14.3, 14.5, 23.36, 23.41, 23.8, 25.5, 25.59, 25.63, 26.4, 30.2, 30.3, 32.4, 32.5, 33.0, 34.8, 34.9, 35.0, 35.2, 63.0 65.2, 66.8, 69.6, 70.3, 70.5, 71.2, 71.3, 72.7, 72.8, 73.3, 73.5, 100.0, 173.76, 173.84, 174.7, 175.0.

Preparation Example 25

(1) Treatment in the same manner as Preparation Example 1 (1) was performed using 0.500 g of a mannosyl sulfoxide compound of Reference Example 1 and 0.342 g of an alcohol (1,2:3,4-di-O-isopropylidene-L-arabinitol) to obtain 0.238 g of a compound (1,2:3,4-di-O-isopropylidene-L-arabinitol-5-yl 3-O-benzyl-4,6-O-benzylidene-2-O-p-methoxybenzyl-β-D-mannopyranoside). Yield was 58%.

Physical and spectroscopic constants of the obtained compound were as follows.

$^{13}C$ NMR (175 MHz, CDCl$_3$) δ: 25.3, 25.5, 26.6, 27.6, 55.2, 66.5, 67.6, 68.5, 68.6, 72.7, 74.1, 74.5, 74.9, 75.7, 78.1, 78.2, 78.7, 101.4, 102.5, 108.9, 109.6, 113.5, 126.0, 127.56, 127.62, 128.2, 128.3, 128.9, 130.25, 130.30, 137.5, 138.3, 159.2.

(2) In the same manner as Preparation Example 1 (2) was treated 328 mg of a compound obtained in the above-described (1) to obtain 250 mg of a compound (1,2:3,4-di-O-isopropylidene-L-arabinitol-5-yl 3-O-benzyl-4,6-O-benzylidene-β-D-mannopyranoside). Yield was 92%.

Physical and spectroscopic constants of the obtained compound were as follows.

$^{13}C$ NMR (100 MHz, CDCl$_3$) δ: 25.36, 25.38, 26.6, 27.7, 66.6, 67.0, 68.0, 68.5, 69.8, 72.7, 74.3, 74.7, 76.6, 78.3, 78.5, 100.8, 101.6, 109.0, 109.7, 126.0, 127.90, 127.94, 128.2, 128.5, 129.0, 137.3, 137.7.

(3) In the same manner as Preparation Example 1 (3) was treated 238 mg of a compound obtained in the above-described (2) to obtain 275 mg of a compound (1,2:3,4-di-O-isopropylidene-L-arabinitol-5-yl 3-O-benzyl-4,6-O-benzylidene-2-O-octanoyl-β-D-mannopyranoside). Yield was 95%.

Physical and spectroscopic constants of the obtained compound were as follows.

$^{13}C$ NMR (100 MHz, CDCl$_3$) δ: 14.1, 22.6, 24.9, 25.3, 25.4, 26.7, 27.7, 28.9, 29.0, 31.7, 34.1, 66.5, 67.3, 68.3, 68.4, 68.5, 71.7, 74.1, 74.8, 75.6, 77.9, 78.6, 100.2, 101.6, 109.0, 109.6, 126.0, 127.7, 128.2, 128.3, 129.0, 137.2, 137.6, 173.1.

(4) In the same manner as Preparation Example 1 (4) was treated 133 mg of a compound obtained in the above-described (3) to obtain 79.0 mg of a compound (1,2:3,4-di-O-isopropylidene-L-arabinitol-5-yl 2-O-octanoyl-β-D-mannopyranoside).

Physical and spectroscopic constants of the obtained compound were as follows.

$^{13}C$ NMR (100 MHz, CD$_3$OD) δ: 14.4, 23.7, 24.9, 25.6, 25.8, 26.0, 27.9, 30.2, 32.9, 35.1, 63.0, 67.6, 68.8, 69.0, 72.8, 73.5, 75.7, 76.5, 78.6, 79.6, 100.5, 109.9, 110.5, 175.0.

(5) In the same manner as Preparation Example 1 (5) was treated 100 mg of a compound obtained in the above-described (4) to obtain 146 mg of a compound (1,2:3,4-di-O-isopropylidene-L-arabinitol-5-yl 3,4,6-tri-O-hexanoyl-2-O-octanoyl-β-D-mannopyranoside).

Physical and spectroscopic constants of the obtained compound were as follows.

$^{13}C$ NMR (100 MHz, CDCl$_3$) δ: 13.8, 13.9, 14.0, 22.2, 22.3, 22.6, 24.2, 24.4, 24.5, 25.0, 25.25, 25.34, 26.7, 27.7, 28.95, 29.00, 31.2, 31.3, 31.7, 33.9, 33.98, 34.02, 34.1, 62.3, 65.6, 66.4, 68.3, 68.6, 70.8, 72.6, 74.1, 74.6, 78.7, 99.3, 109.0, 109.6, 172.2, 172.6, 172.9, 173.4.

(6) In the same manner as Preparation Example 1 (6) was treated 136 mg of a compound obtained in the above-described (5) to obtain 108 mg of L-arabinitol-5-yl 3,4,6-tri-O-hexanoyl-2-O-octanoyl-β-D-mannopyranoside. Yield was 88%.

Physical and spectroscopic constants of the obtained compound were as follows.

$^{13}C$ NMR (100 MHz, CDOD$_3$) δ: 14.2, 14.3, 14.5, 23.39 23.42, 23.8, 25.5, 25.59, 25.62, 26.3, 30.2, 30.3, 32.4, 32.5, 33.0, 34.8, 34.9, 35.0, 35.2, 63.0 64.8, 66.8, 70.5, 71.3 71.7 71.8, 72.7, 73.0, 73.5, 100.1, 173.75, 173.82, 174.7, 174.9.

Preparation Example 26

(1) 5.0 mL (62.0 mmol) of pyridine was added to methylene chloride (155 mL) solution of 4.28 g (15.5 mmol) of a compound (phenyl 1-thio-α-D-mannopyranoside) and 5.68 g (46.5 mmol) of N,N-dimethyl-4-aminopyridine (DMAP), and was stirred. 16.6 mL (77.4 mmol) of hexanoic anhydride was added dropwise thereto and stirred for 1 day. After adding water to the reaction solution, the resultant was extracted with methylene chloride. After washing an organic layer with saturated sodium bicarbonate water, water and saturated saline solution, the resultant was dried with sodium sulphate. Under reduced pressure, the crude product obtained by distilling off a solvent was purified with silica gel column chromatography (hexane:ethyl acetate=30:1), and 9.81 g of an ester (phenyl 2,3,4,6-tetra-O-hexanoyl-1-thio-α-D-mannopyranoside) was obtained. Yield was 94%.

Physical and spectroscopic constants of the obtained compound were as follows.

$[\alpha]_D^{24}$ +73.8 (c=3.51, CHCl$_3$); IR (neat) cm$^{-1}$: 1748; $^1$H NMR (400 MHz, CDCl$_3$) δ. 0.87-0.91 (m), 1.24-1.35 (m), 1.53-1.67 (m), 2.17-2.45 (m), 4.13 (dd, J=12.0, 2.0), 4.26 (dd, J=12.0, 5.6), 4.54 (ddd, J=9.6, 5.6, 2.0), 5.32 (dd, J=9.6, 2.8), 5.37 (dd, J=9.6, 9.6), 5.47 (d, J=1.6), 5.52 (dd, J=2.8, 1.6), 7.29-7.33 (m), 7.48-7.50 (m); $^{13}$C NMR (100 MHz, CDCl$_3$) δ: 13.8, 13.9, 22.2, 22.3, 24.3, 24.4, 24.5, 24.6, 31.15, 31.2, 31.3, 33.9, 34.0, 34.05, 34.09, 62.3, 65.95, 69.3, 69.7, 70.7, 85.8, 128.0, 129.1, 131.9, 132.9, 172.4, 172.5, 172.6, 173.3; MS (FAB) m/z (%): 687 (MNa$^+$, 4); HRMS (FAB) calcd for C$_{56}$H$_{64}$O$_9$SNa (MNa$^+$): 687.3543. found: 687.3564.

(2) 3.50 g of meta-chloroperbenzoic acid was added to 9.81 g of a compound obtained in the above described (1) in methylene chloride (74 mL), and stirred for 3.5 hours. After adding 10% sodium thiosulfate-saturated sodium bicarbonate water to the reaction solution, the resultant was extracted with methylene chloride. After washing an organic layer with saturated saline solution, the resultant was dried with sodium sulphate. Under reduced pressure, the crude product obtained by distilling off a solvent was purified with silica gel column chromatography (hexane:ethyl acetate=5:1), and 7.18 g of a compound (phenyl 2,3,4,6-tetra-O-hexanoyl-1-thio-α-D-mannopyranoside S-oxide) was obtained.

Physical and spectroscopic constants of the obtained compound were as follows.

$[\alpha]_D^{23}$ 54.5 (c=1.61, CHCl$_3$); IR (neat) cm$^{-1}$: 1748; $^1$H NMR (400 MHz, CDCl$_3$) δ. 0.86-0.92 (m), 1.22-1.34 (m), 1.52-1.67 (m), 2.19-2.38 (m), 4.18 (dd, J=12.8, 2.4), 4.24 (dd, J=12.8, 5.2), 4.55 (d, J=2.0), 4.60 (ddd, J=9.6, 5.2, 2.4), 5.38 (dd, J=9.6, 9.6), 5.66 (dd, J=3.6, 2.0), 5.74 (dd, J=9.6, 3.6), 7.55-7.61 (m), 7.70-7.72 (m); $^{13}$C NMR (100 MHz, CDCl$_3$) δ: 13.8, 13.9, 22.21, 22.23, 22.24, 22.3, 24.3, 24.4, 24.45, 24.5, 31.1, 31.16, 31.2, 31.3, 33.9, 33.99, 34.0, 62.3, 65.3, 65.8, 69.3, 74.8, 94.9, 124.4, 129.5, 131.8, 140.1 172.1, 172.2, 172.3, 173.2; MS (FAB) m/z (%): 703 (MNa$^+$, 33); HRMS (FAB) calcd for C$_{36}$H$_{54}$O$_{10}$SNa (MNa$^+$): 703.3492. found: 703.3481.

(3) Treatment in the same manner as Preparation Example 1 (1) was performed using 1.21 g of a compound obtained in the above-described (2) and 1.00 g of an alcohol (6-O-tert-butyldimethylsilyl-2,3:4,5-di-O-isopropylidene-D-mannitol) to obtain 245 mg of a compound (6-O-tert-butyldimethylsilyl-2,3:4,5-di-O-isopropylidene-D-mannitol-1-yl 2,3,4,6-tetra-O-hexanoyl-α-D-mannopyranoside).

Physical and spectroscopic constants of the obtained compound were as follows.

$^1$H NMR (700 MHz, CDCl$_3$) δ: 0.090 (s), 0.093 (s), 0.88 (t, J=7.0 Hz), 0.89 (t, J=7.0 Hz), 0.90 (t, J=7.0 Hz), 0.91 (s), 1.21-1.35 (m), 1.36 (s), 1.38 (s), 1.46 (s), 1.47 (s), 1.52-1.67 (m), 2.18 (dt, J=15.6, 7.6 Hz), 2.21 (dt, J=15.6, 7.6 Hz), 2.24 (dt, J=15.6, 7.6 Hz), 2.28 (dt, J=15.6, 7.6 Hz), 2.34 (dt, J=15.6, 7.6 Hz), 2.368 (dt, J=15.6, 7.6 Hz), 2.374 (dt, J=15.6, 7.6 Hz), 2.41 (dt, J=15.6, 7.6 Hz), 3.64 (dd, J=9.8, 5.6 Hz), 3.68 (dd, J=10.4, 4.0 Hz), 3.73 (dd, J=9.8, 6.0 Hz), 3.81 (dd, J=10.4, 8.6 Hz), 4.06 (ddd, J=10.0, 5.0, 2.2 Hz), 4.11 (dd, J=12.3, 2.2 Hz), 4.22 (ddd, J=8.6, 5.8, 4.0 Hz), 4.25 (dd, J=12.3, 5.0 Hz), 4.28 (dd, J=6.2, 5.8 Hz), 4.39 (ddd, J=6.2, 6.0, 5.6 Hz), 4.43 (dd, J=6.2, 6.2 Hz), 4.83 (d, J=1.6 Hz), 5.24 (dd, J=2.4, 1.6 Hz), 5.33 (dd, J=10.0, 10.0 Hz), 5.35 (dd, J=10.0, 2.4 Hz); $^{13}$C NMR (175 MHz, CDCl$_3$) δ: −5.5, −5.4, 13.8, 13.86, 13.90, 18.4, 22.25, 22.27, 22.29, 24.38, 24.43, 24.5, 24.6, 25.4, 25.9, 27.4, 27.9, 31.16, 31.20, 31.3, 34.01, 34.03, 34.06, 34.10, 62.05, 62.14, 65.6, 67.6, 68.8, 69.0, 69.2, 75.0, 75.1, 75.6, 77.0, 97.8, 108.6, 108.8, 172.3, 172.7, 173.4.

(4) In the same manner as Preparation Example 1 (6) was treated 31.2 mg of a compound obtained in the above-described (3) to obtain 14.6 mg of D-mannitol-1-yl 2,3,4,6-tetra-O-hexanoyl-α-D-mannopyranoside. Yield was 59%.

Physical and spectroscopic constants of the obtained compound were as follows.

$^1$H NMR (700 MHz, CD$_3$OD) δ: 0.89 (t, J=7.2 Hz), 0.90 (t, J=7.2 Hz), 0.925 (t, J=7.2 Hz), 0.931 (t, J=7.2 Hz), 1.23-1.40 (m), 1.51-1.59 (m), 1.62-1.70 (m), 2.199 (dt, J=15.8, 7.4 Hz), 2.203 (dt, J=15.8, 7.4 Hz), 2.27 (dt, J=15.8, 7.4 Hz), 2.31 (dt, J=15.8, 7.4 Hz), 2.34 (dt, J=15.8, 7.4 Hz), 2.36 (dt, J=15.8, 7.4 Hz), 2.39 (dt, J=15.4, 7.2 Hz), 2.44 (dt, J=15.4, 7.2 Hz), 3.63 (dd, J=11.0, 6.0 Hz), 3.69 (ddd, J=8.2, 6.0, 3.7 Hz), 3.74 (dd, J=10.0, 2.0 Hz), 3.80 (d, J=8.2 Hz), 3.81 (dd, J=11.0, 3.7 Hz), 3.85 (ddd, J=8.2, 5.6, 2.0 Hz), 3.88 (dd, J=10.0, 5.6 Hz), 4.12 (dd, J=12.4, 2.2 Hz), 4.18 (ddd, J=9.8, 4.0, 2.2 Hz), 4.25 (dd, J=12.2, 4.0 Hz), 4.86 (brs), 5.32-5.33 (m), 5.34-5.36 (m); $^{13}$C NMR (175 MHz, CD$_3$OD) δ: 14.2, 14.3, 23.3, 23.37, 23.40, 23.45, 25.5, 25.61, 25.63, 25.9, 32.3, 32.4, 34.9, 34.97, 35.01, 35.1, 63.1, 65.2, 66.8, 69.9, 70.6, 70.9, 71.05, 71.12, 71.2, 73.0, 99.2, 173.9, 174.06, 174.13, 175.1.

Furthermore, treatment was performed in the same manner as described above except that hexanoic anhydride used in the above-described (3) was substituted with octanoyl chloride and propionyl chloride to obtain a compound A (D-mannitol-1-yl 2,3,4,6-tetra-O-octanoyl-α-D-mannopyranoside) and a compound B (D-mannitol-1-yl 2,3,4,6-tetra-O-propionyl-α-D-mannopyranoside).

Physical and spectroscopic constants of the obtained compounds A and B were as follows.

Physical and spectroscopic constants of the compound A:
$^1$H NMR (700 MHz, CD$_3$OD) δ: 0.893 (t, J=7.2 Hz), 0.896 (t, J=7.2 Hz), 0.90 (t, J=7.2 Hz), 0.91 (t, J=7.2 Hz), 1.28-1.40 (m), 1.52-1.58 (m), 1.62-1.70 (m), 2.19 (dt, J=15.8, 7.4 Hz), 2.21 (dt, J=15.8, 7.4 Hz), 2.26 (dt, J=15.8, 7.4 Hz), 2.31 (dt, J=15.8, 7.4 Hz), 2.34 (dt, J=15.8, 7.4 Hz), 2.37 (dt, J=15.8, 7.4 Hz), 2.39 (dt, J=15.4, 7.2 Hz), 2.44 (dt, J=15.4, 7.2 Hz), 3.63 (dd, J=11.2, 6.0 Hz), 3.69 (ddd, J=8.6, 6.0, 3.6 Hz), 3.74 (dd, J=10.0, 2.0 Hz), 3.80 (d, J=8.6 Hz), 3.81 (dd, J=11.2, 3.6 Hz), 3.85 (ddd, J=8.6, 5.8, 2.0 Hz), 3.88 (dd, J=10.0, 5.8 Hz), 4.11 (dd, J=12.2, 2.2 Hz), 4.18 (ddd, J=9.8, 3.8, 2.2 Hz), 4.26 (dd, J=12.2, 3.8 Hz), 4.87 (d, J=1.6 Hz), 5.33 (dd, J=3.2, 1.6 Hz), 5.35 (dd, J=9.8, 3.2 Hz), 5.37 (dd, J=9.8, 9.8 Hz); $^{13}$C NMR (175 MHz, CD$_3$OD) δ: 14.4, 14.45, 14.48, 23.7, 23.8, 25.8, 25.96, 25.98, 26.3, 30.1, 30.15 (4C), 30.19, 30.21, 30.25, 32.86, 32.92, 33.0, 34.9, 35.0, 35.1, 35.2, 63.0, 65.2, 66.8, 69.9, 70.6, 70.9, 71.08, 71.14, 71.2, 73.0, 99.2, 173.8, 174.0, 174.1, 175.0. Physical and spectroscopic constants of the compound B: $^1$H NMR (700 MHz, CD$_3$OD) δ: 1.04 (t, J=7.6 Hz), 1.08 (t, J=7.6 Hz), 1.14 (t, J=7.6 Hz), 1.17 (t, J=7.6 Hz), 2.22 (q, J=7.6 Hz), 2.29 (dq, J=16.4, 7.6 Hz), 2.33 (dq, J=16.4, 7.6 Hz), 2.36 (dq, J=16.6, 7.6 Hz), 2.38 (dq, J=16.6, 7.6 Hz), 2.42 (dq, J=16.6, 7.6 Hz), 2.45 (dq, J=16.6, 7.6 Hz), 3.63 (dd, J=11.2, 6.0 Hz), 3.69 (ddd, J=8.2, 6.0, 3.6 Hz), 3.74 (dd, J=9.8, 2.0 Hz), 3.79-3.81 (m), 3.81 (dd, J=11.2, 3.6 Hz), 3.85 (dd, J=8.0, 5.8, 2.0 Hz), 3.88 (dd, J=9.8, 5.8 Hz), 4.13 (dd, J=12.2, 2.2 Hz), 4.18 (ddd, J=10.0, 4.2, 2.2 Hz), 4.27 (dd, J=12.2, 4.2 Hz), 4.87 (d, J=1.6 Hz), 5.32 (dd, J=10.0, 10.0 Hz), 5.33 (dd, J=3.2, 1.6 Hz), 5.36 (dd, J=10.0, 3.2 Hz); $^{13}$C NMR (175 MHz, CD$_3$OD) δ: 9.2, 9.38, 9.41, 9.5, 28.28, 28.30, 28.32, 63.1, 65.2, 67.1, 69.9, 70.7, 71.0, 71.05, 71.14, 71.17, 71.22, 73.1, 99.1, 174.8, 174.85, 174.91, 175.7.

Preparation Example 27

(1) In the same manner as Preparation Example 1 (3) was treated 4.28 g of the compound (phenyl 4,6-O-benzylidene-3-O-p-methoxybenzyl-1-thio-α-D-mannopyranoside) to obtain 9.81 g of a compound (phenyl 4,6-O-benzylidene-3-O-p-methoxybenzyl-2-O-octanoyl-1-thio-α-D-mannopyranoside). Yield was 94%.

Physical and spectroscopic constants of the obtained compound were as follows.

[α]$^{26}_D$ 85.7 (c 1.00, CHCl$_3$); IR (neat) cm$^{-1}$: 1740; $^1$H NMR (400 MHz, CDCl$_3$) δ: 0.87 (t, J=7.2 Hz), 1.24-1.33 (m), 1.64 (tt, J=7.2, 7.2 Hz), 2.40 (t, J=7.2 Hz), 3.80 (s), 3.85 (dd, J=10.0, 10.0 Hz), 3.99 (dd, J=10.0, 3.2 Hz), 4.10 (dd, J=10.0, 10.0 Hz), 4.22 (dd, J=10.0, 4.8 Hz), 4.35 (ddd, J=10.0, 10.0, 4.8 Hz), 4.60 (d, J=11.6 Hz), 4.65 (d, J=11.6 Hz), 5.44 (d, J=1.2 Hz), 5.61 (dd, J=3.2, 1.2 Hz), 5.63 (s), 6.85 (d, J=8.8 Hz), 7.27-7.34 (m), 7.37-7.42 (m), 7.44-7.46 (m), 7.50-7.53 (m); $^{13}$C NMR (100 MHz, CDCl$_3$) δ: 14.1, 22.6, 24.9, 28.9, 29.0, 31.6, 34.2, 55.2, 65.2, 68.4, 71.0, 71.9, 73.7, 78.5, 87.3, 101.6, 113.8, 126.1, 128.0, 128.2, 128.9, 129.2, 129.5, 129.7, 132.1, 133.1, 137.4, 159.3, 172.9; MS (FAB) m/z (%): 629 (MNa$^+$, 6), 73 (100); HRMS (FAB) calcd for C$_{35}$H$_{42}$O$_7$SNa (MNa$^+$): 629.2549. found: 629.2529.

(2) In the same manner as Preparation Example 16 (4) was treated 357 mg of a compound obtained in the above-described (1) to obtain 188 mg of a compound (phenyl 2-O-octanoyl-1-thio-α-D-mannopyranoside). Yield was 80%.

Physical and spectroscopic constants of the obtained compound were as follows.

[α]$^{24}_D$ 114.4 (c 1.01, CHCl$_3$); IR (neat) cm$^{-1}$: 3383, 1740; $^1$H NMR (400 MHz, CDCl$_3$) δ: 0.87 (t, J=6.8 Hz), 1.23-1.34 (m), 1.63 (tt, J=7.2, 7.2 Hz), 1.87 (t, J=6.4 Hz), 2.34 (d, J=6.0 Hz), 2.38 (t, J=7.2 Hz), 2.64 (d, J=2.8 Hz), 3.87-3.91 (m), 3.91 (ddd, J=9.2, 9.2, 2.8 Hz), 4.02 (ddd, J=9.2, 6.0, 2.0 Hz), 4.19 (dt, J=9.2, 6.0 Hz), 5.37 (d, J=2.0 Hz), 5.48 (s), 7.29-7.35 (m), 7.48 (dd, J=7.2, 1.2 Hz); $^{13}$C NMR (100 MHz, CDCl$_3$) δ: 14.0, 22.5, 24.8, 28.9, 29.0, 31.6, 34.2, 62.2, 68.5, 70.8, 72.9, 73.4, 86.3, 128.0, 129.2, 132.2, 133.2, 173.6; MS (FAB) m/z (%): 421 (MNa$^+$, 56), 57 (100); HRMS (FAB) calcd for C$_{20}$H$_{30}$O$_6$SNa (MNa$^+$): 421.1661. found: 421.1678.

(3) In the same manner as Preparation Example 1 (5) was treated 178 mg of a compound obtained in the above-described (2) to obtain 310 mg of a compound (phenyl 3,4,6-tri-O-hexanoyl 2-O-octanoyl-1-thio-α-D-mannopyranoside).

Physical and spectroscopic constants of the obtained compound were as follows.

$[\alpha]^{25}_D$ 71.9 (c 1.07, CHCl$_3$); IR (neat) cm$^{-1}$: 1748; $^1$H NMR (400 MHz, CDCl$_3$) δ: 0.86-0.91 (m), 1.25-1.33 (m), 153-1.68 (m), 2.21-2.41 (m), 4.13 (dd, J=12.4, 1.6 Hz), 4.26 (dd, J=12.4, 5.6 Hz), 4.54 (ddd, J=10.0, 5.6, 1.6 Hz), 5.32 (dd, J=10.0, 3.2 Hz), 5.37 (dd, J=10.0, 10.0 Hz), 5.47 (d, J=1.2 Hz), 5.52 (dd, J=3.2, 1.2 Hz), 7.28-7.33 (m), 7.47-7.50 (m); $^{13}$C NMR (100 MHz, CDCl$_3$) δ: 13.78, 13.84, 14.0, 22.21, 22.2, 22.5, 24.3, 24.4, 24.5, 24.9, 28.9, 29.0, 31.1, 31.2, 31.3, 31.6, 33.89, 33.94, 34.0, 34.1, 62.2, 65.9, 69.3, 69.7, 70.7, 85.8, 128.0, 129.1, 131.9, 132.8, 172.3, 172.5, 172.6, 173.3; MS (FAB) m/z (%): 715 (MNa$^+$, 4), 73 (100); HRMS (FAB) calcd for C$_{38}$H$_{60}$O$_9$SNa (MNa$^+$): 715.3856. found: 715.3867.

(4) In the same manner as Preparation Example 26 (2) was treated 553 mg of a compound obtained in the above-described (3) to obtain 420 mg of a compound (phenyl 3,4,6-tri-O-hexanoyl 2-O-octanoyl-1-thio-α-D-mannopyranoside S-oxide).

Physical and spectroscopic constants of the obtained compound were as follows.

$[\alpha]^{25}_D$ −56.3 (c 1.08, CHCl$_3$); IR (neat) cm$^{-1}$: 1748, 1045; $^1$H NMR (700 MHz, CDCl$_3$) δ: 0.87 (t, J=7.0 Hz), 0.88 (t, J=7.0 Hz), 0.90 (t, J=7.0 Hz), 0.91 (t, J=7.0 Hz), 1.21-1.36 (m), 1.53-1.68 (m), 2.17-2.38 (m), 4.18 (dd, J=12.4, 2.2 Hz), 4.24 (dd, J=12.4, 5.5 Hz), 4.55 (d, J=1.6 Hz), 4.59 (ddd, J=9.8, 5.5, 2.2 Hz), 5.38 (dd, J=9.8, 9.8 Hz), 5.66 (dd, J=3.6, 1.6 Hz), 5.74 (dd, J=9.8, 3.6 Hz), 7.55-7.72 (m); $^{13}$C NMR (175 MHz, CDCl$_3$) δ: 13.8, 13.9, 14.0, 22.2, 22.3, 22.6, 24.35, 24.45, 24.49, 24.8, 28.8, 29.0, 31.17, 31.20, 31.3, 31.6, 33.9, 33.97, 34.00, 34.02, 62.3, 65.3, 65.8, 69.3, 74.8, 94.9, 124.4, 129.5, 131.8, 140.1, 172.1, 172.2, 172.3, 173.2; MS (FAB) m/z (%): 731 (MNa$^+$, 8), 73 (100); HRMS (FAB) calcd for C$_{38}$H$_{60}$O$_{10}$SNa (MNa$^+$): 731.3805. found: 731.3799.

(5) Treatment in the same manner as Preparation Example 1 (1) was performed using 100 mg of a compound obtained in the above-described (4) and 63.6 mg of an alcohol (6-O-tert-butyldimethylsilyl-2,3:4,5-di-O-isopropylidene-D-mannitol) to obtain 17.6 mg of a compound A (6-O-tert-butyldimethylsilyl-2,3:4,5-di-O-isopropylidene-D-mannitol-1-yl 3,4,6-tri-O-hexanoyl-2-O-octanoyl-α-D-mannopyranoside), 50.1 mg of a compound B (3,4,6-tri-O-hexanoyl-2-O-octanoyl-β-D-mannopyranoside-(1→6)-1-O-tert-butyldimethylsilyl-2,3:4,5-di-O-isopropylidene-D-mannitol orthoester) and 23.7 mg of a compound C (3,4,6-tri-O-hexanoyl-2-O-octanoyl-α-D-mannopyranose).

Physical and spectroscopic constants of the obtained compounds A to C were as follows.

Physical and spectroscopic constants of the compound A: $[\alpha]^{24}_D$ 21.2 (c 0.83, CHCl$_3$); IR (neat) cm$^{-1}$: 1748; $^1$H NMR (700 MHz, CDCl$_3$) δ: 0.090 (s), 0.093 (s), 0.87-0.91 (m), 0.91 (s), 1.21-1.35 (m), 1.36 (s), 1.38 (s), 1.46 (s), 1.47 (s), 1.54 (ddt, J=7.6, 7.6, 7.6 Hz), 1.57 (ddt, J=7.6, 7.6, 7.6 Hz), 1.64 (ddt, J=7.6, 7.6, 7.6 Hz), 2.18 (dt, J=15.6, 7.6 Hz), 2.21 (dt, J=15.6, 7.6 Hz), 2.24 (dt, J=15.6, 7.6 Hz), 2.28 (dt, J=15.6, 7.6 Hz), 2.34 (dt, J=15.6, 7.6 Hz), 2.369 (dt, J=15.6, 7.6 Hz), 2.374 (dt, J=15.6, 7.6 Hz), 2.40 (dt, J=15.6, 7.6 Hz), 3.64 (dd, J=9.8, 5.6 Hz), 3.68 (dd, J=10.4, 4.0 Hz), 3.73 (dd, J=9.8, 6.2 Hz), 3.81 (dd, J=10.4, 8.6 Hz), 4.06 (ddd, J=9.8, 5.0, 2.2 Hz), 4.11 (dd, J=12.4, 2.2 Hz), 4.22 (ddd, J=8.6, 6.2, 4.0 Hz), 4.25 (dd, J=12.4, 5.0 Hz), 4.28 (dd, J=6.2, 6.2 Hz), 4.39 (ddd, J=6.2, 6.2, 5.6 Hz), 4.43 (dd, J=6.2, 6.2 Hz), 4.83 (d, J=1.6 Hz), 5.24 (dd, J=2.2, 1.6 Hz), 5.32-5.35 (m); $^{13}$C NMR (175 MHz, CDCl$_3$) δ: −5.56, −5.41, 13.8, 13.9, 14.0, 18.3, 22.2, 22.3, 22.6, 24.38, 24.42, 24.5, 25.0, 25.4, 25.9, 27.4, 27.9, 28.9, 29.0, 31.2, 31.3, 31.7, 34.00, 34.03, 34.1, 62.0, 62.1, 65.6, 67.6, 68.8, 68.9, 69.2, 75.0, 75.1, 75.5, 77.0, 97.8, 108.6, 108.8, 172.3, 172.7, 173.4; MS (FAB) m/z (%): 981 (MNa$^+$, 10), 73 (100); HRMS (FAB) calcd for C$_{50}$H$_{90}$O$_{15}$SiNa (MNa$^+$): 981.5947. found: 981.5952.

Physical and spectroscopic constants of the compound B: $[\alpha]^{26}_D$ −2.21 (c 1.69, CHCl$_3$); IR (neat) cm$^{-1}$: 1748; $^1$H NMR (700 MHz, CDCl$_3$) δ: 0.07 (s), 0.08 (s), 0.87-0.92 (m), 0.89 (s), 1.24-1.35 (m), 1.36 (s), 1.37 (s), 1.456 (s), 1.465 (s), 1.48-1.54 (m), 1.55-1.64 (m), 1.95 (ddd, J=13.8, 10.6, 5.8 Hz), 2.00 (ddd, J=13.8, 10.6, 5.8 Hz), 2.24 (dt, J=15.6, 7.6 Hz), 2.28 (dt, J=15.6, 7.6 Hz), 2.30 (dt, J=15.6, 7.6 Hz), 2.32 (dt, J=15.6, 7.6 Hz), 2.34 (dt, J=15.6, 7.6 Hz), 2.37 (dt, J=15.6, 7.6 Hz), 3.44 (dd, J=9.2, 4.6 Hz), 3.57 (dd, J=10.4, 4.0 Hz), 3.62 (dd, J=9.2, 7.4 Hz), 3.64 (ddd, J=9.8, 4.6, 2.4 Hz), 3.75 (dd, J=10.4, 8.0 Hz), 4.11 (dd, J=12.2, 2.4 Hz), 4.13 (ddd, J=8.0, 5.8, 4.0 Hz), 4.21 (dd, J=12.2, 4.6 Hz), 4.32 (dd, J=7.6, 5.8 Hz), 4.34 (ddd, J=7.4, 5.6, 4.6 Hz), 4.42 (dd, J=7.6, 5.6 Hz), 4.58 (dd, J=4.0, 2.6 Hz), 5.13 (dd, J=9.8, 4.0 Hz), 5.30 (dd, J=9.8, 9.8 Hz), 5.47 (d, J=2.6 Hz); $^{13}$C NMR (175 MHz, CDCl$_3$) δ: −5.6, −5.4, 13.83, 13.84, 13.9, 14.1, 18.3, 22.2, 22.3, 22.6, 23.7, 24.4, 24.5, 25.4, 25.5, 25.9, 27.6, 27.7, 29.2, 29.6, 31.16, 31.18, 31.3, 31.9, 33.96, 33.99, 34.01, 38.2, 61.0, 62.0, 62.2, 65.0, 70.4, 71.4, 75.1, 75.2, 75.3, 76.6, 77.1, 97.2, 108.4, 108.6, 125.4, 172.1, 173.1, 173.4; MS (FAB) m/z (%): 981 (MNa$^+$, 6), 73 (100); HRMS (FAB) calcd for C$_{50}$H$_{90}$O$_{15}$SiNa (MNa$^+$): 981.5947. found: 981.5963. Physical and spectroscopic constants of the compound C: $[\alpha]^{22}_D$ 4.4 (c 1.05, CHCl$_3$); IR (neat) cm$^{-1}$: 3445, 1748; $^1$H NMR (400 MHz, CDCl$_3$) δ: 0.86-0.92 (m), 1.21-1.40 (m), 1.52-1.68 (m), 2.15-2.46 (m), 3.18 (d, J=4.0 Hz), 4.16 (dd, J=12.0, 2.4 Hz), 4.21 (dd, J=12.0, 4.4 Hz), 4.23 (ddd, J=10.0, 4.4, 2.4 Hz), 5.23 (dd, J=4.0, 2.0 Hz), 5.29 (dd, J=3.2, 2.0 Hz), 5.34 (dd, J=10.0, 10.0 Hz), 5.43 (dd, J=10.0, 3.2 Hz); $^{13}$C NMR (100 MHz, CDCl$_3$) δ: 13.8, 13.9, 14.0, 22.2, 22.3, 22.6, 24.3, 24.4, 24.5, 24.9, 28.9, 29.0, 31.2, 31.3, 31.7, 34.01, 34.03, 34.2, 62.3, 65.8, 68.6, 68.8, 69.7, 92.3, 172.4, 172.6, 172.8, 173.5; MS (FAB) m/z (%): 623 (MNa$^+$, 39), 99 (100); HRMS (FAB) calcd for C$_{32}$H$_{56}$O$_{10}$Na (MNa$^+$): 623.3771. found: 623.3765.

(6) In the same manner as Preparation Example 1 (6) was treated 8.3 mg of the compound A obtained in the above-described (5) to obtain 4.6 mg of D-mannitol-1-yl 3,4,6-tri-O-hexanoyl-2-O-octanoyl-α-D-mannopyranoside. Yield was 70%.

Physical and spectroscopic constants of the obtained compound were as follows.

$[\alpha]^{23}_D$ 17.5 (c 0.45, CHCl$_3$); IR (neat) cm$^{-1}$: 3449, 1748; $^1$H NMR (700 MHz, CD$_3$OD) δ: 0.901 (t, J=7.2 Hz), 0.902 (t, J=7.2 Hz), 0.91 (t, J=7.2 Hz), 0.93 (t, J=7.2 Hz), 1.24-1.39 (m), 1.52-1.60 (m), 1.63-1.70 (m), 2.19 (dt, J=15.8, 7.6 Hz), 2.22 (dt, J=15.8, 7.6 Hz), 2.27 (dt, J=15.8, 7.4 Hz), 2.31 (dt, J=15.8, 7.4 Hz), 2.34 (dt, J=15.6, 7.4 Hz), 2.37 (dt, J=15.8, 7.4 Hz), 2.39 (dt, J=15.8, 7.4 Hz), 2.45 (dt, J=15.8, 7.4 Hz), 3.64 (dd, J=11.0, 6.0 Hz), 3.70 (ddd, J=8.2, 6.0, 3.6 Hz), 3.74 (dd, J=10.0, 2.0 Hz), 3.81 (d, J=8.2 Hz and d, J=8.6 Hz), 3.82 (dd, J=11.0, 3.6 Hz), 3.85 (ddd, J=8.6, 5.8, 2.0 Hz), 3.89 (dd, J=10.0, 5.8 Hz), 4.13 (dd, J=12.4, 2.0 Hz), 4.18 (ddd, J=10.0, 4.0, 2.0 Hz), 4.22 (dd, J=12.4, 4.0 Hz), 4.86 (d, J=1.8 Hz), 5.34 (dd, J=3.0, 1.8 Hz), 5.36 (dd, J=10.0, 3.0 Hz), 5.37 (dd, J=10.0, 10.0 Hz, 1H, OCH); $^{13}$C NMR (175 MHz, CD$_3$OD) δ: 14.2, 14.3, 14.4, 23.35, 23.37, 23.4, 23.7, 25.5, 25.62, 25.63, 26.3, 30.16, 30.21, 32.36, 32.44, 32.9, 34.9, 34.99, 35.03, 35.2, 63.1, 65.2, 66.8, 69.9, 70.6, 70.9, 71.06, 71.14, 71.2, 73.0, 99.2, 173.8, 174.06, 174.12, 175.05; MS (FAB) m/z (%): 787 (MNa$^+$, 9), 73 (100); HRMS (FAB) calcd for $C_{38}H_{68}O_{15}Na$ (MNa$^+$): 787.4456. found: 787.4433.

Preparation Example 28

(1) 0.023 mL (0.278 mmol) of pyridine was added to methylene chloride solution (5.6 mL) of 30.0 mg (0.0557 mmol) of a compound (6-O-tert-butyldimethylsilyl-2,3:4,5-di-O-isopropylidene-D-mannitol-1-yl β-D-mannopyranoside) obtained in Preparation Example 12 (2) and 34.0 mg (0.278 mmol) of N,N-dimethyl-4-aminopyridine (DMAP), and stirred. 0.045 mL (0.278) of butyric anhydride was added dropwise thereto and stirred for 8 hours. After adding water to the reaction solution, the resultant was extracted with methylene chloride. After washing an organic layer with saturated sodium bicarbonate water, water and saturated saline solution, the resultant was dried with sodium sulphate. Under reduced pressure, the crude product obtained by distilling off a solvent was purified with silica gel column chromatography (hexane:ethyl acetate=30:1), and 44.6 mg of an ester (6-O-tert-butyldimethylsilyl-2,3:4,5-di-O-isopropylidene-D-mannitol-1-yl 2,3,4,6-tetra-O-butanoyl-β-D-mannopyranoside) was obtained. Yield was 98%.

Physical and spectroscopic constants of the obtained compound were as follows.
$^{13}$C NMR (100 Hz, CDCl$_3$) δ: −5.6, −5.5, 13.53, 13.55, 13.6, 13.7, 18.0, 18.26, 18.29, 18.5, 25.3, 25.5, 25.9, 27.6, 27.9, 35.8, 35.92, 35.94, 36.0, 62.2, 62.3, 65.6, 68.2, 68.5, 71.1, 72.6, 75.0, 75.2, 75.7, 76.8, 98.4, 108.4, 108.7, 172.2, 172.4, 172.6, 173.2.

(2) In the same manner as Preparation Example 1 (6) was treated 31.1 mg of a compound obtained in the above-described (1) to obtain 15.5 mg of D-mannitol-1-yl 2,3,4,6-tetra-O-butanoyl-β-D-mannopyranoside. Yield was 65%.

Physical and spectroscopic constants of the obtained compound were as follows.
$^{13}$C NMR (100 Hz, CD$_3$OD) δ: 13.90, 13.91, 14.02, 14.04, 19.1, 19.3, 19.6, 36.8, 36.9, 37.0, 63.1, 65.2, 66.9, 70.4, 71.0, 71.1, 71.7, 72.7, 73.0, 73.5, 73.7, 100.5, 173.7, 173.8, 174.6, 174.8.

Furthermore, treatment was performed in the same manner as described above except that butyric anhydride used in the above-described (1) was substituted with valeric anhydride and heptanoic anhydride, respectively, to obtain a compound A (D-mannitol-1-yl 2,3,4,6-tetra-O-pentanoyl-β-D-mannopyranoside) and a compound B (D-mannitol-1-yl 2,3,4,6-tetra-O-heptanoyl-β-D-mannopyranoside).

Physical and spectroscopic constants of the obtained compounds A and B were as follows.
Physical and spectroscopic constants of the compound A:
$^{13}$C NMR (100 Hz, CD$_3$OD) δ: 14.0, 14.10, 14.13, 23.2, 23.3, 27.9, 28.02, 28.05, 28.4, 34.7, 34.8, 63.1, 65.2, 66.9, 70.5, 71.0, 71.1, 71.7, 72.7, 73.0, 73.5, 73.7, 100.5, 173.8, 173.9, 174.8, 175.0.
Physical and spectroscopic constants of the compound B:
$^{13}$C NMR (100 Hz, CD$_3$OD) δ: 14.38, 14.42, 14.5, 23.5, 23.6, 23.7, 25.7, 25.87, 25.91, 26.3, 29.85, 29.88, 29.93, 29.95, 32.6, 32.67, 32.69, 32.8, 34.9, 34.97, 35.02, 35.2, 63.0, 65.2, 66.8, 70.5, 71.0, 71.2, 71.7, 72.7, 73.0, 73.5, 73.7, 100.6, 173.76, 173.82, 174.7, 175.0.

Reference Example 1

(1) The compound (300 mg) described in Literature (J. Org. Chem., 2006, 71, 3064-3070) was treated with param-ethoxybenzyl chloride in DMF in the presence of sodium hydride to obtain 316 mg of a compound (phenyl 3-O-benzyl-4,6-O-benzylidene-2-O-p-methoxybenzyl-1-thio-α-D-mannopyranoside). Yield was 63%.

(2) 7.97 g of a compound obtained in the above-described (1) was treated with 3.01 g of meta-chloroperbenzoic acid in methylene chloride to obtain 5.43 g of a mannosyl sulfoxide compound (chemical name: phenyl 3-O-benzyl-4,6-O-benzylidene-2-O-p-methoxybenzyl-1-thio-α-D-mannopyranoside S-oxide).

Physical and spectroscopic constants of the obtained compound were as follows.
$^1$H-NMR (CDCl$_3$) δ: 3.75 (1H, dd, J=10.0, 10.0), 3.78 (3H, s), 4.10 (1H, ddd, J=10.0, 9.2, 4.8), 4.21 (1H, dd, J=10.0, 4.8), 4.27 (1H, dd, J=10.0, 2.8), 4.31 (1H, dd, J=10.0, 9.2), 4.38 (1H, d, J=2.8), 4.47 (1H, brs), 4.51 (2H, s), 4.64 (1H, d, J=12.0), 4.81 (1H, d, J=12.0), 5.62 (1H, s), 7.12-7.14 (2H, m), 7.28-7.56 (17H, m). $^{13}$C-NMR (CDCl$_3$) δ: 55.2, 68.2, 70.0, 72.2, 73.0, 73.1, 76.3, 78.0, 97.7, 101.6, 113.7 (2C), 124.3 (2C), 126.0 (2C), 127.6, 127.7 (3C), 128.2 (2C), 128.3 (3C), 128.9, 129.3 (2C), 129.9 (2C), 131.5, 137.3, 138.3, 159.3.

Reference Example 2

(1) 300 mg of an alcohol described in Literature (Tetrahedron Lett., 2005, 46, 5393-5397) was treated with benzyl bromide in DMF in the presence of sodium hydride to obtain 316 mg of a compound (6-O-benzyl-2,3:4,5-di-O-isoptoypy-lidene-D-mannitol) in which only one hydroxyl group thereof was protected with a benzyl group. Yield was 78%.

Physical and spectroscopic constants of the obtained compound were as follows.
$^1$H NMR (400 MHz, CDCl$_3$) δ: 1.33 (s, 3H, CH$_3$), 1.38 (s, 3H, CH$_3$), 1.48 (s, 3H, CH$_3$), 1.50 (s, 3H, CH$_3$), 2.42 (t, J=6.4 Hz, 1H, OH), 3.55 (dd, J=9.2, 4.8 Hz, 1H, OCH), 3.60-3.69 (m, 3H, 3×OCH), 4.16 (ddd, J=6.4, 6.4, 6.4 Hz, 1H, OCH), 4.22 (dd, J=6.0, 6.0 Hz, 1H, OCH), 4.36-4.42 (m, 2H, 2×OCH), 4.49 (d, J=11.6 Hz, 1H, OCHHPh), 4.58 (d, J=11.6 Hz, 1H, OCHHPh), 7.29-7.38 (m, 5H, Ar); $^{13}$C NMR (100 MHz, CDCl$_3$) δ: 25.2, 25.5, 27.3, 27.4, 61.8, 68.5, 73.7, 74.9, 75.0, 75.2, 77.2, 108.6, 109.0, 128.0, 128.1 (2C), 128.5 (2C), 137.3

Reference Example 3

(1) 5.4 g of D-glucose was treated with ethanethiol in concentrated hydrochloric acid to obtain 3.5 g of a compound in which an aldehyde group was thioacetalized.

(2) 3.4 g of a compound obtained in the above-described (1) was treated in acetone in the presence of concentrated sulfuric acid at room temperature for 1 hour to obtain a compound in which a hydroxyl group has been protected with acetal. Without purifying, the resultant was treated with tert-butyldimethylsilyl chloride in pyridine to obtain a compound in which a hydroxyl group at the 4-position was tert-butyldimethylsilylated. Next, the compound was treated with N-bromosuccinimide in acetone at −78° C. to eliminate a thioacetal group, and was treated with sodium borohydride in ethanol to obtain 879 mg of an alcohol in which an aldehyde was reduced.

Physical and spectroscopic constants of the obtained compound were as follows.

$^1$H-NMR (CDCl$_3$) δ: 0.11 (3H, s), 0.13 (3H, s), 0.90 (9H, s), 1.33 (3H, s), 1.39 (3H, s), 1.41 (6H, s), 3.67-4.60 (8H, m). $^{13}$C-NMR (CDCl$_3$) δ: −4.38, −4.07, 18.2, 25.1, 25.9 (3C), 26.4, 26.9, 27.0, 62.3, 66.4, 72.9, 76.5, 77.2, 79.5, 108.6, 108.8.

Reference Example 4

(1) 1.78 g of an alcohol (2,3-isopropylidene-erythritol) synthesized according to the method described in Literature (Org. Biomol. Chem, 2003, 1, 3692-3697) was treated with tert-butyldimethylsilyl chloride and sodium hydride in DMF to obtain 0.99 g of an alcohol (1-O-tert-butyldimethylsilyl-2,3-O-isopropylidene erythritol and 4-O-tert-butyldimethylsilyl-2,3-O-isopropylidene erythritol).

Physical and spectroscopic constants of the compound: $^1$H-NMR (400 MHz, CDCl$_3$) δ: 0.106 (3H, s), 0.109 (3H, s), 0.91 (9H, s), 1.36 (3H, s), 1.42 (3H, s), 3.68 (1H, dd, J=10.6, 4.0), 3.76 (1H, dd, J=10.6, 6.0), 3.79 (1H, ddd, J=7.8, 7.2, 5.6), 3.81 (1H, dd, J=12.0, 7.2), 4.22 (1H, ddd, J=7.8, 6.0, 4.0), 4.34 (1H, dd, J=12.0, 5.6). $^{13}$C-NMR (100 MHz, CDCl$_3$) δ: −5.68, −5.62, 18.1, 25.1, 25.7 (3C), 27.7, 60.7, 61.5, 76.7, 77.3, 108.3.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

The invention claimed is:

1. An antitumor agent comprising a glycolipid glycoside compound represented by Formula (1) or a pharmacologically acceptable salt thereof as an active ingredient:

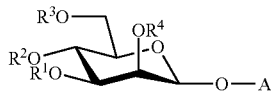

(1)

wherein in Formula (1),

R$^1$ is CH$_3$(CH$_2$)$_m$CO—;

R$^2$ is CH$_3$(CH$_2$)$_n$CO—;

R$^3$ is CH$_3$(CH$_2$)$_h$CO—;

R$^4$ is CH$_3$(CH$_2$)$_f$CO—;

f, h, m, and n each independently represent an integer from 4 to 6; and

A is selected from the group consisting of an erythritol residue, a threitol residue, a ribitol residue, an arabinitol residue, a xylitol residue, a sorbitol residue, a galactitol residue, a perseitol residue, a volemitol residue, a D-glycero-D-glucoheptitol residue, a glycerol residue, and an ethyleneglycol residue.

2. An antitumor combination comprising, as active ingredients, a glycolipid glycoside compound represented by Formula (1) or a pharmacologically acceptable salt thereof, and a second antitumor agent:

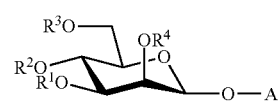

(1)

wherein in Formula (1),

R$^1$ is CH$_3$(CH$_2$)$_m$—CO—;

R$^2$ is CH$_3$(CH$_2$)$_n$CO—;

R$^3$ is CH$_3$(CH$_2$)$_h$CO—;

R$^4$ is CH$_3$(CH$_2$)$_f$CO—;

f, h, m, and n each independently represent an integer 4 to 6; and

A is selected from the group consisting of an erythritol residue, a threitol residue, a ribitol residue, an arabinitol residue, a xylitol residue, a sorbitol residue, a galactitol residue, a perseitol residue, a volemitol residue, a D-glycero-D-glucoheptitol residue, a glycerol residue and an ethyleneglycol residue.

* * * * *